US012404509B2

(12) United States Patent
Kortylewski et al.

(10) Patent No.: US 12,404,509 B2
(45) Date of Patent: Sep. 2, 2025

(54) OLIGONUCLEOTIDE-BASED PROTEOLYSIS TARGETING CHIMERA

(71) Applicant: City of Hope, Duarte, CA (US)

(72) Inventors: Marcin Kortylewski, Monrovia, CA (US); Piotr Marek Swiderski, San Dimas, CA (US); Steven Rosen, Duarte, CA (US)

(73) Assignee: City of Hope, Duarte, CA (US)

( * ) Notice: Subject to any disclaimer, the term of this patent is extended or adjusted under 35 U.S.C. 154(b) by 1272 days.

(21) Appl. No.: 17/251,549

(22) PCT Filed: Jun. 17, 2019

(86) PCT No.: PCT/US2019/037447
§ 371 (c)(1),
(2) Date: Jun. 25, 2021

(87) PCT Pub. No.: WO2019/241766
PCT Pub. Date: Dec. 19, 2019

(65) Prior Publication Data
US 2021/0269803 A1    Sep. 2, 2021

Related U.S. Application Data

(60) Provisional application No. 62/685,810, filed on Jun. 15, 2018.

(51) Int. Cl.
*C12N 15/117* (2010.01)
*A61K 47/54* (2017.01)
*C12N 15/113* (2010.01)

(52) U.S. Cl.
CPC .......... *C12N 15/117* (2013.01); *A61K 47/545* (2017.08); *A61K 47/549* (2017.08); *C12N 15/113* (2013.01); *C12N 2310/13* (2013.01); *C12N 2310/14* (2013.01); *C12N 2310/17* (2013.01); *C12N 2310/315* (2013.01); *C12N 2310/351* (2013.01)

(58) Field of Classification Search
CPC .............. C12N 15/117; C12N 15/113; C12N 2310/13; C12N 2310/14; C12N 2310/17; C12N 2310/315; C12N 2310/351; A61K 47/545; A61K 47/549
See application file for complete search history.

(56) References Cited

U.S. PATENT DOCUMENTS

| 8,748,405 B2 | 6/2014 | Yu et al. |
|---|---|---|
| 9,200,279 B2 | 12/2015 | Yu et al. |
| 9,200,280 B2 | 12/2015 | Yu et al. |
| 9,688,982 B2 | 6/2017 | Yu et al. |
| 9,976,147 B2 | 5/2018 | Kortylewski et al. |
| 10,253,318 B2 | 4/2019 | Yu et al. |
| 10,711,272 B2 | 7/2020 | Yu et al. |
| 10,801,026 B2 | 10/2020 | Kortylewski et al. |
| 10,829,765 B2 | 11/2020 | Kortylewski et al. |
| 11,186,840 B2 | 11/2021 | Yu et al. |
| 11,208,654 B2 | 12/2021 | Yu et al. |
| 11,464,865 B2 | 10/2022 | Kortylewski et al. |
| 11,591,596 B2 | 2/2023 | Kortylewski et al. |
| 11,746,120 B2 * | 9/2023 | Mainolfi .............. C07D 487/04 514/80 |
| 11,801,266 B2 | 10/2023 | Marcucci et al. |
| 11,912,995 B2 | 2/2024 | Yu et al. |
| 2022/0002730 A1 | 1/2022 | Kortylewski et al. |

FOREIGN PATENT DOCUMENTS

| WO | WO-2016197032 A1 * | 12/2016 | ........... A61K 31/426 |
|---|---|---|---|
| WO | WO-2017/004357 A1 | 1/2017 | |
| WO | WO-2018/064589 A1 | 4/2018 | |
| WO | WO-2018/064589 A9 | 4/2018 | |

OTHER PUBLICATIONS

Zheng et al., "Ubiquitin Ligases: Structure, Function and Regulation", Annu. Rev. Biochem., Published Mar. 27, 2017, pp. 129-157. (Year: 2017).*
Vaquerizas et al., "A census of human transcription factors: function, expression and evolution", Nature Reviews Genetics, vol. 10, Published Apr. 2009, pp. 252-263. (Year: 2009).*
Yue et al., "Targeting STAT3 in Cancer: How Successful are we?", Expert Opin Investig Drugs, Published Jan. 2009, pp. 45-56. (Year: 2009).*
Zhao et al., "B Cell Lymphoma Immunotherapy Using TLR9-Targeted Oligonucleotide STAT3 inhibitors", Molecular Therapy vol. 26 No. Mar. 3, 2018, pp. 695-706. (Year: 2018).*
International Search Report mailed on Nov. 6, 2019, for PCT Application No. PCT/US2019/037447, filed Jun. 17, 2019, 5 pages.
Written Opinion mailed on Nov. 6, 2019, for PCT Application No. PCT/US2019/037447, filed Jun. 17, 2019, 7 pages.

* cited by examiner

*Primary Examiner* — Abigail Vanhorn
*Assistant Examiner* — Stephanie L Sullivan
(74) *Attorney, Agent, or Firm* — Mintz, Levin, Cohn, Ferris, Glovsky and Popeo, P.C.

(57) ABSTRACT

Compounds and pharmaceutical compositions useful to treat cancer (e.g., lymphoma), neurodegenerative diseases, and autoimmune disorders include (1) a first nucleic acid sequence capable of binding to a transcription factor, for example, a signal transducer and activator of transcription (STAT) factor, such as STAT3, (2) a second nucleic acid sequence capable of binding a Toll-like receptor protein, for example, a CpG oligodeoxynucleotide, and (3) a ubiquitin ligase binding compound capable of binding a ubiquitin ligase protein, for example, a compound that is capable of binding a cereblon protein, such as lenalidomide, pomalidomide, or thalidomide.

20 Claims, 13 Drawing Sheets
Specification includes a Sequence Listing.

A20-luc

DC2.4 WT

DC2.4/STAT3C

DC2.4/STAT3C

OLIGONUCLEOTIDE-BASED PROTEOLYSIS TARGETING CHIMERA

CROSS-REFERENCE TO RELATED APPLICATIONS

This application is a Section 371 US national phase of International Application No. PCT/US2019/037447 filed Jun. 17, 2019, which claims priority to U.S. Application No. 62/685,810 filed Jun. 15, 2018, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant nos. R01 CA213131 and P50 CA107399 awarded by the National Institutes of Health. The government has certain rights in the invention.

REFERENCE TO A SEQUENCE LISTING

The contents of the text file named 048440-699N01US-Updated-ST25.txt, created on Dec. 18, 2024, having 39,481 bytes, are hereby incorporated by reference in their entireties.

BACKGROUND

Pharmacological inhibition of oncogenic and immunoregulatory transcription factors, such as STAT3, lacking enzymatic activity proved challenging and requires alternative strategies. Disclosed here, inter alia, are solutions to these and other problems in the art.

BRIEF SUMMARY

In an aspect is provided a compound including a first nucleic acid sequence capable of binding to a transcription factor binding site and a ubiquitin ligase binding compound (i.e., a monovalent compound capable of binding a ubiquitin ligase protein) covalently bound to the first nucleic acid. In an aspect is provided a pharmaceutical composition including a pharmaceutically acceptable excipient and a compound, or pharmaceutically acceptable salt thereof, described herein.

In an aspect is provided a compound including a first nucleic acid sequence capable of binding to a transcription factor binding site covalently bound to a second nucleic acid sequence capable of binding a Toll-like receptor protein; and ubiquitin ligase binding compound (i.e., a monovalent compound capable of binding a ubiquitin ligase protein) covalently bound to the first nucleic acid or the second nucleic acid. In an aspect is provided a pharmaceutical composition including a pharmaceutically acceptable excipient and a compound, or pharmaceutically acceptable salt thereof, described herein.

In an aspect is provided a method of treating cancer, an autoimmune disorder, a neurodegenerative disease, or an infectious disease in a patient in need of such treatment, the method including administering a therapeutically effective amount of a compound as described herein.

BRIEF DESCRIPTION OF THE DRAWINGS

FIG. 1A: Protein levels of phosphorylated and total STAT3 in comparison to β-actin used as a loading control were analyzed using Western blotting. FIG. 1B: Quantification of phosphorylated and total STAT3 levels using Biorad Imager software after normalization to β-actin levels.

FIG. 3A: protein levels of phosphorylated and total STAT3 in comparison to β-actin used as a loading control were analyzed using Western blotting. FIG. 3B: Quantification of phosphorylated (top) and total STAT3 (bottom) levels using Biorad Imager software after normalization to β-actin levels.

DETAILED DESCRIPTION

Definitions

Figure 1A:
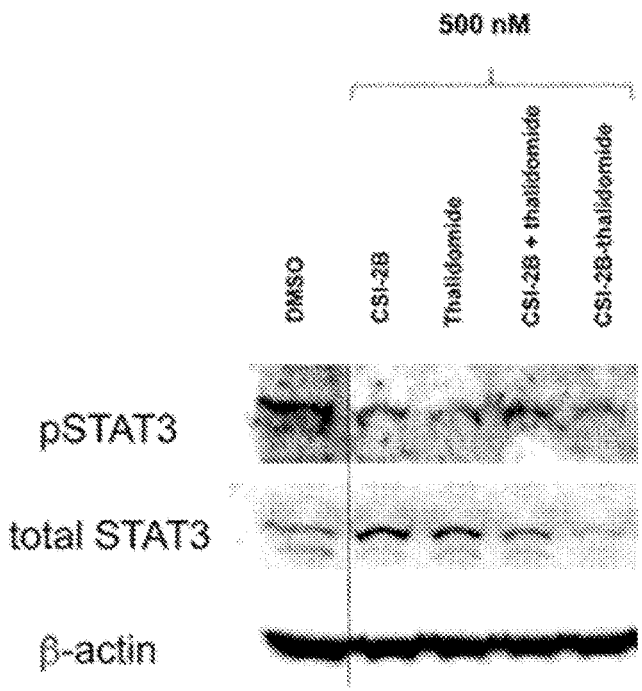
FIGS. 1A-1B show that CSI-2B$^{THAL}$ enhances degradation of total and phosphorylated STAT3 in human Ly10 B-cell lymphoma cells.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatoms may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH═CHO—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms. A heteroalkyl moiety may include three optionally different heteroatoms. A heteroalkyl moiety may include four optionally different heteroatoms. A heteroalkyl moiety may include five optionally different heteroatoms. A heteroalkyl moiety may include up to 8 optionally different heteroatoms. The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$—, —CH$_2$—S—CH$_2$—CH$_2$—NH—CH$_2$—, —PO$_3$OH—(CH$_2$)$_3$—PO$_3$OH, PO$_3$OH—(CH$_2$)$_3$—PO$_3$OH—(CH$_2$)$_6$—, —PO$_3$OH—(CH$_2$)$_3$—PO$_3$OH—(CH$_2$)$_6$—NH—, —CH$_2$PO$_3$OH—(CH$_2$)$_3$—PO$_3$OH—(CH$_2$)$_6$—, and the like. For heteroalkylene groups, heteroatoms (e.g., O, N, S, Si, or P) can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where heteroalkyl is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In aspects, monocyclic ring systems are cyclic hydrocarbon groups containing from 3 to 8 carbon atoms, where such groups can be saturated or unsaturated, but not aromatic. In aspects, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In aspects, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In aspects, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkyl is attached to the parent molecular moiety through any carbon atom contained within the monocyclic cycloalkyl ring. In aspects, cycloalkyl groups are optionally substituted with one or two groups which are independently oxo or thia. In aspects, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkyl is attached to the parent molecular moiety through any carbon atom contained within the base ring. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In aspects, a cycloalkenyl is a monocyclic, bicyclic, or a multicyclic cycloalkenyl ring system. In aspects, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In aspects, bicyclic cycloalkenyl rings are bridged monocyclic rings or a fused bicyclic rings. In aspects, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In aspects, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkenyl is attached to the parent molecular moiety through any carbon atom contained within the monocyclic cycloalkenyl ring. In aspects, cycloalkenyl groups are optionally substituted with one or two groups which are independently oxo or thia. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkenyl is attached to the parent molecular moiety through any carbon atom contained within the base ring. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In aspects, heterocyclyl groups are optionally substituted with one or two groups which are independently oxo or thia. In aspects, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In aspects, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzooxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" or "-" denotes the point of attachment of a chemical moiety to the remainder of a molecule or chemical formula.

The term "oxo" means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In aspects, the alkylarylene group has the formula:

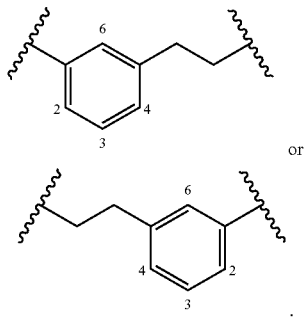

or

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_8$ alkyl or substituted or unsubstituted 2 to 5 membered heteroalkyl). In aspects, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR'SO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$ unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from: (i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$ unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from: (a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In embodiments, each substituted group described in the compounds herein is substituted with at least one substituent group. In aspects, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In aspects, at least one or all of these groups are substituted with at least one size-limited substituent group. In aspects, at least one or all of these groups are substituted with at least one lower substituent group.

In embodiments, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In aspects, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In aspects, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In aspects, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In aspects, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In aspects, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In aspects, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In aspects, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In aspects, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally differently.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate" refers to the resulting association between atoms or molecules of bioconjugate reactive groups. The association can be direct or indirect. For example, a conjugate between a first bioconjugate reactive group (e.g., —NH2, —COOH, —N-hydroxysuccinimide, or -maleimide) and a second bioconjugate reactive group (e.g., sulfhydryl, sulfur-containing amino acid, amine, amine side-chain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In aspects, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982. In aspects, the first bioconjugate reactive group (e.g., maleimide moiety) is covalently attached to the second bioconjugate reactive group (e.g. a sulfhydryl). In aspects, the first bioconjugate reactive group (e.g., haloacetyl moiety) is covalently attached to the second bioconjugate reactive group (e.g. a sulfhydryl). In aspects, the first bioconjugate reactive group (e.g., pyridyl moiety) is covalently attached to the second bioconjugate reactive group (e.g. a sulfhydryl). In aspects, the first bioconjugate reactive group (e.g., —N-hydroxysuccinimide moiety) is covalently attached to the second bioconjugate reactive group (e.g. an amine). In aspects, the first bioconjugate reactive group (e.g., maleimide moiety) is covalently attached to the second bioconjugate reactive group (e.g. a sulfhydryl). In aspects, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In aspects, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as R13A $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158l}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, $T_m$, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga $^{68}$Ga, $^{77}$As, $^{86}$Y $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, $T_m$, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In aspects, two molecules with leaving groups are allowed to contact, and upon a reaction and/or bond formation (e.g., acyloin condensation, aldol condensation, Claisen condensation, Stille reaction) the leaving groups separates from the respective molecule. In aspects, a leaving group is a bioconjugate reactive moiety. In aspects, at least two leaving groups (e.g., $R^1$ and $R^{13}$) are allowed to contact such that the leaving groups are sufficiently proximal to react, interact or physically touch. In aspects, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In aspects the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In aspects the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In aspects be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M); (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be peptide nucleic acids (PNAs), morpholino oligomers, locked nucleic acid (LNA), xeno nucleic acid, ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)$_2$' and any combination of those or any other functional portion of an immunoglobulin peptide capable of binding to target antigen (see, e.g., Fundamental Immunology (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term "antibody" also includes bivalent or bispecific molecules, diabodies, triabodies, and tetrabodies. Bivalent and bispecific molecules are described in, e.g., Kostelny et al. (1992) J. Immunol. 148:1547, Pack and Pluckthun (1992) Biochemistry 31:1579, Hollinger et al. (1993), PNAS. USA 90:6444, Gruber et al. (1994) J Immunol. 152:5368, Zhu et al. (1997) Protein Sci. 6:781, Hu et al. (1996) Cancer Res. 56:3055, Adams et al. (1993) Cancer Res. 53:4026, and McCartney, et al. (1995) Protein Eng. 8:301.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "pharmaceutically acceptable salts" is meant to include salts of the active compounds that are prepared with relatively nontoxic acids or bases, depending on the particular substituents found on the compounds described herein. When compounds contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds contain both basic and acidic functionalities that allow the compounds to be converted into either base or acid addition salts. Other pharmaceutically acceptable carriers known to those of skill in the art are suitable for use. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds may exist as salts, such as with pharmaceutically acceptable acids. Examples of such salts include hydrochlorides, hydrobromides, sulfates, nitrates, citrates, methanesulfonates, maleates, acetates, fumarates, tartrates (e.g., (+)-tartrates, (−)-tartrates, or mixtures thereof including racemic mixtures), succinates, benzoates, and salts with amino acids such as glutamic acid. These salts may be prepared by methods known in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the compounds may be in a prodrug form. Prodrugs of the compounds described herein are those compounds that readily undergo chemical changes under physiological conditions to provide the compounds here. Additionally, prodrugs can be converted to the compounds described herein by chemical or biochemical methods in an ex vivo environment. For example, prodrugs can be slowly converted to the compounds described herein when placed in a transdermal patch reservoir with a suitable enzyme or chemical reagent.

Certain compounds described herein can exist in unsolvated forms as well as solvated forms, including hydrated forms. In general, the solvated forms are equivalent to unsolvated forms and are encompassed within the scope of the disclosure. Certain compounds described herein may exist in multiple crystalline or amorphous forms. In general, all physical forms are equivalent for the uses contemplated herein and are intended to be within the scope of the disclosure.

As used herein, the term "salt" refers to acid or base salts of the compounds used in the methods herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The compounds described herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds, whether radioactive or not, are encompassed within the scope of the disclosure.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. prostate cancer, castration-resistant prostate cancer, breast cancer, triple negative breast cancer, glioblastoma, ovarian cancer, lung cancer, squamous cell carcinoma (e.g. head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, castration-resistant prostate cancer, breast cancer, triple negative breast cancer, glioblastoma, ovarian cancer, lung cancer, squamous cell carcinoma (e.g. head, neck, or esophagus), colorectal cancer, leukemia, acute myeloid leukemia, lymphoma, B cell lymphoma, or multiple myeloma) would be known or may be determined by a person of ordinary skill in the art. The term "treating" and conjugations thereof, include prevention of an injury, pathology, condition, or disease (e.g. preventing the development of one or more symptoms of cancer (e.g. prostate cancer, castration-resistant prostate cancer, breast cancer, triple negative breast cancer, glioblastoma, ovarian cancer, lung cancer, squamous cell carcinoma (e.g. head, neck, or esophagus), colorectal cancer, leukemia, acute myeloid leukemia, lymphoma, B cell lymphoma, or multiple myeloma)). For example certain methods herein treat viral disease (e.g. herpesvirus infection associated disease or hepatitis virus infection associated disease or HIV infection associated disease) by decreasing or reducing or preventing the occurrence, growth, or progression of the virus infection or virus; or treat viral disease (e.g. herpesvirus infection associated disease or hepatitis virus infection associated disease or HIV infection associated disease) by decreasing a symptom of viral disease (e.g. herpesvirus infection associated disease or hepatitis virus infection associated disease or HIV infection associated disease).

An "effective amount" is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "associated" or "associated with" in the context of a substance or substance activity or function associated with a disease (e.g. cancer (e.g. prostate cancer, castration-resistant prostate cancer, breast cancer, triple negative breast cancer, glioblastoma, ovarian cancer, lung cancer, squamous cell carcinoma (e.g. head, neck, or esophagus), colorectal cancer, leukemia, acute myeloid leukemia, lymphoma, B cell lymphoma, or multiple myeloma)) means that the disease (e.g. cancer (e.g. prostate cancer, castration-resistant prostate cancer, breast cancer, triple negative breast cancer, glioblastoma, ovarian cancer, lung cancer, squamous cell carcinoma (e.g. head, neck, or esophagus), colorectal cancer, leukemia, acute myeloid leukemia, lymphoma, B cell lymphoma, or multiple myeloma) or viral disease (e.g. ZIKA virus infection, herpesvirus infection associated disease or hepatitis virus infection associated disease or HIV infection associated disease)) is caused by (in whole or in part), or a symptom of the disease is caused by (in whole or in part) the substance or substance activity or function. For example, a symptom of a disease or condition associated with an increase in STAT3 activity may be a symptom that results (entirely or partially) from an increase in STAT3 activity (e.g. increase in STAT3 transcriptional activation, increase in STAT3 activation of a signal transduction or signalling pathway), which results in altered NF-κB function. As used herein, what is described as being associated with a disease, if a causative agent, could be a target for treatment of the disease. For example, a disease associated with increased STAT3 activity (e.g increase in STAT3 transcriptional activation, increase in STAT3 activation of a signal transduction or signalling pathway), may be treated with an agent (e.g. compound as described herein) effective for decreasing the level of activity of STAT3 or STAT3 pathway. For example, a disease associated with STAT3, may be treated with an agent (e.g. compound as described herein) effective for decreasing the level of activity of STAT3 or a downstream component or effector of STAT3. For example, a symptom of a disease or condition associated with an increase in STAT (e.g. STAT1, STAT2, STAT3, STAT4, STAT5A, STAT5B, or STAT6) activity may be a symptom that results (entirely or partially) from an increase in STAT (e.g. STAT1, STAT2, STAT3, STAT4, STAT5A, STAT5B, or STAT6) activity (e.g increase in STAT (e.g. STAT1, STAT2, STAT3, STAT4, STAT5A, STAT5B, or STAT6) transcriptional activation, increase in STAT (e.g. STAT1, STAT2, STAT3, STAT4, STAT5A, STAT5B, or STAT6) activation of a signal transduction or signalling pathway). As used herein, what is described as being associated with a disease, if a causative agent, could be a target for treatment of the disease. For example, a disease associated with increased STAT (e.g. STAT1, STAT2, STAT3, STAT4, STAT5A, STAT5B, or STAT6) activity (e.g increase in STAT (e.g. STAT1, STAT2, STAT3, STAT4, STAT5A, STAT5B, or STAT6) transcriptional activation, increase in STAT (e.g. STAT1, STAT2, STAT3, STAT4, STAT5A, STAT5B, or STAT6) activation of a signal transduction or signalling pathway), may be treated with an agent (e.g. compound as described herein) effective for decreasing the level of activity of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway. For example, a disease associated with a STAT transcription factor (e.g. STAT1, STAT2, STAT3, STAT4, STAT5A, STAT5B, or STAT6) may be treated with an agent (e.g. compound as described herein) effective for decreasing the level of activity of a STAT transcription factor (e.g. STAT1, STAT2, STAT3, STAT4, STAT5A, STAT5B, or STAT6) or a downstream component or effector of a STAT transcription factor (e.g. STAT1, STAT2, STAT3, STAT4, STAT5A, STAT5B, or STAT6).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. a STAT transcription factor (e.g. STAT1, STAT2, STAT3, STAT4, STAT5A, STAT5B, or STAT6)). In aspects, contacting includes allowing a compound described herein to interact with a protein or enzyme that is involved in a signaling pathway (e.g. a STAT transcription factor (e.g. STAT1, STAT2, STAT3, STAT4, STAT5A, STAT5B, or STAT6) pathway).

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In aspects, inhibition refers to reduction of a disease or symptoms of disease. In aspects, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In aspects, inhibition refers to a decrease in the activity of a signal transduction pathway or signaling pathway (e.g. a STAT transcription factor (e.g. STAT1, STAT2, STAT3, STAT4, STAT5A, STAT5B, or STAT6) activated pathway). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. level of a STAT transcription factor (e.g. STAT1, STAT2, STAT3, STAT4, STAT5A, STAT5B, or STAT6) activity or protein or level or activity of a component of a STAT transcription factor (e.g. STAT1, STAT2, STAT3, STAT4, STAT5A, STAT5B, or STAT6) pathway, wherein each is associated with cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma)) or a viral disease (e.g. herpesvirus infection associated disease or hepatitis virus infection associated disease or HIV infection associated disease). Inhibition may include, at least in part, partially or totally decreasing stimulation, decreasing or reducing activation, or deactivating, desensitizing, or down-regulating signal transduction or enzymatic activity or the amount of a protein (e.g. a STAT transcription factor (e.g. STAT1, STAT2, STAT3, STAT4, STAT5A, STAT5B, or STAT6), protein downstream in a pathway from a STAT transcription factor (e.g. STAT1, STAT2, STAT3, STAT4, STAT5A, STAT5B, or STAT6), protein downstream in a pathway activated by a STAT transcription factor (e.g. STAT1, STAT2, STAT3, STAT4, STAT5A, STAT5B, or STAT6)) that may modulate the level of another protein or increase cell survival (e.g. a STAT transcription factor (e.g. STAT1, STAT2, STAT3, STAT4, STAT5A, STAT5B, or STAT6) pathway activity may increase cell survival in cells that may or may not have an increase in a STAT transcription factor (e.g. STAT1, STAT2, STAT3, STAT4, STAT5A, STAT5B, or STAT6) pathway activity relative to a non-disease control or decrease in a STAT transcription factor (e.g. STAT1, STAT2, STAT3, STAT4, STAT5A, STAT5B, or STAT6) pathway activity may increase cell survival in cells that may or may not have a decrease in a STAT transcription factor (e.g. STAT1, STAT2, STAT3, STAT4, STAT5A, STAT5B, or STAT6) pathway activity relative to a non-disease control). In aspects, the activity or function of a STAT transcription factor (e.g. STAT1, STAT2, STAT3, STAT4, STAT5A, STAT5B, or STAT6) that is inhibited is STAT (e.g. STAT1, STAT2, STAT3, STAT4, STAT5A, STAT5B, or STAT6) transcriptional activation. In aspects, the activity or function of a STAT transcription factor (e.g. STAT1, STAT2, STAT3, STAT4, STAT5A, STAT5B, or STAT6) that is inhibited is STAT (e.g. STAT1, STAT2, STAT3, STAT4, STAT5A, STAT5B, or STAT6) transcriptional inhibition. In aspects, the activity or function of a STAT transcription factor (e.g. STAT1, STAT2, STAT3, STAT4, STAT5A, STAT5B, or STAT6) that is inhibited is STAT transcription factor (e.g. STAT1, STAT2, STAT3, STAT4, STAT5A, STAT5B, or STAT6) binding to genomic DNA. In aspects, the activity or function of a STAT transcription factor (e.g. STAT1, STAT2, STAT3, STAT4, STAT5A, STAT5B, or STAT6) that is inhibited is STAT (e.g. STAT1, STAT2, STAT3, STAT4, STAT5A, STAT5B, or STAT6) binding to a STAT (e.g. STAT1, STAT2, STAT3, STAT4, STAT5A, STAT5B, or STAT6) binding site in genomic DNA.

As defined herein, the term "activation", "activate", "activating" and the like in reference to a protein-activator (e.g. agonist) interaction means positively affecting (e.g. increasing) the activity or function of the protein (e.g. a STAT transcription factor (e.g. STAT1, STAT2, STAT3, STAT4, STAT5A, STAT5B, or STAT6), component of a pathway including a STAT transcription factor (e.g. STAT1, STAT2, STAT3, STAT4, STAT5A, STAT5B, or STAT6), or component of a pathway including a STAT transcription factor (e.g. STAT1, STAT2, STAT3, STAT4, STAT5A, STAT5B, or STAT6)) relative to the activity or function of the protein in the absence of the activator (e.g. compound described herein). In aspects, activation refers to an increase in the activity of a signal transduction pathway or signaling pathway (e.g. a STAT transcription factor (e.g. STAT1, STAT2, STAT3, STAT4, STAT5A, STAT5B, or STAT6) pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of STAT (e.g. STAT1, STAT2, STAT3, STAT4, STAT5A, STAT5B, or STAT6) activity or level of protein or activity decreased by a STAT transcription factor (e.g. STAT1, STAT2, STAT3, STAT4, STAT5A, STAT5B, or STAT6) or protein associated with cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) or viral disease (e.g. herpesvirus infection associated disease or hepatitis virus infection associated disease or HIV infection associated disease)). Activation may include, at least in part, partially or totally increasing stimulation, increasing or enabling activation, or activating, sensitizing, or up-regulating signal transduction or enzymatic activity or the amount of a protein (e.g. a STAT transcription factor (e.g. STAT1, STAT2, STAT3, STAT4, STAT5A, STAT5B, or STAT6), protein downstream of a STAT transcription factor (e.g. STAT1, STAT2, STAT3, STAT4, STAT5A, STAT5B, or STAT6), protein activated or upregulated by a STAT transcription factor (e.g. STAT1, STAT2, STAT3, STAT4, STAT5A, STAT5B, or STAT6)) that may modulate the level of another protein or increase cell survival (e.g. increase in a STAT transcription factor (e.g. STAT1, STAT2, STAT3, STAT4, STAT5A, STAT5B, or STAT6) activity may increase cell survival in cells that may or may not have an increase in a STAT transcription factor (e.g. STAT1, STAT2, STAT3, STAT4, STAT5A, STAT5B, or STAT6) activity relative to a non-disease control).

The term "modulator" refers to a composition that increases or decreases the level of a target molecule or the function of a target molecule (e.g. a STAT transcription factor (e.g. STAT1, STAT2, STAT3, STAT4, STAT5A, STAT5B, or STAT6) transcriptional activation or a STAT transcription factor (e.g. STAT1, STAT2, STAT3, STAT4, STAT5A, STAT5B, or STAT6) binding to genomic DNA, or a STAT transcription factor (e.g. STAT1, STAT2, STAT3, STAT4, STAT5A, STAT5B, or STAT6) binding to a STAT transcription factor (e.g. STAT1, STAT2, STAT3, STAT4, STAT5A, STAT5B, or STAT6) binding site on DNA). In some embodiments, a modulator of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway is a compound that reduces the severity of one or more symptoms of a disease associated with a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway (e.g. disease associated with an increase in the level of a STAT transcription factor (e.g. STAT1, STAT2, STAT3, STAT4, STAT5A, STAT5B, or STAT6) activity or protein or a STAT transcription factor (e.g. STAT1, STAT2, STAT3, STAT4, STAT5A, STAT5B, or STAT6) pathway activity or protein, for example cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) or viral disease (e.g. herpesvirus infection associated disease or hepatitis virus infection associated disease or HIV infection associated disease)) or a disease that is not caused by a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway but may benefit from modulation of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway activity (e.g. decreasing in level or level of activity of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway). In aspects, a modulator of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway is an anti-cancer agent. In aspects, a modulator of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway is an anti-viral agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In aspects, a patient is human. In aspects, a patient is a mammal. In aspects, a patient is a mouse. In aspects, a patient is an experimental animal. In aspects, a patient is a rat. In aspects, a patient is a test animal.

"Disease" or "condition" refer to a state of being or health status of a patient or subject capable of being treated with a compound, pharmaceutical composition, or method provided herein. In aspects, the disease is a disease related to (e.g. caused by) an increase in the level of a STAT transcription factor (e.g. STAT1, STAT2, STAT3, STAT4, STAT5A, STAT5B, or STAT6), STAT (e.g. STAT1, STAT2, STAT3, STAT4, STAT5A, STAT5B, or STAT6) phosphorylation, or a STAT transcription factor (e.g. STAT1, STAT2, STAT3, STAT4, STAT5A, STAT5B, or STAT6) pathway activity, or pathway activated by a STAT transcription factor (e.g. STAT1, STAT2, STAT3, STAT4, STAT5A, STAT5B, or STAT6). In aspects, the disease is cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma). In aspects, the disease is a viral disease (e.g. herpesvirus infection associated disease or hepatitis virus infection associated disease or HIV infection associated disease) associated with STAT3-dependent immunosuppression.

Examples of diseases, disorders, or conditions include, but are not limited to, cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma). In some instances, "disease" or "condition" refers to cancer. In aspects, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In aspects, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, *Lentigo maligna* melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

Further examples of diseases, disorders, or conditions include, but are not limited to viral diseases (e.g., Zika virus infection, herpesvirus infection associated disease or hepatitis virus infection associated disease or HIV infection associated disease) associated with STAT3-dependent immunosuppression. A viral disease associated with STAT3-dependent immunosuppression is a disease wherein the causative agent is a virus and wherein a symptom of the viral disease (i.e. virus infection) is immunosuppression dependent on STAT3. For example, Asian ZIKA virus infection is known to be an IL-10/STAT3-dependent disease (showed in Nature Microbiology 2017; DOI: 10.1038/s41564-017-0016-3, which is incorporated herein by reference in its entirety). A herpesvirus infection associated disease is a disease wherein the causative agent is a herpesvirus (e.g. HHV-1, HHV-2, HHV-3, HHV-4, HHV-5, HHV-6A, HHV-6B, HHV-7, or HHV-8). A hepatitis infection associated disease is a disease wherein the causative agent is a hepatitis virus (e.g. hepatitis A virus, hepatitis B virus, hepatitis C virus, hepatitis D virus, or hepatitis E virus). An HIV infection associated disease is a disease wherein the causative agent is HIV. In aspects, the viral disease associated with STAT3-dependent immunosuppression is HSV-1 infection and the causative agent is HHV-1 (herpes simplex virus-1, HSV-1). In aspects, the viral disease associated with STAT3-dependent immunosuppression is HSV-2 infection and the causative agent is HHV-2 (herpes simplex virus-2, HSV-2). In aspects, the viral disease associated with STAT3-dependent immunosuppression is chickenpox, shingles, or VZV infection, and the causative agent is HHV-3 (varicella zoster virus, VZV). In aspects, the viral disease associated with STAT3-dependent immunosuppression is infectious mononucleosis, Burkitt's lymphoma, CNS lymphoma, post-transplant lymphoproliferative syndrome (PTLD), nasopharyngeal carcinoma, hairy leukoplakia, or CMV infection, and the causative agent is HHV-5 (cytomegalovirus, CMV). In aspects, the viral disease associated with STAT3-dependent immunosuppression is sixth disease, roseola infantum, exanthema subitum, or HHV-6 infection and the causative agent is HHV-6A or HHV-6B (roseolovirus, herpes lymphotropic virus). In aspects, the viral disease associated with STAT3-dependent immunosuppression is roseola infantum, exanthema subitum, or HHV-7 infection and the causative agent is HHV-7 (*Pityriasis rosea*). In aspects, the viral disease associated with STAT3-dependent immunosuppression is Kaposi's sarcoma, primary effusion lymphoma, multicentric Castleman's disease, or HHV-8 infection and the causative agent is HHV-8 (Kaposi's sarcoma-associated herpesvirus, KSHV). In aspects, the viral disease associated with STAT3-dependent immunosuppression is hepatitis A and the causative agent is hepatitis A virus. In aspects, the viral disease associated with STAT3-dependent immunosuppression is hepatitis B and the causative agent is hepatitis B virus. In aspects, the viral disease associated with STAT3-dependent immunosuppression is hepatitis C and the causative agent is hepatitis C virus. In aspects, the viral disease associated with STAT3-dependent immunosuppression is hepatitis D and the causative agent is hepatitis D virus. In aspects, the viral disease associated with STAT3-dependent immunosuppression is hepatitis E and the causative agent is hepatitis E virus. In aspects, the viral disease associated with STAT3-dependent immunosuppression is HIV infection or AIDS and the causative agent is HIV (human immunodeficiency virus) (e.g. HIV-1 or HIV-2). In aspects, the viral disease associated with STAT3-dependent immunosuppression is ZIKA infection and the causative agent is ZIKV (e.g., Zika virus).

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. One of skill in the art will recognize that other pharmaceutical excipients are useful herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In aspects, administration includes direct administration to a tumor. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The compound described herein can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The compositions described herein can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In aspects, the formulations of the compositions described herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions described herein into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions can also be delivered as nanoparticles.

Pharmaceutical compositions provided herein include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. a STAT transcription factor (e.g. STAT1, STAT2, STAT3, STAT4, STAT5A, STAT5B, or STAT6)), and/or reducing, eliminating, or slowing the progression of disease symptoms (e.g. symptoms of cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) or viral disease (e.g. herpesvirus infection associated disease or hepatitis virus infection associated disease or HIV infection associated disease)). Determination of a therapeutically effective amount of a compound described herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma)), kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma), or with other active agents known to be useful in treating viral disease (e.g. herpesvirus infection associated disease or hepatitis virus infection associated disease or HIV infection associated disease), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In aspects, the active agents can be formulated separately. In aspects, the active and/or adjunctive agents may be linked or conjugated to one another. In aspects, the compounds described herein may be combined with treatments for cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) such as surgery or with other treatments known to be useful in treating viral disease (e.g. herpesvirus infection associated disease or hepatitis virus infection associated disease or HIV infection associated disease).

The term "STAT" or "STAT transcription factor" are used interchangeably and refer to a "Signal transducer and activator of transcription" protein and homologs thereof (e.g. STAT1, STAT2, STAT3, STAT4, STAT5A, STAT5B, or STAT6). In aspects, "STAT transcription factor" refers to a human protein (e.g. STAT1, STAT2, STAT3, STAT4, STAT5A, STAT5B, or STAT6). Included in the term "STAT transcription factor" are the wildtype and mutant forms of the protein (e.g. STAT1, STAT2, STAT3, STAT4, STAT5A, STAT5B, or STAT6). In aspects, "STAT transcription factor" refers to the wildtype protein (e.g. STAT1, STAT2, STAT3, STAT4, STAT5A, STAT5B, or STAT6). In aspects, "STAT transcription factor" refers to a mutant protein (e.g. STAT1, STAT2, STAT3, STAT4, STAT5A, STAT5B, or STAT6). "Phosphorylated STAT" refers to a STAT protein (e.g. STAT1, STAT2, STAT3, STAT4, STAT5A, STAT5B, or STAT6) that is phosphorylated and activated by the phosphorylation. In aspects, activation of a STAT transcription factor (e.g. STAT1, STAT2, STAT3, STAT4, STAT5A, STAT5B, or STAT6) means the STAT (e.g. STAT1, STAT2, STAT3, STAT4, STAT5A, STAT5B, or STAT6) is capable of activating transcription. In aspects, activated STAT (e.g. STAT1, STAT2, STAT3, STAT4, STAT5A, STAT5B, or STAT6) is phosphorylated on STAT1 Y701, STAT2, Y690, STAT3 Y705, STAT4 Y693, STAT5A Y694, STAT5B Y694, STAT6 Y641, or a residue corresponding to one of those residues, forms dimers (e.g. homodimers or heterodimers), translocates to the nucleus, and activates transcription. In aspects, activated STAT (e.g. STAT1, STAT2, STAT3, STAT4, STAT5A, STAT5B, or STAT6) forms homodimers. In aspects, activated STAT (e.g. STAT1, STAT2, STAT3, STAT4, STAT5A, STAT5B, or STAT6) forms heterodimers. An example of a protein that phosphorylates STAT (e.g. STAT1, STAT2, STAT3, STAT4, STAT5A, STAT5B, or STAT6) and thereby activate a STAT (e.g. STAT1, STAT2, STAT3, STAT4, STAT5A, STAT5B, or STAT6) includes JAK.

The term "STAT-binding nucleic acid sequence" refers to a nucleic acid capable of binding to a STAT (e.g. STAT1, STAT2, STAT3, STAT4, STAT5A, STAT5B, or STAT6) or a nucleic acid that forms part of a STAT-binding substituent (e.g. STAT1-, STAT2-, STAT3-, STAT4-, STAT5A-, STAT5B—, or STAT6-binding substituent). A STAT3-binding nucleic acid sequence is a nucleic acid capable of binding to STAT3 or a nucleic acid that forms part of a STAT3-binding substituent (STAT3-binding nucleic acid substituent).

The term "STAT1" refers to a "Signal transducer and activator of transcription 1" protein and homologs thereof. In aspects, "STAT1" refers to the protein associated with Entrez Gene 6772, OMIM 600555, UniProt P42224, and/or RefSeq (protein) NP_009330. In aspects, the reference numbers immediately above refer to the protein, and associated nucleic acids, known as of the date of filing of this application.

The term "STAT2" refers to a "Signal transducer and activator of transcription 2" protein and homologs thereof. In aspects, "STAT2" refers to the protein associated with Entrez Gene 6773, OMIM 600556, UniProt P52630, and/or RefSeq (protein) NP_005410. In aspects, the reference numbers immediately above refer to the protein, and associated nucleic acids, known as of the date of filing of this application.

The term "STAT4" refers to a "Signal transducer and activator of transcription 4" protein and homologs thereof. In aspects, "STAT4" refers to the protein associated with Entrez Gene 6775, OMIM 600558, UniProt Q14765, and/or RefSeq (protein) NP_001230764. In aspects, the reference numbers immediately above refer to the protein, and associated nucleic acids, known as of the date of filing of this application.

The term "STAT5A" refers to a "Signal transducer and activator of transcription 5A" protein and homologs thereof. In aspects, "STAT5A" refers to the protein associated with Entrez Gene 6776, OMIM 601511, UniProt P42229, and/or RefSeq (protein) NP_003143. In aspects, the reference numbers immediately above refer to the protein, and associated nucleic acids, known as of the date of filing of this application.

The term "STAT5B" refers to a "Signal transducer and activator of transcription 5B" protein and homologs thereof. In aspects, "STAT5B" refers to the protein associated with Entrez Gene 6777, OMIM 604260, UniProt P51692, and/or RefSeq (protein) NP_036580. In aspects, the reference numbers immediately above refer to the protein, and associated nucleic acids, known as of the date of filing of this application.

The term "STAT6" refers to a "Signal transducer and activator of transcription 6" protein and homologs thereof. In aspects, "STAT6" refers to the protein associated with Entrez Gene 6778, OMIM 601512, UniProt P42226, and/or RefSeq (protein) NP_001171549. In aspects, the reference numbers immediately above refer to the protein, and associated nucleic acids, known as of the date of filing of this application.

The term "STAT3" refers to the protein "Signal transducer and activator of transcription 3" and homologs thereof. In aspects, "STAT3" refers to the human protein. Included in the term "STAT3" are the wildtype and mutant forms of the protein. In aspects, "STAT3" refers to the wildtype protein. In aspects, "STAT3" refers to a mutant protein. In aspects, "STAT3" refers to the protein associated with Entrez Gene 6774, OMIM 102582, UniProt P40763, and/or RefSeq (protein) NP_003141. In aspects, the reference numbers immediately above refer to the protein, and associated nucleic acids, known as of the date of filing of this application. "Phosphorylated STAT3" refers to a STAT3 protein that is phosphorylated and activated by the phosphorylation. In aspects, a phosphorylated STAT3 is phosphorylated on tyrosine 705 or the residue corresponding to tyrosine 705 in homologs. In aspects, activation of STAT3 means the STAT3 is capable of activating transcription. In aspects, activated STAT3 is phosphorylated on tyrosine 705, or the residue corresponding to tyrosine 705, forms dimers (e.g. homodimers or heterodimers), translocates to the nucleus, and/or activates transcription. In aspects, activated STAT3 forms homodimers. Examples of proteins that phosphorylate STAT3 and thereby activate STAT3 include JAK2, EGFR, c-MET, and PDGF-R.

"Anti-viral agent" is used in accordance with its plain ordinary meaning and refers to a composition (e.g. compound, drug, antagonist, inhibitor, modulator) having anti-infective properties or the ability to inhibit the growth or proliferation of virus. In aspects, an anti-viral agent is an agent identified herein having utility in methods of treating viral disease (e.g. herpesvirus infection associated disease or hepatitis virus infection associated disease or HIV infection associated disease). In aspects, an anti-viral agent is an agent approved by the FDA or similar regulatory agency of a country other than the USA, for treating viral disease (e.g. herpesvirus infection associated disease or hepatitis virus infection associated disease or HIV infection associated disease). Examples of anti-viral agents are well known in the art and include agents for treating herpesvirus infection associated disease, hepatitis virus infection associated disease, and HIV infection associated disease. In aspects, an anti-viral agent is an agent identified herein having utility in methods of treating viral disease (e.g. Zika virus infection).

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In aspects, an anti-cancer agent is a chemotherapeutic. In aspects, an anti-cancer agent is an agent identified herein having utility in methods of treating cancer. In aspects, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/ trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, melphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$I, $^{90}$Y, or $^{131}$I, etc.).

In embodiments, the compounds described herein can be co-administered with conventional radiotherapeutic agents including, but not limited to, radionuclides such as $^{4}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In aspects, the nucleic acids herein contain phosphodiester bonds. In aspects, nucleic acid analogs are included that may have alternate backbones (e.g. phosphodiester derivatives), including, e.g., phosphoramidate, phosphorodiamidate, phosphorothioate (also know as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

A particular nucleic acid sequence also encompasses "splice variants." Similarly, a particular protein encoded by a nucleic acid encompasses any protein encoded by a splice variant of that nucleic acid. Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An amino acid residue in a protein "corresponds" to a given residue when it occupies the same essential structural position within the protein as the given residue. For example, a selected residue in a selected protein (e.g. homolog of human STAT, STAT1, STAT2, STAT4, STAT5A, STAT5B, or STAT6) corresponds to STAT1 Y701, STAT2, Y690, STAT3 Y705, STAT4 Y693, STAT5A Y694, STAT5B Y694, or STAT6 Y641 when the selected residue occupies the same essential spatial or other structural relationship as STAT1 Y701, STAT2, Y690, STAT3 Y705, STAT4 Y693, STAT5A Y694, STAT5B Y694, or STAT6 Y641 in each respective STAT protein. In some embodiments, where a selected protein is aligned for maximum homology with the a STAT protein, the position in the aligned selected protein aligning with STAT1 Y701, STAT2, Y690, STAT3 Y705, STAT4 Y693, STAT5A Y694, STAT5B Y694, or STAT6 Y641 is said to correspond to STAT1 Y701, STAT2, Y690, STAT3 Y705, STAT4 Y693, STAT5A Y694, STAT5B Y694, or STAT6 Y641 respectively. Instead of a primary sequence alignment, a three dimensional structural alignment can also be used, e.g., where the structure of the selected protein is aligned for maximum correspondence with the a human STAT protein and the overall structures compared. In this case, an amino acid that occupies the same essential position as STAT1 Y701, STAT2, Y690, STAT3 Y705, STAT4 Y693, STAT5A Y694, STAT5B Y694, or STAT6 Y641 in the structural model is said to correspond to STAT1 Y701, STAT2, Y690, STAT3 Y705, STAT4 Y693, STAT5A Y694, STAT5B Y694, or STAT6 Y641.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

A "label" or a "detectable moiety" is a composition detectable by spectroscopic, photochemical, biochemical, immunochemical, chemical, magnetic resonance imaging, or other physical means. For example, useful detectable moieties include $^{32}P$, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline SPIO, monochrystalline SPIO aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g. compound described herein). Any method known in the art for conjugating an oligonucleotide or protein to the label may be employed, e.g., using methods described in Hermanson, Bioconjugate Techniques 1996, Academic Press, Inc., San Diego.

MRI can be used to non-invasively acquire tissue images with high resolution. Paramagnetic agents or USPIO nanoparticles or aggregates thereof enhance signal attenuation on $T_2$-weighted magnetic resonance images, and conjugation of such nanoparticles to binding ligands permits the detection of specific molecules at the cellular level. For example, MRI with nanoparticle detection agents can detect small foci of cancer. See e.g., Y. W. Jun et al., 2005, *J. Am. Chern. Soc.* 127:5732-5733; Y. M. Huh et al., 2005, *J. Am. Chern. Soc.* 127:12387-12391. Contrast-enhanced MRI is well-suited for the dynamic non-invasive imaging of macromolecules or of molecular events, but it requires ligands that specifically bind to the molecule of interest. J. W. Bulte et al., 2004, *NMR Biomed.* 17:484-499. Fluorescent dyes and fluorophores (e.g. fluorescein, fluorescein isothiocyanate, and fluorescein derivatives) can be used to non-invasively acquire tissue images with high resolution, with for example spectrophotometry, two-photon fluorescence, two-photon laser microscopy, or fluorescence microscopy (e.g. of tissue biopsies). MRI can be used to non-invasively acquire tissue images with high resolution, with for example paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents. MRI can be used to non-invasively acquire tissue images with high resolution, with for example Gadolinium, including liposomes or other delivery vehicles containing Gadolinium chelate ("Gd-chelate") molecules. Positron emission tomography (PET), PET/computed tomography (CT), single photon emission computed tomography (SPECT), and SPECT/CT can be used to non-invasively acquire tissue images with high resolution, with for example radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia. Ultrasound (ultrasonography) and contrast enhanced ultrasound (contrast enhanced ultrasonography) can be used to non-invasively acquire tissue images with high resolution, with for example biocolloids or microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.). X-ray imaging (radiography) or CT can be used to non-invasively acquire tissue images with high resolution, with for example iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, or gold nanoparticle aggregates. These detection methods and instruments and detectable moieties capable of being measured or detected by the corresponding method are non-limiting examples.

As used herein, the term "ultrasmall superparamagnetic iron oxide nanoparticle" or "USPIO nanoparticle" refers to superparamagnetic iron oxide particles ranging from 1 to 50 nm in diameter, more typically between 5 and 40 nm in diameter (excluding any coating applied after synthesis). USPIO nanoparticles are commonly made of maghemite ($Fe_2O_3$) or magnetite ($Fe_3O_4$) having crystal-containing regions of unpaired spins. Those magnetic domains are disordered in the absence of a magnetic field, but when a field is applied (i.e., while taking an MRI), the magnetic domains align to create a magnetic moment much greater than the sum of the individual unpaired electrons without resulting in residual magnetization of the particles.

As used herein, the term "TLR-binding nucleic acid substituent" refers to a substituent or moiety capable of binding to a toll-like receptor ("TLR") or activating a toll-like receptor, including at least one nucleic acid. In aspects, a TLR-binding nucleic acid substituent is capable of binding a TLR. In aspects, a TLR-binding nucleic acid substituent is capable of activating a TLR. In aspects, a TLR-binding nucleic acid substituent is capable of activating a TLR without directly binding the TLR. In aspects, a TLR-binding nucleic acid substituent is capable of binding a TLR without activating the TLR. In aspects, a TLR-binding nucleic acid substituent is a nucleic acid. In aspects, the TLR-binding nucleic acid substituent includes at least one nucleic acid analog. In aspects, the TLR-binding nucleic acid substituent includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In aspects, a TLR-binding nucleic acid substituent includes or is DNA. In aspects, a TLR-binding nucleic acid substituent includes or is RNA. In aspects, a TLR-binding nucleic acid substituent includes or is a nucleic acid having internucleotide linkages selected from phosphodiesters and phosphodiester derivatives (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof). In aspects, a TLR-binding nucleic acid substituent consists of a nucleic acid having internucleotide linkages selected from phosphodiesters and phosphorothioates. In aspects, a TLR-binding nucleic acid substituent includes or is a nucleic acid having backbone linkages selected from phosphodiesters and phosphorodithioates. In aspects, a TLR-binding nucleic acid substituent includes or is a nucleic acid having phosphodiester backbone linkages. In aspects, a TLR-binding nucleic acid substituent includes or is a nucleic acid having phosphorothioate backbone linkages. In aspects, a TLR-binding nucleic acid substituent includes or is a nucleic acid having phosphorodithioate backbone linkages. In aspects, a TLR-binding nucleic acid substituent preferentially binds TLR9 over other TLR. In aspects, a TLR-binding nucleic acid substituent specifically binds TLR9. In aspects, a TLR-binding nucleic acid substituent preferentially binds TLR3 over other TLR. In aspects, a TLR-binding nucleic acid substituent specifically binds TLR3. In aspects, a TLR-binding nucleic acid substituent preferentially binds TLR7 over other TLR. In aspects, a TLR-binding nucleic acid substituent specifically binds TLR7. In aspects, a TLR-binding nucleic acid substituent preferentially binds TLR8 over other TLR. In aspects, a TLR-binding nucleic acid substituent specifically binds TLR8. In aspects, a TLR-binding nucleic acid substituent specifically binds a cellular subcompartment (e.g. endosome) associated TLR (e.g. TLR3, TLR7, TLR8, or TLR9). In aspects, a TLR-binding nucleic acid substituent includes or is a G-rich nucleic acid (e.g. about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% G nucleotides; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% G nucleotides). In aspects, a TLR-binding nucleic acid substituent includes single stranded RNA (including phosphodiester internucleotide linkages, phosphodiester derivative internucleotide linkages, or a combination both). In aspects, a TLR-binding nucleic acid substituent includes double stranded RNA (including phosphodiester internucleotide linkages, phosphodiester derivative internucleotide linkages, or a combination both) (e.g. poly (I:C). In aspects, a TLR-binding nucleic acid substituent is a TLR3-binding nucleic acid substituent. In aspects, a TLR-binding nucleic acid substituent is a TLR7-binding nucleic acid substituent. In aspects, a TLR-binding nucleic acid substituent is a TLR8-binding nucleic acid substituent. In aspects, a TLR-binding nucleic acid substituent is a TLR9-binding nucleic acid substituent. In aspects, a TLR-binding nucleic acid substituent is a TLR-binding DNA substituent. In aspects, a TLR-binding nucleic acid substituent is a TLR9-binding DNA substituent.

As used herein, the term "TLR-binding DNA substituent" refers to a substituent or moiety capable of binding to a toll-like receptor ("TLR"), including at least one deoxyribonucleic acid. In aspects, a TLR-binding DNA substituent is a nucleic acid. In aspects, the TLR-binding DNA substituent includes at least one nucleic acid analog. In aspects, the TLR-binding DNA substituent includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In aspects, a TLR-binding DNA substituent includes DNA. In aspects, all nucleotide sugars in a TLR-binding DNA substituent are deoxyribose (e.g., all nucleotides are DNA). In aspects, a TLR-binding DNA substituent consists of DNA. In aspects, a TLR-binding DNA substituent includes or is DNA having internucleotide linkages selected from phosphodiesters and phosphodiester derivatives (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof). In aspects, a TLR-binding DNA substituent consists of DNA having internucleotide linkages selected from phosphodiesters and phosphorothioates. In aspects, a TLR-binding DNA substituent includes or is DNA having backbone linkages selected from phosphodiesters and phosphorodithioates. In aspects, a TLR-binding DNA substituent includes or is DNA including phosphodiester backbone linkages. In aspects, a TLR-binding DNA substituent includes or is DNA including phosphorothioate backbone linkages. In aspects, a TLR-binding DNA substituent includes or is DNA including phosphorodithioate backbone linkages. In aspects, a TLR-binding DNA substituent preferentially binds TLR9 over other TLR. In aspects, a TLR-binding DNA substituent specifically binds TLR9. In aspects, a TLR-binding DNA substituent specifically binds TLR3. In aspects, a TLR-binding DNA substituent specifically binds TLR7. In aspects, a TLR-binding DNA substituent specifically binds TLR8. In aspects, a TLR-binding DNA substituent specifically binds a cellular subcompartment (e.g. endosome) associated TLR (e.g. TLR3, TLR7, TLR8, or TLR9). In aspects, a TLR-binding DNA substituent includes or is a G-rich oligonucleotide (e.g. about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% G nucleotides). In aspects, a TLR-binding DNA substituent includes a CpG motif, wherein C and G are nucleotides and p is the phosphate connecting the C and G. In aspects, the CpG motif is unmethylated. In aspects, a TLR-binding DNA substituent is a Class A CpG oligodeoxynucleotide (ODN). In aspects, a TLR-binding DNA substituent is a Class B CpG oligodeoxynucleotide (ODN). In aspects, a TLR-binding DNA substituent is a Class C CpG oligodeoxynucleotide (ODN). In aspects, a TLR-binding DNA substituent (e.g., TLR9-binding DNA substituent) consists of deoxyribonucleic acids with A, G, C, or T bases and phosphodiester linkages and/or phosphodiester derivative linkages (e.g., phosphorothioate linkage(s)).

As used herein, the term "CpG motif" refers to a 5' C nucleotide connected to a 3' G nucleotide through a phosphodiester internucleotide linkage or a phosphodiester derivative internucleotide linkage. In aspects, a CpG motif includes a phosphodiester internucleotide linkage. In aspects, a CpG motif includes a phosphodiester derivative internucleotide linkage.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide including one or more of poly-G sequence at the 5', 3', or both ends; an internal palindrome sequence including CpG motif, or one or more phosphodiester derivatives linking deoxynucleotides. In aspects, a Class A CpG ODN includes poly-G sequence at the 5', 3', or both ends; an internal palindrome sequence including CpG motif; and one or more phosphodiester derivatives linking deoxynucleotides. In aspects, the phosphodiester derivative is phosphorothioate. Examples of Class A CpG ODNs include ODN D19 (e.g., SEQ ID NO:15 or SEQ ID NO:16), ODN 1585 (e.g., SEQ ID NO:11 or SEQ ID NO:12), ODN 2216 (e.g., SEQ ID NO:13 or SEQ ID NO:14), and ODN 2336 (e.g., SEQ ID NO:17 or SEQ ID NO:18).

As used herein, the term "Class B CpG ODN" or "B-class CpG ODN" or "K-type CpG ODN" or "Class B CpG DNA sequence" is used in accordance with its common meaning in the biological and chemical sciences and refers to a CpG motif including oligodeoxynucleotide including one or more of a 6mer motif including a CpG motif, phosphodiester derivatives linking all deoxynucleotides. In aspects, a Class B CpG ODN includes one or more copies of a 6mer motif including a CpG motif and phosphodiester derivatives linking all deoxynucleotides. In aspects, the phosphodiester derivative is phosphorothioate. In aspects, a Class B CpG ODN includes one 6mer motif including a CpG motif. In aspects, a Class B CpG ODN includes two copies of a 6mer motif including a CpG motif. In aspects, a Class B CpG ODN includes three copies of a 6mer motif including a CpG motif. In aspects, a Class B CpG ODN includes four copies of a 6mer motif including a CpG motif. Examples of Class B CpG ODNs include ODN 1668 (e.g., SEQ ID NO:19), ODN 1826 (e.g., SEQ ID NO:20), ODN 2006 (e.g., SEQ ID NO:21), and ODN 2007 (e.g., SEQ ID NO:22).

As used herein, the term "Class C CpG ODN" or "C-class CpG ODN"" or "C-type CpG DNA sequence" is used in accordance with its common meaning in the biological and chemical sciences and refers to an oligodeoxynucleotide including a palindrome sequence including a CpG motif and phosphodiester derivatives (phosphorothioate) linking all deoxynucleotides. Examples of Class C CpG ODNs include ODN 2395 (e.g., SEQ ID NO:23) and ODN M362 (e.g., SEQ ID NO:24).

As used herein, the term "STAT-binding substituent" or "STAT-binding nucleic acid substituent" refers to a composition including one or more nucleic acids capable of binding to a STAT transcription factor (e.g. STAT1, STAT2, STAT3, STAT4, STAT5A, STAT5B, or STAT6). In aspects, a STAT-binding substituent includes DNA (e.g. including phosphodiester internucleotide linkages, phosphodiester derivative internucleotide linkages, or a combination of phosphodiester and phosphodiester derivative internucleotide linkages). In aspects, a STAT-binding substituent (e.g. STAT1-, STAT2-, STAT3-, STAT4-, STAT5A-, STAT5B—, or STAT6-binding substituent) includes a DNA sequence identical (except that it may include one or more phosphodiester derivative linkage(s)) to the genomic DNA sequence a STAT transcription factor (e.g. STAT1, STAT2, STAT3, STAT4, STAT5A, STAT5B, or STAT6) binds when modulating transcription. In aspects, a STAT-binding substituent (e.g. STAT1-, STAT2-, STAT3-, STAT4-, STAT5A-, STAT5B—, or STAT6-binding substituent) is a DNA sequence identical (except that it may include one or more phosphodiester derivative linkage(s)) to the genomic DNA sequence a STAT transcription factor (e.g. STAT1, STAT2, STAT3, STAT4, STAT5A, STAT5B, or STAT6) binds when modulating transcription. In aspects, a STAT-binding substituent (e.g. STAT1-, STAT2-, STAT3-, STAT4-, STAT5A-, STAT5B—, or STAT6-binding substituent) includes a DNA sequence identical (except that it may include one or more phosphodiester derivative linkage(s)) to the genomic DNA sequence phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, or STAT6) binds when modulating transcription. In aspects, a STAT-binding substituent (e.g. STAT1-, STAT2-, STAT3-, STAT4-, STAT5A-, STAT5B—, or STAT6-binding substituent) is a DNA sequence identical (except that it may include one or more phosphodiester derivative linkage(s)) to the genomic DNA sequence phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, or STAT6) binds when modulating transcription. In aspects, a STAT-binding substituent (e.g. STAT1-, STAT2-, STAT3-, STAT4-, STAT5A-, STAT5B—, or STAT6-binding substituent) includes a DNA sequence identical (except that it may include one or more phosphodiester derivative linkage(s)) to the genomic DNA sequence a STAT (e.g. STAT1, STAT2, STAT3, STAT4, STAT5A, STAT5B, STAT6, or combinations thereof) dimer binds when modulating transcription. In aspects, a STAT-binding substituent (e.g. STAT1-, STAT2-, STAT3-, STAT4-, STAT5A-, STAT5B—, or STAT6-binding substituent) is a DNA sequence identical (except that it may include one or more phosphodiester derivative linkage(s)) to the genomic DNA sequence a STAT (e.g. STAT1, STAT2, STAT3, STAT4, STAT5A, STAT5B, STAT6, or combinations thereof) dimer binds when modulating transcription. In aspects, a STAT-binding substituent (e.g. STAT1-, STAT2-, STAT3-, STAT4-, STAT5A-, STAT5B—, or STAT6-binding substituent) includes a DNA sequence identical (except that it may include one or more phosphodiester derivative linkage(s)) to the genomic DNA sequence a phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, STAT6, or combinations thereof) dimer binds when modulating transcription. In aspects, a STAT-binding substituent (e.g. STAT1-, STAT2-, STAT3-, STAT4-, STAT5A-, STAT5B—, or STAT6-binding substituent) is a DNA sequence identical (except that it may include one or more phosphodiester derivative linkage(s)) to the genomic DNA sequence a phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, STAT6, or combinations thereof) dimer binds when modulating transcription.

As used herein, the term "STAT3-binding nucleic acid substituent" or "STAT3-binding substituent" refers to a composition including one or more nucleic acids capable of binding to STAT3. In aspects, a STAT3-binding substituent includes DNA (e.g. including phosphodiester internucleotide linkages, phosphodiester derivative internucleotide linkages, or a combination of phosphodiester and phosphodiester derivative internucleotide linkages) (a "STAT3-binding DNA substituent"). In aspects, all nucleotide sugars in a STAT3-binding DNA substituent are deoxyribose (e.g., all nucleotides are DNA). In aspects, a STAT3-binding substituent is DNA (e.g. including phosphodiester internucleotide linkages, phosphodiester derivative internucleotide linkages, or a combination of phosphodiester and phosphodiester derivative internucleotide linkages). In aspects, a STAT3-binding substituent includes a DNA sequence identical (except that it may include one or more phosphodiester derivative linkage(s)) to the genomic DNA sequence STAT3 binds when modulating transcription. In aspects, a STAT3-binding substituent is a DNA sequence identical (except that it may include one or more phosphodiester derivative linkage(s)) to the genomic DNA sequence STAT3 binds when modulating transcription. In aspects, a STAT3-binding substituent includes a DNA sequence identical (except that it may include one or more phosphodiester derivative linkage(s)) to the genomic DNA sequence phosphorylated (e.g. on Y705 or residue corresponding to human STAT3 Y705) STAT3 binds when modulating transcription. In aspects, a STAT3-binding substituent is a DNA sequence identical (except that it may include one or more phosphodiester derivative linkage(s)) to the genomic DNA sequence phosphorylated (e.g. on Y705 or residue corresponding to human STAT3 Y705) STAT3 binds when modulating transcription. In aspects, a STAT3-binding substituent includes a DNA sequence identical (except that it may include one or more phosphodiester derivative linkage(s)) to the genomic DNA sequence a STAT3 dimer binds when modulating transcription. In aspects, a STAT3-binding substituent is a DNA sequence identical (except that it may include one or more phosphodiester derivative linkage(s)) to the genomic DNA sequence a STAT3 dimer binds when modulating transcription. In aspects, a STAT3-binding substituent includes a DNA sequence identical (except that it may include one or more phosphodiester derivative linkage(s)) to the genomic DNA sequence a phosphorylated (e.g. on Y705 or residue corresponding to human STAT3 Y705) STAT3 dimer binds when modulating transcription. In aspects, a STAT3-binding substituent is a DNA sequence identical (except that it may include one or more phosphodiester derivative linkage(s)) to the genomic DNA sequence a phosphorylated (e.g. on Y705 or residue corresponding to human STAT3 Y705) STAT3 dimer binds when modulating transcription.

As used herein, the term "preferentially binds" as applied to a STAT-binding substituent (e.g. STAT1-, STAT2-, STAT3-, STAT4-, STAT5A-, STAT5B—, or STAT6-binding substituent) or STAT3-binding nucleic acid substituent (e.g. STAT3-binding DNA substituent) binding to a specific form of a STAT transcription factor (e.g. STAT1, STAT2, STAT3, STAT4, STAT5A, STAT5B, or STAT6) or STAT3 respectively, means binds more strongly to the specific form compared to the binding to another form of a STAT transcription factor (e.g. STAT1, STAT2, STAT3, STAT4, STAT5A, STAT5B, or STAT6). In aspects, preferentially binds means binds more strongly to the specific form compared to the binding to other forms of a STAT transcription factor (e.g. STAT1, STAT2, STAT3, STAT4, STAT5A, STAT5B, or STAT6). In aspects, preferential binding is measured as an IC50. In aspects, preferential binding is measured as a dissociation constant. In aspects, preferential binding is measured as an association constant. In aspects, preferential binding is measured as an on rate. In aspects, preferential binding is measured as an off rate. In aspects, preferential binding is measured as a lowered concentration needed to bind to the preferred form to the same extent as binding to a non-preferred form at a greater concentration. In aspects, preferentially binds means binds 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000 fold, 100,000-fold, or 1,000,000-fold greater to the preferred form compared to another form.

As used herein, the term "conjugated" when referring to two moieties means the two moieties are bonded, wherein the bond or bonds connecting the two moieties may be covalent or non-covalent. In aspects, the two moieties are covalently bonded to each other (e.g. directly or through a covalently bonded intermediary). In aspects, the two moieties are non-covalently bonded (e.g. through ionic bond(s), van der waal's bond(s)/interactions, hydrogen bond(s), polar bond(s), or combinations or mixtures thereof).

As used herein, the term "about" means a range of values including the specified value, which a person of ordinary skill in the art would consider reasonably similar to the specified value. In aspects, about means within a standard deviation using measurements generally acceptable in the art. In aspects, about means a range extending to +/−10% of the specified value. In aspects, about means the specified value.

The term "capable of binding" as used herein refers to a moiety (e.g. a compound as described herein) that is able to measurably bind to a target (e.g., a transcription factor binding site, a Toll-like receptor protein, or a ubiquitin ligase protein). In aspects, where a moiety is capable of binding a target, the moiety is capable of binding with a Kd of less than about 10 µM, 5 µM, 1 µM, 500 nM, 250 nM, 100 nM, 75 nM, 50 nM, 25 nM, 15 nM, 10 nM, 5 nM, 1 nM, or about 0.1 nM.

The term "RNA virus" as used herein refers, in the usual and customary sense, to a a virus that has RNA (ribonucleic acid) as its genetic material. In aspects, the RNA is single-stranded RNA (e.g., ssRNA). In aspects, the RNA is positive (+) single-stranded RNA (e.g., Bymoviruses, comoviruses, nepoviruses, nodaviruses, picornaviruses, potyviruses, sobemoviruses, luteoviruses (e.g., beet western yellows virus, barley yellow dwarf virus, potato leafroll virus), Carmoviruses, dianthoviruses, flaviviruses, pestiviruses, statoviruses, tombusviruses, single-stranded RNA bacteriophages, hepatitis C virus, Alphaviruses, carlaviruses, furoviruses, hordeiviruses, potexviruses, rubiviruses, tobraviruses, tricornaviruses, tymoviruses, apple chlorotic leaf spot virus, or hepatitis E virus). In aspects, the RNA is double-stranded RNA (e.g., dsRNA). In aspects, the RNA virus is a Picornavirata virus. In aspects, the RNA virus is a Flavivirata virus. In aspects, the RNA virus is a Rubivirata virus. In aspects, the RNA virus is a Zika virus.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, or L$^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

A "polyglycol" as used herein refers to a poly alkyl ether. In aspects, the polyglycol is substituted (e.g., e.g., substituted with a substituent group, a size-limited substituent group, or lower substituent group). In aspects, the polyglycol has the formula

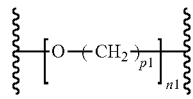

wherein p1 is an integer from 1 to 20; n1 is an integer from 1 to 100. In aspects, wherein p1 is 2, the polyglycol may be referred to as polyethylene glycol. In aspects, wherein p1 is 3, the polyglycol may be referred to as polypropylene glycol.

Compounds

In an aspect is provided a compound including a first nucleic acid sequence capable of binding to a transcription factor binding site and a ubiquitin ligase binding compound covalently bound to the first nucleic acid. In aspects the first nucleic acid sequence binds to the transcription factor binding site. In aspects the first nucleic acid sequence non-covalently binds to the transcription factor binding site. In aspects, the ubiquitin ligase binding compound is bonded to the 3'-terminus of the first nucleic acid. In aspects, the ubiquitin ligase binding compound is bonded to the 5'-terminus of the first nucleic acid. In aspects, the ubiquitin ligase binding compound is bonded to any nucleotide in the first nucleic acid. In aspects, the ubiquitin ligase binding compound is bonded to the first nucleic acid via a linker of the formula -L$^1$-L$^2$-L$^3$-L$^4$-MC, where the substituents are as defined herein.

In embodiments, the compound further includes second nucleic acid sequence capable of binding a Toll-like receptor protein (TLR). In aspects, the second nucleic acid sequence binds to the Toll-like receptor protein. In aspects, the second nucleic acid sequence non-covalently binds to the Toll-like receptor protein. In aspects, the compound comprises a first nucleic acid sequence capable of binding to a transcription factor binding site covalently bound to a second nucleic acid sequence capable of binding a Toll-like receptor protein; and a ubiquitin ligase binding compound covalently bound to the first nucleic acid or the second nucleic acid. In aspects, the compound comprises a first nucleic acid sequence capable of binding to a transcription factor binding site covalently bound to a second nucleic acid sequence capable of binding a Toll-like receptor protein; and a ubiquitin ligase binding compound covalently bound to the first nucleic acid or the second nucleic acid via a linker of the formula -L$^1$-L$^2$-L$^3$-L$^4$-MC, where the substituents are as defined herein. In aspects, the first nucleic acid sequence is bonded to the second nucleic acid sequence by a spacer, as defined herein. In aspects, the first nucleic acid sequence is bonded to the second nucleic acid sequence by a spacer or linker, as defined herein. In aspects, the ubiquitin ligase binding compound is bonded to the 3'-terminus of the first nucleic acid or the second nucleic acid. In aspects, the ubiquitin ligase binding compound is bonded to the 5'-terminus of the first nucleic acid or the second nucleic acid. In aspects, the ubiquitin ligase binding compound is bonded to any nucleotide in the first nucleic acid or the second nucleic acid. In aspects, the ubiquitin ligase binding compound is bonded to the first nucleic acid or the second nucleic acid via a linker of the formula -L$^1$-L$^2$-L$^3$-L$^4$-MC, where the substituents are as defined herein. In aspects, the ubiquitin ligase binding compound is bonded to the spacer (defined herein) which links the first nucleic acid and the second nucleic acid. In aspects, the 3'-terminus of the first nucleic acid is bonded to the 3'-terminus of the second nucleic acid via a spacer or linker. In aspects, the 3'-terminus of the first nucleic acid is bonded to the 5'-terminus of the second nucleic acid via a spacer or linker. In aspects, the 3'-terminus of the first nucleic acid is bonded to any nucleotide in the second nucleic acid via a spacer or linker. In aspects, the 5'-terminus of the first nucleic acid is bonded to the 3'-terminus of the second nucleic acid via a spacer or linker. In aspects, the 5'-terminus of the first nucleic acid is bonded to the 5'-terminus of the second nucleic acid via a spacer or linker. In aspects, the 5'-terminus of the first nucleic acid is bonded to any nucleotide in the second nucleic acid via a spacer or linker.

In an aspect is provided a compound including a first nucleic acid sequence capable of binding to a transcription factor binding site covalently bound to a second nucleic acid sequence capable of binding a Toll-like receptor protein; and a ubiquitin ligase binding compound covalently bound to the first nucleic acid or the second nucleic acid. In aspects, the first nucleic acid sequence is bonded to the second nucleic acid sequence by a spacer, as defined herein. In aspects, the first nucleic acid sequence is bonded to the second nucleic acid sequence by a linker, as defined herein. In aspects, the ubiquitin ligase binding compound is bonded to the 3'-terminus of the first nucleic acid or the second nucleic acid. In aspects, the ubiquitin ligase binding compound is bonded to the 5'-terminus of the first nucleic acid or the second nucleic acid. In aspects, the ubiquitin ligase binding compound is bonded to any nucleotide in the first nucleic acid or the second nucleic acid.

In embodiments, the ubiquitin ligase binding compound is covalently bound to the first nucleic acid, the second nucleic acid, or the spacer. In aspects, the ubiquitin ligase binding compound is covalently bound to the first nucleic acid. In aspects, the ubiquitin ligase binding compound is covalently bound to the second nucleic acid. In aspects, the ubiquitin ligase binding compound is covalently bound to the spacer. In aspects, the ubiquitin ligase binding compound is covalently bound to the linker (e.g., the linker between the TLR-binding nucleic acid (e.g. endosomal TLR-, TLR3-, TLR7-, TLR8-, or TLR9-binding nucleic acid) substituent and the STAT-binding nucleic acid substituent (e.g. STAT1-, STAT2-, STAT3-, STAT4-, STAT5A-, STAT5B—, or STAT6-binding nucleic acid substituent).

In embodiments, the Toll-like receptor protein is human Toll-like receptor 3 (TLR3), human Toll-like receptor 7 (TLR7), human Toll-like receptor 8 (TLR8), or human Toll-like receptor 9 (TLR9). In aspects, the Toll-like receptor protein is human Toll-like receptor 3 (TLR3). In aspects, the Toll-like receptor protein is human Toll-like receptor 7 (TLR7). In aspects, the Toll-like receptor protein is human Toll-like receptor 8 (TLR8). In aspects, the Toll-like receptor protein is human Toll-like receptor 9 (TLR9).

In embodiments, the first nucleic acid sequence includes a CpG motif, a GpC motif, or a phosphorothioated nucleic acid sequence having at least 10 nucleotides. In aspects, the first nucleic acid sequence includes a CpG motif. In aspects, the first nucleic acid sequence includes a GpC motif. In aspects, the first nucleic acid sequence includes a phosphorothioated nucleic acid sequence having at least 10 nucleotides. In embodiments, the first nucleic acid sequence includes an unmethylated CpG motif.

In embodiments, the second nucleic acid sequence includes a CpG motif, a GpC motif, or a phosphorothioated nucleic acid sequence having at least 10 nucleotides. In aspects, the second nucleic acid sequence includes a CpG motif. In aspects, the second nucleic acid sequence includes a GpC motif. In aspects, the second nucleic acid sequence includes a phosphorothioated nucleic acid sequence having at least 10 nucleotides. In embodiments, the second nucleic acid sequence includes an unmethylated CpG motif.

In embodiments, the compound includes a CpG motif. In aspects, the compound includes an unmethylated CpG motif. In aspects, the compound includes a CpG motif wherein the CpG is not methylated. In aspects, the compound includes a nucleic acid sequence capable of forming a G-quadruplex. In aspects, the compound includes a DNA sequence capable of forming a G-quadruplex. In aspects, the compound includes a Class A CpG DNA sequence. In aspects, the compound includes a Class B CpG DNA sequence. In aspects, the compound includes a C-type CpG DNA sequence. In aspects, the compound binds an endosomal TLR. In aspects, the compound preferentially binds an endosomal TLR over other TLR. In aspects, the compound specifically binds an endosomal TLR. In aspects, the compound binds TLR3. In aspects, the compound preferentially binds TLR3 over other TLR. In aspects, the compound specifically binds TLR3. In aspects, the compound binds TLR7. In aspects, the compound preferentially binds TLR7 over other TLR. In aspects, the compound specifically binds TLR7. In aspects, the compound binds TLR8. In aspects, the compound preferentially binds TLR8 over other TLR. In aspects, the compound specifically binds TLR8. In aspects, the compound binds TLR9. In aspects, the compound preferentially binds TLR9 over other TLR. In aspects, the compound specifically binds TLR9. In aspects, the compound includes CpG, wherein C and G are nucleotides connected by a phosphodiester internucleotide linkage or phosphodiester derivative internucleotide linkage. In aspects, the compound includes CpG, wherein C and G are nucleotides connected by a phosphodiester internucleotide linkage. In aspects, the compound includes CpG, wherein C and G are nucleotides connected by a phosphodiester derivative internucleotide linkage. In aspects, the CpG is unmethylated. In aspects, the compound preferentially binds phosphorylated STAT (e.g. STAT1, STAT2, STAT3, STAT4, STAT5A, STAT5B, or STAT6) over unphosphorylated STAT (e.g. STAT1, STAT2, STAT3, STAT4, STAT5A, STAT5B, or STAT6). In aspects, the compound binds phosphorylated STAT (e.g. STAT1, STAT2, STAT3, STAT4, STAT5A, STAT5B, or STAT6). In aspects, the compound binds STAT3 phosphorylated on tyrosine 705. In aspects, the compound binds a STAT transcription factor (e.g. STAT1, STAT2, STAT3, STAT4, STAT5A, STAT5B, or STAT6) phosphorylated on STAT1 Y701, STAT2, Y690, STAT3 Y705, STAT4 Y693, STAT5A Y694, STAT5B Y694, STAT6 Y641, or a residue corresponding to one of those residues. In aspects, the compound binds human STAT (e.g. STAT1, STAT2, STAT3, STAT4, STAT5A, STAT5B, or STAT6). In aspects, the compound binds STAT (e.g. STAT1, STAT2, STAT3, STAT4, STAT5A, STAT5B, STAT6, or combinations thereof) dimers. In aspects, the compound binds dimers of phosphorylated STAT (e.g. STAT1, STAT2, STAT3, STAT4, STAT5A, STAT5B, STAT6, or combinations thereof) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues). In aspects, the compound binds activated STAT (e.g. STAT1, STAT2, STAT3, STAT4, STAT5A, STAT5B, or STAT6). In aspects, the compound binds a scavenger receptor.

In embodiments, the compound enters a cell following administration (e.g. to a patient, to the blood stream of a patient, or to the extracellular milieu of the cell). In aspects, the compound enters a cell following administration (e.g. to a patient, to the blood stream of a patient, or to the extracellular milieu of the cell) without co-administration of an agent to facilitate transfection (e.g. an agent with the sole purpose of assisting the compound to enter a cell). In aspects, the cell is a plasmacytoid dendritic cell, myeloid dendritic cell, myeloid-derived suppressor cell, granulocytic myeloid-derived suppressor cell, macrophage, B cell, activated NK cell, or activated neutrophil. In aspects, the cell is in the brain, an organ, bone, or bone marrow of a subject. In embodiments, the compound is not degraded (e.g. in a patient, in the blood stream, at the site of administration, or in the extracellular milieu).

In embodiments, the second nucleic acid sequence includes a Class A CpG DNA sequence, Class B CpG DNA sequence, or Class C CpG DNA sequence. In aspects, the second nucleic acid sequence includes a Class A CpG DNA sequence. In aspects, the second nucleic acid sequence includes Class B CpG DNA sequence. In aspects, the second nucleic acid sequence includes Class C CpG DNA sequence. In aspects, the second nucleic acid sequence is a Class A CpG DNA sequence, Class B CpG DNA sequence, or Class C CpG DNA sequence. In aspects, the second nucleic acid sequence is a Class A CpG DNA sequence. In aspects, the second nucleic acid sequence is Class B CpG DNA sequence. In aspects, the second nucleic acid sequence is Class C CpG DNA sequence.

In aspects, the compound comprises one of SEQ ID NOS:1-24. In aspects, the first nucleic acid sequence and/or the second nucleic acid sequence is one of SEQ ID NOS: 1-24.

In embodiments, the transcription factor is signal transducer and activator of transcription protein or nuclear factor kappa-light-chain-enhancer of activated B cells. In aspects, the transcription factor is signal transducer and activator of transcription protein. In aspects, the transcription factor is nuclear factor kappa-light-chain-enhancer of activated B cells.

In embodiments, the transcription factor is signal transducer and activator of transcription 3 (STAT3) protein. In aspects, the first nucleic acid sequence is a STAT-binding nucleic acid substituent. In aspects, the first nucleic acid sequence is a STAT3-binding nucleic acid substituent.

In embodiments, the STAT3-binding nucleic acid substituent (e.g. STAT3-binding DNA substituent) includes a first STAT3-binding nucleic acid sequence (e.g. STAT3-binding DNA sequence) bound to a second STAT3-binding nucleic acid sequence (e.g. STAT3-binding DNA sequence) by a spacer. In aspects, the STAT3-binding nucleic acid substituent (e.g. STAT3-binding DNA substituent) includes a first STAT3-binding nucleic acid sequence (e.g. STAT3-binding DNA sequence) covalently bound to a second STAT3-binding nucleic acid sequence (e.g. STAT3-binding DNA sequence) by a spacer. In aspects, the STAT-binding nucleic acid substituent (e.g. STAT1-, STAT2-, STAT3-, STAT4-, STAT5A-, STAT5B—, or STAT6-binding nucleic acid substituent) includes a first STAT-binding nucleic acid sequence (e.g. STAT1-, STAT2-, STAT3-, STAT4-, STAT5A-, STAT5B—, or STAT6-binding nucleic acid sequence) bound to a second STAT-binding nucleic acid sequence (e.g. STAT1-, STAT2-, STAT3-, STAT4-, STAT5A-, STAT5B—, or STAT6-binding nucleic acid sequence) by a spacer. In aspects, the STAT-binding nucleic acid substituent (e.g. STAT1-, STAT2-, STAT3-, STAT4-, STAT5A-, STAT5B—, or STAT6-binding nucleic acid substituent) includes a first STAT-binding nucleic acid sequence (e.g. STAT1-, STAT2-, STAT3-, STAT4-, STAT5A-, STAT5B—, or STAT6-binding nucleic acid sequence) covalently bound to a second STAT-binding nucleic acid sequence (e.g. STAT1-, STAT2-, STAT3-, STAT4-, STAT5A-, STAT5B—, or STAT6-binding nucleic acid sequence) by a spacer.

In embodiments, the STAT3-binding DNA substituent includes a first STAT3-binding DNA sequence bound to a second STAT3-binding DNA sequence by a spacer. In aspects, the STAT3-binding DNA substituent includes a first STAT3-binding DNA sequence covalently bound to a second STAT3-binding DNA sequence by a spacer. In aspects, the STAT-binding DNA substituent (e.g. STAT1-, STAT2-, STAT3-, STAT4-, STAT5A-, STAT5B—, or STAT6-binding DNA substituent) includes a first STAT-binding DNA sequence (e.g. STAT1-, STAT2-, STAT3-, STAT4-, STAT5A-, STAT5B—, or STAT6-binding DNA sequence) bound to a second STAT-binding DNA sequence (e.g. STAT1-, STAT2-, STAT3-, STAT4-, STAT5A-, STAT5B—, or STAT6-binding DNA sequence) by a spacer. In aspects, the STAT-binding DNA substituent (e.g. STAT1-, STAT2-, STAT3-, STAT4-, STAT5A-, STAT5B—, or STAT6-binding DNA substituent) includes a first STAT-binding DNA sequence (e.g. STAT1-, STAT2-, STAT3-, STAT4-, STAT5A-, STAT5B—, or STAT6-binding DNA sequence) covalently bound to a second STAT-binding DNA sequence (e.g. STAT1-, STAT2-, STAT3-, STAT4-, STAT5A-, STAT5B—, or STAT6-binding DNA sequence) by a spacer.

In embodiments, the second nucleic acid sequence is a TLR-binding nucleic acid substituent. In aspects, the second nucleic acid sequence is a TLR-binding DNA substituent. In aspects, the second nucleic acid sequence is a TLR9-binding nucleic acid substituent. In aspects, the second nucleic acid sequence is a TLR9-binding DNA substituent.

In embodiments, the TLR9-binding DNA substituent includes a CpG motif. In aspects, the TLR9-binding DNA substituent includes an unmethylated CpG motif. In aspects, the TLR9-binding DNA substituent includes a CpG motif wherein the CpG is not methylated. In aspects, the TLR9-binding DNA substituent includes a DNA sequence capable of forming a G-quadruplex. In aspects, the TLR9-binding DNA substituent includes a Class A CpG DNA sequence. In aspects, the TLR9-binding DNA substituent includes a Class B CpG DNA sequence. In aspects, the TLR9-binding DNA substituent includes a C-type CpG DNA sequence.

In embodiments, the TLR-binding DNA substituent binds TLR9. In aspects, the TLR-binding DNA substituent preferentially binds TLR9 over other TLR. In aspects, the TLR-binding DNA substituent specifically binds TLR9. In aspects, the TLR-binding DNA substituent includes CpG, wherein C and G are nucleotides connected by a phosphodiester internucleotide linkage or phosphodiester derivative internucleotide linkage. In aspects, the compound includes CpG, wherein C and G are nucleotides connected by a phosphodiester internucleotide linkage. In aspects, the compound includes CpG, wherein C and G are nucleotides connected by a phosphodiester derivative internucleotide linkage. In aspects, the CpG is unmethylated. In aspects, the TLR-binding DNA substituent is a Class A CpG oligodeoxynucleotide (ODN). In aspects, the TLR-binding DNA substituent is a Class B CpG oligodeoxynucleotide (ODN). In aspects, the TLR-binding DNA substituent is a Class C CpG oligodeoxynucleotide (ODN). In aspects, the TLR-binding DNA substituent is ODN 1585 (e.g., SEQ ID NO:11 or SEQ ID NO:12), ODN 2216 (e.g., SEQ ID NO:13 or SEQ ID NO:14), ODN D19 (e.g., SEQ ID NO:15 or SEQ ID NO:16), or ODN 2336 (e.g., SEQ ID NO:17 or SEQ ID NO:18). In aspects, the TLR-binding DNA substituent is ODN 1668 (e.g., SEQ ID NO:19), ODN 1826 (e.g., SEQ ID NO:20), ODN 2006 (e.g., SEQ ID NO:21), or ODN 2007 (e.g., SEQ ID NO:22). In aspects, the TLR-binding DNA substituent is ODN 2395 (e.g., SEQ ID NO:23) or ODN M362 (e.g., SEQ ID NO:24). In aspects, the TLR-binding DNA substituent is a derivative of ODN 1585 (e.g., SEQ ID NO:11 or SEQ ID NO:12), ODN 2216 (e.g., SEQ ID NO:13 or SEQ ID NO:14), ODN D19 (e.g., SEQ ID NO:15 or SEQ ID NO:16), ODN 2336 (e.g., SEQ ID NO:17 or SEQ ID NO:18), ODN 1668 (e.g., SEQ ID NO:19), ODN 1826 (e.g., SEQ ID NO:20), ODN 2006 (e.g., SEQ ID NO:21), ODN 2007 (e.g., SEQ ID NO:22), ODN 2395 (e.g., SEQ ID NO:23) or ODN M362 (e.g., SEQ ID NO:24). In aspects, a derivative of ODN 1585 (e.g., SEQ ID NO:11 or SEQ ID NO:12), ODN 2216 (e.g., SEQ ID NO:13 or SEQ ID NO:14), ODN D19 (e.g., SEQ ID NO:15 or SEQ ID NO:16), ODN 2336 (e.g., SEQ ID NO:17 or SEQ ID NO:18), ODN 1668 (e.g., SEQ ID NO:19), ODN 1826 (e.g., SEQ ID NO:20), ODN 2006 (e.g., SEQ ID NO:21), ODN 2007 (e.g., SEQ ID NO:22), ODN 2395 (e.g., SEQ ID NO:23) or ODN M362 (e.g., SEQ ID NO:24) includes one or more nucleotide substitutions (e.g. A, C, G, or T substituted with a different nucleotide). In aspects, a derivative of ODN 1585 (e.g., SEQ ID NO:11 or SEQ ID NO:12), ODN 2216 (e.g., SEQ ID NO:13 or SEQ ID NO:14), ODN D19 (e.g., SEQ ID NO:15 or SEQ ID NO:16), ODN 2336 (e.g., SEQ ID NO:17 or SEQ ID NO:18), ODN 1668 (e.g., SEQ ID NO:19), ODN 1826 (e.g., SEQ ID NO:20), ODN 2006 (e.g., SEQ ID NO:21), ODN 2007 (e.g., SEQ ID NO:22), ODN 2395 (e.g., SEQ ID NO:23) or ODN M362 (e.g., SEQ ID NO:24) includes one or more internucleotide linkage replacements (e.g. phosphodiester replaced with a phosphodiester derivative or a phosphodiester derivative replaced with a phosphodiester). In aspects, a derivative of ODN 1585 (e.g., SEQ ID NO:11 or SEQ ID NO:12), ODN 2216 (e.g., SEQ ID NO:13 or SEQ ID NO:14), ODN D19 (e.g., SEQ ID NO:15 or SEQ ID NO:16), ODN 2336 (e.g., SEQ ID NO:17 or SEQ ID NO:18), ODN 1668 (e.g., SEQ ID NO:19), ODN 1826 (e.g., SEQ ID NO:20), ODN 2006 (e.g., SEQ ID NO:21), ODN 2007 (e.g., SEQ ID NO:22), ODN 2395 (e.g., SEQ ID NO:23) or ODN M362 (e.g., SEQ ID NO:24) includes one or more nucleotide deletions. In aspects, a derivative of ODN 1585 (e.g., SEQ ID NO:11 or SEQ ID NO:12), ODN 2216 (e.g., SEQ ID NO:13 or SEQ ID NO:14), ODN D19 (e.g., SEQ ID NO:15 or SEQ ID NO:16), ODN 2336 (e.g., SEQ ID NO:17 or SEQ ID NO:18), ODN 1668 (e.g., SEQ ID NO:19), ODN 1826 (e.g., SEQ ID NO:20), ODN 2006 (e.g., SEQ ID NO:21), ODN 2007 (e.g., SEQ ID NO:22), ODN 2395 (e.g., SEQ ID NO:23) or ODN M362 (e.g., SEQ ID NO:24) includes one or more nucleotide additions.

In embodiments, the first nucleic acid sequence includes a first transcription factor binding site nucleic acid sequence and a second transcription factor binding side nucleic acid sequence connected through a spacer, wherein the spacer is a substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the second nucleic acid sequence comprises a first Toll-like receptor binding site nucleic acid sequence and a second Toll-like receptor binding side nucleic acid sequence connected through a spacer, wherein the spacer is a substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In the compounds described herein, a spacer between a first nucleic acid and a second nucleic acid is a bond, nucleic acid sequence, two nucleic acid sequences, DNA sequence, two DNA sequences, nucleic acid analog sequence, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the spacer between a first nucleic acid and a second nucleic acid is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In aspects, the spacer is a substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In aspects, the spacer is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In aspects, the spacer is an unsubstituted $C_1$-$C_{20}$ alkylene. In aspects, the spacer is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In aspects, the spacer is a substituted or unsubstituted $C_1$-$C_{40}$ alkylene. In aspects, the spacer is a substituted or unsubstituted 2 to 40 membered heteroalkylene. In aspects, the spacer is a substituted 2 to 40 membered heteroalkylene. In aspects, the spacer includes alkyl phosphates (e.g., propyl phosphates). In aspects, the spacer consists of alkyl phosphates (e.g., propyl phosphates) bonded to the reminder of the compound by phosphates at both ends. In aspects, the spacer consists of 1-5 alkyl phosphates (e.g., propyl phosphates) bonded to the reminder of the compound by phosphates at both ends. In aspects, the spacer consists of 1-4 alkyl phosphates (e.g., propyl phosphates) bonded to the reminder of the compound by phosphates at both ends. In aspects, the spacer consists of 4 alkyl phosphates (e.g., propyl phosphates) bonded to the reminder of the compound by phosphates at both ends. A person having ordinary skill in the art will recognize that a spacer consisting of alkyl phosphates that is bonded to the remainder of the compound by phosphates on both ends will have one more phosphate than alkylene groups (e.g., a spacer consisting of 4 alkyl phosphates that is bonded to the reminder of the compound by phosphates at both ends will have five phosphates and four alkyl groups with alternating phosphate groups and alkyl groups).

In embodiments, the spacer between a first nucleic acid and a second nucleic acid includes a first single nucleic acid strand connected to the first STAT3-binding nucleic acid sequence (e.g. STAT3-binding DNA sequence) and a second single nucleic acid strand connected to the second STAT3-binding nucleic acid sequence (e.g. STAT3-binding DNA sequence), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang." In aspects, the spacer includes a first single nucleic acid strand connected to the first STAT-binding nucleic acid sequence (e.g. STAT1-, STAT2-, STAT3-, STAT4-, STAT5A-, STAT5B—, or STAT6-binding nucleic acid sequence) and a second single nucleic acid strand connected to the STAT-binding nucleic acid sequence (e.g. STAT1-, STAT2-, STAT3-, STAT4-, STAT5A-, STAT5B—, or STAT6-binding nucleic acid sequence), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang." In aspects, the first and second single nucleic acid strands in the hybridized nucleic acid overhang are complementary throughout their entire lengths. In aspects, the spacer is an unsubstituted $C_1$-$C_{20}$ alkylene. In aspects, the spacer is an unsubstituted linear $C_1$-$C_{20}$ alkylene. In aspects, the spacer is an unsubstituted $C_3$-$C_{21}$ alkylene. In aspects, the spacer is an unsubstituted $C_3$-$C_{15}$ alkylene. In aspects, the spacer is an unsubstituted linear $C_3$-$C_{15}$ alkylene. In aspects, the spacer is an unsubstituted linear $C_6$-$C_{21}$ alkylene. In aspects, the spacer is an unsubstituted linear $C_9$-$C_{21}$ alkylene. In aspects, the spacer is an unsubstituted linear $C_9$-$C_{15}$ alkylene. In aspects, the spacer is an unsubstituted linear $C_9$-$C_{15}$ alkylene. In aspects, the spacer is an unsubstituted linear $C_{12}$-$C_{15}$ alkylene. In aspects, the spacer is an unsubstituted linear $C_{12}$ alkylene. In aspects, the spacer is an unsubstituted linear $C_{13}$ alkylene. In aspects, the spacer is an unsubstituted linear $C_{14}$ alkylene. In aspects, the spacer is an unsubstituted linear $C_{15}$ alkylene. A STAT3-binding nucleic acid (e.g. DNA) sequence or STAT-binding nucleic acid (e.g. DNA) sequence is a nucleic acid (e.g. DNA) including phosphodiester linkages, phosphodiester derivative linkages, and/or nucleic acid analogs, capable of binding STAT3 or a STAT transcription factor respectively. In aspects, the spacer is a substituted 2 to 40 membered heteroalkylene. In aspects, the spacer is a substituted 10 to 50 membered heteroalkylene. In aspects, the spacer is a substituted 20 to 40 membered heteroalkylene. In aspects, the spacer is a substituted 25 to 40 membered heteroalkylene. In aspects, the spacer is a substituted 30 to 40 membered heteroalkylene. In aspects, the spacer is a substituted liner 2 to 40 membered heteroalkylene. In aspects, the spacer is a substituted liner 10 to 50 membered heteroalkylene. In aspects, the spacer is a substituted liner 20 to 40 membered heteroalkylene. In aspects, the spacer is a substituted liner 25 to 40 membered heteroalkylene. In aspects, the spacer is a substituted liner 30 to 40 membered heteroalkylene.

In embodiments, the STAT-binding nucleic acid substituent (e.g. STAT1-, STAT2-, STAT3-, STAT4-, STAT5A-, STAT5B—, or STAT6-binding nucleic acid substituent) preferentially binds phosphorylated STAT (e.g. STAT1, STAT2, STAT3, STAT4, STAT5A, STAT5B, or STAT6) over unphosphorylated STAT (e.g. STAT1, STAT2, STAT3, STAT4, STAT5A, STAT5B, or STAT6). In aspects, the first STAT-binding nucleic acid sequence (e.g. STAT1-, STAT2-, STAT3-, STAT4-, STAT5A-, STAT5B—, or STAT6-binding nucleic acid sequence) and second STAT-binding nucleic acid sequence (e.g. STAT1-, STAT2-, STAT3-, STAT4-, STAT5A-, STAT5B—, or STAT6-binding nucleic acid sequence) form a double-stranded STAT-binding nucleic acid sequence (e.g. STAT1-, STAT2-, STAT3-, STAT4-, STAT5A-, STAT5B—, or STAT6-binding nucleic acid sequence). In aspects, the STAT-binding nucleic acid substituent (e.g. STAT1-, STAT2-, STAT3-, STAT4-, STAT5A-, STAT5B—, or STAT6-binding nucleic acid substituent) includes a STAT-binding nucleic acid sequence (e.g. STAT1-, STAT2-, STAT3-, STAT4-, STAT5A-, STAT5B—, or STAT6-binding nucleic acid sequence) covalently bonded to a terminal moiety. In aspects, the STAT-binding nucleic acid substituent (e.g. STAT1-, STAT2-, STAT3-, STAT4-, STAT5A-, STAT5B—, or STAT6-binding nucleic acid substituent) binds phosphorylated STAT (e.g. STAT1, STAT2, STAT3, STAT4, STAT5A, STAT5B, or STAT6). In aspects, the STAT3-binding nucleic acid substituent binds STAT3 phosphorylated on tyrosine 705. In aspects, the STAT-binding nucleic acid substituent (e.g. STAT1-, STAT2-, STAT3-, STAT4-, STAT5A-, STAT5B—, or STAT6-binding nucleic acid substituent) binds a STAT transcription factor (e.g. STAT1, STAT2, STAT3, STAT4, STAT5A, STAT5B, or STAT6) phosphorylated on STAT1 Y701, STAT2, Y690, STAT3 Y705, STAT4 Y693, STAT5A Y694, STAT5B Y694, STAT6 Y641, or a residue corresponding to one of those residues. In aspects, the STAT-binding nucleic acid substituent (e.g. STAT1-, STAT2-, STAT3-, STAT4-, STAT5A-, STAT5B—, or STAT6-binding nucleic acid substituent) binds human STAT (e.g. STAT1, STAT2, STAT3, STAT4, STAT5A, STAT5B, or STAT6). In aspects, the STAT-binding nucleic acid substituent (e.g. STAT1-, STAT2-, STAT3-, STAT4-, STAT5A-, STAT5B—, or STAT6-binding nucleic acid substituent) binds STAT (e.g. STAT1, STAT2, STAT3, STAT4, STAT5A, STAT5B, STAT6, or combinations thereof) dimers. In aspects, the STAT-binding nucleic acid substituent (e.g. STAT1-, STAT2-, STAT3-, STAT4-, STAT5A-, STAT5B—, or STAT6-binding nucleic acid substituent) binds dimers of phosphorylated STAT (e.g. STAT1, STAT2, STAT3, STAT4, STAT5A, STAT5B, STAT6, or combinations thereof) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues). In aspects, the STAT-binding nucleic acid substituent (e.g. STAT1-, STAT2-, STAT3-, STAT4-, STAT5A-, STAT5B—, or STAT6-binding nucleic acid substituent) binds activated STAT (e.g. STAT1, STAT2, STAT3, STAT4, STAT5A, STAT5B, or STAT6). In aspects, the STAT-binding nucleic acid substituent (e.g. STAT1-, STAT2-, STAT3-, STAT4-, STAT5A-, STAT5B—, or STAT6-binding nucleic acid substituent) includes the nucleic acid sequence recognized by a STAT transcription factor (e.g. apo-STAT (e.g. STAT1, STAT2, STAT3, STAT4, STAT5A, STAT5B, or STAT6), activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In aspects, the STAT-binding nucleic acid substituent (e.g. STAT1-, STAT2-, STAT3-, STAT4-, STAT5A-, STAT5B—, or STAT6-binding nucleic acid substituent) includes the nucleic acid sequence contacted by a STAT transcription factor (e.g. STAT1, STAT2, STAT3, STAT4, STAT5A, STAT5B, or STAT6) that is associated with STAT (e.g. STAT1, STAT2, STAT3, STAT4, STAT5A, STAT5B, or STAT6) transcriptional activation activity). In aspects, the STAT-binding nucleic acid substituent (e.g. STAT1-, STAT2-, STAT3-, STAT4-, STAT5A-, STAT5B—, or STAT6-binding nucleic acid substituent) includes a STAT-binding derivative of the nucleic acid sequence recognized by a STAT transcription factor (e.g. apo-STAT3, activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In aspects, the STAT-binding nucleic acid substituent (e.g. STAT1-, STAT2-, STAT3-, STAT4-, STAT5A-, STAT5B—, or STAT6-binding nucleic acid substituent) includes a STAT-binding derivative of the nucleic acid sequence contacted by a STAT transcription factor and associated with STAT (e.g. STAT1, STAT2, STAT3, STAT4, STAT5A, STAT5B, or STAT6) transcriptional activation activity). In aspects, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotide substitutions (e.g. A, C, G, or T substituted with a different nucleotide). In aspects, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) internucleotide linkage replacements (e.g. phosphodiester replaced with a phosphodiester derivative or a phosphodiester derivative replaced with a phosphodiester). In aspects, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) nucleotide deletions. In aspects, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide additions.

In embodiments, the spacer between a first nucleic acid and a second nucleic acid includes a first single DNA strand connected to the first STAT3-binding DNA sequence and a second single DNA strand connected to the second STAT3-binding DNA sequence, wherein the first DNA strand includes a DNA sequence that is complementary to a DNA sequence included in the second single DNA strand (both single DNA strands including their respective complementary sequences being collectively a "hybridized DNA overhang." In aspects, the spacer includes a first single DNA strand connected to the first STAT-binding DNA sequence (e.g. STAT1-, STAT2-, STAT3-, STAT4-, STAT5A-, STAT5B—, or STAT6-binding DNA sequence) and a second single DNA strand connected to the STAT-binding DNA sequence (e.g. STAT1-, STAT2-, STAT3-, STAT4-, STAT5A-, STAT5B—, or STAT6-binding DNA sequence), wherein the first DNA strand includes a DNA sequence that is complementary to a DNA sequence included in the second single DNA strand (both single DNA strands including their respective complementary sequences being collectively a "hybridized DNA overhang." In aspects, the hybridized DNA overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In aspects, the complementary DNA sequence in the hybridized DNA overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. A STAT3-binding DNA sequence or STAT-binding DNA sequence is a DNA including phosphodiester linkages, phosphodiester derivative linkages, and/or nucleic acid analogs, capable of binding STAT3 or a STAT transcription factor respectively.

In embodiments, the STAT-binding DNA substituent (e.g. STAT1-, STAT2-, STAT3-, STAT4-, STAT5A-, STAT5B—, or STAT6-binding DNA substituent) preferentially binds phosphorylated STAT (e.g. STAT1, STAT2, STAT3, STAT4, STAT5A, STAT5B, or STAT6) over unphosphorylated STAT (e.g. STAT1, STAT2, STAT3, STAT4, STAT5A, STAT5B, or STAT6). In aspects, the first STAT-binding DNA sequence (e.g. STAT1-, STAT2-, STAT3-, STAT4-, STAT5A-, STAT5B—, or STAT6-binding DNA sequence) and second STAT-binding DNA sequence (e.g. STAT1-, STAT2-, STAT3-, STAT4-, STAT5A-, STAT5B—, or STAT6-binding DNA sequence) form a double-stranded STAT-binding DNA sequence (e.g. STAT1-, STAT2-, STAT3-, STAT4-, STAT5A-, STAT5B—, or STAT6-binding DNA sequence). In aspects, the STAT-binding DNA substituent (e.g. STAT1-, STAT2-, STAT3-, STAT4-, STAT5A-, STAT5B—, or STAT6-binding DNA substituent) includes a STAT-binding DNA sequence (e.g. STAT1-, STAT2-, STAT3-, STAT4-, STAT5A-, STAT5B—, or STAT6-binding DNA sequence) covalently bonded to a terminal moiety. In aspects, the STAT-binding DNA substituent (e.g. STAT1-, STAT2-, STAT3-, STAT4-, STAT5A-, STAT5B—, or STAT6-binding DNA substituent) binds phosphorylated STAT (e.g. STAT1, STAT2, STAT3, STAT4, STAT5A, STAT5B, or STAT6). In aspects, the STAT3-binding DNA substituent binds STAT3 phosphorylated on tyrosine 705. In aspects, the STAT-binding DNA substituent (e.g. STAT1-, STAT2-, STAT3-, STAT4-, STAT5A-, STAT5B—, or STAT6-binding DNA substituent) binds a STAT transcription factor (e.g. STAT1, STAT2, STAT3, STAT4, STAT5A, STAT5B, or STAT6) phosphorylated on STAT1 Y701, STAT2, Y690, STAT3 Y705, STAT4 Y693, STAT5A Y694, STAT5B Y694, STAT6 Y641, or a residue corresponding to one of those residues. In aspects, the STAT-binding DNA substituent (e.g. STAT1-, STAT2-, STAT3-, STAT4-, STAT5A-, STAT5B—, or STAT6-binding DNA substituent) binds human STAT (e.g. STAT1, STAT2, STAT3, STAT4, STAT5A, STAT5B, or STAT6). In aspects, the STAT-binding DNA substituent (e.g. STAT1-, STAT2-, STAT3-, STAT4-, STAT5A-, STAT5B—, or STAT6-binding DNA substituent) binds STAT (e.g. STAT1, STAT2, STAT3, STAT4, STAT5A, STAT5B, STAT6, or combinations thereof) dimers. In aspects, the STAT-binding DNA substituent (e.g. STAT1-, STAT2-, STAT3-, STAT4-, STAT5A-, STAT5B—, or STAT6-binding DNA substituent) binds dimers of phosphorylated STAT (e.g. STAT1, STAT2, STAT3, STAT4, STAT5A, STAT5B, STAT6, or combinations thereof) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues). In aspects, the STAT-binding DNA substituent (e.g. STAT1-, STAT2-, STAT3-, STAT4-, STAT5A-, STAT5B—, or STAT6-binding DNA substituent) binds activated STAT (e.g. STAT1, STAT2, STAT3, STAT4, STAT5A, STAT5B, or STAT6). In aspects, the STAT-binding DNA substituent (e.g. STAT1-, STAT2-, STAT3-, STAT4-, STAT5A-, STAT5B—, or STAT6-binding DNA substituent) includes the DNA sequence recognized by a STAT transcription factor (e.g. apo-STAT (e.g. STAT1, STAT2, STAT3, STAT4, STAT5A, STAT5B, or STAT6), activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In aspects, the STAT-binding DNA substituent (e.g. STAT1-, STAT2-, STAT3-, STAT4-, STAT5A-, STAT5B—, or STAT6-binding DNA substituent) includes the DNA sequence contacted by a STAT transcription factor associated with STAT (e.g. STAT1, STAT2, STAT3, STAT4, STAT5A, STAT5B, or STAT6) transcriptional activation activity). In aspects, the STAT-binding DNA substituent (e.g. STAT1-, STAT2-, STAT3-, STAT4-, STAT5A-, STAT5B—, or STAT6-binding DNA substituent) includes a STAT-binding derivative of the DNA sequence recognized by a STAT transcription factor (e.g. apo-STAT (e.g. STAT1, STAT2, STAT3, STAT4, STAT5A, STAT5B, or STAT6), activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In aspects, the STAT-binding DNA substituent (e.g. STAT1-, STAT2-, STAT3-, STAT4-, STAT5A-, STAT5B—, or STAT6-binding DNA substituent) includes a STAT-binding derivative of the DNA sequence contacted by a STAT transcription factor (e.g. STAT1, STAT2, STAT3, STAT4, STAT5A, STAT5B, or STAT6) associated with STAT (e.g. STAT1, STAT2, STAT3, STAT4, STAT5A, STAT5B, or STAT6) transcriptional activation activity). In aspects, the STAT-binding derivative (e.g. STAT1-, STAT2-, STAT3-, STAT4-, STAT5A-, STAT5B—, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotide substitutions (e.g. A, C, G, or T substituted with a different nucleotide). In aspects, the STAT-binding derivative (e.g. STAT1-, STAT2-, STAT3-, STAT4-, STAT5A-, STAT5B—, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) internucleotide linkage replacements (e.g. phosphodiester replaced with a phosphodiester derivative or a phosphodiester derivative replaced with a phosphodiester). In aspects, the STAT-binding derivative (e.g. STAT1-, STAT2-, STAT3-, STAT4-, STAT5A-, STAT5B—, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) nucleotide deletions. In aspects, the STAT-binding derivative (e.g. STAT1-, STAT2-, STAT3-, STAT4-, STAT5A-, STAT5B—, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide additions.

A terminal moiety is hydrogen, nucleic acid sequence, DNA sequence, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In aspects, a terminal moiety is a chemically reactive moiety, detectable moiety, therapeutic moiety (e.g. anti-cancer agent or anti-viral agent), nucleic acid sequence, DNA sequence, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In aspects, a terminal moiety is a detectable moiety. In aspects, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In aspects, a terminal moiety is a therapeutic moiety (e.g. anti-cancer agent or anti-viral agent).

In embodiments, the terminal moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In aspects, the terminal moiety is a substituted or unsubstituted $C_1$-$C_{40}$ alkyl, substituted or unsubstituted 2 to 40 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In aspects, the terminal moiety is a substituted $C_1$-$C_{40}$ alkyl, substituted 2 to 40 membered heteroalkyl, substituted $C_3$-$C_8$ cycloalkyl, substituted 3 to 8 membered heterocycloalkyl, substituted $C_6$-$C_{10}$ aryl, or substituted 5 to 10 membered heteroaryl.

In embodiments, the compound includes a linker between the TLR-binding nucleic acid (e.g. endosomal TLR-, TLR3-, TLR7-, TLR8-, or TLR9-binding nucleic acid) substituent and the STAT-binding nucleic acid substituent (e.g. STAT1-, STAT2-, STAT3-, STAT4-, STAT5A-, STAT5B—, or STAT6-binding nucleic acid substituent). In aspects, the compound includes a linker between the TLR9-binding DNA substituent and the STAT3-binding nucleic acid substituent. In aspects, the compound includes a linker between the TLR9-binding nucleic acid substituent and the STAT-binding DNA substituent (e.g. STAT1-, STAT2-, STAT3-, STAT4-, STAT5A-, STAT5B—, or STAT6-binding DNA substituent). In aspects, the STAT-binding nucleic acid substituent is a STAT1-binding nucleic acid substituent. In aspects, the STAT-binding nucleic acid substituent is a STAT2-binding nucleic acid substituent. In aspects, the STAT-binding nucleic acid substituent is a STAT3-binding nucleic acid substituent. In aspects, the STAT-binding nucleic acid substituent is a STAT4-binding nucleic acid substituent. In aspects, the STAT-binding nucleic acid substituent is a STAT5A-binding nucleic acid substituent. In aspects, the STAT-binding nucleic acid substituent is a STAT5B-binding nucleic acid substituent. In aspects, the STAT-binding nucleic acid substituent is a STAT6-binding nucleic acid substituent.

In embodiments, the compound includes a linker between the TLR-binding nucleic acid (e.g. endosomal TLR-, TLR3-, TLR7-, TLR8-, or TLR9-binding nucleic acid) substituent and the STAT-binding DNA substituent (e.g. STAT1-, STAT2-, STAT3-, STAT4-, STAT5A-, STAT5B—, or STAT6-binding DNA substituent). In aspects, the compound includes a linker between the TLR9-binding DNA substituent and the STAT3-binding DNA substituent. In aspects, the compound includes a linker between the TLR9-binding DNA substituent and the STAT-binding DNA substituent (e.g. STAT1-, STAT2-, STAT3-, STAT4-, STAT5A-, STAT5B—, or STAT6-binding DNA substituent). In aspects, the STAT-binding DNA substituent is a STAT1-binding DNA substituent. In aspects, the STAT-binding DNA substituent is a STAT2-binding DNA substituent. In aspects, the STAT-binding DNA substituent is a STAT3-binding DNA substituent. In aspects, the STAT-binding DNA substituent is a STAT4-binding DNA substituent. In aspects, the STAT-binding DNA substituent is a STAT5A-binding DNA substituent. In aspects, the STAT-binding DNA substituent is a STAT5B-binding DNA substituent. In aspects, the STAT-binding DNA substituent is a STAT6-binding DNA substituent.

A linker is a bond, nucleic acid sequence, two nucleic acid sequences, DNA sequence, two DNA sequences, nucleic acid analog sequence, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In aspects, the linker is a substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In aspects, the linker is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In aspects, the linker is an unsubstituted $C_1$-$C_{20}$ alkylene. In aspects, the linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In aspects, the linker is a substituted or unsubstituted $C_1$-$C_{40}$ alkylene. In aspects, the linker is a substituted or unsubstituted 2 to 40 membered heteroalkylene. In aspects, the linker is a substituted 2 to 40 membered heteroalkylene. In aspects, the linker includes alkyl phosphates (e.g., propyl phosphates). In aspects, the linker consists of alkyl phosphates (e.g., propyl phosphates) bonded to the reminder of the compound by phosphates at both ends. In aspects, the linker consists of 1-6 alkyl phosphates (e.g., propyl phosphates) bonded to the remainder of the compound by phosphates on both ends. In aspects, the linker consists of 4-6 alkyl phosphates (e.g., propyl phosphates) bonded to the remainder of the compound by phosphates on both ends. In aspects, the linker consists of 5 alkyl phosphates (e.g., propyl phosphates) bonded to the remainder of the compound by phosphates on both ends. A person having ordinary skill in the art will recognize that a linker consisting of alkyl phosphates that is bonded to the remainder of the compound by phosphates on both ends will have one more phosphate than alkylene groups (e.g., a linker consisting of 4 alkyl phosphates that is bonded to the reminder of the compound by phosphates at both ends will have five phosphates and four alkyl groups with alternating phosphate groups and alkyl groups).

In embodiments, the linker includes a first single nucleic acid strand connected to the TLR9-binding nucleic acid substituent and a second single nucleic acid strand connected to the STAT-binding nucleic acid substituent (e.g. STAT1-, STAT2-, STAT3-, STAT4-, STAT5A-, STAT5B—, or STAT6-binding nucleic acid substituent), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In aspects, the linker includes a first single nucleic acid strand connected to the TLR-binding nucleic acid (e.g. endosomal TLR-, TLR3-, TLR7-, TLR8-, or TLR9-binding nucleic acid) substituent and a second single nucleic acid strand connected to the STAT-binding nucleic acid substituent (e.g. STAT1-, STAT2-, STAT3-, STAT4-, STAT5A-, STAT5B—, or STAT6-binding nucleic acid substituent), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In aspects, the linker includes a first single nucleic acid strand connected to the TLR9-binding nucleic acid substituent and a second single nucleic acid strand connected to the STAT3-binding nucleic acid substituent, wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In aspects, the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In aspects, the complementary nucleic acid sequence in the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In aspects, the first and second single nucleic acid strands in the hybridized nucleic acid overhang are complementary throughout their entire lengths. In aspects, the linker is an unsubstituted $C_1$-$C_{20}$ alkylene. In aspects, the linker is an unsubstituted linear $C_1$-$C_{20}$ alkylene. In aspects, the linker is an unsubstituted $C_3$-$C_{21}$ alkylene. In aspects, the linker is an unsubstituted $C_3$-$C_{15}$ alkylene. In aspects, the linker is an unsubstituted linear $C_3$-$C_{15}$ alkylene. In aspects, the linker is an unsubstituted linear $C_6$-$C_{21}$ alkylene. In aspects, the linker is an unsubstituted linear $C_9$-$C_{21}$ alkylene. In aspects, the linker is an unsubstituted linear $C_9$-$C_{15}$ alkylene. In aspects, the linker is an unsubstituted linear $C_9$-$C_{15}$ alkylene. In aspects, the linker is an unsubstituted linear $C_{12}$-$C_{15}$ alkylene. In aspects, the linker is an unsubstituted linear $C_{12}$ alkylene. In aspects, the linker is an unsubstituted linear $C_{13}$ alkylene. In aspects, the linker is an unsubstituted linear $C_{14}$ alkylene. In aspects, the linker is an unsubstituted linear $C_{15}$ alkylene. In aspects, the linker is a substituted 2 to 40 membered heteroalkylene. In aspects, the linker is a substituted 10 to 50 membered heteroalkylene. In aspects, the linker is a substituted 20 to 40 membered heteroalkylene. In aspects, the linker is a substituted 25 to 40 membered heteroalkylene. In aspects, the linker is a substituted 30 to 40 membered heteroalkylene. In aspects, the linker is a substituted liner 2 to 40 membered heteroalkylene. In aspects, the linker is a substituted liner 10 to 50 membered heteroalkylene. In aspects, the linker is a substituted liner 20 to 40 membered heteroalkylene. In aspects, the linker is a substituted liner 25 to 40 membered heteroalkylene. In aspects, the linker is a substituted liner 30 to 40 membered heteroalkylene.

In embodiments, the linker includes a first single DNA strand connected to the TLR9-binding DNA substituent and a second single DNA strand connected to the STAT-binding DNA substituent (e.g. STAT1-, STAT2-, STAT3-, STAT4-, STAT5A-, STAT5B—, or STAT6-binding DNA substituent), wherein the first DNA strand includes a DNA sequence that is complementary to a DNA sequence included in the second single DNA strand (both single DNA strands including their respective complementary sequences being collectively a "hybridized DNA overhang." In aspects, the linker includes a first single DNA strand connected to the TLR-binding nucleic acid (e.g. endosomal TLR-, TLR3-, TLR7-, TLR8-, or TLR9-binding nucleic acid) substituent and a second single DNA strand connected to the STAT-binding DNA substituent (e.g. STAT1-, STAT2-, STAT3-, STAT4-, STAT5A-, STAT5B—, or STAT6-binding DNA substituent), wherein the first DNA strand includes a DNA sequence that is complementary to a DNA sequence included in the second single DNA strand (both single DNA strands including their respective complementary sequences being collectively a "hybridized DNA overhang." In aspects, the linker includes a first single DNA strand connected to the TLR9-binding DNA substituent and a second single DNA strand connected to the STAT3-binding DNA substituent, wherein the first DNA strand includes a DNA sequence that is complementary to a DNA sequence included in the second single DNA strand (both single DNA strands including their respective complementary sequences being collectively a "hybridized DNA overhang." In aspects, the hybridized DNA overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In aspects, the complementary DNA sequence in the hybridized DNA overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In aspects, the first and second single DNA strands in the hybridized DNA overhang are complementary throughout their entire lengths.

In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In aspects, the compound includes a plurality of phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof). In aspects, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the second nucleic acid sequence (e.g., TLR9-binding DNA substituent). In aspects, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the first nucleic acid sequence (e.g., STAT3-binding nucleic acid substituent). In aspects, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)). In aspects, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT3-binding DNA substituent. In aspects, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)).

In embodiments, the compound includes a phosphorothioate linkage. In aspects, the compound includes a plurality of phosphorothioate linkages. In aspects, the compound includes a phosphorothioate linkage in the second nucleic acid sequence (e.g., TLR9-binding DNA substituent). In aspects, the compound includes a phosphorothioate linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphorothioate linkage in the first nucleic acid sequence (e.g., STAT3-binding nucleic acid substituent). In aspects, the compound includes a phosphorothioate linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphorothioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorothioate linkages). In aspects, the compound includes a phosphorothioate linkage in the STAT3-binding DNA substituent. In aspects, the compound includes a phosphorothioate linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphorothioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorothioate linkages).

In embodiments, the compound includes a phosphoramidate linkage. In aspects, the compound includes a plurality of phosphoramidate linkages. In aspects, the compound includes a phosphoramidate linkage in the second nucleic acid sequence (e.g., TLR9-binding DNA substituent). In aspects, the compound includes a phosphoramidate linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphoramidate linkage in the first nucleic acid sequence (e.g., STAT3-binding nucleic acid substituent). In aspects, the compound includes a phosphoramidate linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphoramidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphoramidate linkages). In aspects, the compound includes a phosphoramidate linkage in the STAT3-binding DNA substituent. In aspects, the compound includes a phosphoramidate linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphoramidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphoramidate linkages).

In embodiments, the compound includes a phosphorodiamidate linkage. In aspects, the compound includes a plurality of phosphorodiamidate linkages. In aspects, the compound includes a phosphorodiamidate linkage in the second nucleic acid sequence (e.g., TLR9-binding DNA substituent). In aspects, the compound includes a phosphorodiamidate linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphorodiamidate linkage in the first nucleic acid sequence (e.g., STAT3-binding nucleic acid substituent). In aspects, the compound includes a phosphorodiamidate linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphorodiamidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodiamidate linkages). In aspects, the compound includes a phosphorodiamidate linkage in the STAT3-binding DNA substituent. In aspects, the compound includes a phosphorodiamidate linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphorodiamidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodiamidate linkages).

In embodiments, the compound includes a phosphorodithioate linkage. In aspects, the compound includes a plurality of phosphorodithioate linkages. In aspects, the compound includes a phosphorodithioate linkage in the second nucleic acid sequence (e.g., TLR9-binding DNA substituent). In aspects, the compound includes a phosphorodithioate linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphorodithioate linkage in the first nucleic acid sequence (e.g., STAT3-binding nucleic acid substituent). In aspects, the compound includes a phosphorodithioate linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphorodithioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodithioate linkages). In aspects, the compound includes a phosphorodithioate linkage in the STAT3-binding DNA substituent. In aspects, the compound includes a phosphorodithioate linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphorodithioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodithioate linkages).

In embodiments, the compound includes a phosphonocarboxylic acid linkage. In aspects, the compound includes a plurality of phosphonocarboxylic acid linkages. In aspects, the compound includes a phosphonocarboxylic acid linkage in the second nucleic acid sequence (e.g., TLR9-binding DNA substituent). In aspects, the compound includes a phosphonocarboxylic acid linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphonocarboxylic acid linkage in the first nucleic acid sequence (e.g., STAT3-binding nucleic acid substituent). In aspects, the compound includes a phosphonocarboxylic acid linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphonocarboxylic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylic acid linkages). In aspects, the compound includes a phosphonocarboxylic acid linkage in the STAT3-binding DNA substituent. In aspects, the compound includes a phosphonocarboxylic acid linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphonocarboxylic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylic acid linkages).

In embodiments, the compound includes a phosphonocarboxylate linkage. In aspects, the compound includes a plurality of phosphonocarboxylate linkages. In aspects, the compound includes a phosphonocarboxylate linkage in the second nucleic acid sequence (e.g., TLR9-binding DNA substituent). In aspects, the compound includes a phosphonocarboxylate linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphonocarboxylate linkage in the first nucleic acid sequence (e.g., STAT3-binding nucleic acid substituent). In aspects, the compound includes a phosphonocarboxylate linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphonocarboxylate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylate linkages). In aspects, the compound includes a phosphonocarboxylate linkage in the STAT3-binding DNA substituent. In aspects, the compound includes a phosphonocarboxylate linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphonocarboxylate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylate linkages).

In embodiments, the compound includes a phosphonoacetic acid linkage. In aspects, the compound includes a plurality of phosphonoacetic acid linkages. In aspects, the compound includes a phosphonoacetic acid linkage in the second nucleic acid sequence (e.g., TLR9-binding DNA substituent). In aspects, the compound includes a phosphonoacetic acid linkage in the second nucleic acid sequence (e.g., TLR-binding nucleic acid) (e.g. endosomal TLR-, TLR3-TLR7-, TLR8-, or TLR9-binding nucleic acid) substituent. In aspects, the compound includes a phosphonoacetic acid linkage in the first nucleic acid sequence (e.g., STAT3-binding nucleic acid substituent). In aspects, the compound includes a phosphonoacetic acid linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphonoacetic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoacetic acid linkages). In aspects, the compound includes a phosphonoacetic acid linkage in the STAT3-binding DNA substituent. In aspects, the compound includes a phosphonoacetic acid linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphonoacetic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoacetic acid linkages).

In embodiments, the compound includes a phosphonoformic acid linkage. In aspects, the compound includes a plurality of phosphonoformic acid linkages. In aspects, the compound includes a phosphonoformic acid linkage in the second nucleic acid sequence (e.g., TLR9-binding DNA substituent). In aspects, the compound includes a phosphonoformic acid linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a phosphonoformic acid linkage in the first nucleic acid sequence (e.g., STAT3-binding nucleic acid substituent). In aspects, the compound includes a phosphonoformic acid linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a phosphonoformic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoformic acid linkages). In aspects, the compound includes a phosphonoformic acid linkage in the STAT3-binding DNA substituent. In aspects, the compound includes a phosphonoformic acid linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a phosphonoformic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoformic acid linkages).

In embodiments, the compound includes a methyl phosphonate linkage. In aspects, the compound includes a plurality of methyl phosphonate linkages. In aspects, the compound includes a methyl phosphonate linkage in the second nucleic acid sequence (e.g., TLR9-binding DNA substituent). In aspects, the compound includes a methyl phosphonate linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a methyl phosphonate linkage in the first nucleic acid sequence (e.g., STAT3-binding nucleic acid substituent). In aspects, the compound includes a methyl phosphonate linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a methyl phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are methyl phosphonate linkages). In aspects, the compound includes a methyl phosphonate linkage in the STAT3-binding DNA substituent. In aspects, the compound includes a methyl phosphonate linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a methyl phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are methyl phosphonate linkages).

In embodiments, the compound includes a boron phosphonate linkage. In aspects, the compound includes a plurality of boron phosphonate linkages. In aspects, the compound includes a boron phosphonate linkage in the second nucleic acid sequence (e.g., TLR9-binding DNA substituent). In aspects, the compound includes a boron phosphonate linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes a boron phosphonate linkage in the first nucleic acid sequence (e.g., STAT3-binding nucleic acid substituent). In aspects, the compound includes a boron phosphonate linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a boron phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are boron phosphonate linkages). In aspects, the compound includes a boron phosphonate linkage in the STAT3-binding DNA substituent. In aspects, the compound includes a boron phosphonate linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a boron phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are boron phosphonate linkages).

In embodiments, the compound includes an O-methylphosphoroamidite linkage. In aspects, the compound includes a plurality of O-methylphosphoroamidite linkages. In aspects, the compound includes an O-methylphosphoroamidite linkage in the second nucleic acid sequence (e.g., TLR9-binding DNA substituent). In aspects, the compound includes an O-methylphosphoroamidite linkage in the second nucleic acid sequence (e.g., TLR-binding nucleic acid) (e.g. endosomal TLR-, TLR3-, TLR7-, TLR8-, or TLR9-binding nucleic acid) substituent. In aspects, the compound includes an O-methylphosphoroamidite linkage in the first nucleic acid sequence (e.g., STAT3-binding nucleic acid substituent). In aspects, the compound includes an O-methylphosphoroamidite linkage in the first nucleic acid sequence (e.g., STAT-binding nucleic acid substituent, for example STAT1-, STAT2-, STAT3-, STAT4-, STAT5A-, STAT5B—, or STAT6-binding nucleic acid substituent). In aspects, one or more of the nucleic acid internucleotide linkages in the compound is a O-methylphosphoroamidite linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are O-methylphosphoroamidite linkages). In aspects, the compound includes an O-methylphosphoroamidite linkage in the STAT3-binding DNA substituent. In aspects, the compound includes an O-methylphosphoroamidite linkage in the STAT-binding DNA substituent (e.g. STAT1-, STAT2-, STAT3-, STAT4-, STAT5A-, STAT5B—, or STAT6-binding DNA substituent). In aspects, one or more of the DNA internucleotide linkages in the compound is a O-methylphosphoroamidite linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are O-methylphosphoroamidite linkages).

In embodiments, the linker or the spacer is:

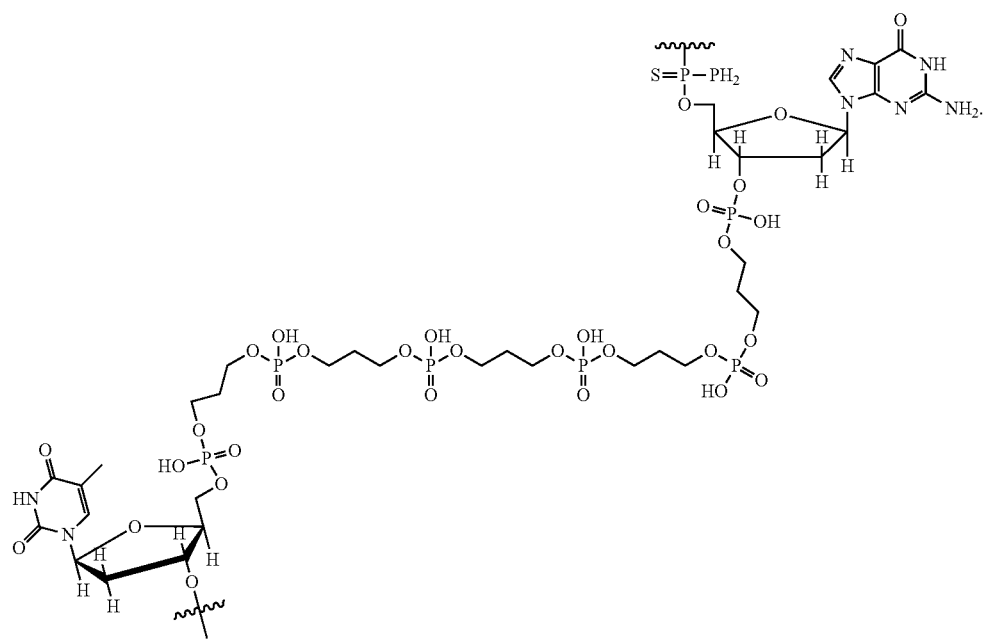

In embodiments, the linker or the spacer is:

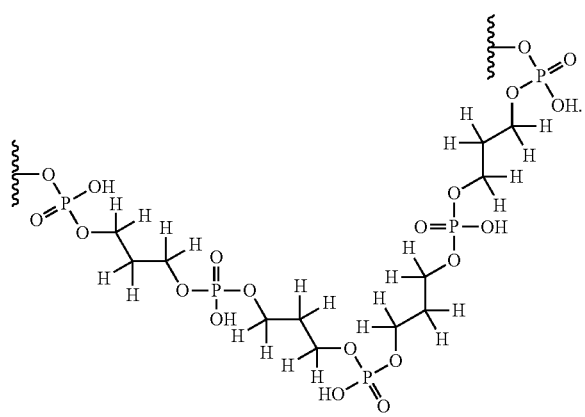 [SMILES: *OP(=O)(O)OCCCOP(=O)(O)OCCCOP(=O)(O)OCCCOP(=O)(O)OCCCOP(=O)(O)O*]

In embodiments, the linker or the spacer is:

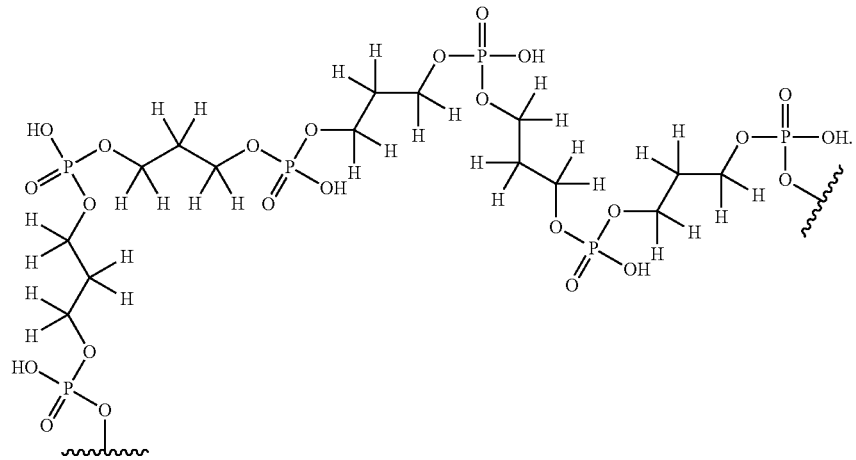 [SMILES: *OP(=O)(O)OCCCOP(=O)(O)OCCCOP(=O)(O)OCCCOP(=O)(O)OCCCOP(=O)(O)OCCCOP(=O)(O)O*]

In embodiments, the spacer is substituted with a ubiquitin ligase binding compound. In embodiments, the ubiquitin ligase protein is von Hippel-Lindau tumor suppressor, Cereblon, Mouse Double Minute 2 homologue, or Cellular Inhibitor of Apoptosis. In aspects, the ubiquitin ligase protein is von Hippel-Lindau tumor suppressor. In aspects, the ubiquitin ligase protein is Cereblon. In aspects, the ubiquitin ligase protein is Mouse Double Minute 2 homologue. In aspects, the ubiquitin ligase protein is a Cellular Inhibitor of Apoptosis.

In embodiments, the compound further includes a phosphorothioate linkage in the first nucleic acid sequence and/or the second nucleic acid sequence. In aspects, the compound further includes a plurality of phosphorothioate linkages (e.g., a plurality of phosphorothioate linkages in the first nucleic acid sequence and/or a plurality of phosphorothioate linkages in the second nucleic acid sequence). In aspects, the compound further includes a phosphorothioate linkage in the first nucleic acid sequence. In aspects, the compound further a phosphorothioate linkage in the second nucleic acid sequence.

In embodiments, the ubiquitin ligase binding compound is covalently bonded to the first nucleic acid and/or the second nucleic acid through a linker having the formula:

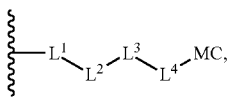

wherein, MC is the ubiquitin ligase binding compound; and $L^1, L^2, L^3$, and $L^4$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In aspects, $L^1, L^2, L^3$, and $L^4$ are each independently a polyglycol (e.g., aliphatic polyether). In aspects, $L^1, L^2, L^3$, and $L^4$ each independently includes PEG. In aspects, $L^4$ comprises PEG. In aspects, the linker is bound to the 3'-end of the nucleic acid. In aspects, the linker is bound to the '5-end of the nucleic acid.

In embodiments, $L^1$, $L^2$, $L^3$, and $L^4$ are each independently substituted or unsubstituted polyglycol, substituted or unsubstituted $C_1$-$C_{16}$ alkylene, substituted or unsubstituted 2 to 16 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 6 to 20 membered heteroarylene.

In embodiments, $L^1$, $L^2$, $L^3$, and $L^4$ are each independently substituted or unsubstituted polyglycol, substituted or unsubstituted $C_1$-$C_{16}$ alkylene, substituted or unsubstituted 2 to 16 membered heteroalkylene, substituted or unsubstituted $C_3$-$C_{12}$ cycloalkylene, substituted or unsubstituted 3 to 20 membered heterocycloalkylene, substituted or unsubstituted $C_6$-$C_{12}$ arylene, or substituted or unsubstituted 6 to 12 membered heteroarylene. In aspects, $L^1$ is a bond. In aspects, $L^2$ is a bond. In aspects, $L^3$ is a bond. In aspects, $L^4$ is a bond.

In embodiments, $L^1$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^1$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene.

In embodiments, $L^1$ is unsubstituted alkylene, unsubstituted heteroalkylene, unsubstituted cycloalkylene, unsubstituted heterocycloalkylene, unsubstituted arylene, or unsubstituted heteroarylene.

In embodiments, $L^1$ is substituted (e.g., substituted with a substituent group, a size-limited substituent group, or lower substituent group) or unsubstituted alkylene. In aspects, $L^1$ is substituted (e.g., substituted with a substituent group, a size-limited substituent group, or lower substituent group) alkylene. In aspects, $L^1$ is unsubstituted alkylene. In aspects, $L^1$ is substituted or unsubstituted alkylene (e.g., $C_1$-$C_8$, $C_1$-$C_6$, $C_1$-$C_4$, or $C_1$-$C_2$). In aspects, $L^1$ is substituted alkylene (e.g., $C_1$-$C_8$, $C_1$-$C_6$, $C_1$-$C_4$, or $C_1$-$C_2$). In aspects, $L^1$ is unsubstituted alkylene (e.g., $C_1$-$C_8$, $C_1$-$C_6$, $C_1$-$C_4$, or $C_1$-$C_2$).

In embodiments, $L^1$ is substituted (e.g., substituted with a substituent group, a size-limited substituent group, or lower substituent group) or unsubstituted heteroalkylene. In aspects, $L^1$ is substituted (e.g., substituted with a substituent group, a size-limited substituent group, or lower substituent group) heteroalkylene. In aspects, $L^1$ is unsubstituted heteroalkylene. In aspects, $L^1$ is substituted or unsubstituted heteroalkylene (e.g., 2 to 8 membered, 2 to 6 membered, 4 to 6 membered, 2 to 3 membered, or 4 to 5 membered). In aspects, $L^1$ is substituted heteroalkylene (e.g., 2 to 8 membered, 2 to 6 membered, 4 to 6 membered, 2 to 3 membered, or 4 to 5 membered). In aspects, $L^1$ is an unsubstituted heteroalkylene (e.g., 2 to 8 membered, 2 to 6 membered, 4 to 6 membered, 2 to 3 membered, or 4 to 5 membered).

In embodiments, $L^1$ is substituted (e.g., substituted with a substituent group, a size-limited substituent group, or lower substituent group) or unsubstituted cycloalkylene. In aspects, $L^1$ is substituted (e.g., substituted with a substituent group, a size-limited substituent group, or lower substituent group) cycloalkylene. In aspects, $L^1$ is an unsubstituted cycloalkylene. In aspects, $L^1$ is substituted or unsubstituted cycloalkylene (e.g., $C_3$-$C_8$, $C_3$-$C_6$, $C_4$-$C_6$, or $C_5$-$C_6$). In aspects, $L^1$ is substituted cycloalkylene (e.g., $C_3$-$C_8$, $C_3$-$C_6$, $C_4$-$C_6$, or $C_5$-$C_6$). In aspects, $L^1$ is unsubstituted cycloalkylene (e.g., $C_3$-$C_8$, $C_3$-$C_6$, $C_4$-$C_6$, or $C_5$-$C_6$).

In embodiments, $L^1$ is substituted (e.g., substituted with a substituent group, a size-limited substituent group, or lower substituent group) or unsubstituted heterocycloalkylene. In aspects, $L^1$ is substituted (e.g., substituted with a substituent group, a size-limited substituent group, or lower substituent group) heterocycloalkylene. In aspects, $L^1$ is an unsubstituted heterocycloalkylene. In aspects, $L^1$ is substituted or unsubstituted heterocycloalkylene (e.g., 3 to 8 membered, 3 to 6 membered, 4 to 6 membered, 4 to 5 membered, or 5 to 6 membered). In aspects, $L^1$ is substituted heterocycloalkylene (e.g., 3 to 8 membered, 3 to 6 membered, 4 to 6 membered, 4 to 5 membered, or 5 to 6 membered). In aspects, $L^1$ an unsubstituted heterocycloalkylene (e.g., 3 to 8 membered, 3 to 6 membered, 4 to 6 membered, 4 to 5 membered, or 5 to 6 membered).

In embodiments, $L^1$ is substituted (e.g., substituted with a substituent group, a size-limited substituent group, or lower substituent group) or unsubstituted arylene. In aspects, $L^1$ is substituted (e.g., substituted with a substituent group, a size-limited substituent group, or lower substituent group) arylene. In aspects, $L^1$ is an unsubstituted arylene. In aspects, $L^1$ is substituted or unsubstituted arylene (e.g., $C_6$-$C_{10}$ or phenylene). In aspects, $L^1$ is substituted arylene (e.g., $C_6$-$C_{10}$ or phenylene). In aspects, $L^1$ is an unsubstituted arylene (e.g., $C_6$-$C_{10}$ or phenylene).

In embodiments, $L^1$ is substituted (e.g., substituted with a substituent group, a size-limited substituent group, or lower substituent group) or unsubstituted heteroarylene. In aspects, $L^1$ is substituted (e.g., substituted with a substituent group, a size-limited substituent group, or lower substituent group) heteroarylene. In aspects, $L^1$ is an unsubstituted heteroarylene. In aspects, $L^1$ is substituted or unsubstituted heteroarylene (e.g., 5 to 10 membered, 5 to 9 membered, or 5 to 6 membered). In aspects, $L^1$ is substituted heteroarylene (e.g., 5 to 10 membered, 5 to 9 membered, or 5 to 6 membered). In aspects, $L^1$ is an unsubstituted heteroarylene (e.g., 5 to 10 membered, 5 to 9 membered, or 5 to 6 membered).

In embodiments, $L^1$ is substituted or unsubstituted alkylene (e.g., $C_1$-$C_{30}$, $C_1$-$C_{25}$, $C_{10}$-$C_{20}$, or $C_1$-$C_8$), substituted or unsubstituted heteroalkylene (e.g., 2 to 30 membered, 6 to 30 membered, 12 to 24 membered, 10 to 22 membered, or 18 to 22 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^1$ is substituted (e.g., substituted with a substituent group, a size-limited substituent group, or lower substituent group) or unsubstituted alkylene. In aspects, $L^1$ is substituted (e.g., substituted with a substituent group, a size-limited substituent group, or lower substituent group) alkylene. In aspects, $L^1$ is unsubstituted alkylene. In aspects, $L^1$ is substituted or unsubstituted alkylene (e.g., $C_1$-$C_{30}$, $C_1$-$C_{25}$, $C_{10}$-$C_{20}$, or $C_1$-$C_8$). In aspects, $L^1$ is substituted alkylene (e.g., $C_1$-$C_{30}$, $C_1$-$C_{25}$, $C_{10}$-$C_{20}$, or $C_1$-$C_8$). In aspects, $L^1$ is unsubstituted alkylene (e.g., $C_1$-$C_{30}$, $C_1$-$C_{25}$, $C_{10}$-$C_{20}$, or $C_1$-$C_8$).

In embodiments, $L^1$ is substituted (e.g., substituted with a substituent group, a size-limited substituent group, or lower substituent group) or unsubstituted heteroalkylene. In aspects, $L^1$ is substituted (e.g., substituted with a substituent group, a size-limited substituent group, or lower substituent group) heteroalkylene. In aspects, $L^1$ is unsubstituted heteroalkylene. In aspects, $L^1$ is substituted or unsubstituted heteroalkylene (e.g., 2 to 30 membered, 6 to 30 membered, 12 to 24 membered, 10 to 22 membered, or 18 to 22 membered). In aspects, $L^1$ is substituted heteroalkylene (e.g., 2 to 30 membered, 6 to 30 membered, 12 to 24 membered, 10 to 22 membered, or 18 to 22 membered). In aspects, $L^1$ is an unsubstituted heteroalkylene (e.g., 2 to 30 membered, 6 to 30 membered, 12 to 24 membered, 10 to 22 membered, or 18 to 22 membered).

In embodiments, $L^1$ is a substituted or unsubstituted 2 to 30 membered heteroalkylene. In aspects, $L^1$ is a substituted 2 to 30 membered heteroalkylene. In aspects, $L^1$ is an unsubstituted 2 to 30 membered heteroalkylene. In aspects, $L^1$ is a substituted or unsubstituted 2 to 25 membered heteroalkylene. In aspects, $L^1$ is a substituted 2 to 25 membered heteroalkylene. In aspects, $L^1$ is an unsubstituted 2 to 25 membered heteroalkylene. In aspects, $L^1$ is a substituted or unsubstituted 10 to 30 membered heteroalkylene. In aspects, $L^1$ is a substituted 10 to 30 membered heteroalkylene. In aspects, $L^1$ is an unsubstituted 10 to 30 membered heteroalkylene. In aspects, $L^1$ is a substituted or unsubstituted 15 to 30 membered heteroalkylene. In aspects, $L^1$ is a substituted 15 to 30 membered heteroalkylene. In aspects, $L^1$ is an unsubstituted 15 to 30 membered heteroalkylene. In aspects, $L^1$ is a substituted or unsubstituted 15 to 25 membered heteroalkylene. In aspects, $L^1$ is a substituted 15 to 25 membered heteroalkylene. In aspects, $L^1$ is an unsubstituted 15 to 25 membered heteroalkylene. In aspects, $L^1$ is a substituted or unsubstituted 20 membered heteroalkylene. In aspects, $L^1$ is a substituted 20 membered heteroalkylene. In aspects, $L^1$ is an unsubstituted 20 membered heteroalkylene. In aspects, $L^1$ is a substituted or unsubstituted 21 membered heteroalkylene. In aspects, $L^1$ is a substituted 21 membered heteroalkylene. In aspects, $L^1$ is an unsubstituted 21 membered heteroalkylene.

In embodiments, $L^1$ is: —$(CH_2)_6$—NH—

In embodiments, $L^1$ is: —$(PO_3OH$—$(CH_2)_{pm})_{pn}$—$PO_3OH$—, where pm is an integer from 1 to 8; and pn is an integer from 1 to 10. In aspects, pm is an integer from 1 to 4. In aspects pm is 2 or 3. In aspects, pn is 1, 2, 3, or 4.

In embodiments, $L^1$ is: —$(CH_2)_{pc}$—$(PO_3OH$—$(CH_2)_{pm})_{pn}$—$PO_3OH$—, where pc is an integer from 0 to 6; pm is an integer from 1 to 8; and pn is an integer from 1 to 10. In aspects, pc is an integer from 1 to 4. In aspects, pc is 1 or 2. In aspects, pm is an integer from 1 to 4. In aspects pm is 2 or 3. In aspects, pn is 1, 2, 3, or 4.

In embodiments, $L^1$ is: —$(CH_2)_{pc}$—$(PO_3OH$—$(CH_2)_{pm})_{pn}$—, where pc is an integer from 0 to 6; pm is an integer from 1 to 8; and pn is an integer from 1 to 10. In aspects, pc is an integer from 1 to 4. In aspects, pc is 1 or 2. In aspects, pm is an integer from 1 to 4. In aspects pm is 2 or 3. In aspects, pn is 1, 2, 3, or 4.

In embodiments, $L^1$ is: —$(PO_3OH$—$(CH_2)_{pm})_{pn}$—$PO_3OH$—$(CH_2)_{po}$—NH—, where pm is an integer from 1 to 8; pn is an integer from 1 to 10; and po is an integer from 1 to 12. In aspects, pm is an integer from 1 to 4. In aspects pm is 2 or 3. In aspects, pn is 1, 2, 3, or 4. In aspects, po is an integer from 2 to 10. In aspects, po is an integer from 4 to 8. In aspects, po is 2. In aspects, po is 4. In aspects, po is 6. In aspects, po is 8.

In embodiments, $L^1$ is: —$(PO_3OH$—$(CH_2)_{pm})_{pn}$—$PO_3OH$—$[(CH_2)_{pa}$—$O]_{pb}$—$(CH_2)_{po}$—NH—, where pm is an integer from 1 to 8; pn is an integer from 1 to 10; po is an integer from 1 to 12; pa is an integer from 1 to 4; and pb is 0, 1, or 2. In aspects, pm is an integer from 1 to 4. In aspects pm is 2 or 3. In aspects, pn is 1, 2, 3, or 4. In aspects, po is an integer from 2 to 10. In aspects, po is an integer from 4 to 8. In aspects, po is 2. In aspects, po is 4. In aspects, po is 6. In aspects, po is 8. In aspects, pa is 1 or 2. In aspects, pb is 0. In aspects, pb is 1. In aspects, pb is 2.

In embodiments, $L^1$ is:

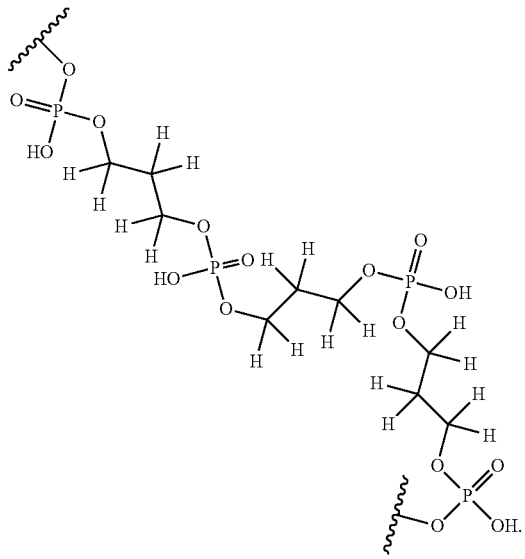 [SMILES: *OP(=O)(O)OCCCOP(=O)(O)OCCCOP(=O)(O)OCCCOP(=O)(O)O*]

In embodiments, $L^1$ is:

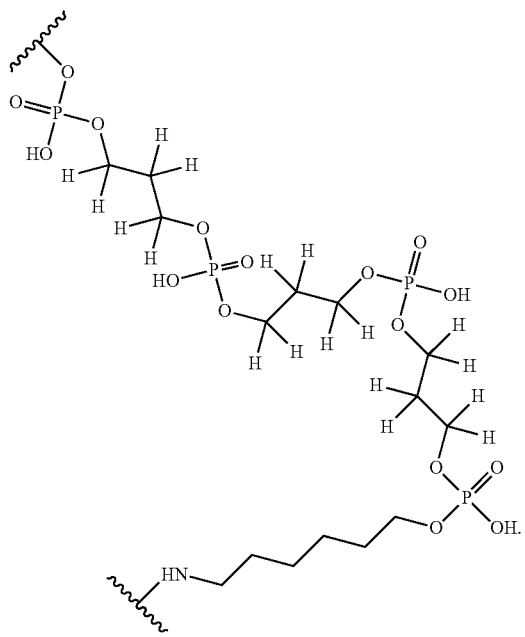 [SMILES: *NCCCCCCOP(=O)(O)OCCCOP(=O)(O)OCCCOP(=O)(O)OCCCOP(=O)(O)O*]

In aspects, $L^1$ is —$PO_3OH$—$CH_2CH_2CH_2$—$PO_3OH$—. In aspects, $L^1$ is —$PO_3OH$—$CH_2CH_2$—$PO_3OH$—. In aspects, $L^1$ is —$CH_2$—$PO_3OH$—$CH_2CH_2CH_2$—$PO_3OH$—. In aspects, $L^1$ is —$CH_2$—$PO_3OH$—$CH_2CH_2$—$PO_3OH$—. In aspects, $L^1$ is —$CH_2$—$PO_3OH$—In aspects, $L^1$ is —$CH_2CH_2$—$PO_3OH$—. In aspects, $L^1$ is —$PO_3OH$—$(CH_2)_3$—$PO_3OH$—. In aspects, $L^1$ is —$PO_3OH$—$(CH_2)_3$—$PO_3OH$—$(CH_2)_2$—$PO_3OH$—. In aspects, $L^1$ is —$PO_3OH$—$(CH_2)_2$—$PO_3OH$—$(CH_2)_2$—$PO_3OH$—. In aspects, $L^1$ is —$PO_3OH$—$(CH_2)_3$—$PO_3OH$—$(CH_2)_3$—$PO_3OH$—. In aspects, $L^1$ is —$PO_3OH$—$(CH_2)_3$—$PO_3OH$—$(CH_2)_3$—$PO_3OH$—$(CH_2)_3$—$PO_3OH$—. In aspects, $L^1$ is —$PO_3OH$—$(CH_2)_3$—$PO_3OH$—$(CH_2)_2$—

$PO_3OH$—$(CH_2)_3$—$PO_3OH$—. In aspects, $L^1$ is —$PO_3OH$—$(CH_2)_3$—$PO_3OH$—$(CH_2)_2$—$PO_3OH$—$(CH_2)_3$—$PO_3OH$—$(CH_2)_2$—$PO_3OH$—. In aspects, $L^1$ is —$PO_3OH$—$(CH_2)_3$—$PO_3OH$—$(CH_2)_2$—$PO_3OH$—$(CH_2)_3$—$PO_3OH$—$(CH_2)_2$—$PO_3OH$—$(CH_2)_3$—$PO_3OH$—. In aspects, $L^1$ is —$PO_3OH$—$(CH_2)_3$—$PO_3OH$—$(CH_2)_2$—$PO_3OH$—$(CH_2)_3$—$PO_3OH$—$(CH_2)_2$—$PO_3OH$—$(CH_2)_3$—$PO_3OH$—$(CH_2)_2$—$PO_3OH$—.

In embodiments, $L^2$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocyclo-alkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^2$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene.

In embodiments, $L^2$ is unsubstituted alkylene, unsubstituted heteroalkylene, unsubstituted cycloalkylene, unsubstituted heterocycloalkylene, unsubstituted arylene, or unsubstituted heteroarylene.

In embodiments, $L^2$ is substituted (e.g., substituted with a substituent group, a size-limited substituent group, or lower substituent group) or unsubstituted alkylene. In aspects, $L^2$ is substituted (e.g., substituted with a substituent group, a size-limited substituent group, or lower substituent group) alkylene. In aspects, $L^2$ is unsubstituted alkylene. In aspects, $L^2$ is substituted or unsubstituted alkylene (e.g., $C_1$-$C_8$, $C_1$-$C_6$, $C_1$-$C_4$, or $C_1$-$C_2$). In aspects, $L^2$ is substituted alkylene (e.g., $C_1$-$C_8$, $C_1$-$C_6$, $C_1$-$C_4$, or $C_1$-$C_2$). In aspects, $L^2$ is unsubstituted alkylene (e.g., $C_1$-$C_8$, $C_1$-$C_6$, $C_1$-$C_4$, or $C_1$-$C_2$).

In embodiments, $L^2$ is substituted (e.g., substituted with a substituent group, a size-limited substituent group, or lower substituent group) or unsubstituted heteroalkylene. In aspects, $L^2$ is substituted (e.g., substituted with a substituent group, a size-limited substituent group, or lower substituent group) heteroalkylene. In aspects, $L^2$ is unsubstituted heteroalkylene. In aspects, $L^2$ is substituted or unsubstituted heteroalkylene (e.g., 2 to 8 membered, 2 to 6 membered, 4 to 6 membered, 2 to 3 membered, or 4 to 5 membered). In aspects, $L^2$ is substituted heteroalkylene (e.g., 2 to 8 membered, 2 to 6 membered, 4 to 6 membered, 2 to 3 membered, or 4 to 5 membered). In aspects, $L^2$ is an unsubstituted heteroalkylene (e.g., 2 to 8 membered, 2 to 6 membered, 4 to 6 membered, 2 to 3 membered, or 4 to 5 membered).

In embodiments, $L^2$ is substituted (e.g., substituted with a substituent group, a size-limited substituent group, or lower substituent group) or unsubstituted cycloalkylene. In aspects, $L^2$ is substituted (e.g., substituted with a substituent group, a size-limited substituent group, or lower substituent group) cycloalkylene. In aspects, $L^2$ is an unsubstituted cycloalkylene. In aspects, $L^2$ is substituted or unsubstituted cycloalkylene (e.g., $C_3$-$C_8$, $C_3$-$C_6$, $C_4$-$C_6$, or $C_5$-$C_6$). In aspects, $L^2$ is substituted cycloalkylene (e.g., $C_3$-$C_8$, $C_3$-$C_6$, $C_4$-$C_6$, or $C_5$-$C_6$). In aspects, $L^2$ is unsubstituted cycloalkylene (e.g., $C_3$-$C_8$, $C_3$-$C_6$, $C_4$-$C_6$, or $C_5$-$C_6$).

In embodiments, $L^2$ is substituted (e.g., substituted with a substituent group, a size-limited substituent group, or lower substituent group) or unsubstituted heterocycloalkylene. In aspects, $L^2$ is substituted (e.g., substituted with a substituent group, a size-limited substituent group, or lower substituent group) heterocycloalkylene. In aspects, $L^2$ is an unsubstituted heterocycloalkylene. In aspects, $L^2$ is substituted or unsubstituted heterocycloalkylene (e.g., 3 to 8 membered, 3 to 6 membered, 4 to 6 membered, 4 to 5 membered, or 5 to 6 membered). In aspects, $L^2$ is substituted heterocycloalkylene (e.g., 3 to 8 membered, 3 to 6 membered, 4 to 6 membered, 4 to 5 membered, or 5 to 6 membered). In aspects, $L^2$ an unsubstituted heterocycloalkylene (e.g., 3 to 8 membered, 3 to 6 membered, 4 to 6 membered, 4 to 5 membered, or 5 to 6 membered).

In embodiments, $L^2$ is substituted (e.g., substituted with a substituent group, a size-limited substituent group, or lower substituent group) or unsubstituted arylene. In aspects, $L^2$ is substituted (e.g., substituted with a substituent group, a size-limited substituent group, or lower substituent group) arylene. In aspects, $L^2$ is an unsubstituted arylene. In aspects, $L^2$ is substituted or unsubstituted arylene (e.g., $C_6$-$C_{10}$ or phenylene). In aspects, $L^2$ is substituted arylene (e.g., $C_6$-$C_{10}$ or phenylene). In aspects, $L^2$ is an unsubstituted arylene (e.g., $C_6$-$C_{10}$ or phenylene).

In embodiments, $L^2$ is substituted (e.g., substituted with a substituent group, a size-limited substituent group, or lower substituent group) or unsubstituted heteroarylene. In aspects, $L^2$ is substituted (e.g., substituted with a substituent group, a size-limited substituent group, or lower substituent group) heteroarylene. In aspects, $L^2$ is an unsubstituted heteroarylene. In aspects, $L^2$ is substituted or unsubstituted heteroarylene (e.g., 5 to 10 membered, 5 to 9 membered, or 5 to 6 membered). In aspects, $L^2$ is substituted heteroarylene (e.g., 5 to 10 membered, 5 to 9 membered, or 5 to 6 membered). In aspects, $L^2$ is an unsubstituted heteroarylene (e.g., 5 to 10 membered, 5 to 9 membered, or 5 to 6 membered).

In embodiments, $L^2$ is substituted or unsubstituted alkylene (e.g., $C_1$-$C_{30}$, $C_1$-$C_{25}$, $C_{10}$-$C_{20}$, or $C_1$-$C_8$), substituted or unsubstituted heteroalkylene (e.g., 2 to 30 membered, 6 to 30 membered, 12 to 24 membered, 10 to 22 membered, or 18 to 22 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^2$ is substituted (e.g., substituted with a substituent group, a size-limited substituent group, or lower substituent group) or unsubstituted alkylene. In aspects, $L^2$ is substituted (e.g., substituted with a substituent group, a size-limited substituent group, or lower substituent group) alkylene. In aspects, $L^2$ is unsubstituted alkylene. In aspects, $L^2$ is substituted or unsubstituted alkylene (e.g., $C_1$-$C_{30}$, $C_1$-$C_{25}$, $C_{10}$-$C_{20}$, or $C_1$-$C_8$). In aspects, $L^2$ is substituted alkylene (e.g., $C_1$-$C_{30}$, $C_1$-$C_{25}$, $C_{10}$-$C_{20}$, or $C_1$-$C_8$). In aspects, $L^2$ is unsubstituted alkylene (e.g., $C_1$-$C_{30}$, $C_1$-$C_{25}$, $C_{10}$-$C_{20}$, or $C_1$-$C_8$).

In embodiments, $L^2$ is substituted (e.g., substituted with a substituent group, a size-limited substituent group, or lower substituent group) or unsubstituted heteroalkylene. In aspects, $L^2$ is substituted (e.g., substituted with a substituent group, a size-limited substituent group, or lower substituent group) heteroalkylene. In aspects, $L^2$ is unsubstituted heteroalkylene. In aspects, $L^2$ is substituted or unsubstituted heteroalkylene (e.g., 2 to 30 membered, 6 to 30 membered, 12 to 24 membered, 10 to 22 membered, or 18 to 22 membered). In aspects, $L^2$ is substituted heteroalkylene (e.g., 2 to 30 membered, 6 to 30 membered, 12 to 24 membered, 10 to 22 membered, or 18 to 22 membered). In aspects, $L^2$ is an unsubstituted heteroalkylene (e.g., 2 to 30 membered, 6 to 30 membered, 12 to 24 membered, 10 to 22 membered, or 18 to 22 membered).

In embodiments where $L^2$ comprises a moiety with one or more substituents, one or more substituents is -$L^{11}$-$L^{12}$-$L^{13}$-$L^{14}$-MC, wherein $L^{11}$ has the same definition as $L^1$; $L^{12}$ has the same definition as $L^2$; $L^{13}$ has the same definition of $L^3$; $L^{14}$ has the same definition of $L^4$; and MC is as defined herein. In aspects, $L^{12}$ is substituted with -$L^{101}$-$L^{102}$-$L^{103}$-$L^{104}$-MC, wherein $L^{101}$ has the same definition as $L^1$; $L^{102}$ has the same definition as $L^2$; $L^{103}$ has the same definition of $L^3$; $L^{104}$ has the same definition of $L^4$; and MC is as defined herein. In aspects, $L^{102}$ is substituted with -$L^{110}$-$L^{120}$-$L^{130}$-$L^{140}$-MC, wherein $L^{110}$ has the same definition as $L^1$; $L^{120}$ has the same definition as $L^2$; $L^{130}$ has the same definition of $L^3$; $L^{140}$ has the same definition of $L^4$; and MC is as defined herein. In aspects, $L^{120}$ is substituted with -$L^{111}$-$L^{122}$-$L^{133}$-$L^{144}$-MC, wherein $L^{111}$ has the same definition as $L^1$; $L^{122}$ has the same definition as $L^2$; $L^{133}$ has the same definition of $L^3$; $L^{144}$ has the same definition of $L^4$; and MC is as defined herein. In aspects, $L^{122}$ is substituted with -$L^{1111}$-$L^{1222}$-$L^{1333}$-$L^{1444}$-MC, wherein $L^{1111}$ has the same definition as $L^1$; $L^{1222}$ has the same definition as $L^2$; $L^{1333}$ has the same definition of L3; $L^{1444}$ has the same definition of $L^4$; and MC is as defined herein.

In aspects, $L^{11}$, $L^{101}$, $L^{110}$, and $L^{111}$ have the same definition as $L^1$. In aspects, $L^{11}$, $L^{101}$, $L^{110}$, and $L^{111}$ are each independently selected from the group consisting of —($PO_3OH$)—($CH_2$)$_{pm}$)$_{pn}$—$PO_3OH$—, —($CH_2$)$_{pc}$—($PO_3OH$—($CH_2$)$_{pm}$)$_{pn}$—$PO_3OH$—, —($CH_2$)$_{pc}$—($PO_3OH$—($CH_2$)$_{pm}$)$_{pn}$—($PO_3OH$—($CH_2$)$_{pm}$)$_{pn}$—$PO_3OH$—($CH_2$)$_{po}$—NH—, and —($PO_3OH$—($CH_2$)$_{pm}$)$_{pn}$—$PO_3OH$—[($CH_2$)$_{pa}$—O]$_{pb}$—($CH_2$)$_{po}$—NH—; wherein pc is an integer from 0 to 6; pm is an integer from 1 to 8; pn is an integer from 1 to 10; po is an integer from 1 to 12; pa is an integer from 1 to 4; and pb is 0, 1, or 2. In aspects, $L^{12}$, $L^{102}$, $L^{120}$, and $L^{122}$ have the same definition of $L^2$. In aspects, $L^{12}$, $L^{102}$, $L^{120}$, and $L^{122}$ are each independently selected from the group consisting of —C(=O)$CH_2CH_2$C(=O)NH—($CH_2$)$_6$—; —($CH_2$)$_3$—O—($CH_2$)$_3$NH—C(=O)($CH_2$)$_2$C(=O)—; and —($CH_2$)$_2$—O—($CH_2$)$_3$NH—C(=O)($CH_2$)$_2$C(=O)—. In aspects, $L^{13}$, $L^{103}$, $L^{130}$, and $L^{133}$ have the same definition of $L^3$. In aspects, $L^{14}$, $L^{104}$, $L^{140}$, and $L^{144}$ have the same definition of $L^4$.

In embodiments, $L^2$ has the formula: —C(=O)—$CH_2CH_2$—(C=O)—.

In embodiments, $L^2$ has the formula: —C(=O)—($CH_2$)$_{k1}$—NH—($CH_2$)$_{k2}$—, wherein k1 is an integer from 1 to 6, and wherein k2 is an integer from 1 to 12. In aspects, k1 is an integer from 1 to 4. In aspects, k1 is 2. In aspects, k1 is 3. In aspects k1 is 4. In aspects k2 is an integer from 2 to 10. In aspects, k2 is an integer from 4 to 8. In aspects, k2 is 4. In aspects, k2 is 5. In aspects, k2 is 6. In aspects, k2 is 7. In aspects, k2 is 8. In aspects, L2 has the formula —C(=O)—($CH_2$)$_{k1}$—NH—($CH_2$)$_{k1}$—O—($CH_2$)$_{k1}$—, wherein k1 is an integer from 1 to 6. In aspects, k1 is an integer from 1 to 4. In aspects, k1 is 2. In aspects, k1 is 3. In aspects, k1 is 4. In aspects, $L^2$ has the formula:

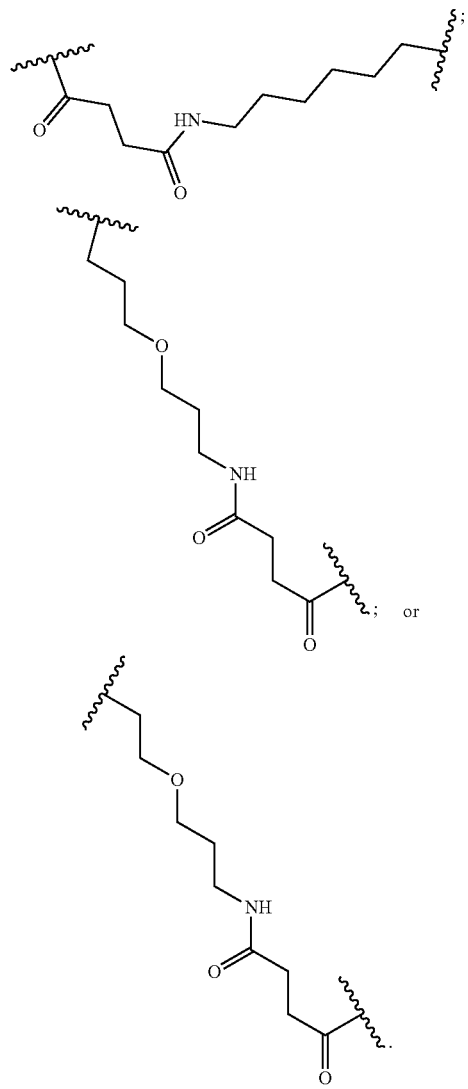

In aspects, this formula of $L^2$ is optionally substituted with -$L^{11}$-$L^{12}$-$L^{13}$-$L^{14}$-MC, wherein $L^{11}$ has the same definition as $L^1$; $L^{12}$ has the same definition as $L^2$; $L^{13}$ has the same definition of $L^3$; $L^{14}$ has the same definition of $L^4$; and MC is as defined herein. In aspects, $L^{12}$ is substituted with -$L^{101}$-$L^{102}$-$L^{103}$-$L^{104}$-MC, wherein $L^{101}$ has the same definition as $L^1$; $L^{102}$ has the same definition as $L^2$; $L^{103}$ has the same definition of $L^3$; $L^{104}$ has the same definition of $L^4$; and MC is as defined herein. In aspects, $L^{102}$ is substituted with -$L^{110}$-$L^{120}$-$L^{130}$-$L^{140}$-MC, wherein $L^{110}$ has the same definition as $L^1$; $L^{120}$ has the same definition as $L^2$; $L^{130}$ has the same definition of $L^3$; $L^{140}$ has the same definition of $L^4$; and MC is as defined herein. In aspects, $L^{120}$ is substituted with -$L^{111}$-$L^{122}$-$L^{133}$-$L^{144}$-MC, wherein $L^{111}$ has the same definition as $L^1$; $L^{122}$ has the same definition as $L^2$; $L^{133}$ has the same definition of $L^3$; $L^{144}$ has the same definition of $L^4$; and MC is as defined herein. In aspects, $L^{122}$ is substituted with -$L^{1111}$-$L^{122}$-$L^{1333}$-$L^{1444}$-MC, wherein $L^{1111}$ has the same definition as $L^1$; $L^{1222}$ has the same definition as $L^2$; $L^{1333}$ has the same definition of L3; $L^{1444}$ has the same definition of $L^4$; and MC is as defined herein.

In embodiments, $L^3$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^3$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene.

In embodiments, $L^3$ is unsubstituted alkylene, unsubstituted heteroalkylene, unsubstituted cycloalkylene, unsubstituted heterocycloalkylene, unsubstituted arylene, or unsubstituted heteroarylene.

In embodiments, $L^3$ is substituted (e.g., substituted with a substituent group, a size-limited substituent group, or lower substituent group) or unsubstituted alkylene. In aspects, $L^3$ is substituted (e.g., substituted with a substituent group, a size-limited substituent group, or lower substituent group) alkylene. In aspects, $L^3$ is unsubstituted alkylene. In aspects, $L^3$ is substituted or unsubstituted alkylene (e.g., $C_1$-$C_8$, $C_1$-$C_6$, $C_1$-$C_4$, or $C_1$-$C_2$). In aspects, $L^3$ is substituted alkylene (e.g., $C_1$-$C_8$, $C_1$-$C_6$, $C_1$-$C_4$, or $C_1$-$C_2$). In aspects, $L^3$ is unsubstituted alkylene (e.g., $C_1$-$C_8$, $C_1$-$C_6$, $C_1$-$C_4$, or $C_1$-$C_2$).

In embodiments, $L^3$ is substituted (e.g., substituted with a substituent group, a size-limited substituent group, or lower substituent group) or unsubstituted heteroalkylene. In aspects, $L^3$ is substituted (e.g., substituted with a substituent group, a size-limited substituent group, or lower substituent group) heteroalkylene. In aspects, $L^3$ is unsubstituted heteroalkylene. In aspects, $L^3$ is substituted or unsubstituted heteroalkylene (e.g., 2 to 8 membered, 2 to 6 membered, 4 to 6 membered, 2 to 3 membered, or 4 to 5 membered). In aspects, $L^3$ is substituted heteroalkylene (e.g., 2 to 8 membered, 2 to 6 membered, 4 to 6 membered, 2 to 3 membered, or 4 to 5 membered). In aspects, $L^3$ is an unsubstituted heteroalkylene (e.g., 2 to 8 membered, 2 to 6 membered, 4 to 6 membered, 2 to 3 membered, or 4 to 5 membered).

In embodiments, $L^3$ is substituted (e.g., substituted with a substituent group, a size-limited substituent group, or lower substituent group) or unsubstituted cycloalkylene. In aspects, $L^3$ is substituted (e.g., substituted with a substituent group, a size-limited substituent group, or lower substituent group) cycloalkylene. In aspects, $L^3$ is substituted or unsubstituted cycloalkylene (e.g., $C_3$-$C_8$, $C_3$-$C_6$, $C_4$-$C_6$, or $C_5$-$C_6$). In aspects, $L^3$ is substituted cycloalkylene (e.g., $C_3$-$C_8$, $C_3$-$C_6$, $C_4$-$C_6$, or $C_5$-$C_6$). In aspects, $L^3$ is unsubstituted cycloalkylene (e.g., $C_3$-$C_8$, $C_3$-$C_6$, $C_4$-$C_6$, or $C_5$-$C_6$).

In embodiments, $L^3$ is substituted (e.g., substituted with a substituent group, a size-limited substituent group, or lower substituent group) or unsubstituted heterocycloalkylene. In aspects, $L^3$ is substituted (e.g., substituted with a substituent group, a size-limited substituent group, or lower substituent group) heterocycloalkylene. In aspects, $L^3$ is an unsubstituted heterocycloalkylene. In aspects, $L^3$ is substituted or unsubstituted heterocycloalkylene (e.g., 3 to 8 membered, 3 to 6 membered, 4 to 6 membered, 4 to 5 membered, or 5 to 6 membered). In aspects, $L^3$ is substituted heterocycloalkylene (e.g., 3 to 8 membered, 3 to 6 membered, 4 to 6 membered, 4 to 5 membered, or 5 to 6 membered). In aspects, $L^3$ an unsubstituted heterocycloalkylene (e.g., 3 to 8 membered, 3 to 6 membered, 4 to 6 membered, 4 to 5 membered, or 5 to 6 membered).

In embodiments, $L^3$ is substituted (e.g., substituted with a substituent group, a size-limited substituent group, or lower substituent group) or unsubstituted arylene. In aspects, $L^3$ is substituted (e.g., substituted with a substituent group, a size-limited substituent group, or lower substituent group) arylene. In aspects, $L^3$ is an unsubstituted arylene. In aspects, $L^3$ is substituted or unsubstituted arylene (e.g., $C_6$-$C_{10}$ or phenylene). In aspects, $L^3$ is substituted arylene (e.g., $C_6$-$C_{10}$ or phenylene). In aspects, $L^3$ is an unsubstituted arylene (e.g., $C_6$-$C_{10}$ or phenylene).

In embodiments, $L^3$ is substituted (e.g., substituted with a substituent group, a size-limited substituent group, or lower substituent group) or unsubstituted heteroarylene. In aspects, $L^3$ is substituted (e.g., substituted with a substituent group, a size-limited substituent group, or lower substituent group) heteroarylene. In aspects, $L^3$ is an unsubstituted heteroarylene. In aspects, $L^3$ is substituted or unsubstituted heteroarylene (e.g., 5 to 10 membered, 5 to 9 membered, or 5 to 6 membered). In aspects, $L^3$ is substituted heteroarylene (e.g., 5 to 10 membered, 5 to 9 membered, or 5 to 6 membered). In aspects, $L^3$ is an unsubstituted heteroarylene (e.g., 5 to 10 membered, 5 to 9 membered, or 5 to 6 membered).

In embodiments, $L^3$ is substituted or unsubstituted alkylene (e.g., $C_1$-$C_{30}$, $C_1$-$C_{25}$, $C_{10}$-$C_{20}$, or $C_1$-$C_8$), substituted or unsubstituted heteroalkylene (e.g., 2 to 30 membered, 6 to 30 membered, 12 to 24 membered, 10 to 22 membered, or 18 to 22 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^3$ is substituted (e.g., substituted with a substituent group, a size-limited substituent group, or lower substituent group) or unsubstituted alkylene. In aspects, $L^3$ is substituted (e.g., substituted with a substituent group, a size-limited substituent group, or lower substituent group) alkylene. In aspects, $L^3$ is unsubstituted alkylene. In aspects, $L^3$ is substituted or unsubstituted alkylene (e.g., $C_1$-$C_{30}$, $C_1$-$C_{25}$, $C_{10}$-$C_{20}$, or $C_1$-$C_8$). In aspects, $L^3$ is substituted alkylene (e.g., $C_1$-$C_{30}$, $C_1$-$C_{25}$, $C_{10}$-$C_{20}$, or $C_1$-$C_8$). In aspects, $L^3$ is unsubstituted alkylene (e.g., $C_1$-$C_{30}$, $C_1$-$C_{25}$, $C_{10}$-$C_{20}$, or $C_1$-$C_8$).

In embodiments, $L^3$ is substituted (e.g., substituted with a substituent group, a size-limited substituent group, or lower substituent group) or unsubstituted heteroalkylene. In aspects, $L^3$ is substituted (e.g., substituted with a substituent group, a size-limited substituent group, or lower substituent group) heteroalkylene. In aspects, $L^3$ is unsubstituted heteroalkylene. In aspects, $L^3$ is substituted or unsubstituted heteroalkylene (e.g., 2 to 30 membered, 6 to 30 membered, 12 to 24 membered, 10 to 22 membered, or 18 to 22 membered). In aspects, $L^3$ is substituted heteroalkylene (e.g., 2 to 30 membered, 6 to 30 membered, 12 to 24 membered, 10 to 22 membered, or 18 to 22 membered). In aspects, $L^3$ is an unsubstituted heteroalkylene (e.g., 2 to 30 membered, 6 to 30 membered, 12 to 24 membered, 10 to 22 membered, or 18 to 22 membered).

In embodiments, $L^3$ has the formula:

In embodiments, $L^4$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^4$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene.

In embodiments, $L^4$ is unsubstituted alkylene, unsubstituted heteroalkylene, unsubstituted cycloalkylene, unsubstituted heterocycloalkylene, unsubstituted arylene, or unsubstituted heteroarylene.

In embodiments, $L^4$ is substituted (e.g., substituted with a substituent group, a size-limited substituent group, or lower substituent group) or unsubstituted alkylene. In aspects, $L^4$ is substituted (e.g., substituted with a substituent group, a size-limited substituent group, or lower substituent group) alkylene. In aspects, $L^4$ is unsubstituted alkylene. In aspects, $L^4$ is substituted or unsubstituted alkylene (e.g., $C_1$-$C_8$, $C_1$-$C_6$, $C_1$-$C_4$, or $C_1$-$C_2$). In aspects, $L^4$ is substituted alkylene (e.g., $C_1$-$C_8$, $C_1$-$C_6$, $C_1$-$C_4$, or $C_1$-$C_2$). In aspects, $L^4$ is unsubstituted alkylene (e.g., $C_1$-$C_8$, $C_1$-$C_6$, $C_1$-$C_4$, or $C_1$-$C_2$).

In embodiments, $L^4$ is substituted (e.g., substituted with a substituent group, a size-limited substituent group, or lower substituent group) or unsubstituted heteroalkylene. In aspects, $L^4$ is substituted (e.g., substituted with a substituent group, a size-limited substituent group, or lower substituent group) heteroalkylene. In aspects, $L^4$ is unsubstituted heteroalkylene. In aspects, $L^4$ is substituted or unsubstituted heteroalkylene (e.g., 2 to 8 membered, 2 to 6 membered, 4 to 6 membered, 2 to 3 membered, or 4 to 5 membered). In aspects, $L^4$ is substituted heteroalkylene (e.g., 2 to 8 membered, 2 to 6 membered, 4 to 6 membered, 2 to 3 membered, or 4 to 5 membered). In aspects, $L^4$ is an unsubstituted heteroalkylene (e.g., 2 to 8 membered, 2 to 6 membered, 4 to 6 membered, 2 to 3 membered, or 4 to 5 membered).

In embodiments, $L^4$ is substituted (e.g., substituted with a substituent group, a size-limited substituent group, or lower substituent group) or unsubstituted cycloalkylene. In aspects, $L^4$ is substituted (e.g., substituted with a substituent group, a size-limited substituent group, or lower substituent group) cycloalkylene. In aspects, $L^4$ is an unsubstituted cycloalkylene. In aspects, $L^4$ is substituted or unsubstituted cycloalkylene (e.g., $C_3$-$C_8$, $C_3$-$C_6$, $C_4$-$C_6$, or $C_5$-$C_6$). In aspects, $L^4$ is substituted cycloalkylene (e.g., $C_3$-$C_8$, $C_3$-$C_6$, $C_4$-$C_6$, or $C_5$-$C_6$). In aspects, $L^4$ is unsubstituted cycloalkylene (e.g., $C_3$-$C_8$, $C_3$-$C_6$, $C_4$-$C_6$, or $C_5$-$C_6$).

In embodiments, $L^4$ is substituted (e.g., substituted with a substituent group, a size-limited substituent group, or lower substituent group) or unsubstituted heterocycloalkylene. In aspects, $L^4$ is substituted (e.g., substituted with a substituent group, a size-limited substituent group, or lower substituent group) heterocycloalkylene. In aspects, $L^4$ is an unsubstituted heterocycloalkylene. In aspects, $L^4$ is substituted or unsubstituted heterocycloalkylene (e.g., 3 to 8 membered, 3 to 6 membered, 4 to 6 membered, 4 to 5 membered, or 5 to 6 membered). In aspects, $L^4$ is substituted heterocycloalkylene (e.g., 3 to 8 membered, 3 to 6 membered, 4 to 6 membered, 4 to 5 membered, or 5 to 6 membered). In aspects, $L^4$ an unsubstituted heterocycloalkylene (e.g., 3 to 8 membered, 3 to 6 membered, 4 to 6 membered, 4 to 5 membered, or 5 to 6 membered).

In embodiments, $L^4$ is substituted (e.g., substituted with a substituent group, a size-limited substituent group, or lower substituent group) or unsubstituted arylene. In aspects, $L^4$ is substituted (e.g., substituted with a substituent group, a size-limited substituent group, or lower substituent group) arylene. In aspects, $L^4$ is an unsubstituted arylene. In aspects, $L^4$ is substituted or unsubstituted arylene (e.g., $C_6$-$C_{10}$ or phenylene). In aspects, $L^4$ is substituted arylene (e.g., $C_6$-$C_{10}$ or phenylene). In aspects, $L^4$ is an unsubstituted arylene (e.g., $C_6$-$C_{10}$ or phenylene).

In embodiments, $L^4$ is substituted (e.g., substituted with a substituent group, a size-limited substituent group, or lower substituent group) or unsubstituted heteroarylene. In aspects, $L^4$ is substituted (e.g., substituted with a substituent group, a size-limited substituent group, or lower substituent group) heteroarylene. In aspects, $L^4$ is an unsubstituted heteroarylene. In aspects, $L^4$ is substituted or unsubstituted heteroarylene (e.g., 5 to 10 membered, 5 to 9 membered, or 5 to 6 membered). In aspects, $L^4$ is substituted heteroarylene (e.g., 5 to 10 membered, 5 to 9 membered, or 5 to 6 membered). In aspects, $L^4$ is an unsubstituted heteroarylene (e.g., 5 to 10 membered, 5 to 9 membered, or 5 to 6 membered).

In embodiments, $L^4$ is substituted or unsubstituted alkylene (e.g., $C_1$-$C_{30}$, $C_1$-$C_{25}$, $C_{10}$-$C_{20}$, or $C_1$-$C_8$), substituted or unsubstituted heteroalkylene (e.g., 2 to 30 membered, 6 to 30 membered, 12 to 24 membered, 10 to 22 membered, or 18 to 22 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^4$ is substituted (e.g., substituted with a substituent group, a size-limited substituent group, or lower substituent group) or unsubstituted alkylene. In aspects, $L^4$ is substituted (e.g., substituted with a substituent group, a size-limited substituent group, or lower substituent group) alkylene. In aspects, $L^4$ is unsubstituted alkylene. In aspects, $L^4$ is substituted or unsubstituted alkylene (e.g., $C_1$-$C_{30}$, $C_1$-$C_{25}$, $C_{10}$-$C_{20}$, or $C_1$-$C_8$). In aspects, $L^4$ is substituted alkylene (e.g., $C_1$-$C_{30}$, $C_1$-$C_{25}$, $C_{10}$-$C_{20}$, or $C_1$-$C_8$). In aspects, $L^4$ is unsubstituted alkylene (e.g., $C_1$-$C_{30}$, $C_1$-$C_{25}$, $C_{10}$-$C_{20}$, or $C_1$-$C_8$).

In embodiments, $L^4$ is substituted (e.g., substituted with a substituent group, a size-limited substituent group, or lower substituent group) or unsubstituted heteroalkylene. In aspects, $L^4$ is substituted (e.g., substituted with a substituent group, a size-limited substituent group, or lower substituent group) heteroalkylene. In aspects, $L^4$ is unsubstituted heteroalkylene. In aspects, $L^4$ is substituted or unsubstituted heteroalkylene (e.g., 2 to 30 membered, 6 to 30 membered, 12 to 24 membered, 10 to 22 membered, or 18 to 22 membered). In aspects, $L^4$ is substituted heteroalkylene (e.g., 2 to 30 membered, 6 to 30 membered, 12 to 24 membered, 10 to 22 membered, or 18 to 22 membered). In aspects, $L^4$ is an unsubstituted heteroalkylene (e.g., 2 to 30 membered, 6 to 30 membered, 12 to 24 membered, 10 to 22 membered, or 18 to 22 membered).

In embodiments, $L^4$ has the formula:

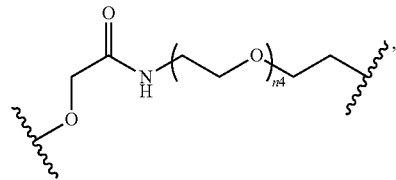

wherein n4 is an integer from 0 to 6.

In embodiments, $L^4$ has the formula:

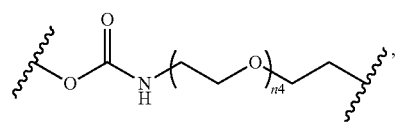

wherein n4 is an integer from 0 to 6.

In embodiments, $L^4$ has the formula:

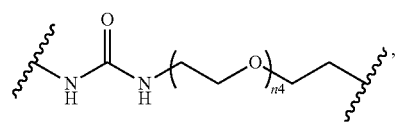

wherein n4 is an integer from 0 to 6.

In embodiments, $L^4$ has the formula:

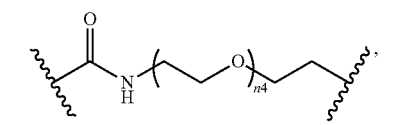

wherein n4 is an integer from 0 to 6.

In embodiments, -$L^1$-$L^2$-$L^3$-$L^4$- has the formula:

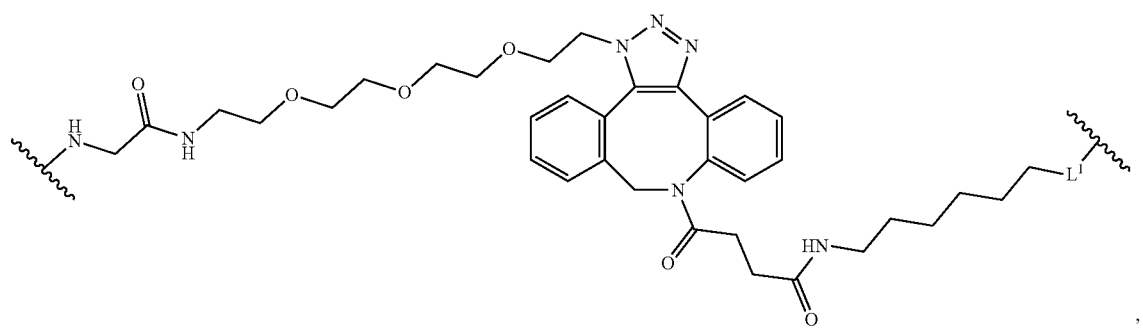

wherein $L^1$ is as described herein. In aspects, $L^1$ is $-(PO_3OH-(CH_2)_{pm})_{pn}-PO_3OH-$, $-(CH_2)_{pc}-(PO_3OH-(CH_2)_{pm})_{pn}-PO_3OH-$, $-(CH_2)_{pc}-(PO_3OH-(CH_2)_{pm})_{pn}-$, $-(PO_3OH-(CH_2)_{pm})_{pn}-PO_3OH-(CH_2)_{po}-NH-$, or $-(PO_3OH-(CH_2)_{pm})_{pn}-PO_3OH-[(CH_2)_{pa}-O]_{pb}-(CH_2)_{po}-NH-$; wherein pc is an integer from 0 to 6; pm is an integer from 1 to 8; pn is an integer from 1 to 10; po is an integer from 1 to 12; pa is an integer from 1 to 4; and pb is 0, 1, or 2.

In embodiments, $-L^1-L^2-L^3-L^4-$ has the formula:

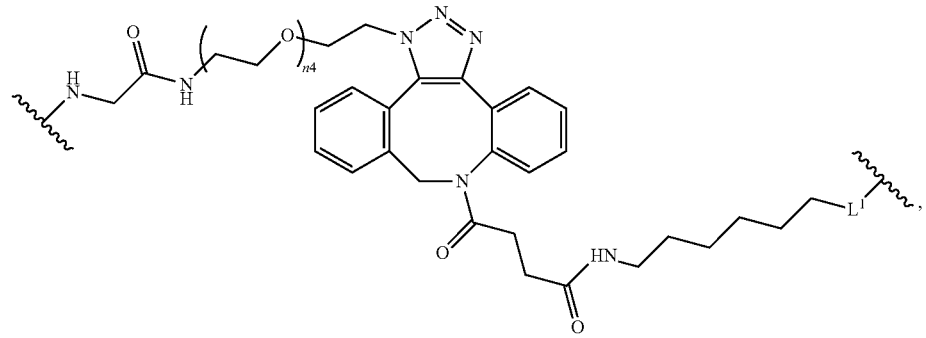

wherein $L^1$ and n4 are as described herein. In aspects, n4 is 0. In aspects, n4 is 1. In aspects, n4 is 2. In aspects, n4 is 3. In aspects, n4 is 4. In aspects, n4 is 5. In aspects, n4 is 6. In aspects, $L^1$ is $-(PO_3OH-(CH_2)_{pm})_{pn}-PO_3OH-$, $-(CH_2)_{pc}-(PO_3OH-(CH_2)_{pm})_{pn}-PO_3OH-$, $-(CH_2)_{pc}-(PO_3OH-(CH_2)_{pm})_{pn}-$, $-(PO_3OH-(CH_2)_{pm})_{pn}-PO_3OH-(CH_2)_{po}-NH-$, or $-(PO_3OH-(CH_2)_{pm})_{pn}-PO_3OH-[(CH_2)_{pa}-O]_{pb}-(CH_2)_{po}-NH-$; wherein pc is an integer from 0 to 6; pm is an integer from 1 to 8; pn is an integer from 1 to 10; po is an integer from 1 to 12; pa is an integer from 1 to 4; and pb is 0, 1, or 2.

In embodiments, $-L^1-L^2-L^3-L^4-$ has the formula:

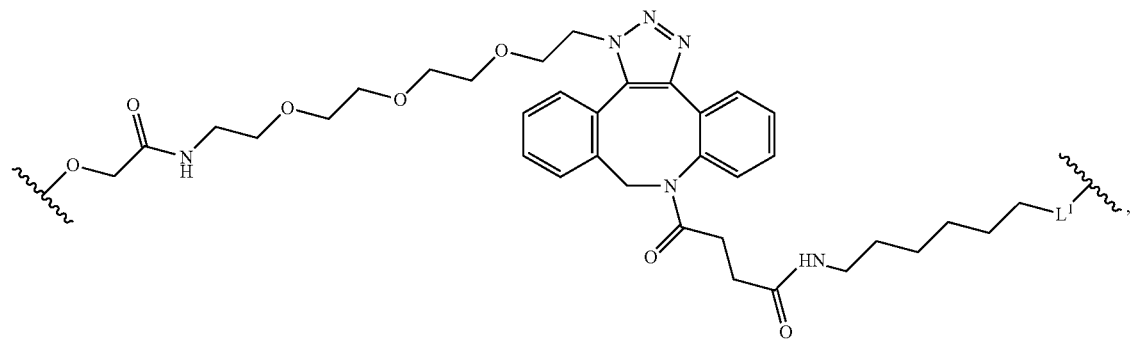

wherein $L^1$ is as described herein. In aspects, $L^1$ is $-(PO_3OH-(CH_2)_{pm})_{pn}-PO_3OH-$, $-(CH_2)_{pc}-(PO_3OH-(CH_2)_{pm})_{pn}-PO_3OH-$, $-(CH_2)_{pc}-(PO_3OH-(CH_2)_{pm})_{pn}-$, $-(PO_3OH-(CH_2)_{pm})_{pn}-PO_3OH-(CH_2)_{po}-NH-$, or $-(PO_3OH-(CH_2)_{pm})_{pn}-PO_3OH-[(CH_2)_{pa}-O]_{pb}-(CH_2)_{po}-NH-$; wherein pc is an integer from 0 to 6; pm is an integer from 1 to 8; pn is an integer from 1 to 10; po is an integer from 1 to 12; pa is an integer from 1 to 4; and pb is 0, 1, or 2.

In embodiments, -L$^1$-L$^2$-L$^3$-L$^4$- has the formula:

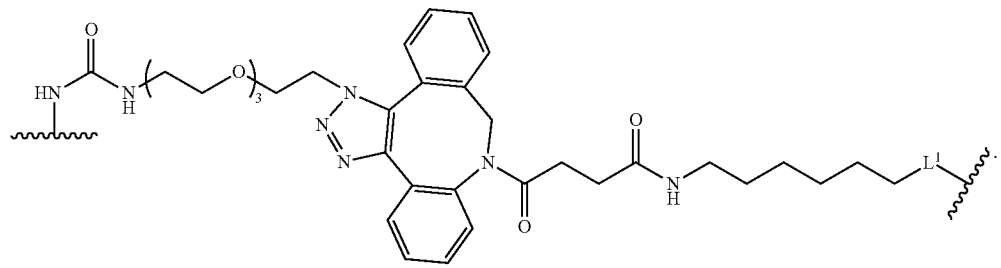

In aspects, L$^1$ is —(PO$_3$OH—(CH$_2$)$_{pm}$)$_{pn}$—PO$_3$OH—, —(CH$_2$)$_{pc}$—(PO$_3$OH—(CH$_2$)$_{pm}$)$_{pn}$—PO$_3$OH—, —(CH$_2$)$_{pc}$—(PO$_3$OH—(CH$_2$)$_{pm}$)$_{pn}$—, —(PO$_3$OH—(CH$_2$)$_{pm}$)$_{pn}$—PO$_3$OH—(CH$_2$)$_{po}$—NH—, or —(PO$_3$OH—(CH$_2$)$_{pm}$)$_{pn}$—PO$_3$OH—[(CH$_2$)$_{pa}$—O]$_{pb}$—(CH$_2$)$_{po}$—NH—; wherein pc is an integer from 0 to 6; pm is an integer from 1 to 8; pn is an integer from 1 to 10; po is an integer from 1 to 12; pa is an integer from 1 to 4; and pb is 0, 1, or 2.

In embodiments, -L$^1$-L$^2$-L$^3$-L$^4$- has the formula:

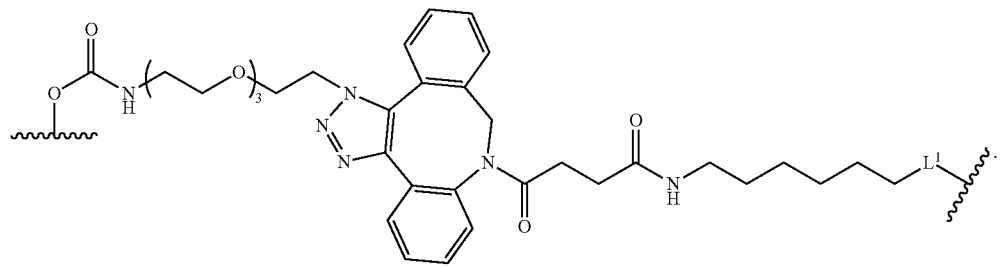

In aspects, L$^1$ is —(PO$_3$OH—(CH$_2$)$_{pm}$)$_{pn}$—PO$_3$OH—, —(CH$_2$)$_{pc}$—(PO$_3$OH—(CH$_2$)$_{pm}$)$_{pn}$—PO$_3$OH—, —(CH$_2$)$_{pc}$—(PO$_3$OH—(CH$_2$)$_{pm}$)$_{pn}$—, —(PO$_3$OH—(CH$_2$)$_{pm}$)$_{pn}$—PO$_3$OH—(CH$_2$)$_{po}$—NH—, or —(PO$_3$OH—(CH$_2$)$_{pm}$)$_{pn}$—PO$_3$OH—[(CH$_2$)$_{pa}$—O]$_{pb}$—(CH$_2$)$_{po}$—NH—; wherein pc is an integer from 0 to 6; pm is an integer from 1 to 8; pn is an integer from 1 to 10; po is an integer from 1 to 12; pa is an integer from 1 to 4; and pb is 0, 1, or 2.

In embodiments, -L$^1$-L$^2$-L$^3$-L$^4$- has the formula:

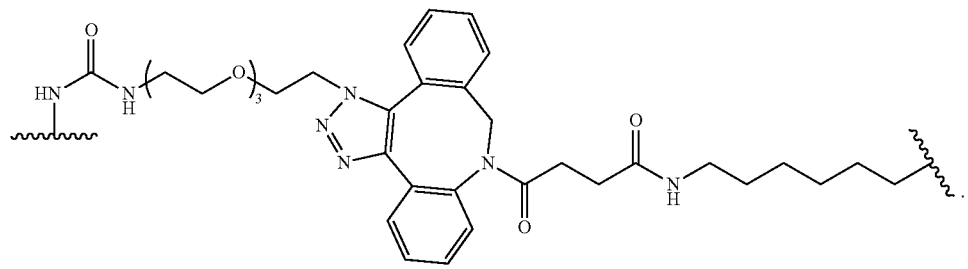

In embodiments, -L¹-L²-L³-L⁴- has the formula:

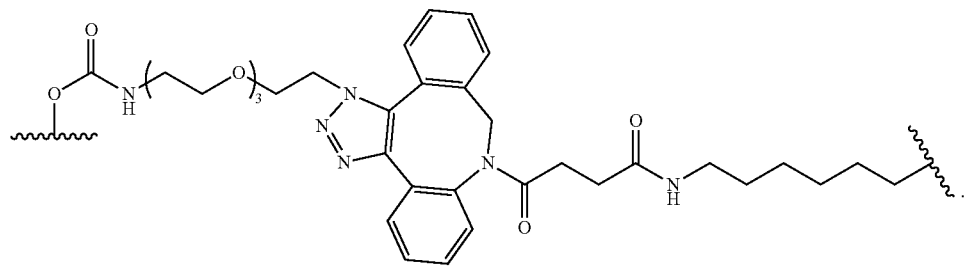

A "ubiquitin ligase binding compound" refers to any compound capable of binding a ubiquitin ligase protein. In aspects, the ubiquitin ligase binding compound is a monovalent compound capable of binding a ubiquitin ligase protein. Exemplary ubiquitin ligase proteins include von Hippel-Lindau tumor suppressor, cereblon, mouse double minute 2 homologue (E3 ubiquitin-protein ligase Mdm2), and cellular inhibitor of apoptosis (e.g., cellular inhibitor of apoptosis protein-1, cellular inhibitor of apoptosis protein-2). In aspects, the ubiquitin ligase binding compound comprises a phthalimide moiety.

The skilled art will recognize compounds that are capable of binding a ubiquitin ligase protein.

In embodiments, the ubiquitin ligase binding compound is a thalidomide moiety, or a stereoisomer thereof, represented by the structure:

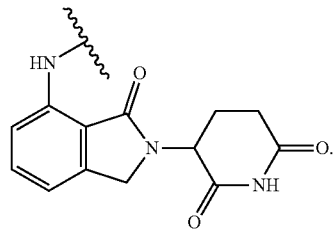 [SMILES: *Nc1cccc2c1C(=O)N(C1CCC(=O)NC1=O)C2]

In embodiments, the ubiquitin ligase binding compound is a lenalidomide moiety, or a stereoisomer thereof, represented by the structure:

In embodiments, the ubiquitin ligase binding compound is a pomalidomide moiety, or a stereoisomer thereof, represented by the structure:

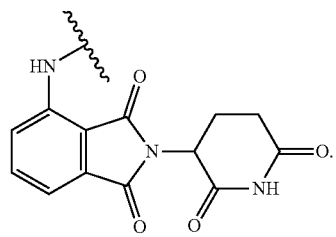 [SMILES: *Nc1cccc2c1C(=O)N(C1CCC(=O)NC1=O)C2=O]

In embodiments, the ubiquitin ligase binding compound is

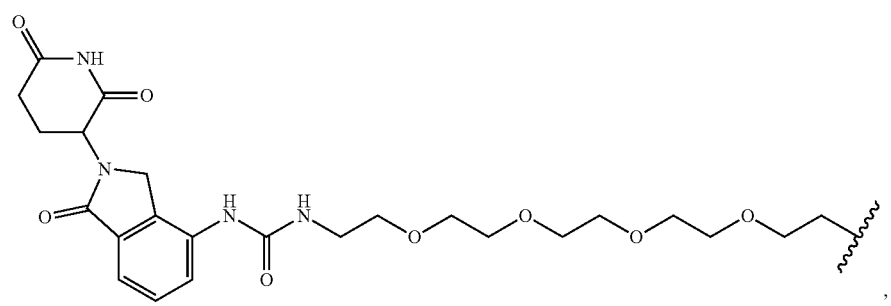

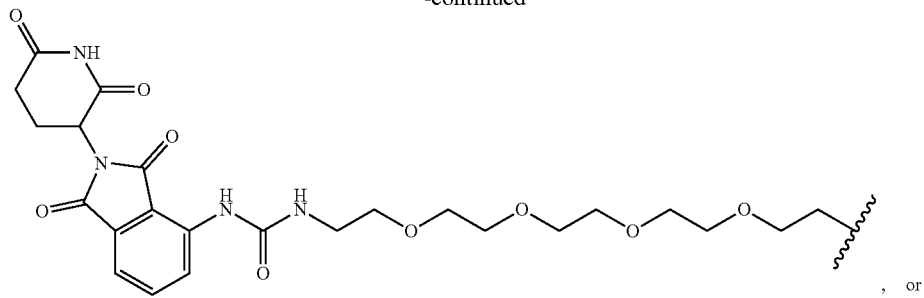
, or
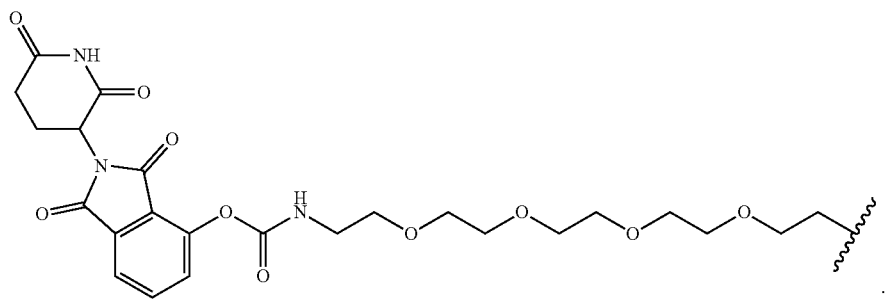
.
In embodiments, the ubiquitin ligase binding compound is VH032, or a stereoisomer thereof, which has the formula:
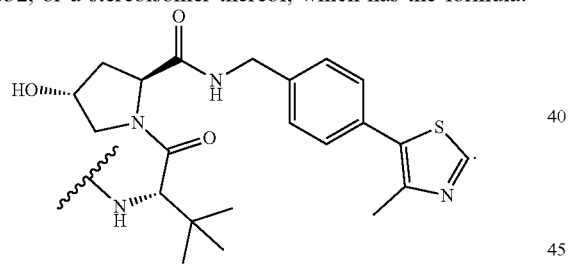
In embodiments, the ubiquitin ligase binding compound is VH298, or a stereoisomer thereof, which has the formula:
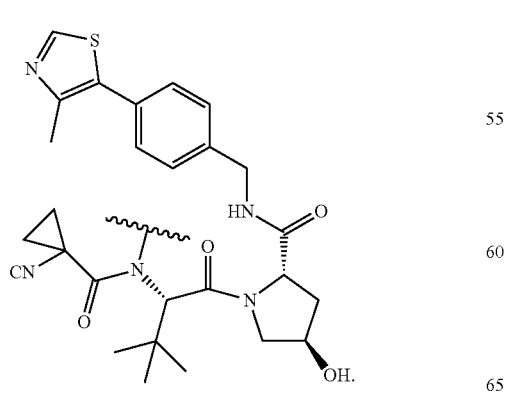

In embodiments, the ubiquitin ligase binding compound is
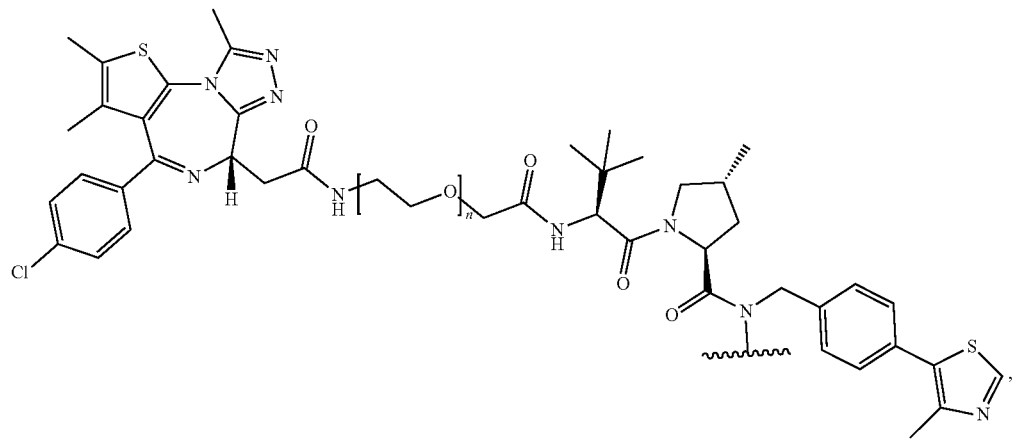
or a stereoisomer thereof, wherein n is an integer from 2 to 4.
In embodiments, the ubiquitin ligase binding compound is
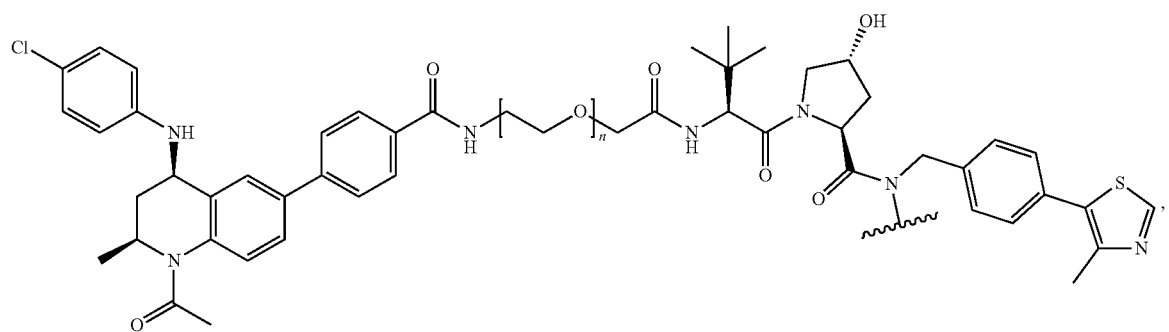
or a stereoisomer thereof, wherein n is an integer from 2 to 4. In aspects, n is 2. In aspects, n is 3. In aspects, n is 4.

In embodiments, -L¹-L2-L³-L⁴-MC is:
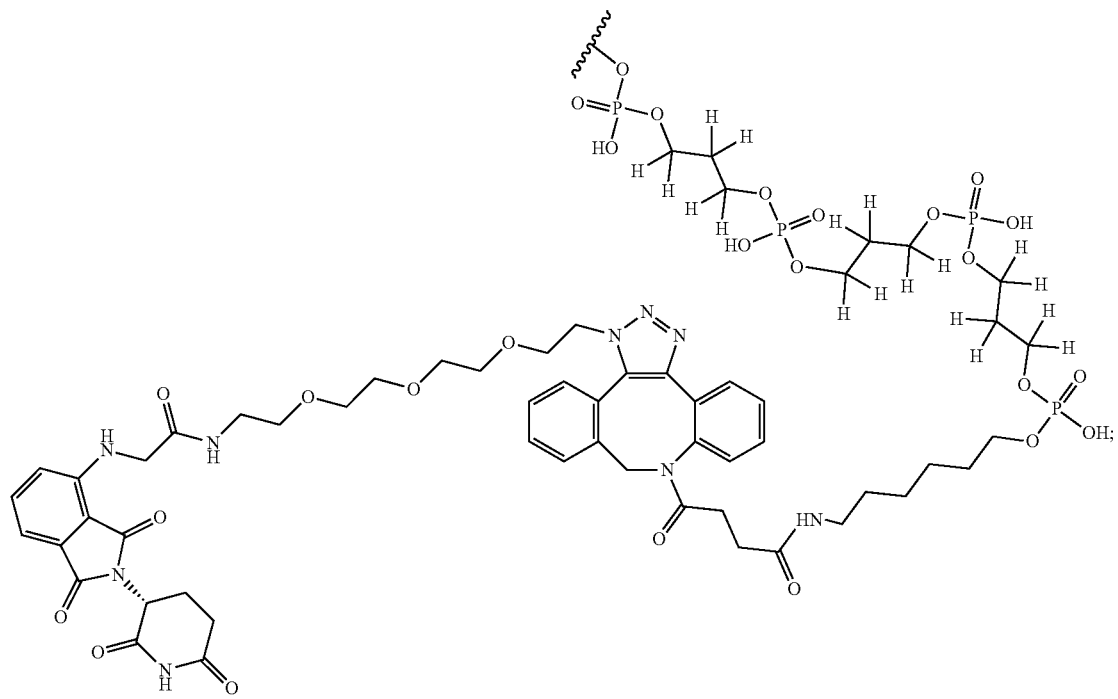 [SMILES: *OP(=O)(O)OCCCOP(=O)(O)OCCCOP(=O)(O)OCCCOP(=O)(O)OCCCCCCNC(=O)CCC(=O)N1Cc2ccccc2-c2c(nnn2CCOCCOCCOCCNC(=O)CNc2cccc3c2C(=O)N([C@@H]2CCC(=O)NC2=O)C3=O)-c2ccccc21]
wherein the nucleic acid is linked at the bond adjacent to the —PO₃OH moiety. In aspects, the nucleic acid is any one of SEQ ID NOS:1-24 or a homolog of any one of SEQ ID NOS:1-24.
In embodiments, -L¹-L²-L³-L⁴-MC is:

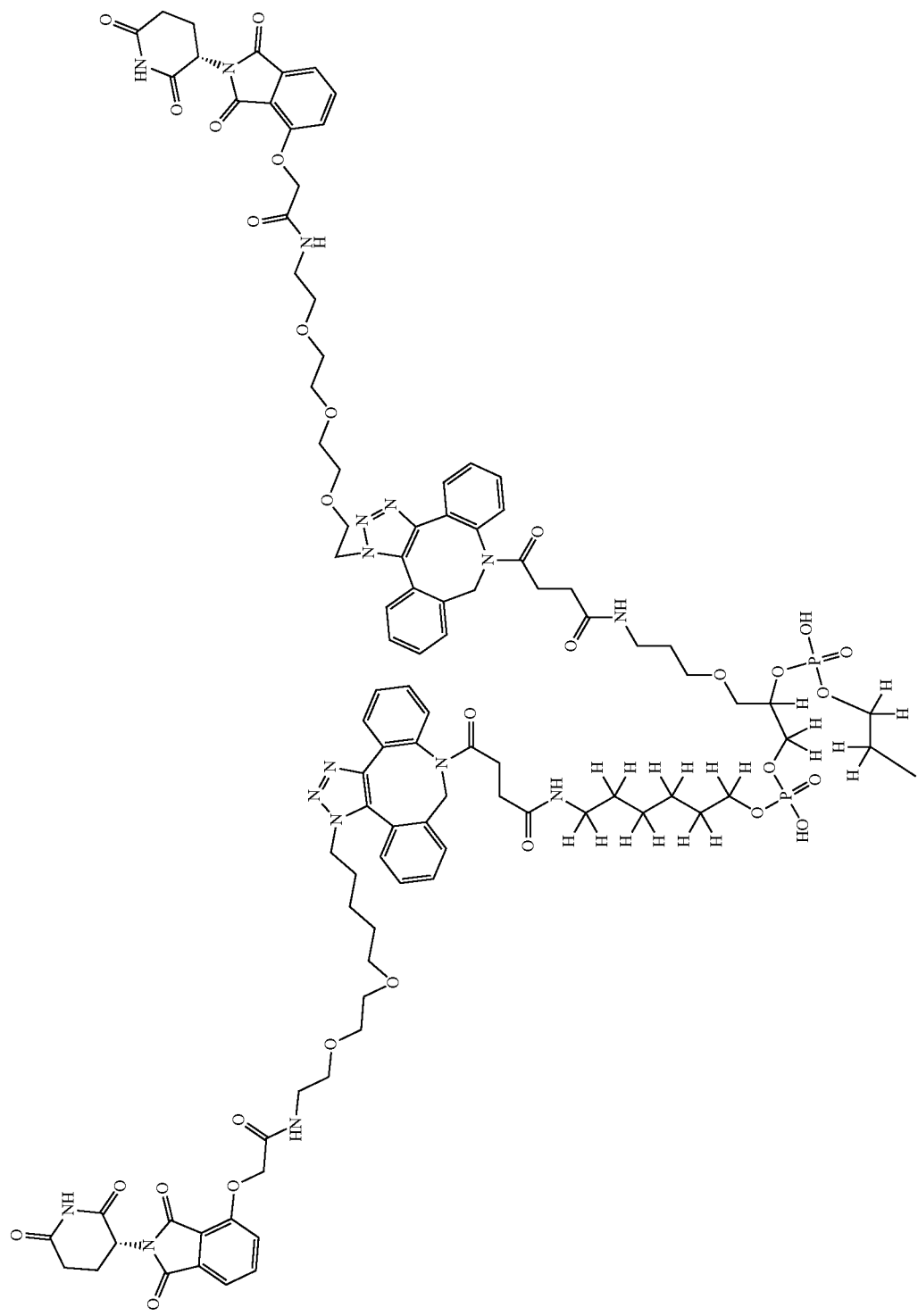

-continued
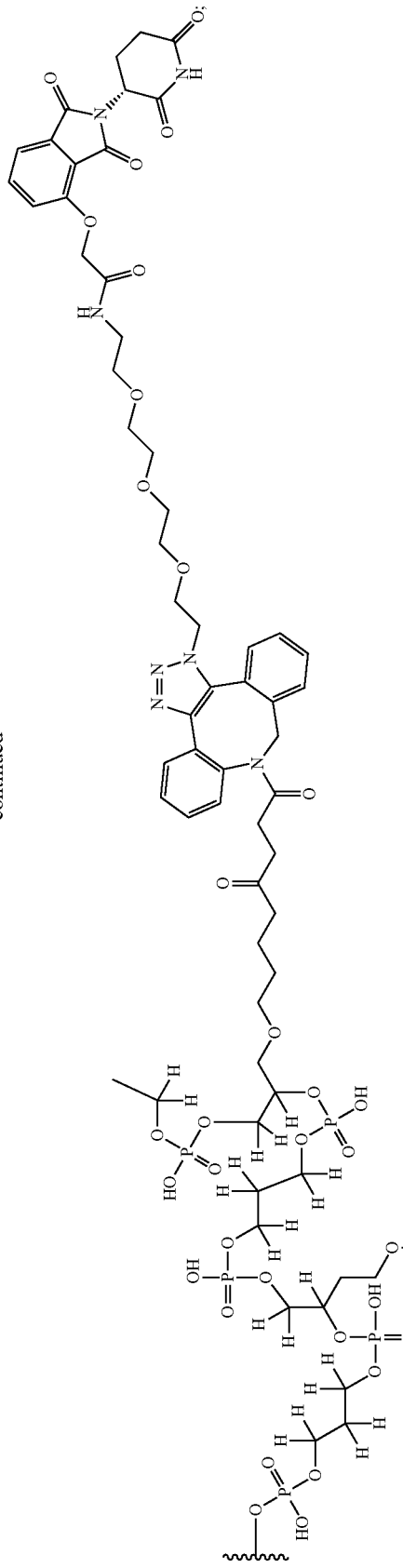
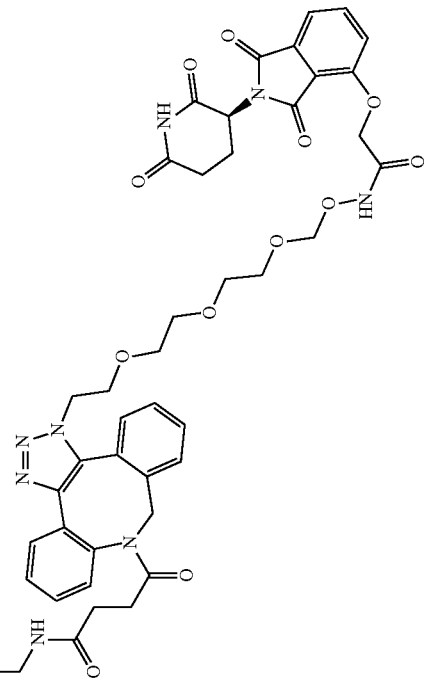

wherein the nucleic acid is linked at the bond adjacent the —$PO_3OH$ moiety. In aspects, the nucleic acid is any one of SEQ ID NOS: 1-24 or a homolog of any one of SEQ ID NOS: 1-24.

In embodiments, In embodiments, -$L^1$-$L^2$-$L^3$-$L^4$- is:

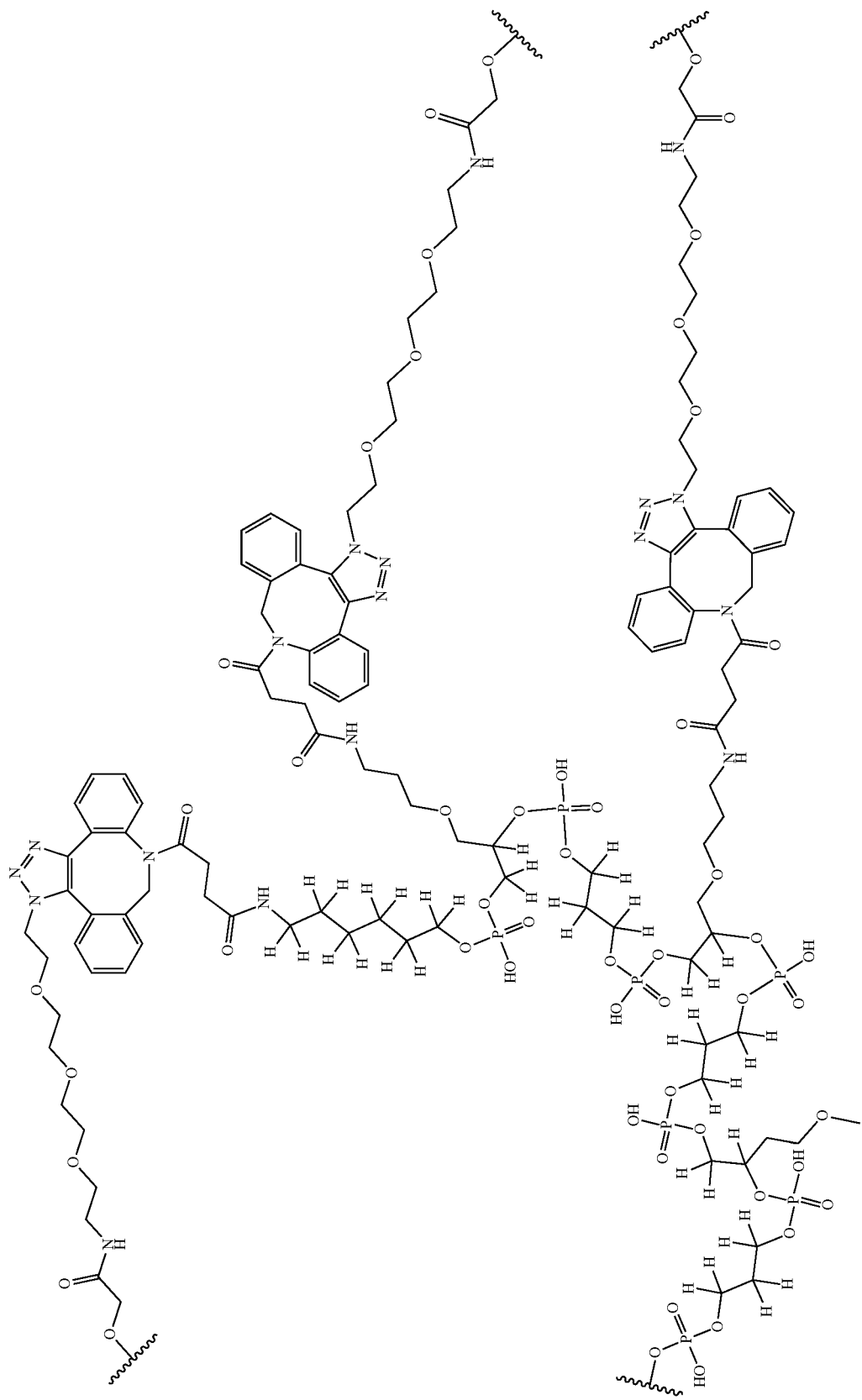

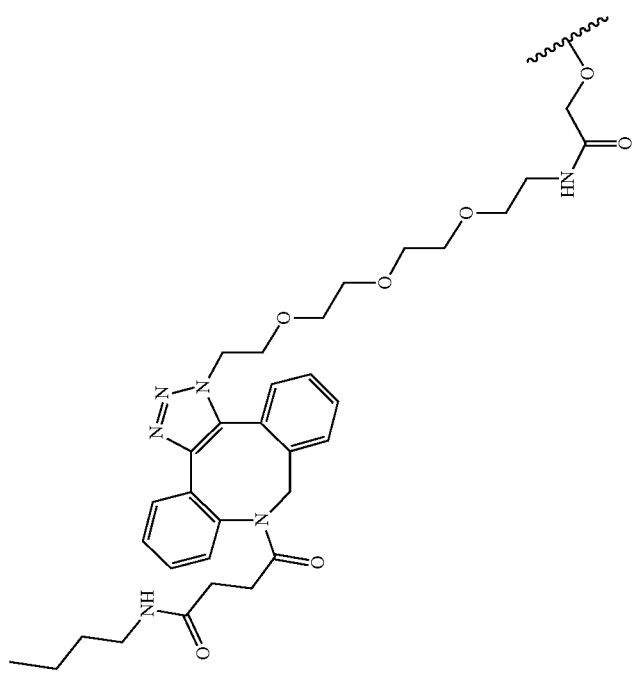

wherein the nucleic acid is linked at the bond adjacent the —$PO_3OH$ moiety; and the ubiquitin ligase binding compounds are linked at the bonds adjacent the —$OCH_2C(=O)NH$— moiety. In aspects, the nucleic acid is any one of SEQ ID NOS:1-24 or a homolog of any one of SEQ ID NOS:1-24.

In embodiments, -$L^1$-$L^2$-$L^3$-$L^4$-is:

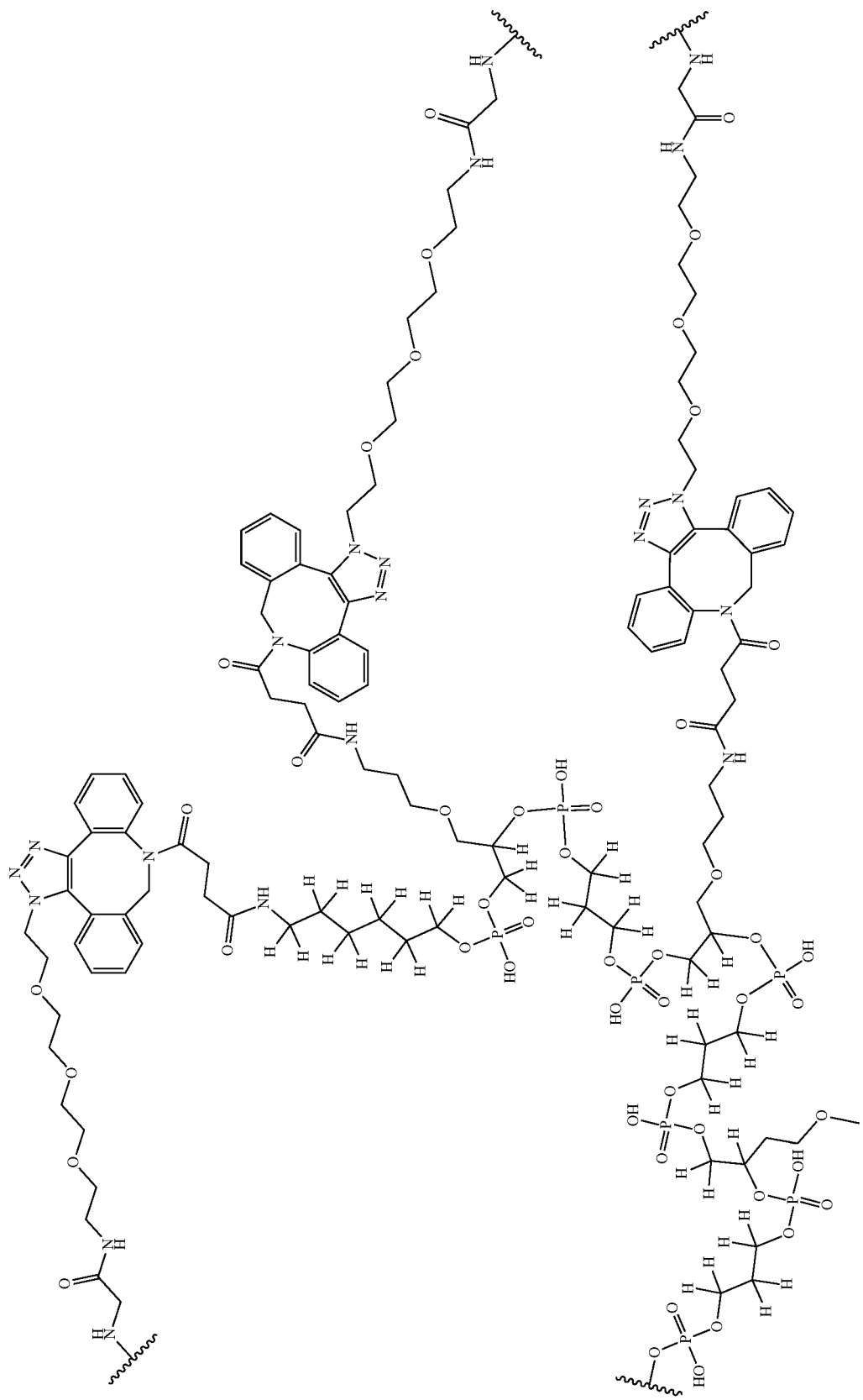

-continued
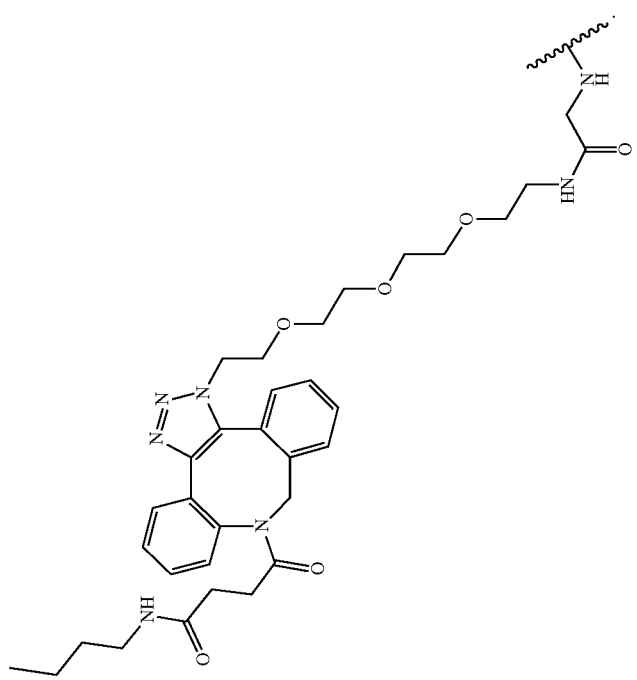

wherein the nucleic acid is linked at the bond adjacent the —PO₃OH moiety; and the ubiquitin ligase binding compounds are linked at the bonds adjacent the —NHCH₂C(=O)NH— moiety. In aspects, the nucleic acid is any one of SEQ ID NOS:1-24 or a homolog of any one of SEQ ID NOS:1-24.

In embodiments, -L¹-L²-L³-L⁴- is:

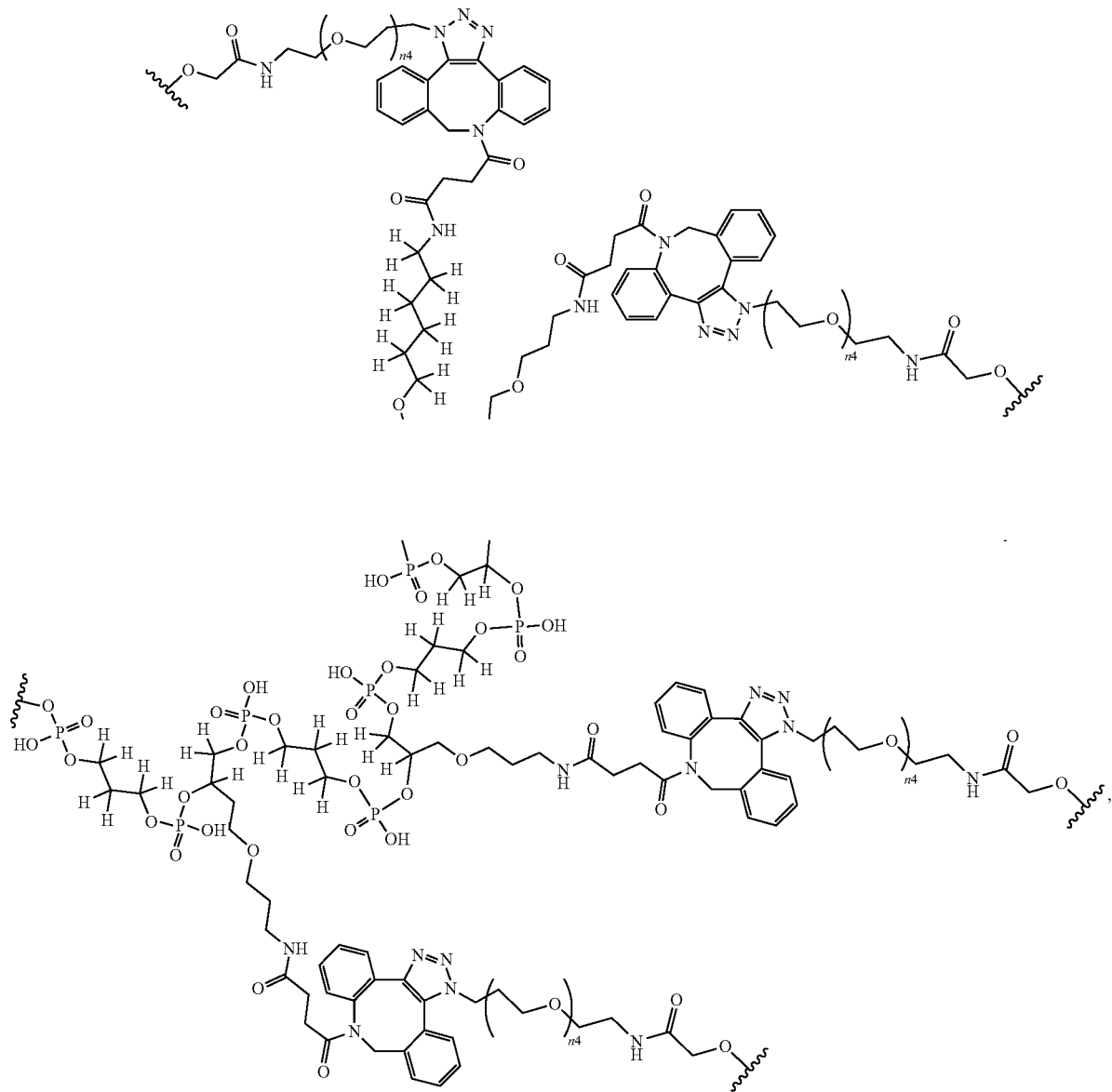

wherein each instance of n4 is independently an integer from 0 to 6; the nucleic acid is linked at the bond adjacent the —PO₃OH moiety; and the ubiquitin ligase binding compounds are linked at the bonds adjacent the —OCH₂C(=O)NH— moiety. In aspects, the nucleic acid is any one of SEQ TD NOS: 1-24 or a homolog of any one of SEQ TD NOS: 1-24.

In embodiments, In embodiments, -L$^1$-L$^2$-L$^3$-L$^4$-MC is:
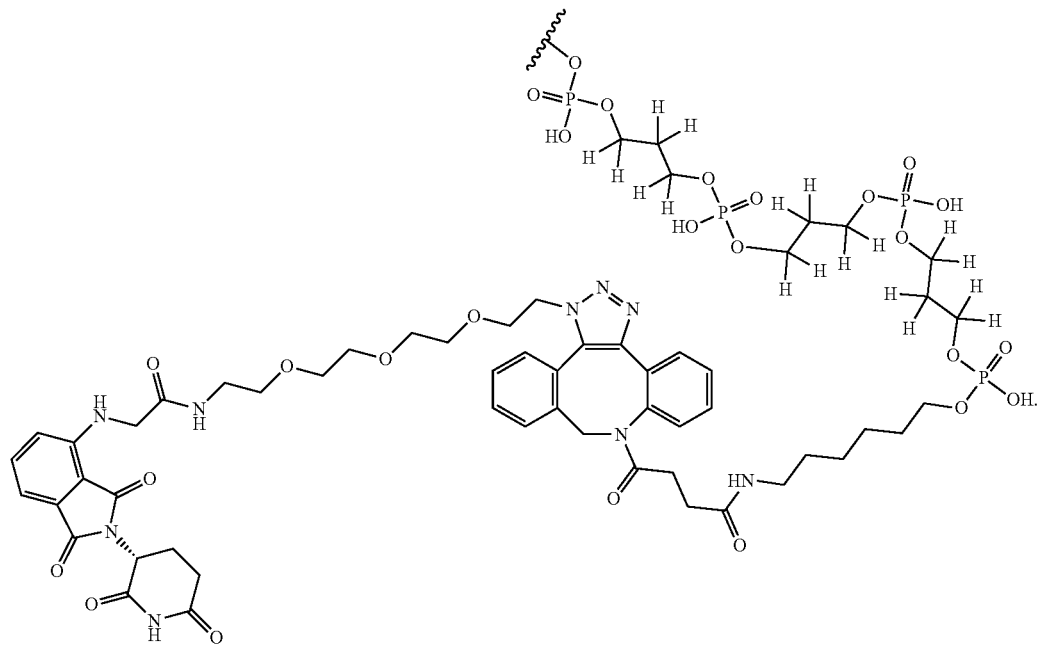 [SMILES: *OP(=O)(O)OCCCOP(=O)(O)OCCCOP(=O)(O)OCCCOP(=O)(O)OCCCCCCNC(=O)CCC(=O)N1Cc2ccccc2-c2c(nnn2CCOCCOCCOCCNC(=O)CNc2cccc3c2C(=O)N([C@@H]2CCC(=O)NC2=O)C3=O)-c2ccccc21]
wherein the nucleic acid is linked at the bond adjacent the —PO$_3$OH moiety. In aspects, the nucleic acid is any one of SEQ ID NOS:1-24 or a homolog of any one of SEQ ID NOS:1-24.
In embodiments, -L$^1$-L$^2$-L$^3$-L$^4$- is:
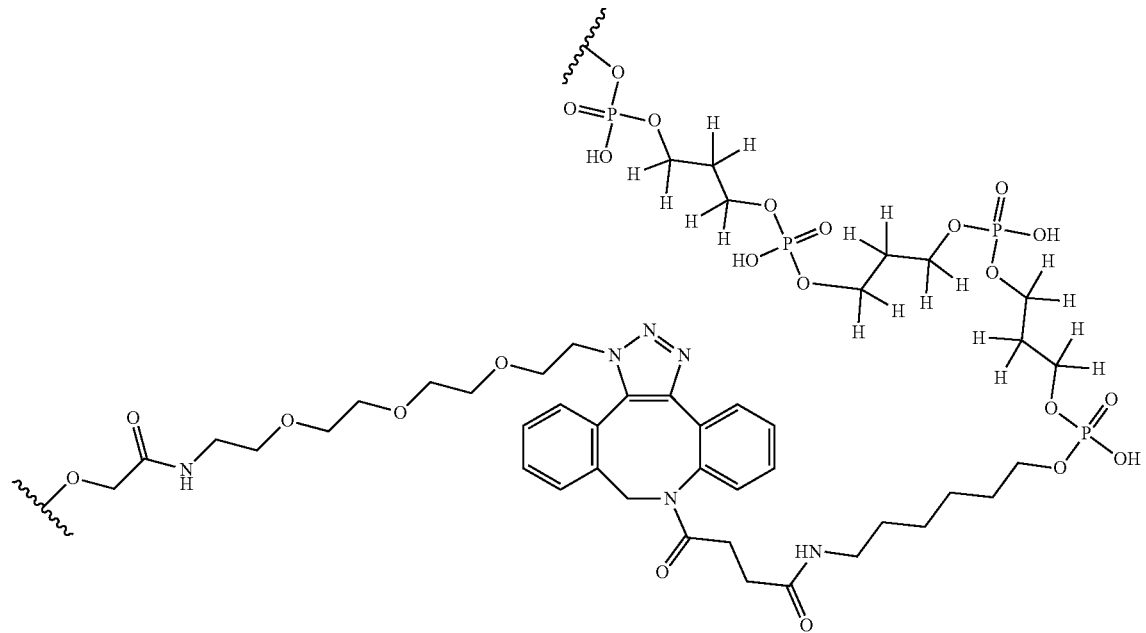 [SMILES: *OCC(=O)NCCOCCOCCOCCn1nnc2c1-c1ccccc1CN(C(=O)CCC(=O)NCCCCCCOP(=O)(O)OCCCOP(=O)(O)OCCCOP(=O)(O)OCCCOP(=O)(O)O*)c1ccccc1-2]

wherein the nucleic acid is linked at the bond adjacent the —$PO_3OH$ moiety; and the ubiquitin ligase binding compounds are linked at the bonds adjacent the —$OCH_2C(=O)NH$— moiety. In aspects, the nucleic acid is any one of SEQ ID NOS:1-24 or a homolog of any one of SEQ ID NOS:1-24.

In embodiments, -$L^1$-$L^2$-$L^3$-$L^4$-MC is:

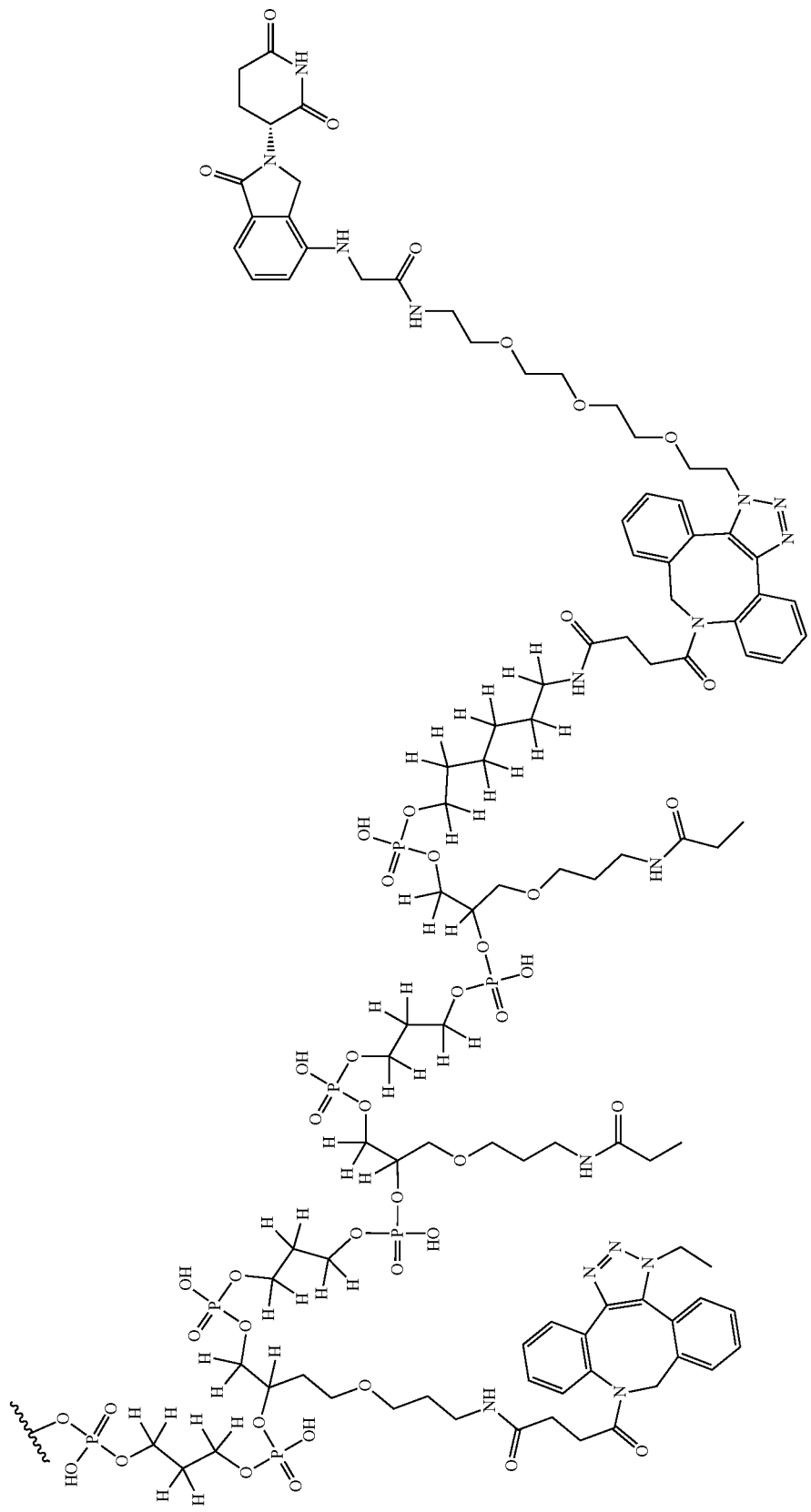

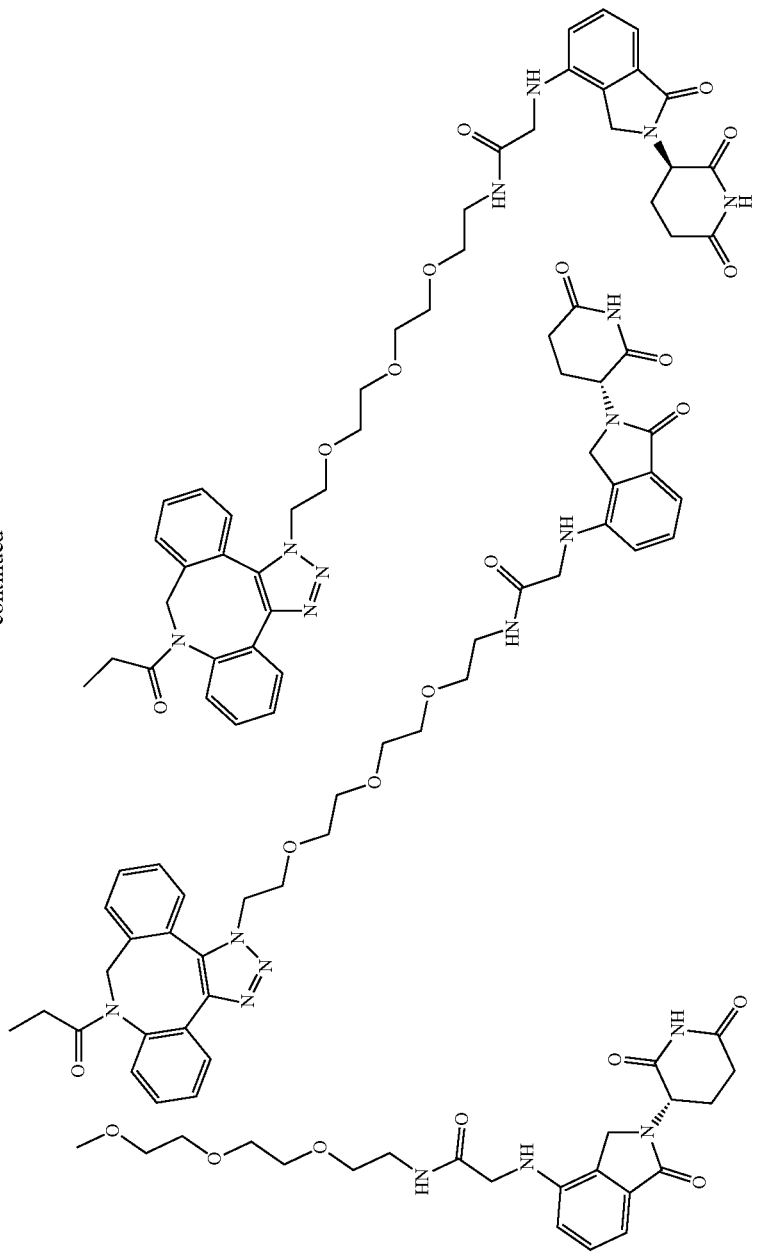

wherein the nucleic acid is linked at the bond adjacent the —PO₃OH moiety. In aspects, the nucleic acid is any one of SEQ ID NOS: 1-24 or a homolog of any one of SEQ ID NOS: 1-24.

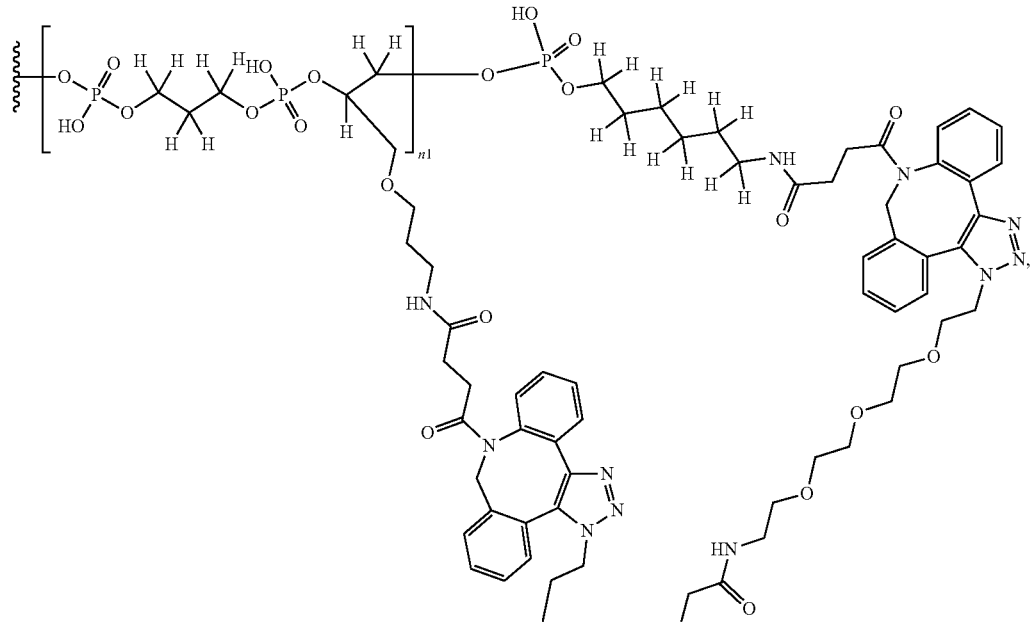

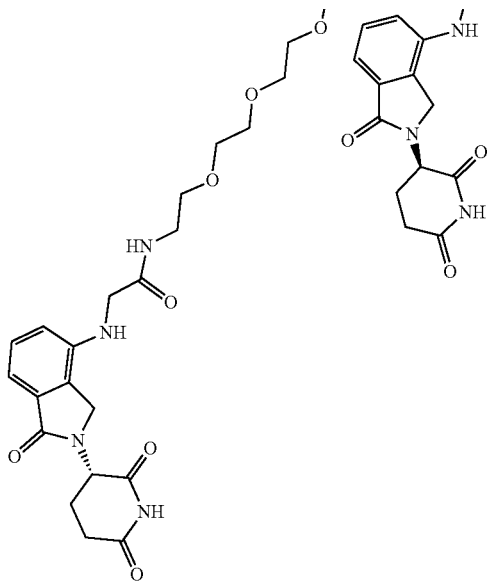

60 wherein n1 is an integer from 0 to 4; and wherein the nucleic acid is linked at the bond adjacent the —PO₃OH moiety. In aspects, n1 is 0. In aspects, n1 is 2. In aspects n1 is 3. In aspects, n1 is 4. In aspects, the nucleic acid is any one of SEQ ID NOS:1-24 or a homolog of any one of SEQ ID NOS:1-24.

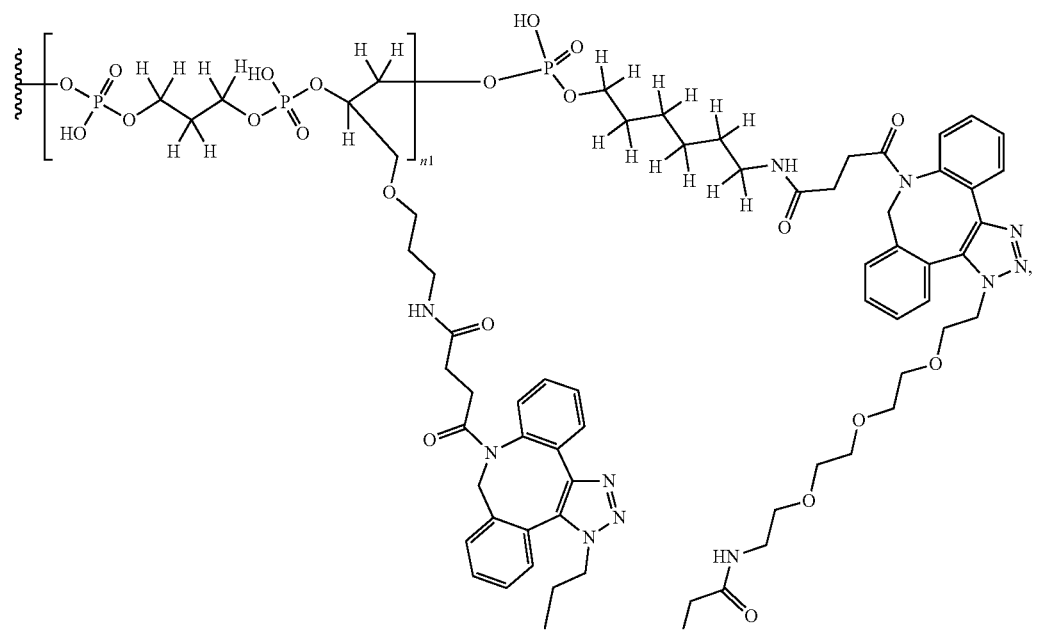
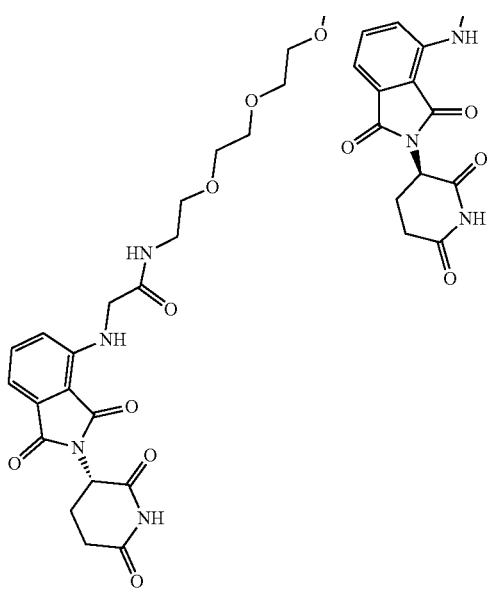
wherein n1 is an integer from 0 to 4; and wherein the nucleic acid is linked at the bond adjacent the —PO₃OH moiety. In aspects, n1 is 0. In aspects, n1 is 2. In aspects n1 is 3. In aspects, n1 is 4. In aspects, the nucleic acid is any one of SEQ ID NOS:1-24 or a homolog of any one of SEQ ID NOS:1-24.

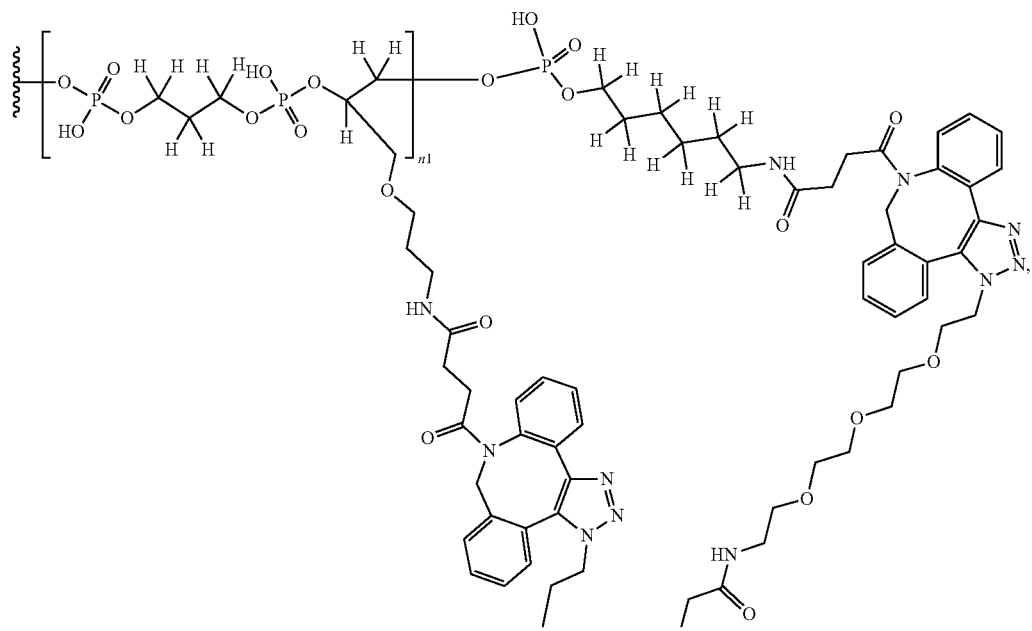
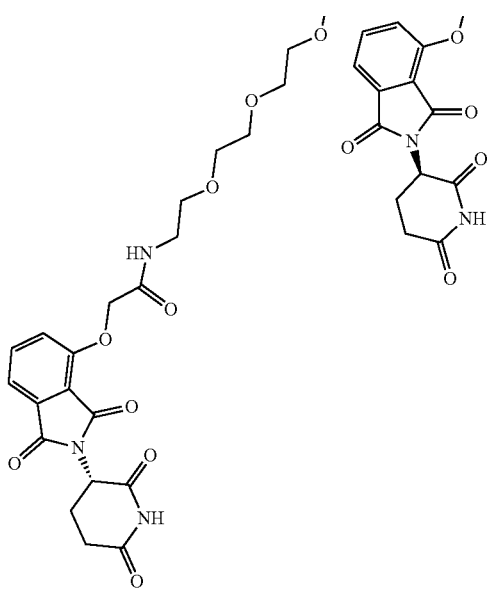
wherein n1 is an integer from 0 to 4; and wherein the nucleic acid is linked at the bond adjacent the —PO₃OH moiety. In aspects, n1 is 0. In aspects, n1 is 2. In aspects n1 is 3. In aspects, n1 is 4. In aspects, the nucleic acid is any one of SEQ TD NOS:1-24 or a homolog of any one of SEQ TD NOS:1-24.

In embodiments, -L$^1$-L$^2$-L$^3$-L$^4$-M is:
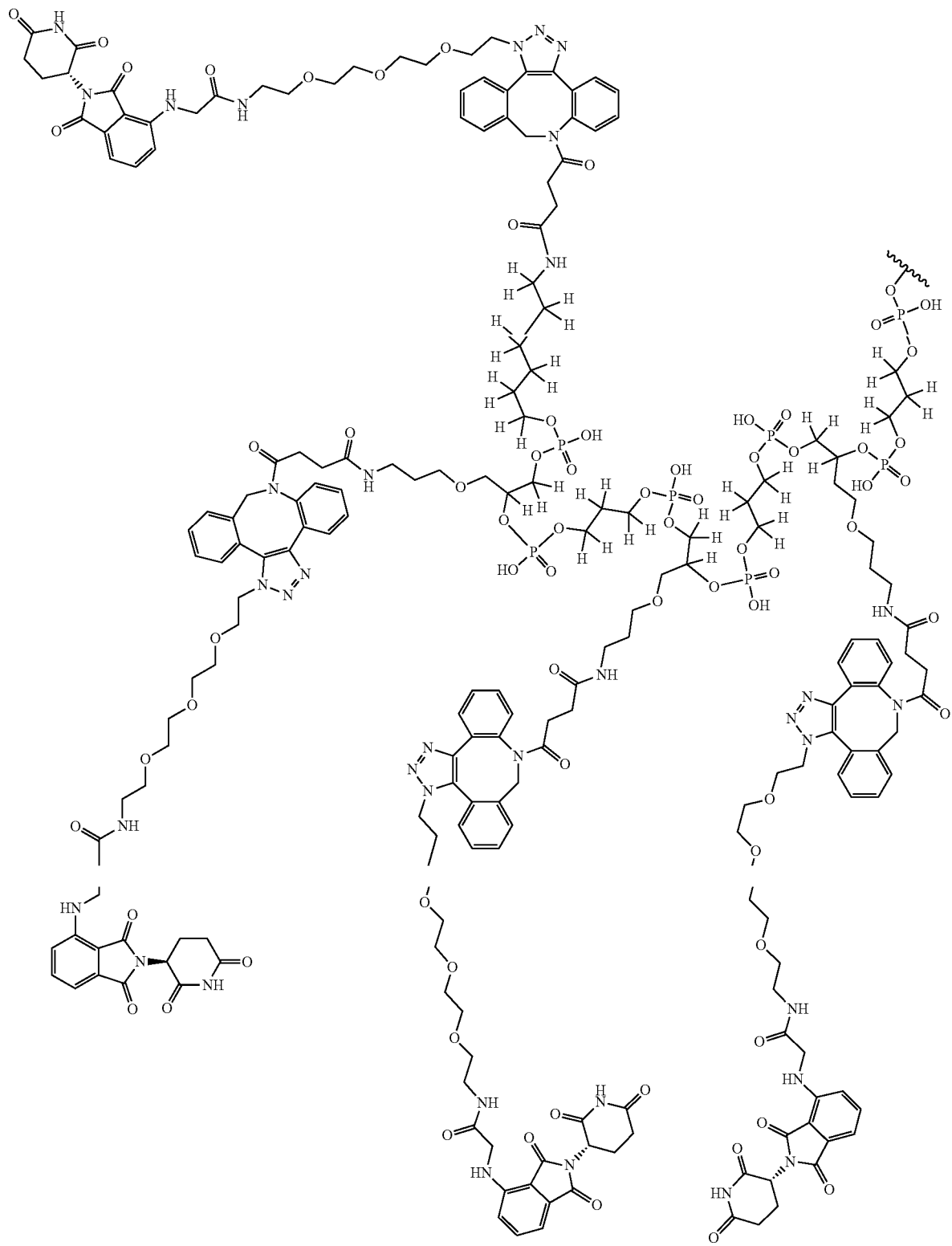
wherein the nucleic acid is linked at the bond adjacent the —PO$_3$OH moiety. In aspects, the nucleic acid is any one of SEQ ID NOS: 1-24 or a homolog of any one of SEQ ID NOS: 1-24.

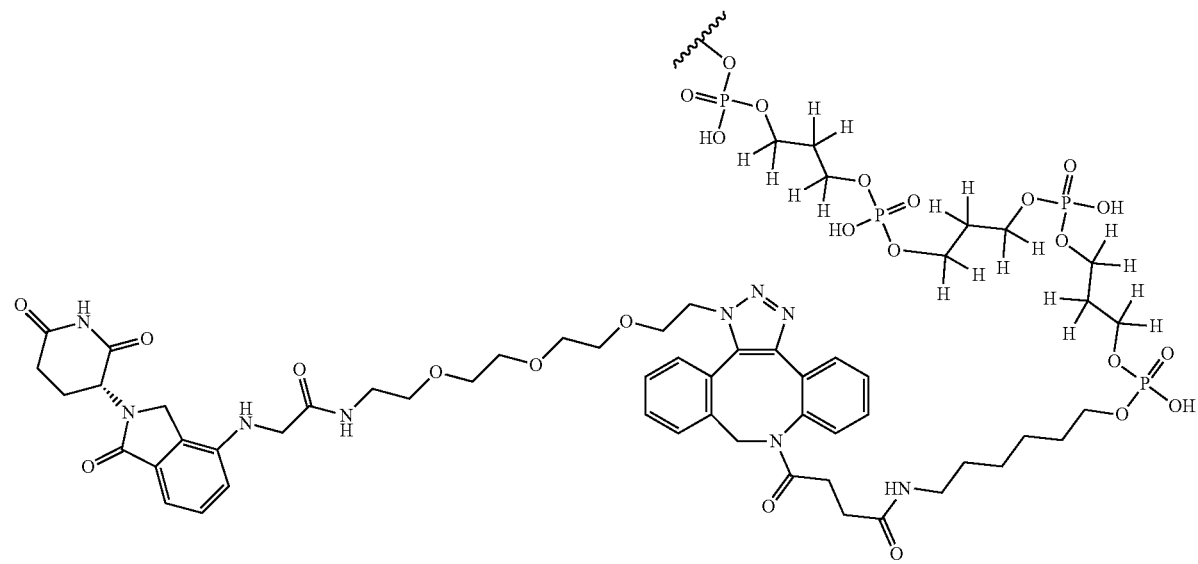 [SMILES: *OP(=O)(O)OCCCOP(=O)(O)OCCCOP(=O)(O)OCCCOP(=O)(O)OCCCCCCNC(=O)CCC(=O)N1Cc2ccccc2-c2c(nnn2CCOCCOCCOCCNC(=O)CNc2cccc3c2CN([C@@H]2CCC(=O)NC2=O)C3=O)-c2ccccc21]
wherein the nucleic acid is linked at the bond adjacent the —PO$_3$OH moiety. In aspects, the nucleic acid is any one of SEQ ID NOS:1-24 or a homolog of any one of SEQ ID NOS:1-24.

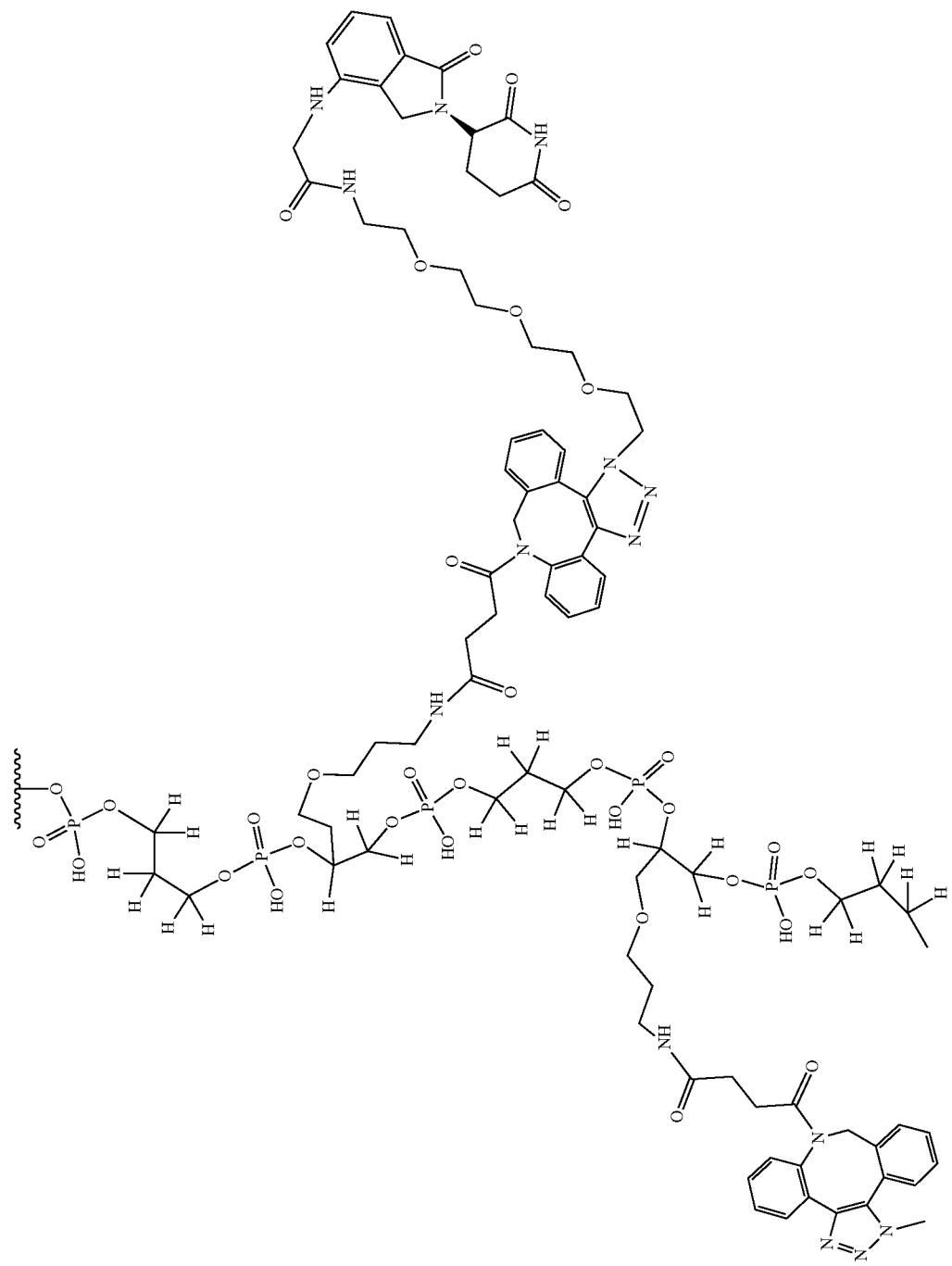

-continued
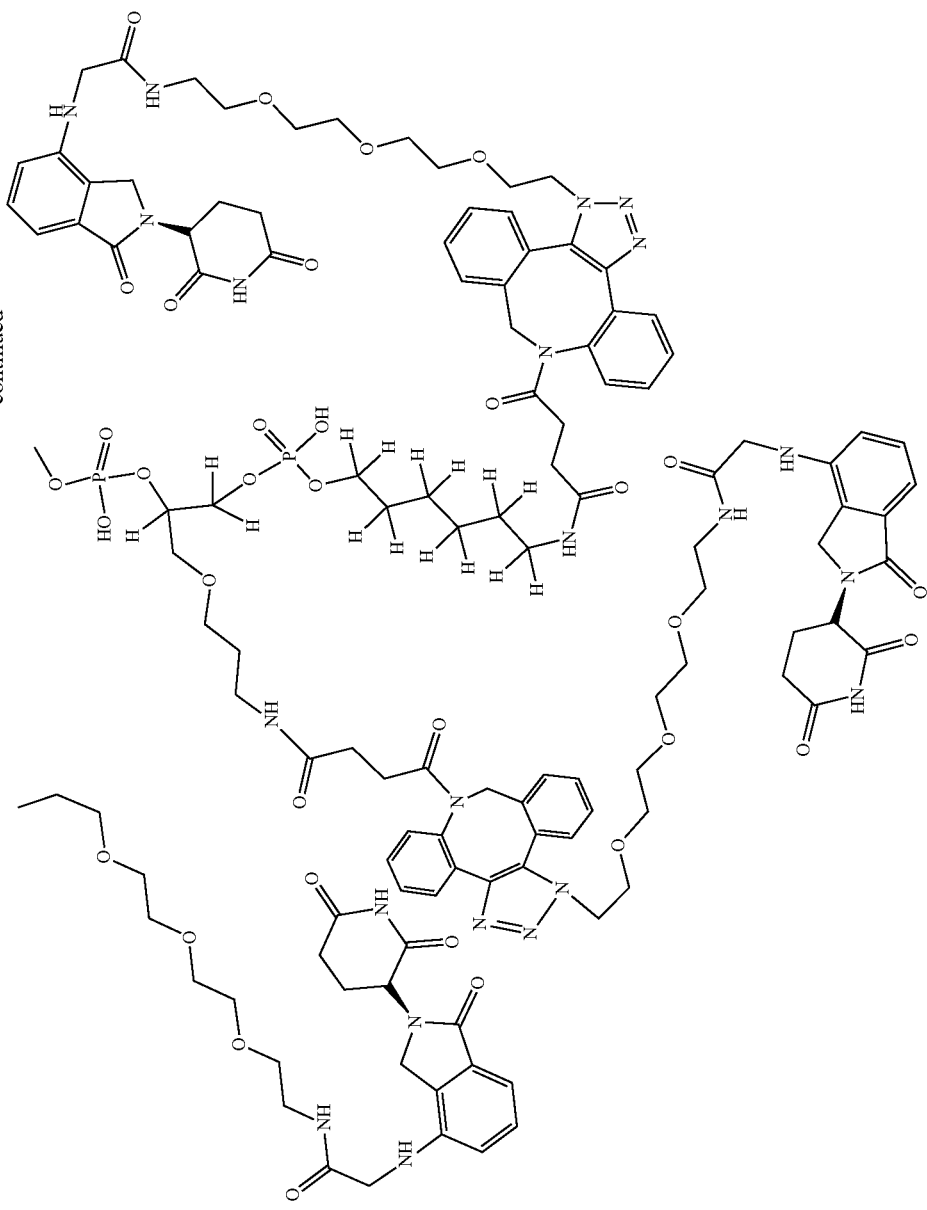

wherein the nucleic acid is linked at the bond adjacent the —$PO_3OH$ moiety. In aspects, the nucleic acid is any one of SEQ ID NOS:1-24 or a homolog of any one of SEQ ID NOS:1-24.

In embodiments, -$L^1$-$L^2$-$L^3$-$L^4$-MC is:

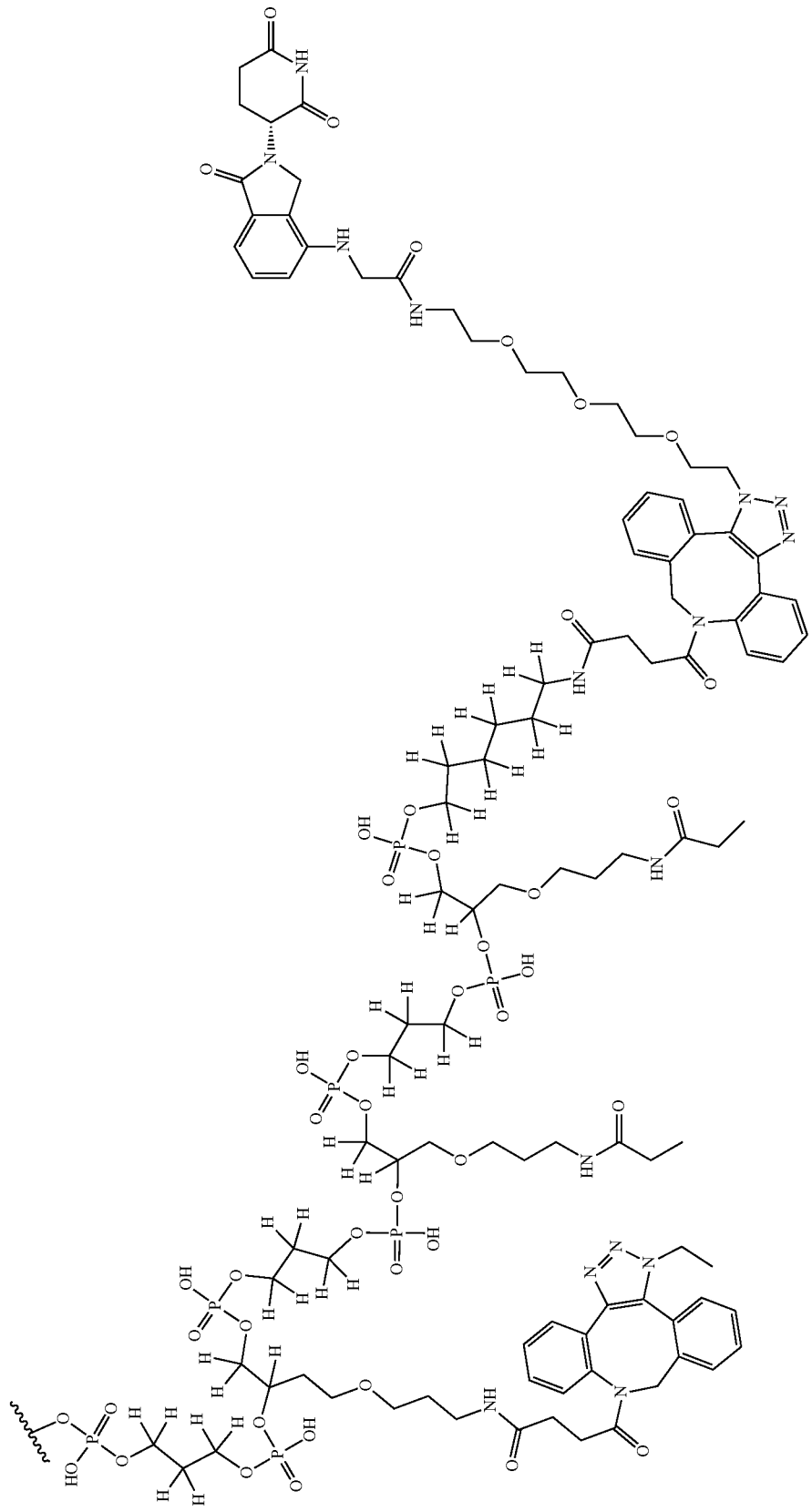

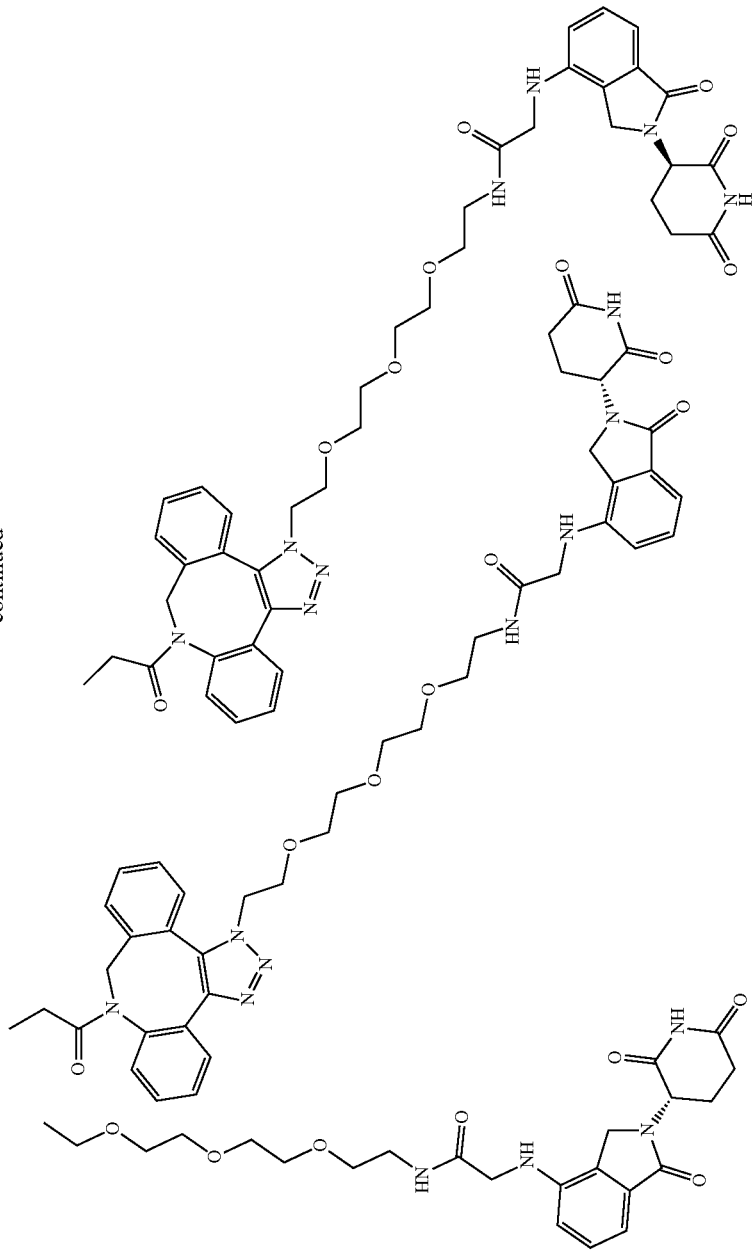

wherein the nucleic acid is linked at the bond adjacent the —PO$_3$OH moiety. In aspects, the nucleic acid is any one of SEQ ID NOS: 1-24 or a homolog of any one of SEQ ID NOS: 1-24.

In embodiments described herein, the nucleic acid sequence (e.g., first and/or second nucleic acid sequence) is bonded to the L$^1$ portion of the -L$^1$-L$^2$-L$^3$-L$^4$-MC linker. The nucleic acid sequence can be any described herein. In aspects, L$^1$ is bonded to the nucleic acid sequence at the 3'-terminus. In aspects, L$^1$ is bonded to the nucleic acid sequence at the 5'-terminus. In aspects, L$^1$ is bonded to any nucleotide in the nucleic acid sequence. In aspects where the compound contains two nucleic acid sequences, L$^1$ is bonded to the first nucleic acid, L$^1$ is bonded to the second nucleic acid, or L$^1$ is bonded to the spacer between the first nucleic acid sequence and the second nucleic acid sequence. In aspects, where the compound contains two nucleic acid sequences and two or more -L$^1$-L$^2$-L$^3$-L$^4$-MC linkers, the linking groups can all be bound to the first nucleic acid or to the second nucleic acid or to the spacer between the first nucleic acid and the second nucleic acid. In aspects, the linking groups can be bonded to the first nucleic acid and the spacer; to the first nucleic acid and the second nucleic acid; to the second nucleic acid and the spacer; or to the first nucleic acid, the second nucleic acid, and the spacer.

In embodiments, the nucleic acid sequence (e.g., first or second nucleic acid sequence) is any one of SEQ ID NOS:1-24 or homologs thereof. In aspects, the nucleic acid sequence (e.g., first or second nucleic acid sequence) is SEQ ID NO:1 or a homolog thereof. In aspects, the nucleic acid sequence (e.g., first or second nucleic acid sequence) is SEQ ID NO:2 or a homolog thereof. In aspects, the nucleic acid sequence (e.g., first or second nucleic acid sequence) is SEQ ID NO:3 or a homolog thereof. In aspects, the nucleic acid sequence (e.g., first or second nucleic acid sequence) is SEQ ID NO:4 or a homolog thereof. In aspects, the nucleic acid sequence (e.g., first or second nucleic acid sequence) is SEQ ID NO:5 or a homolog thereof. In aspects, the nucleic acid sequence (e.g., first or second nucleic acid sequence) is SEQ ID NO:6 or a homolog thereof. In aspects, the nucleic acid sequence (e.g., first or second nucleic acid sequence) is SEQ ID NO:7 or a homolog thereof. In aspects, the nucleic acid sequence (e.g., first or second nucleic acid sequence) is SEQ ID NO:8 or a homolog thereof. In aspects, the nucleic acid sequence (e.g., first or second nucleic acid sequence) is SEQ ID NO:9 or a homolog thereof. In aspects, the nucleic acid sequence (e.g., first or second nucleic acid sequence) is SEQ ID NO:10 or a homolog thereof. In aspects, the nucleic acid sequence (e.g., first or second nucleic acid sequence) is SEQ ID NO:11 or a homolog thereof. In aspects, the nucleic acid sequence (e.g., first or second nucleic acid sequence) is SEQ ID NO:12 or a homolog thereof. In aspects, the nucleic acid sequence (e.g., first or second nucleic acid sequence) is SEQ ID NO:13 or a homolog thereof. In aspects, the nucleic acid sequence (e.g., first or second nucleic acid sequence) is SEQ ID NO:14 or a homolog thereof. In aspects, the nucleic acid sequence (e.g., first or second nucleic acid sequence) is SEQ ID NO:15 or a homolog thereof. In aspects, the nucleic acid sequence (e.g., first or second nucleic acid sequence) is SEQ ID NO:16 or a homolog thereof. In aspects, the nucleic acid sequence (e.g., first or second nucleic acid sequence) is SEQ ID NO:17 or a homolog thereof. In aspects, the nucleic acid sequence (e.g., first or second nucleic acid sequence) is SEQ ID NO:18 or a homolog thereof. In aspects, the nucleic acid sequence (e.g., first or second nucleic acid sequence) is SEQ ID NO:19 or a homolog thereof. In aspects, the nucleic acid sequence (e.g., first or second nucleic acid sequence) is SEQ ID NO:20 or a homolog thereof. In aspects, the nucleic acid sequence (e.g., first or second nucleic acid sequence) is SEQ ID NO:21 or a homolog thereof. In aspects, the nucleic acid sequence (e.g., first or second nucleic acid sequence) is SEQ ID NO:22 or a homolog thereof. In aspects, the nucleic acid sequence (e.g., first or second nucleic acid sequence) is SEQ ID NO:23 or a homolog thereof. In aspects, the nucleic acid sequence (e.g., first or second nucleic acid sequence) is SEQ ID NO:24 or a homolog thereof.

In embodiments, the disclosure provides a compound shown in FIG. 2, FIG. 4, FIG. 5, FIG. 6, FIG. 7, FIG. 8, FIG. 9, or FIG. 10. In aspects, the compound has at least 80% sequence identity to the nucleic acid in the compound shown in FIG. 2, FIG. 4, FIG. 5, FIG. 6, FIG. 7, FIG. 8, FIG. 9, or FIG. 10. In aspects, the compound has at least 85% sequence identity to the nucleic acid in the compound shown in FIG. 2, FIG. 4, FIG. 5, FIG. 6, FIG. 7, FIG. 8, FIG. 9, or FIG. 10. In aspects, the compound has at least 90% sequence identity to the nucleic acid in the compound shown in FIG. 2, FIG. 4, FIG. 5, FIG. 6, FIG. 7, FIG. 8, FIG. 9, or FIG. 10. In aspects, the compound has at least 92% sequence identity to the nucleic acid in the compound shown in FIG. 2, FIG. 4, FIG. 5, FIG. 6, FIG. 7, FIG. 8, FIG. 9, or FIG. 10. In aspects, the compound has at least 94% sequence identity to the nucleic acid in the compound shown in FIG. 2, FIG. 4, FIG. 5, FIG. 6, FIG. 7, FIG. 8, FIG. 9, or FIG. 10. In aspects, the compound has at least 95% sequence identity to the nucleic acid in the compound shown in FIG. 2, FIG. 4, FIG. 5, FIG. 6, FIG. 7, FIG. 8, FIG. 9, or FIG. 10. In aspects, the compound has at least 96% sequence identity to the nucleic acid in the compound shown in FIG. 2, FIG. 4, FIG. 5, FIG. 6, FIG. 7, FIG. 8, FIG. 9, or FIG. 10. In aspects, the compound has at least 98% sequence identity to the nucleic acid in the compound shown in FIG. 2, FIG. 4, FIG. 5, FIG. 6, FIG. 7, FIG. 8, FIG. 9, or FIG. 10. In aspects, the disclosure provides a compound shown in FIG. 2 or a homolog thereof. In aspects, the disclosure provides a compound shown in FIG. 4 or a homolog thereof. In aspects, the disclosure provides a compound shown in FIG. 5 or a homolog thereof. In aspects, the disclosure provides a compound shown in FIG. 6 or a homolog thereof. In aspects, the disclosure provides a compound shown in FIG. 7 or a homolog thereof. In aspects, the disclosure provides a compound shown in FIG. 8 or a homolog thereof. In aspects, the disclosure provides a compound shown in FIG. 9 or a homolog thereof. In aspects, the disclosure provides a compound shown in FIG. 10 or a homolog thereof.

In embodiments, the disclosure provides a compound comprising: (i) a nucleic acid selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and a homolog of any one of the foregoing; and (ii) one or more ubiquitin ligase binding compounds selected from the group consisting of:

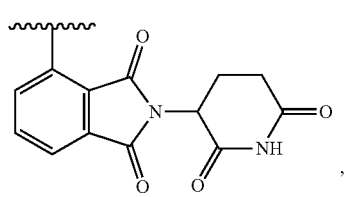
(A)
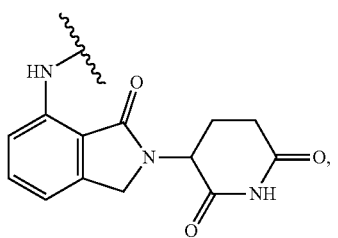
(B)
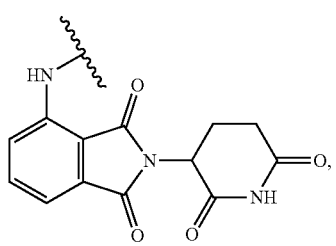
(C)
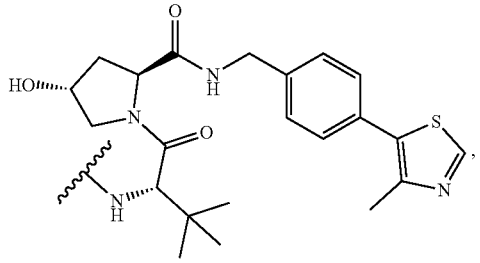
(D)
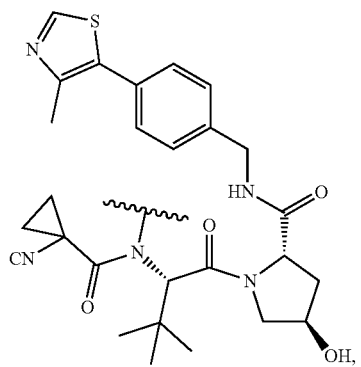
(E)
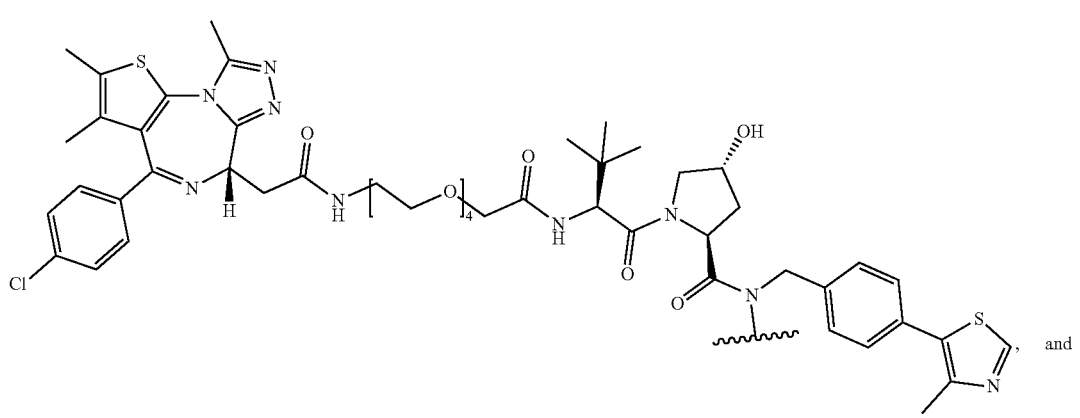
(F)
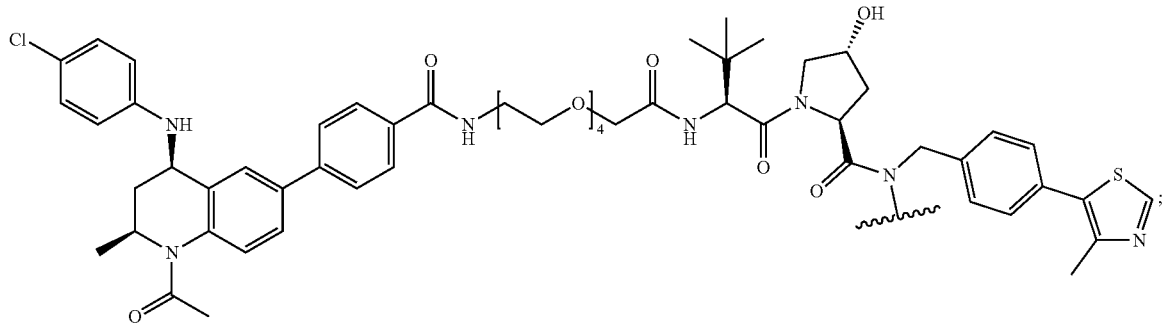
and (G)

wherein the nucleic acid is covalently bonded (optionally via a spacer or a linker, such as -L¹-L²-L³-L⁴-) to the one or more ubiquitin ligase binding compounds. In aspects, the disclosure provides a compound comprising: (i) a nucleic acid having at least 90% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24, and (ii) one or more ubiquitin ligase binding compounds selected from the group consisting of (A), (B), (C), (D), (E), (F), and (G); wherein the nucleic acid is covalently bonded to the ubiquitin ligase binding compound optionally via a spacer or a linker, such as -L¹-L²-L³-L⁴-. In aspects, the disclosure provides a compound comprising: (i) a nucleic acid having at least 92% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24, and (ii) one or more ubiquitin ligase binding compounds selected from the group consisting of (A), (B), (C), (D), (E), (F), and (G); wherein the nucleic acid is covalently bonded to the ubiquitin ligase binding compound optionally via a spacer or a linker, such as -L¹-L²-L³-L⁴-. In aspects, the disclosure provides a compound comprising: (i) a nucleic acid having at least 94% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24, and (ii) one or more ubiquitin ligase binding compounds selected from the group consisting of (A), (B), (C), (D), (E), (F), and (G); wherein the nucleic acid is covalently bonded to the ubiquitin ligase binding compound optionally via a spacer or a linker, such as -L¹-L²-L³-L⁴-. In aspects, the disclosure provides a compound comprising: (i) a nucleic acid having at least 96% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24, and (ii) one or more ubiquitin ligase binding compounds selected from the group consisting of (A), (B), (C), (D), (E), (F), and (G); wherein the nucleic acid is covalently bonded to the ubiquitin ligase binding compound optionally via a spacer or a linker, such as -L¹-L²-L³-L⁴-. In aspects, the disclosure provides a compound comprising: (i) a nucleic acid having at least 98% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24, and (ii) one or more ubiquitin ligase binding compounds selected from the group consisting of (A), (B), (C), (D), (E), (F), and (G); wherein the nucleic acid is covalently bonded to the ubiquitin ligase binding compound optionally via a spacer or a linker, such as -L¹-L²-L³-L⁴-. In aspects, the nucleic acid is SEQ ID NO:1. In aspects, the nucleic acid is SEQ ID NO:2. In aspects, the nucleic acid is SEQ ID NO:3. In aspects, the nucleic acid is SEQ ID NO: 4. In aspects, the nucleic acid is SEQ ID NO: 5. In aspects, the nucleic acid is SEQ ID NO:6. In aspects, the nucleic acid is SEQ ID NO:7. In aspects, the nucleic acid is SEQ ID NO: 8. In aspects, the nucleic acid is SEQ ID NO: 9. In aspects, the nucleic acid is SEQ ID NO: 10. In aspects, the nucleic acid is SEQ ID NO: 11. In aspects, the nucleic acid is SEQ ID NO: 12. In aspects, the nucleic acid is SEQ ID NO: 13. In aspects, the nucleic acid is SEQ ID NO: 14. In aspects, the nucleic acid is SEQ ID NO: 15. In aspects, the nucleic acid is SEQ ID NO: 16. In aspects, the nucleic acid is SEQ ID NO: 17. In aspects, the nucleic acid is SEQ ID NO: 18. In aspects, the nucleic acid is SEQ ID NO: 19. In aspects, the nucleic acid is SEQ ID NO:20. In aspects, the nucleic acid is SEQ ID NO:21. In aspects, the nucleic acid is SEQ ID NO:22. In aspects, the nucleic acid is SEQ ID NO:23. In aspects, the nucleic acid is SEQ ID NO:24. In aspects, the ubiquitin ligase binding compound is (A). In aspects, the ubiquitin ligase binding compound is (B). In aspects, the ubiquitin ligase binding compound is (C). In aspects, the ubiquitin ligase binding compound is (D). In aspects, the ubiquitin ligase binding compound is (E). In aspects, the ubiquitin ligase binding compound is (F). In aspects, the ubiquitin ligase binding compound is (G). In aspects, the nucleic acid is covalently bonded to the one or more ubiquitin ligase binding compounds through a linking group, such as -L¹-L²-L³-L⁴-. In aspects, the one or more ubiquitin ligase binding compounds are bonded to the 3'-terminus of the nucleic acid, optionally through a linking group, such as -L¹-L²-L³-L⁴-. In aspects, the one or more ubiquitin ligase binding compounds are bonded to the 5'-terminus of the nucleic acid, optionally through a linking group, such as -L¹-L²-L³-L⁴-. In aspects, the one or more ubiquitin ligase binding compounds are bonded to any nucleotide in the nucleic acid, optionally through a linking group, such as -L¹-L²-L³-L⁴-. In aspects, the one or more ubiquitin ligase binding compounds are bonded to a spacer between the first nucleic acid and the second nucleic acid, optionally through a linking group, such as -L¹-L²-L³-L⁴-. In aspects, 1 to 10 ubiquitin ligase binding compounds are bonded to the nucleic acid, optionally through a linking group, such as -L¹-L²-L³-L⁴-. In aspects, 1 to 8 ubiquitin ligase binding compounds are bonded to the nucleic acid, optionally through a linking group, such as -L¹-L²-L³-L⁴-. In aspects, 1 to 6 ubiquitin ligase binding compounds are bonded to the nucleic acid, optionally through a linking group, such as -L¹-L²-L³-L⁴-. In aspects, 1 to 5 ubiquitin ligase binding compounds are bonded to the nucleic acid, optionally through a linking group, such as -L¹-L²-L³-L⁴-. In aspects, 1 to 4 ubiquitin ligase binding compounds are bonded to the nucleic acid, optionally through a linking group, such as -L¹-L²-L³-L⁴-. In aspects, 1 ubiquitin ligase binding compound is bonded to the nucleic acid, optionally through a linking group, such as -L¹-L²-L³-L⁴-. In aspects, 2 ubiquitin ligase binding compounds are bonded to the nucleic acid, optionally through a linking group, such as -L¹-L²-L³-L⁴-. In aspects, 3 ubiquitin ligase binding compounds are bonded to the nucleic acid, optionally through a linking group, such as -L¹-L²-L³-L⁴-.

In aspects, 4 ubiquitin ligase binding compounds are bonded to the nucleic acid, optionally through a linking group, such as -L¹-L²-L³-L⁴-. In aspects, 5 ubiquitin ligase binding compounds are bonded to the nucleic acid, optionally through a linking group, such as -L¹-L²-L³-L⁴-. In aspects, 6 ubiquitin ligase binding compounds are bonded to the nucleic acid, optionally through a linking group, such as -L¹-L²-L³-L⁴-.

In aspects, the compound comprises the nucleic acid of SEQ ID NO:1 (or a homolog thereof) and ubiquitin ligase binding compound (A). In aspects, the compound comprises the nucleic acid of SEQ ID NO:1 (or a homolog thereof) and ubiquitin ligase binding compound (B). In aspects, the compound comprises the nucleic acid of SEQ ID NO:1 (or a homolog thereof) and ubiquitin ligase binding compound (C). In aspects, the compound comprises the nucleic acid of SEQ ID NO:1 (or a homolog thereof) and ubiquitin ligase binding compound (D). In aspects, the compound comprises the nucleic acid of SEQ ID NO:1 (or a homolog thereof) and ubiquitin ligase binding compound (E). In aspects, the compound comprises the nucleic acid of SEQ ID NO:1 (or a homolog thereof) and ubiquitin ligase binding compound (F). In aspects, the compound comprises the nucleic acid of SEQ ID NO:1 (or a homolog thereof) and ubiquitin ligase binding compound (G). In aspects, the compound comprises the nucleic acid of SEQ ID NO:2 (or a homolog thereof) and ubiquitin ligase binding compound (A). In aspects, the compound comprises the nucleic acid of SEQ ID NO:2 (or a homolog thereof) and ubiquitin ligase binding compound (B). In aspects, the compound comprises the nucleic acid of SEQ ID NO:2 (or a homolog thereof) and ubiquitin ligase binding compound (C). In aspects, the compound comprises the nucleic acid of SEQ ID NO:2 (or a homolog thereof) and ubiquitin ligase binding compound (D). In aspects, the compound comprises the nucleic acid of SEQ ID NO:2 (or a homolog thereof) and ubiquitin ligase binding compound (E). In aspects, the compound comprises the nucleic acid of SEQ ID NO:2 (or a homolog thereof) and ubiquitin ligase binding compound (F). In aspects, the compound comprises the nucleic acid of SEQ ID NO:2 (or a homolog thereof) and ubiquitin ligase binding compound (G). In aspects, the compound comprises the nucleic acid of SEQ ID NO:3 (or a homolog thereof) and ubiquitin ligase binding compound (A). In aspects, the compound comprises the nucleic acid of SEQ ID NO:3 (or a homolog thereof) and ubiquitin ligase binding compound (B). In aspects, the compound comprises the nucleic acid of SEQ ID NO:3 (or a homolog thereof) and ubiquitin ligase binding compound (C). In aspects, the compound comprises the nucleic acid of SEQ ID NO:3 (or a homolog thereof) and ubiquitin ligase binding compound (D). In aspects, the compound comprises the nucleic acid of SEQ ID NO:3 (or a homolog thereof) and ubiquitin ligase binding compound (E). In aspects, the compound comprises the nucleic acid of SEQ ID NO:3 (or a homolog thereof) and ubiquitin ligase binding compound (F). In aspects, the compound comprises the nucleic acid of SEQ ID NO:3 (or a homolog thereof) and ubiquitin ligase binding compound (G). In aspects, the compound comprises the nucleic acid of SEQ ID NO:4 (or a homolog thereof) and ubiquitin ligase binding compound (A). In aspects, the compound comprises the nucleic acid of SEQ ID NO:4 (or a homolog thereof) and ubiquitin ligase binding compound (B). In aspects, the compound comprises the nucleic acid of SEQ ID NO:4 (or a homolog thereof) and ubiquitin ligase binding compound (C). In aspects, the compound comprises the nucleic acid of SEQ ID NO:4 (or a homolog thereof) and ubiquitin ligase binding compound (D). In aspects, the compound comprises the nucleic acid of SEQ ID NO:4 (or a homolog thereof) and ubiquitin ligase binding compound (E). In aspects, the compound comprises the nucleic acid of SEQ ID NO:4 (or a homolog thereof) and ubiquitin ligase binding compound (F). In aspects, the compound comprises the nucleic acid of SEQ ID NO:5 (or a homolog thereof) and ubiquitin ligase binding compound (A). In aspects, the compound comprises the nucleic acid of SEQ ID NO:5 (or a homolog thereof) and ubiquitin ligase binding compound (B). In aspects, the compound comprises the nucleic acid of SEQ ID NO:5 (or a homolog thereof) and ubiquitin ligase binding compound (C). In aspects, the compound comprises the nucleic acid of SEQ ID NO:5 (or a homolog thereof) and ubiquitin ligase binding compound (D). In aspects, the compound comprises the nucleic acid of SEQ ID NO:5 (or a homolog thereof) and ubiquitin ligase binding compound (E). In aspects, the compound comprises the nucleic acid of SEQ ID NO:5 (or a homolog thereof) and ubiquitin ligase binding compound (F). In aspects, the compound comprises the nucleic acid of SEQ ID NO:5 (or a homolog thereof) and ubiquitin ligase binding compound (G). In aspects, the compound comprises the nucleic acid of SEQ ID NO:6 (or a homolog thereof) and ubiquitin ligase binding compound (A). In aspects, the compound comprises the nucleic acid of SEQ ID NO:6 (or a homolog thereof) and ubiquitin ligase binding compound (B). In aspects, the compound comprises the nucleic acid of SEQ ID NO:6 (or a homolog thereof) and ubiquitin ligase binding compound (C). In aspects, the compound comprises the nucleic acid of SEQ ID NO:6 (or a homolog thereof) and ubiquitin ligase binding compound (D). In aspects, the compound comprises the nucleic acid of SEQ ID NO:6 (or a homolog thereof) and ubiquitin ligase binding compound (E). In aspects, the compound comprises the nucleic acid of SEQ ID NO:6 (or a homolog thereof) and ubiquitin ligase binding compound (F). In aspects, the compound comprises the nucleic acid of SEQ ID NO:6 (or a homolog thereof) and ubiquitin ligase binding compound (G). In aspects, the compound comprises the nucleic acid of SEQ ID NO:7 (or a homolog thereof) and ubiquitin ligase binding compound (A). In aspects, the compound comprises the nucleic acid of SEQ ID NO:7 (or a homolog thereof) and ubiquitin ligase binding compound (B). In aspects, the compound comprises the nucleic acid of SEQ ID NO:7 (or a homolog thereof) and ubiquitin ligase binding compound (C). In aspects, the compound comprises the nucleic acid of SEQ ID NO:7 (or a homolog thereof) and ubiquitin ligase binding compound (D). In aspects, the compound comprises the nucleic acid of SEQ ID NO:7 (or a homolog thereof) and ubiquitin ligase binding compound (E). In aspects, the compound comprises the nucleic acid of SEQ ID NO:7 (or a homolog thereof) and ubiquitin ligase binding compound (F). In aspects, the compound comprises the nucleic acid of SEQ ID NO:7 (or a homolog thereof) and ubiquitin ligase binding compound (G). In aspects, the compound comprises the nucleic acid of SEQ ID NO:8 (or a homolog thereof) and ubiquitin ligase binding compound (A). In aspects, the compound comprises the nucleic acid of SEQ ID NO:8 (or a homolog thereof) and ubiquitin ligase binding compound (B). In aspects, the compound comprises the nucleic acid of SEQ ID NO:8 (or a homolog thereof) and ubiquitin ligase binding compound (C). In aspects, the compound comprises the nucleic acid of SEQ ID NO:8 (or a homolog thereof) and ubiquitin ligase binding compound (D). In aspects, the compound comprises the nucleic acid of SEQ ID NO:8 (or a homolog thereof) and ubiquitin ligase binding compound (E). In aspects, the compound comprises the nucleic acid of SEQ ID NO:8 (or a homolog thereof) and ubiquitin ligase binding compound (F). In aspects, the compound comprises the nucleic acid of SEQ ID NO:8 (or a homolog thereof) and ubiquitin ligase binding compound (G). In aspects, the compound comprises the nucleic acid of SEQ ID NO:9 (or a homolog thereof) and ubiquitin ligase binding compound (A). In aspects, the compound comprises the nucleic acid of SEQ ID NO:9 (or a homolog thereof) and ubiquitin ligase binding compound (B). In aspects, the compound comprises the nucleic acid of SEQ ID NO:9 (or a homolog thereof) and ubiquitin ligase binding compound (C). In aspects, the compound comprises the nucleic acid of SEQ ID NO:9 (or a homolog thereof) and ubiquitin ligase binding compound (D). In aspects, the compound comprises the nucleic acid of SEQ ID NO:9 (or a homolog thereof) and ubiquitin ligase binding compound (E). In aspects, the compound comprises the nucleic acid of SEQ ID NO:9 (or a homolog thereof) and ubiquitin ligase binding compound (F). In aspects, the compound comprises the nucleic acid of SEQ ID NO:9 (or a homolog thereof) and ubiquitin ligase binding compound (G). In aspects, the compound comprises the nucleic acid of SEQ ID NO:10 (or a homolog thereof) and ubiquitin ligase binding compound (A). In aspects, the compound comprises the nucleic acid of SEQ ID NO:10 (or a homolog thereof) and ubiquitin ligase binding compound (B). In aspects, the compound comprises the nucleic acid of SEQ ID NO:10 (or a homolog thereof) and ubiquitin ligase binding compound (C). In aspects, the compound comprises the nucleic acid of SEQ ID NO:10 (or a homolog thereof) and ubiquitin ligase binding compound (D). In aspects, the compound comprises the nucleic acid of SEQ ID NO:10 (or a homolog thereof) and ubiquitin ligase binding compound (E). In aspects, the compound comprises the nucleic acid of SEQ ID NO:10 (or a homolog thereof) and ubiquitin ligase binding compound (F). In aspects, the compound comprises the nucleic acid of SEQ ID NO:10 (or a homolog thereof) and ubiquitin ligase binding compound (G). In aspects, the compound comprises the nucleic acid of SEQ ID NO:11 (or a homolog thereof) and ubiquitin ligase binding compound (A). In aspects, the compound comprises the nucleic acid of SEQ ID NO:11 (or a homolog thereof) and ubiquitin ligase binding compound (B). In aspects, the compound comprises the nucleic acid of SEQ ID NO:11 (or a homolog thereof) and ubiquitin ligase binding compound (C). In aspects, the compound comprises the nucleic acid of SEQ ID NO:11 (or a homolog thereof) and ubiquitin ligase binding compound (D). In aspects, the compound comprises the nucleic acid of SEQ ID NO:11 (or a homolog thereof) and ubiquitin ligase binding compound (E). In aspects, the compound comprises the nucleic acid of SEQ ID NO:11 (or a homolog thereof) and ubiquitin ligase binding compound (F). In aspects, the compound comprises the nucleic acid of SEQ ID NO:11 (or a homolog thereof) and ubiquitin ligase binding compound (G). In aspects, the compound comprises the nucleic acid of SEQ ID NO:12 (or a homolog thereof) and ubiquitin ligase binding compound (A). In aspects, the compound comprises the nucleic acid of SEQ ID NO:12 (or a homolog thereof) and ubiquitin ligase binding compound (B). In aspects, the compound comprises the nucleic acid of SEQ ID NO:12 (or a homolog thereof) and ubiquitin ligase binding compound (C). In aspects, the compound comprises the nucleic acid of SEQ ID NO:12 (or a homolog thereof) and ubiquitin ligase binding compound (D). In aspects, the compound comprises the nucleic acid of SEQ ID NO:12 (or a homolog thereof) and ubiquitin ligase binding compound (E). In aspects, the compound comprises the nucleic acid of SEQ ID NO:12 (or a homolog thereof) and ubiquitin ligase binding compound (F). In aspects, the compound comprises the nucleic acid of SEQ ID NO:12 (or a homolog thereof) and ubiquitin ligase binding compound (G). In aspects, the compound comprises the nucleic acid of SEQ ID NO:13 (or a homolog thereof) and ubiquitin ligase binding compound (A). In aspects, the compound comprises the nucleic acid of SEQ ID NO:13 (or a homolog thereof) and ubiquitin ligase binding compound (B). In aspects, the compound comprises the nucleic acid of SEQ ID NO:13 (or a homolog thereof) and ubiquitin ligase binding compound (C). In aspects, the compound comprises the nucleic acid of SEQ ID NO:13 (or a homolog thereof) and ubiquitin ligase binding compound (D). In aspects, the compound comprises the nucleic acid of SEQ ID NO:13 (or a homolog thereof) and ubiquitin ligase binding compound (E). In aspects, the compound comprises the nucleic acid of SEQ ID NO:13 (or a homolog thereof) and ubiquitin ligase binding compound (F). In aspects, the compound comprises the nucleic acid of SEQ ID NO:13 (or a homolog thereof) and ubiquitin ligase binding compound (G). In aspects, the compound comprises the nucleic acid of SEQ ID NO:14 (or a homolog thereof) and ubiquitin ligase binding compound (A). In aspects, the compound comprises the nucleic acid of SEQ ID NO:14 (or a homolog thereof) and ubiquitin ligase binding compound (B). In aspects, the compound comprises the nucleic acid of SEQ ID NO:14 (or a homolog thereof) and ubiquitin ligase binding compound (C). In aspects, the compound comprises the nucleic acid of SEQ ID NO:14 (or a homolog thereof) and ubiquitin ligase binding compound (D). In aspects, the compound comprises the nucleic acid of SEQ ID NO:14 (or a homolog thereof) and ubiquitin ligase binding compound (E). In aspects, the compound comprises the nucleic acid of SEQ ID NO:14 (or a homolog thereof) and ubiquitin ligase binding compound (F). In aspects, the compound comprises the nucleic acid of SEQ ID NO:14 (or a homolog thereof) and ubiquitin ligase binding compound (G). In aspects, the compound comprises the nucleic acid of SEQ ID NO:15 (or a homolog thereof) and ubiquitin ligase binding compound (A). In aspects, the compound comprises the nucleic acid of SEQ ID NO:15 (or a homolog thereof) and ubiquitin ligase binding compound (B). In aspects, the compound comprises the nucleic acid of SEQ ID NO:15 (or a homolog thereof) and ubiquitin ligase binding compound (C). In aspects, the compound comprises the nucleic acid of SEQ ID NO:15 (or a homolog thereof) and ubiquitin ligase binding compound (D). In aspects, the compound comprises the nucleic acid of SEQ ID NO:15 (or a homolog thereof) and ubiquitin ligase binding compound (E). In aspects, the compound comprises the nucleic acid of SEQ ID NO:15 (or a homolog thereof) and ubiquitin ligase binding compound (F). In aspects, the compound comprises the nucleic acid of SEQ ID NO:15 (or a homolog thereof) and ubiquitin ligase binding compound (G). In aspects, the compound comprises the nucleic acid of SEQ ID NO:16 (or a homolog thereof) and ubiquitin ligase binding compound (A). In aspects, the compound comprises the nucleic acid of SEQ ID NO:16 (or a homolog thereof) and ubiquitin ligase binding compound (B). In aspects, the compound comprises the nucleic acid of SEQ ID NO:16 (or a homolog thereof) and ubiquitin ligase binding compound (C). In aspects, the compound comprises the nucleic acid of SEQ ID NO:16 (or a homolog thereof) and ubiquitin ligase binding compound (D). In aspects, the compound comprises the nucleic acid of SEQ ID NO:16 (or a homolog thereof) and ubiquitin ligase binding compound (E). In aspects, the compound comprises the nucleic acid of SEQ ID NO:16 (or a homolog thereof) and ubiquitin ligase binding compound (F). In aspects, the compound comprises the nucleic acid of SEQ ID NO:16 (or a homolog thereof) and ubiquitin ligase binding compound (G). In aspects, the compound comprises the nucleic acid of SEQ ID NO:17 (or a homolog thereof)

and ubiquitin ligase binding compound (A). In aspects, the compound comprises the nucleic acid of SEQ ID NO:17 (or a homolog thereof) and ubiquitin ligase binding compound (B). In aspects, the compound comprises the nucleic acid of SEQ ID NO:17 (or a homolog thereof) and ubiquitin ligase binding compound (C). In aspects, the compound comprises the nucleic acid of SEQ ID NO:17 (or a homolog thereof) and ubiquitin ligase binding compound (D). In aspects, the compound comprises the nucleic acid of SEQ ID NO:17 (or a homolog thereof) and ubiquitin ligase binding compound (E). In aspects, the compound comprises the nucleic acid of SEQ ID NO:17 (or a homolog thereof) and ubiquitin ligase binding compound (F). In aspects, the compound comprises the nucleic acid of SEQ ID NO:17 (or a homolog thereof) and ubiquitin ligase binding compound (G). In aspects, the compound comprises the nucleic acid of SEQ ID NO:18 (or a homolog thereof) and ubiquitin ligase binding compound (A). In aspects, the compound comprises the nucleic acid of SEQ ID NO:18 (or a homolog thereof) and ubiquitin ligase binding compound (B). In aspects, the compound comprises the nucleic acid of SEQ ID NO:18 (or a homolog thereof) and ubiquitin ligase binding compound (C). In aspects, the compound comprises the nucleic acid of SEQ ID NO:18 (or a homolog thereof) and ubiquitin ligase binding compound (D). In aspects, the compound comprises the nucleic acid of SEQ ID NO:18 (or a homolog thereof) and ubiquitin ligase binding compound (E). In aspects, the compound comprises the nucleic acid of SEQ ID NO:18 (or a homolog thereof) and ubiquitin ligase binding compound (F). In aspects, the compound comprises the nucleic acid of SEQ ID NO:18 (or a homolog thereof) and ubiquitin ligase binding compound (G). In aspects, the compound comprises the nucleic acid of SEQ ID NO:19 (or a homolog thereof) and ubiquitin ligase binding compound (A). In aspects, the compound comprises the nucleic acid of SEQ ID NO:19 (or a homolog thereof) and ubiquitin ligase binding compound (B). In aspects, the compound comprises the nucleic acid of SEQ ID NO:19 (or a homolog thereof) and ubiquitin ligase binding compound (C). In aspects, the compound comprises the nucleic acid of SEQ ID NO:19 (or a homolog thereof) and ubiquitin ligase binding compound (D). In aspects, the compound comprises the nucleic acid of SEQ ID NO:19 (or a homolog thereof) and ubiquitin ligase binding compound (E). In aspects, the compound comprises the nucleic acid of SEQ ID NO:19 (or a homolog thereof) and ubiquitin ligase binding compound (F). In aspects, the compound comprises the nucleic acid of SEQ ID NO:19 (or a homolog thereof) and ubiquitin ligase binding compound (G). In aspects, the compound comprises the nucleic acid of SEQ ID NO:20 (or a homolog thereof) and ubiquitin ligase binding compound (A). In aspects, the compound comprises the nucleic acid of SEQ ID NO:20 (or a homolog thereof) and ubiquitin ligase binding compound (B). In aspects, the compound comprises the nucleic acid of SEQ ID NO:20 (or a homolog thereof) and ubiquitin ligase binding compound (C). In aspects, the compound comprises the nucleic acid of SEQ ID NO:20 (or a homolog thereof) and ubiquitin ligase binding compound (D). In aspects, the compound comprises the nucleic acid of SEQ ID NO:20 (or a homolog thereof) and ubiquitin ligase binding compound (E). In aspects, the compound comprises the nucleic acid of SEQ ID NO:20 (or a homolog thereof) and ubiquitin ligase binding compound (F). In aspects, the compound comprises the nucleic acid of SEQ ID NO:20 (or a homolog thereof) and ubiquitin ligase binding compound (G). In aspects, the compound comprises the nucleic acid of SEQ ID NO:21 (or a homolog thereof) and ubiquitin ligase binding compound (A). In aspects, the compound comprises the nucleic acid of SEQ ID NO:21 (or a homolog thereof) and ubiquitin ligase binding compound (B). In aspects, the compound comprises the nucleic acid of SEQ ID NO:21 (or a homolog thereof) and ubiquitin ligase binding compound (C). In aspects, the compound comprises the nucleic acid of SEQ ID NO:21 (or a homolog thereof) and ubiquitin ligase binding compound (D). In aspects, the compound comprises the nucleic acid of SEQ ID NO:21 (or a homolog thereof) and ubiquitin ligase binding compound (E). In aspects, the compound comprises the nucleic acid of SEQ ID NO:21 (or a homolog thereof) and ubiquitin ligase binding compound (F). In aspects, the compound comprises the nucleic acid of SEQ ID NO:21 (or a homolog thereof) and ubiquitin ligase binding compound (G). In aspects, the compound comprises the nucleic acid of SEQ ID NO:22 (or a homolog thereof) and ubiquitin ligase binding compound (A). In aspects, the compound comprises the nucleic acid of SEQ ID NO:22 (or a homolog thereof) and ubiquitin ligase binding compound (B). In aspects, the compound comprises the nucleic acid of SEQ ID NO:22 (or a homolog thereof) and ubiquitin ligase binding compound (C). In aspects, the compound comprises the nucleic acid of SEQ ID NO:22 (or a homolog thereof) and ubiquitin ligase binding compound (D). In aspects, the compound comprises the nucleic acid of SEQ ID NO:22 (or a homolog thereof) and ubiquitin ligase binding compound (E). In aspects, the compound comprises the nucleic acid of SEQ ID NO:22 (or a homolog thereof) and ubiquitin ligase binding compound (F). In aspects, the compound comprises the nucleic acid of SEQ ID NO:22 (or a homolog thereof) and ubiquitin ligase binding compound (G). In aspects, the compound comprises the nucleic acid of SEQ ID NO:23 (or a homolog thereof) and ubiquitin ligase binding compound (A). In aspects, the compound comprises the nucleic acid of SEQ ID NO:23 (or a homolog thereof) and ubiquitin ligase binding compound (B). In aspects, the compound comprises the nucleic acid of SEQ ID NO:23 (or a homolog thereof) and ubiquitin ligase binding compound (C). In aspects, the compound comprises the nucleic acid of SEQ ID NO:23 (or a homolog thereof) and ubiquitin ligase binding compound (D). In aspects, the compound comprises the nucleic acid of SEQ ID NO:23 (or a homolog thereof) and ubiquitin ligase binding compound (E). In aspects, the compound comprises the nucleic acid of SEQ ID NO:23 (or a homolog thereof) and ubiquitin ligase binding compound (F). In aspects, the compound comprises the nucleic acid of SEQ ID NO:23 (or a homolog thereof) and ubiquitin ligase binding compound (G). In aspects, the compound comprises the nucleic acid of SEQ ID NO:24 (or a homolog thereof) and ubiquitin ligase binding compound (A). In aspects, the compound comprises the nucleic acid of SEQ ID NO:24 (or a homolog thereof) and ubiquitin ligase binding compound (B). In aspects, the compound comprises the nucleic acid of SEQ ID NO:24 (or a homolog thereof) and ubiquitin ligase binding compound (C). In aspects, the compound comprises the nucleic acid of SEQ ID NO:24 (or a homolog thereof) and ubiquitin ligase binding compound (D). In aspects, the compound comprises the nucleic acid of SEQ ID NO:24 (or a homolog thereof) and ubiquitin ligase binding compound (E). In aspects, the compound comprises the nucleic acid of SEQ ID NO:24 (or a homolog thereof) and ubiquitin ligase binding compound (F). In aspects, the compound comprises the nucleic acid of SEQ ID NO:24 (or a homolog thereof) and ubiquitin ligase binding compound (G). In aspects, the nucleic acid is covalently bonded to the one or more ubiquitin ligase binding compounds through a linking group. In aspects, the nucleic acid is covalently bonded to the one or more ubiquitin ligase binding compounds through a linking group of the formula -$L^1$-$L^2$-$L^3$-

$L^4$-. In aspects, the one or more ubiquitin ligase binding compounds are bonded to the 3'-terminus of the nucleic acid, optionally through a linking group, e.g., of the formula -$L^1$-$L^2$-$L^3$-$L^4$-. In aspects, the one or more ubiquitin ligase binding compounds are bonded to the 5'-terminus of the nucleic acid, optionally through a linking group, e.g., of the formula -$L^1$-$L^2$-$L^3$-$L^4$-. In aspects, the one or more ubiquitin ligase binding compounds are bonded to any nucleotide in the nucleic acid, optionally through a linking group, e.g., of the formula -$L^1$-$L^2$-$L^3$-$L^4$-. In aspects, 1 to 10 ubiquitin ligase binding compounds are bonded to the nucleic acid, optionally through a linking group, e.g., of the formula -$L^1$-$L^2$-$L^3$-$L^4$-. In aspects, 1 to 8 ubiquitin ligase binding compounds are bonded to the nucleic acid. In aspects, 1 to 6 ubiquitin ligase binding compounds are bonded to the nucleic acid, optionally through a linking group, e.g., of the formula -$L^1$-$L^2$-$L^3$-$L^4$-. In aspects, 1 to 5 ubiquitin ligase binding compounds are bonded to the nucleic acid, optionally through a linking group, e.g., of the formula -$L^1$-$L^2$-$L^3$-$L^4$-. In aspects, 1 to 4 ubiquitin ligase binding compounds are bonded to the nucleic acid, optionally through a linking group, e.g., of the formula -$L^1$-$L^2$-$L^3$-$L^4$-. In aspects, 1 ubiquitin ligase binding compound is bonded to the nucleic acid, optionally through a linking group, e.g., of the formula -$L^1$-$L^2$-$L^3$-$L^4$—In aspects, 2 ubiquitin ligase binding compounds are bonded to the nucleic acid, optionally through a linking group, e.g., of the formula -$L^L$-$L^2$-$L^3$-$L^4$-. In aspects, 3 ubiquitin ligase binding compounds are bonded to the nucleic acid. In aspects, 4 ubiquitin ligase binding compounds are bonded to the nucleic acid, optionally through a linking group, e.g., of the formula -$L^L$-$L^2$-$L^3$-$L^4$-. In aspects, 5 ubiquitin ligase binding compounds are bonded to the nucleic acid, optionally through a linking group, e.g., of the formula -$L^L$-$L^2$-$L^3$-$L^4$-. In aspects, 6 ubiquitin ligase binding compounds are bonded to the nucleic acid, optionally through a linking group, e.g., of the formula -$L^L$-$L^2$-$L^3$-$L^4$-.

In aspects, the nucleic acid of any one of SEQ ID NOS:1-24 or homologs thereof is covalently bonded to the one or more ubiquitin ligase binding compounds (MC) represented by (A)-(G) through the following linking group: -$L^L$-$L^2$-$L^3$-$L^4$-MC, wherein $L^1$, $L^2$, $L^3$. $L^4$ are as defined herein.

In aspects, the nucleic acid of any one of SEQ ID NOS:1-24 or homologs thereof is covalently bonded to the one or more ubiquitin ligase binding compounds (MC) represented by (A)-(G) through a linking group of the formula:

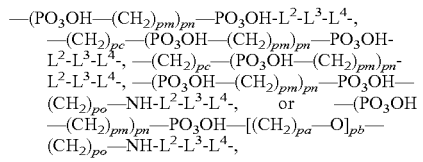

wherein $L^2$, $L^3$, and $L^4$, are as defined herein, and wherein pc is an integer from 0 to 6; pm is an integer from 1 to 8; pn is an integer from 1 to 10; po is an integer from 1 to 12; pa is an integer from 1 to 4; and pb is 0, 1, or 2. In aspects, $L^2$ is optionally substituted with -$L^{11}$-$L^{12}$-$L^{13}$-$L^{14}$-MC, wherein $L^{11}$ has the same definition as $L^1$; $L^{12}$ has the same definition as $L^2$; $L^{13}$ has the same definition of $L^3$; $L^{14}$ has the same definition of $L^{4t}$ and MC is as defined herein. In aspects, $L^{12}$ is optionally substituted with -$L^{101}$-$L^{102}$-$L^{103}$-$L^{104}$-MC, wherein $L^{101}$ has the same definition as $L^1$; $L^{102}$ has the same definition as $L^2$; $L^{103}$ has the same definition of $L^3$; $L^{104}$ has the same definition of $L^4$; and MC is as defined herein. In aspects, $L^{102}$ is substituted with -$L^{110}$-$L^{120}$-$L^{130}$-$L^{140}$-MC, wherein $L^{110}$ has the same definition as $L^1$; $L^{120}$ has the same definition as $L^2$; $L^{130}$ has the same definition of $L^3$; $L^{140}$ has the same definition of $L^4$; and MC is as defined herein. In aspects, $L^{120}$ is substituted with -$L^{111}$-$L^{122}$-$L^{133}$-$L^{144}$-MC, wherein $L^{111}$ has the same definition as $L^1$; $L^{122}$ has the same definition as $L^2$; $L^{133}$ has the same definition of $L^3$; $L^{144}$ has the same definition of $L^4$; and MC is as defined herein. In aspects, $L^{122}$ is substituted with -$L^{1111}$-$L^{1222}$-$L^{1333}$-$L^{1444}$-MC, wherein $L^{1111}$ has the same definition as $L^1$; $L^{1222}$ has the same definition as $L^2$; $L^{1333}$ has the same definition of $L^3$; $L^{1444}$ has the same definition of $L^4$; and MC is as defined herein.

In embodiments, the compound further comprises a second nucleic acid selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24; wherein the first nucleic acid and the second nucleic acid are the same or different; where the first nucleic acid is covalently bonded to the second nucleic acid optionally by a spacer or linking group; and wherein the first nucleic acid and/or the second nucleic acid is covalently bonded to one or more ubiquitin ligase binding compounds. In aspects, the spacer between the first nucleic acid and the second nucleic acid is a bond, a nucleic acid sequence, two nucleic acid sequences, a DNA sequence, two DNA sequences, a nucleic acid analog sequence, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In aspects, the spacer is any spacer described herein. In aspects, the second nucleic acid has at least 90% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In aspects, the second nucleic acid has at least 92% sequence identity to S SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In aspects, the second nucleic acid has at least 94% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In aspects, the second nucleic acid has at least 96% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In aspects, the second nucleic acid has at least 98% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In aspects, the first nucleic acid is covalently bonded to the second nucleic acid by a spacer. In aspects, the first nucleic acid or the second nucleic acid is covalently bonded to the one or more ubiquitin ligase binding compounds through a linking group of the formula -$L^1$-$L^2$-$L^3$-$L^4$-MC, where the substituents are as defined herein. In aspects, the linking group is any linking group described herein. In aspects, the ubiquitin ligase binding compound is bonded to the first nucleic acid via a linking group. In aspects, the ubiquitin ligase binding compound is bonded to the second nucleic acid via a linking group. In aspects, the ubiquitin ligase binding compound is bonded to the spacer between the first and second nucleic acid via a linking group. In aspects, the ubiquitin ligase binding compounds are bonded to the first nucleic acid via a linking group, and to the second nucleic acid via a linking group. In aspects, the ubiquitin ligase binding compounds are bonded to the first nucleic acid via a linking group, and to the spacer between the first and second nucleic acids via a linking group. In aspects, the ubiquitin ligase binding compounds are bonded to the second nucleic acid via a linking group, and to the spacer between the first and second nucleic acids via a linking group. In aspects, the ubiquitin ligase binding compounds are bonded to the first nucleic acid via a linking group, to the second nucleic acid via a linking group, and to the spacer between the first and second nucleic acids via a linking group. In aspects, the first and/or second nucleic acid and/or spacer between the first and second nucleic acids is covalently bonded to one or more of the same ubiquitin ligase binding compound. In aspects, the first and/or second nucleic acid and/or spacer between the first and second nucleic acids is covalently bonded to two or more different ubiquitin ligase binding compounds. In aspects, the first and/or second nucleic acid and/or spacer between the first and second nucleic acids is covalently bonded to 1 to 10 ubiquitin ligase binding compounds. In aspects, the first and/or second nucleic acid is covalently bonded to 1 to 5 ubiquitin ligase binding compounds. In aspects, the first and/or second nucleic acid is covalently bonded to 1 to 4 ubiquitin ligase binding compounds. In aspects, the nucleic acid is covalently bonded to 1 ubiquitin ligase binding compound. In aspects, the first and/or second nucleic acid is covalently bonded to 2 ubiquitin ligase binding compounds. In aspects, the nucleic acid is covalently bonded to 3 ubiquitin ligase binding compounds. In aspects, the first and/or second nucleic acid is covalently bonded to 4 ubiquitin ligase binding compounds. In aspects, the first and/or second nucleic acid is covalently bonded to 5 ubiquitin ligase binding compounds.

Pharmaceutical Compositions

In an aspect is provided a pharmaceutical composition including a pharmaceutically acceptable excipient and a compound, or pharmaceutically acceptable salt thereof, described herein (including in an aspect, embodiment, table, figure, claim, sequence listing, or example). In aspects of the pharmaceutical compositions, the compound, or pharmaceutically acceptable salt thereof, as described herein (including in an aspect, embodiment, table, figure, claim, sequence listing, or example), is included in a therapeutically effective amount.

In embodiments, the pharmaceutical composition further includes a second agent (e.g. therapeutic agent). In aspects, the second agent is an anti-cancer agent. In aspects, the second agent is an anti-viral agent. In aspects of the pharmaceutical compositions, the pharmaceutical composition includes a second agent (e.g. therapeutic agent) in a therapeutically effective amount. In aspects, the antigenic component is a cancer antigenic component. In aspects, the antigenic component is a tumor-associated antigen.

Methods of Use

In an aspect is provided a method of treating cancer in a patient in need of such treatment, the method including administering a therapeutically effective amount of a compound as described herein, including in an aspect, embodiment, table, figure, claim, sequence listing, or example, to the patient. In aspects, the cancer is a hematopoietic cell cancer. In aspects, the cancer is not a hematopoietic cell cancer. In aspects, the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma. In aspects, the cancer is prostate cancer (e.g. castration-resistant). In aspects, the cancer is breast cancer (e.g. triple negative). In aspects, the cancer is glioblastoma. In aspects, the cancer is ovarian cancer. In aspects, the cancer is lung cancer. In aspects, the cancer is head and neck cancer. In aspects, the cancer is esophageal cancer. In aspects, the cancer is skin cancer. In aspects, the cancer is melanoma. In aspects, the cancer is brain cancer. In aspects, the cancer is colorectal cancer. In aspects, the cancer is leukemia (e.g. AML, ALL, or CML). In aspects, the cancer is lymphoma. In aspects, the cancer is myeloma (e.g. multiple myeloma). In aspects, the cancer is squamous cell carcinoma (e.g. head and neck cancer or esophageal cancer). In aspects, the cancer is metastatic cancer. In aspects, the cancer is acute myeloid leukemia. In aspects, the cancer is B cell lymphoma. In aspects, the cancer is multiple myeloma. In aspects, the cancer is prostate cancer. In aspects, the cancer is glioblastoma.

In aspects, the cancer has an increased level of STAT3 (e.g. activity, mRNA, or protein) relative to a control (e.g. non-cancerous cell of the same type as the cancer cell). In aspects, the cancer has an increased level of TLR9 relative to a control (e.g. non-cancerous cell of the same type as the cancer cell). In aspects, the cancer has an increased level of TLR (e.g. endosomal TLR, TLR3, TLR7, TLR8, or TLR9) relative to a control (e.g. non-cancerous cell of the same type as the cancer cell). In aspects, the cancer has an increased level of phosphorylated STAT3 relative to a control (e.g. non-cancerous cell of the same type as the cancer cell). In aspects, the cancer has an increased level of a STAT transcription factor (e.g. STAT1, STAT2, STAT3, STAT4, STAT5A, STAT5B, or STAT6) (e.g. activity, mRNA, or protein) relative to a control (e.g. non-cancerous cell of the same type as the cancer cell). In aspects, the cancer has an increased level of phosphorylated STAT (e.g. STAT1, STAT2, STAT3, STAT4, STAT5A, STAT5B, or STAT6) relative to a control (e.g. non-cancerous cell of the same type as the cancer cell). In aspects, the STAT is STAT1. In aspects, the STAT is STAT2. In aspects, the STAT is STAT3. In aspects, the STAT is STAT4. In aspects, the STAT is STAT5A. In aspects, the STAT is STAT5B. In aspects, the STAT is STAT6. In aspects, the STAT is human.

In an aspect is provided a method of treating an autoimmune disorder in a patient in need of such treatment, the method including administering a therapeutically effective amount of a compound as described herein to the patient. As used herein, the term "autoimmune disorder" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), graft-vs-host disease, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Systemic lupus erythematosus (SLE), Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA). In aspects, the autoimmune disorder is graft-vs-host disease, Systemic lupus erythematosus (SLE), or Crohn's disease.

In an aspect is provided a method of treating a neurodegenerative disease in a patient in need of such treatment, the method including administering a therapeutically effective amount of a compound as described herein to the patient. As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis. In aspects, the neurodegenerative disease is Huntington Disease, Alzheimer Disease, or Parkinson's Disease.

In embodiments, the method includes systemic administration of the compound. In aspects, the method includes parenteral administration of the compound. In aspects, the method includes intravenous administration of the compound. In aspects, the method includes infusion of the compound over a period of 30 minutes to 6 hours. In aspects, the method includes administration directly to a tumor.

In an aspect is provided a method of inhibiting the growth of a cancer cell including contacting the cancer cell with a compound described herein (including in an aspect, embodiment, table, figure, claim, sequence listing, or example). In aspects, the cell forms part of an organism. In aspects, the organism is a mammal.

In embodiments, the cancer cell includes a level of TLR (e.g. endosomal TLR, TLR3, TLR7, TLR8, or TLR9) greater than a non-cancerous cell control. In aspects, the cancer cell includes a level of TLR9 greater than a non-cancerous cell control. In aspects, the cancer cell includes a level of a STAT transcription factor (e.g. STAT1, STAT2, STAT3, STAT4, STAT5A, STAT5B, or STAT6) greater than a non-cancerous cell control. In aspects, the STAT is STAT1. In aspects, the STAT is STAT2. In aspects, the STAT is STAT3. In aspects, the STAT is STAT4. In aspects, the STAT is STAT5A. In aspects, the STAT is STAT5B. In aspects, the STAT is STAT6. In aspects, the TLR is an endosomal TLR. In aspects, the TLR is TLR3. In aspects, the TLR is TLR7. In aspects, the TLR is TLR8. In aspects, the TLR is TLR9. In aspects, the cancer cell includes a level of STAT3 greater than a non-cancerous cell control. In aspects, the method or use includes inducing apoptosis of the cancer cell. In aspects, the method or use includes inducing apoptosis in a cancer cell but not a non-cancer cell. In aspects, the method or use includes inducing apoptosis in a cancer cell in a patient but not a non-cancer cell in the same patient. In aspects, the method or use includes inducing apoptosis in a cancer cell but not a non-cancer cell of the same cell type as the cancer cell (e.g. lung cell, breast cell, pancreatic cell, colorectal cell, prostate cell, hematopoietic cell). In aspects, the cancer cell is in the brain. In aspects, the cancer cell is in an organ. In aspects, the cancer cell is in a bone. In aspects, the cancer cell is in bone marrow.

In an aspect is provided a method of treating a viral disease in a patient in need of the treatment, the method including administering a compound, or pharmaceutically acceptable salt thereof, described herein (including in an aspect, embodiment, table, figure, claim, sequence listing, or example). The terms "viral infection" or "viral disease" or "viral infectious disease" or "virus infection" as used interchangeably herein refers, in the usual and customary sense, to the presence of a virus (e.g., RNA virus) within a subject. In aspects, a viral infection refers to the presence of a virus (e.g., RNA virus) within a subject that is capable of replicating and/or generating virus particles. In aspects, the viral infection refers to the presence of a virus (e.g., RNA virus) within a subject that is capable of infecting a second subject. A viral infection can be present in any body issue and the subject may present symptoms such as fever, red eyes, joint pain, headache, and a maculopapular rash, or the subject may be asymptomatic. Diagnosis of a viral infection may be determined by testing bodily fluids (e.g., blood, urine, or saliva) for the presence of the virus's RNA or for antibodies. In aspects, the virus may be present within a subject but may be latent. In aspects, the methods of treatment described herein refer to a reduction in viral shedding from a subject. The term "viral shedding" is used according to its plain ordinary meaning in Medicine and Virology and refers to the production and release of virus from an infected cell. In aspects, the virus is released from a cell of a subject. In aspects, virus is released into the environment from an infected subject. In aspects, the virus is released from a cell within a subject. In aspects, the viral disease is a Zika viral infection.

In an aspect is provided a method of treating a viral disease associated with STAT3-dependent immunosuppression in a patient in need of the treatment, the method including administering a compound, or pharmaceutically acceptable salt thereof, described herein (including in an aspect, embodiment, table, figure, claim, sequence listing, or example). In embodiments, the viral disease associated with STAT3-dependent immunosuppression is HHV-1 infection. In aspects, the viral disease associated with STAT3-dependent immunosuppression is HHV-2 infection. In aspects, the viral disease associated with STAT3-dependent immunosuppression is HHV-3 infection. In aspects, the viral disease associated with STAT3-dependent immunosuppression is HHV-4 infection. In aspects, the viral disease associated with STAT3-dependent immunosuppression is HHV-5 infection. In aspects, the viral disease associated with STAT3-dependent immunosuppression is HHV-6A infection. In aspects, the viral disease associated with STAT3-dependent immunosuppression is HHV-6B infection. In aspects, the viral disease associated with STAT3-dependent immunosuppression is HHV-7 infection. In aspects, the viral disease associated with STAT3-dependent immunosuppression is HHV-8 infection. In aspects, the viral disease associated with STAT3-dependent immunosuppression is hepatitis A virus infection. In aspects, the viral disease associated with STAT3-dependent immunosuppression is hepatitis B virus infection. In aspects, the viral disease associated with STAT3-dependent immunosuppression is hepatitis C virus infection. In aspects, the viral disease associated with STAT3-dependent immunosuppression is hepatitis D virus infection. In aspects, the viral disease associated with STAT3-dependent immunosuppression is hepatitis E virus infection. In aspects, the viral disease associated with STAT3-dependent immunosuppression is HIV infection. In aspects, the viral disease associated with STAT3-dependent immunosuppression is ZIKA infection.

EMBODIMENTS

Embodiment 1

A compound comprising a first nucleic acid sequence capable of binding to a transcription factor binding site and a ubiquitin ligase binding compound covalently bound to the first nucleic acid.

Embodiment 2

The compound of Embodiment 1, further comprising a second nucleic acid sequence capable of binding a Toll-like receptor protein.

Embodiment 3

The compound of Embodiment 2, wherein the ubiquitin ligase binding compound is covalently bound to the first nucleic acid or the second nucleic acid.

Embodiment 4

The compound of Embodiment 2 or 3, wherein the Toll-like receptor protein is human Toll-like receptor 3, Toll-like receptor 7, Toll-like receptor 8, or Toll-like receptor 9.

Embodiment 5

The compound of any one of Embodiments 2 to 4, wherein the second nucleic acid sequence comprises a CpG motif, a GpC motif, or a phosphorothioated nucleic acid sequence having at least 10 nucleotides.

Embodiment 6

The compound of any one of Embodiments 2 to 4, wherein the second nucleic acid sequence comprises an unmethylated CpG motif.

Embodiment 7

The compound of any one of Embodiments 2 to 4, wherein the second nucleic acid sequence comprises a Class A CpG DNA sequence, Class B CpG DNA sequence, or Class C CpG DNA sequence.

Embodiment 8

The compound of any one of Embodiments 1 to 7, wherein the transcription factor is signal transducer and activator of transcription protein or nuclear factor kappa-light-chain-enhancer of activated B cells.

Embodiment 9

The compound of any one of Embodiments 1 to 7, wherein the transcription factor is signal transducer and activator of transcription 3 protein.

Embodiment 10

The compound of any one of Embodiments 1 to 9, wherein the first nucleic acid sequence comprises a first transcription factor binding site nucleic acid sequence and a second transcription factor binding side nucleic acid sequence connected through a spacer, wherein the spacer is a substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 11

The compound of any one of Embodiments 1 to 11, wherein the second nucleic acid sequence comprises a first Toll-like receptor binding site nucleic acid sequence and a second Toll-like receptor binding side nucleic acid sequence connected through a spacer, wherein the spacer is a substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 12

The compound of any one of Embodiments 1 to 11, wherein the ubiquitin ligase binding compound is covalently bound to the first nucleic acid or the second nucleic acid through a linker having the formula: -$L^1$-$L^2$-$L^3$-$L^4$-MC; wherein, MC is the ubiquitin ligase binding compound; and $L^1$, $L^2$, $L^3$, and $L^4$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 13

The compound of Embodiment 12, wherein $L^1$, $L^2$, $L^3$, and $L^4$ are each independently substituted or unsubstituted polyglycol, substituted or unsubstituted $C_1$-$C_{16}$ alkylene, substituted or unsubstituted 2 to 16 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 6 to 20 membered heteroarylene.

Embodiment 14

The compound of Embodiment 12 or 13, wherein $L^1$ is: —$(PO_3OH$—$(CH_2)_{pm})_{pn}$—$PO_3OH$—, wherein pm is an integer from 1 to 8; and pn is an integer from 1 to 10.

Embodiment 15

The compound of Embodiment 12 or 13, wherein $L^1$ is: —$(CH_2)_{pc}$—$(PO_3OH$—$(CH_2)_{pm})_{pn}$—$PO_3OH$—; wherein pc is an integer from 0 to 6; pm is an integer from 1 to 8; and pn is an integer from 1 to 10.

Embodiment 16

The compound of Embodiment 12 or 13, wherein $L^1$ is: —$(CH_2)_{pc}$—$(PO_3OH$—$(CH_2)_{pm})_{pn}$—; wherein pc is an integer from 0 to 6; pm is an integer from 1 to 8; and pn is an integer from 1 to 10.

Embodiment 17

The compound of Embodiment 12 or 13, wherein $L^1$ is: —$(PO_3OH$—$(CH_2)_{pm})_{pn}$—$PO_3OH$—$(CH_2)_{po}$—NH—; wherein pm is an integer from 1 to 8; pn is an integer from 1 to 10; and po is an integer from 1 to 12.

Embodiment 18

The compound of Embodiment 12 or 13, wherein $L^1$ is: —$(PO_3OH$—$(CH_2)_{pm})_{pn}$—$PO_3OH$—$[(CH_2)_{pa}$—$O]_{pb}$—$(CH_2)_{po}$—NH—; wherein pm is an integer from 1 to 8; pn is an integer from 1 to 10; po is an integer from 1 to 12; pa is an integer from 1 to 4; and pb is 0, 1, or 2.

Embodiment 19

The compound of Embodiment 12 or 13, wherein $L^1$ has the formula:

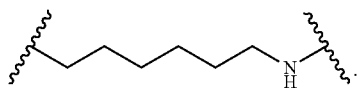 [SMILES: *CCCCCCN*]

Embodiment 20

The compound of any one of Embodiments 12 to 19, wherein $L^2$ is:

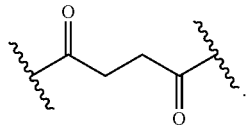 [SMILES: *C(=O)CCC(*)=O]

Embodiment 21

The compound any one of Embodiments 12 to 20, wherein $L^3$ is:

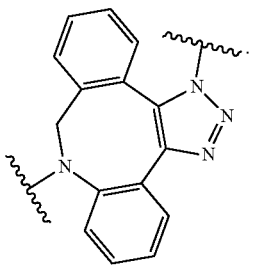 [SMILES: *N1Cc2ccccc2-c2c(nnn2*)-c2ccccc21]

Embodiment 22

The compound of any one of Embodiments 12 to 21, wherein $L^4$ is:

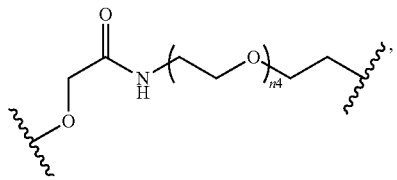

wherein n4 is an integer from 0 to 6.

Embodiment 23

The compound of Embodiment 12 or 13, wherein -$L^1$-$L^2$-$L^3$-$L^4$- is:

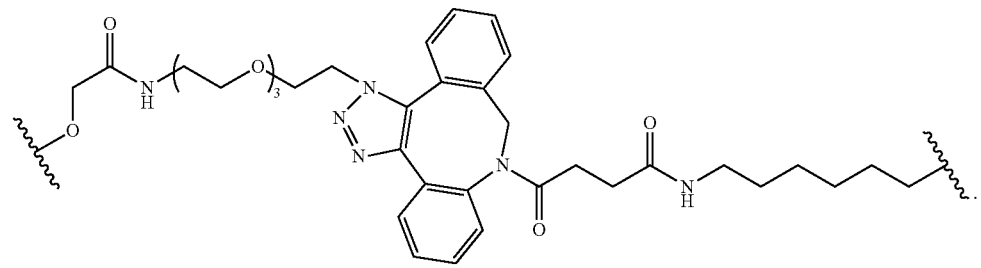

Embodiment 24

The compound of any one of Embodiments 12 to 18, wherein -$L^2$-$L^3$-$L^4$- is:

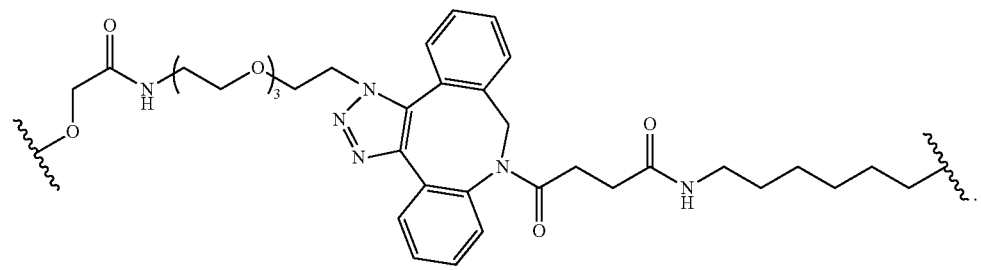

Embodiment 25

The compound of any one of Embodiments 12 to 24, wherein $L^2$ is substituted with -$L^{11}$-$L^{12}$-$L^{13}$-$L^{14}$-MC; wherein MC is the ubiquitin ligase binding compound; and $L^{11}$, $L^{12}$, $L^{13}$, and $L^{14}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 26

The compound of Embodiment 25, wherein $L^{12}$ is substituted with -$L^{101}$-$L^{102}$-$L^{103}$-$L^{104}$-MC; wherein MC is the ubiquitin ligase binding compound; and $L^{101}$, $L^{102}$, $L^{103}$, and $L^{104}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 27

The compound of Embodiment 26, wherein $L^{102}$ is substituted with -$L^{110}$-$L^{120}$-$L^{130}$-$L^{140}$-MC; wherein MC is the ubiquitin ligase binding compound; and $L^{110}$, $L^{120}$, $L^{130}$, and $L^{140}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 28

The compound of Embodiment 27, wherein $L^{120}$ is substituted with -$L^{111}$-$L^{122}$-$L^{133}$-$L^{144}$-MC; wherein MC is the ubiquitin ligase binding compound; and $L^{11}$, $L^{12}$, $L^{133}$, and $L^{144}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 29

The compound of any one of Embodiments 10 to 28, wherein the spacer is substituted with a ubiquitin ligase binding compound.

Embodiment 30

The compound of any one of Embodiments 10 to 28, further comprising a plurality of ubiquitin ligase binding compounds covalently bound to the spacer.

Embodiment 31

The compound of any one of Embodiments 1 to 30, wherein the ubiquitin ligase protein is von Hippel-Lindau tumor suppressor, Cereblon, Mouse Double Minute 2 homologue, or Cellular Inhibitor of Apoptosis.

Embodiment 32

The compound of any one of Embodiments 1 to 31, wherein the ubiquitin ligase binding compound is

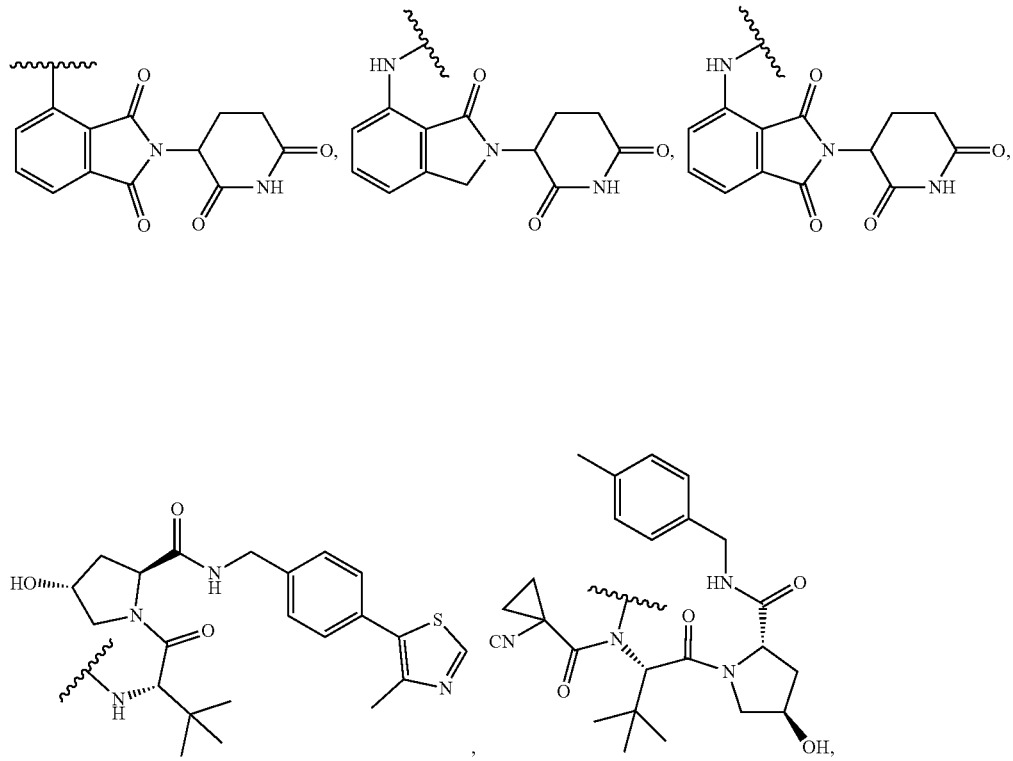

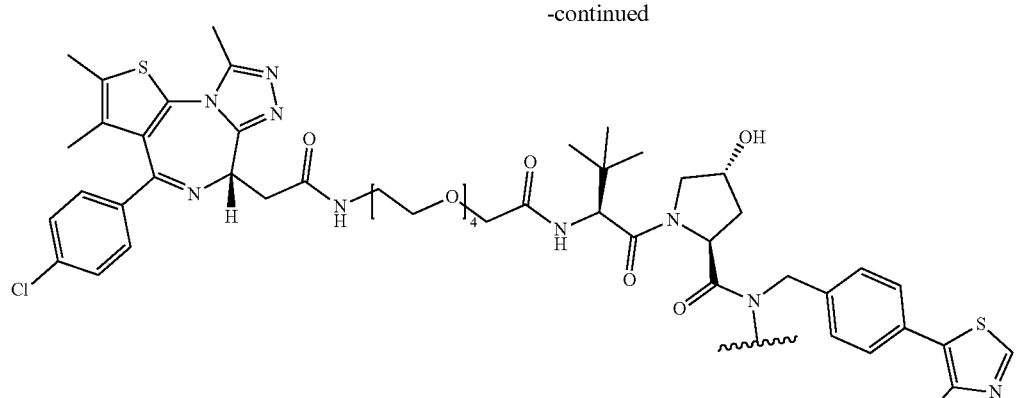

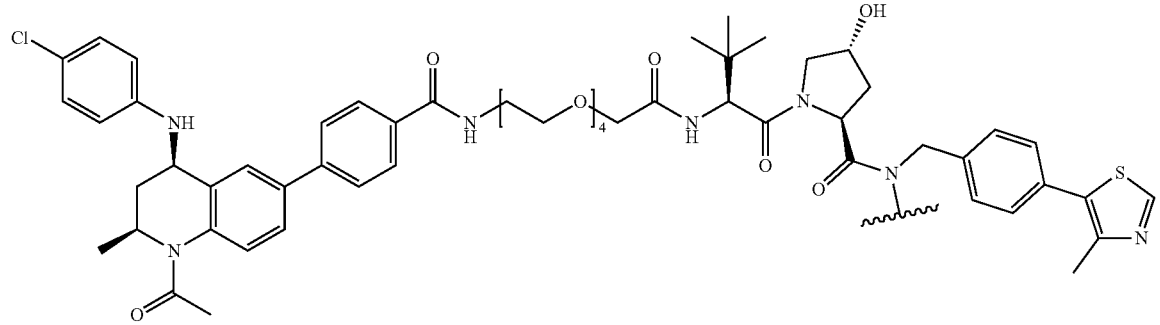

, or

Embodiment 33

The compound of any one of Embodiments 2 to 32, further comprising a phosphorothioate linkage in the first nucleic acid sequence and/or the second nucleic acid sequence.

Embodiment 34

The compound of any one of Embodiment 33, further comprising a plurality of phosphorothioate linkages.

Embodiment 35

The compound of any one of Embodiments 1 to 32, further comprising a phosphorothioate linkage in the first nucleic acid sequence.

Embodiment 36

The compound of any one of Embodiments 2 to 35, further comprising a phosphorothioate linkage in the second nucleic acid sequence.

Embodiment 37

A pharmaceutical composition comprising the compound of any one of Embodiments 1 to 36 and a pharmaceutically acceptable excipient.

Embodiment 38

A method of treating cancer in a patient in need of such treatment, the method comprising administering to the patient a therapeutically effective amount of a compound of any one of Embodiments 1 to 36 or the pharmaceutical composition of claim 37.

Embodiment 39

The method of Embodiment 38, wherein the cancer is a hematopoietic cell cancer, prostate cancer, bladder cancer, renal cancer, breast cancer, glioblastoma, ovarian cancer, lung cancer, head and neck cancer, esophageal cancer, skin cancer, melanoma, brain cancer, colorectal cancer, leukemia, lymphoma, or myeloma

Embodiment 40

A method of treating a neurodegenerative disease in a patient in need of such treatment, the method comprising administering to the patient a therapeutically effective amount of a compound of any one of Embodiments 1 to 36 or the pharmaceutical composition of claim 37.

Embodiment 41

A method of treating an autoimmune disorder in a patient in need of such treatment, the method comprising administering to the patient a therapeutically effective amount of a compound of any one of Embodiments 1 to 36 or the pharmaceutical composition of claim 37.

Embodiment 42

A compound comprising: (i) a nucleic acid having at least 90% sequence identity to a nucleic acid selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24; and
(ii) one or more ubiquitin ligase binding compounds selected from the group consisting of:
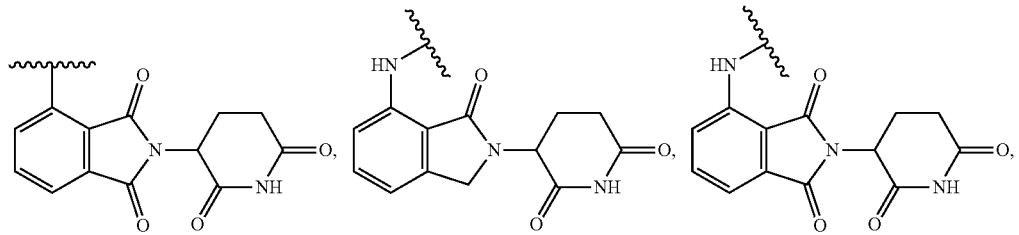
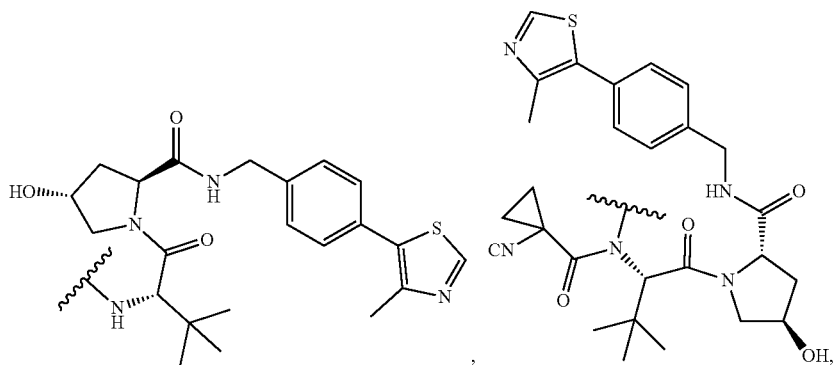
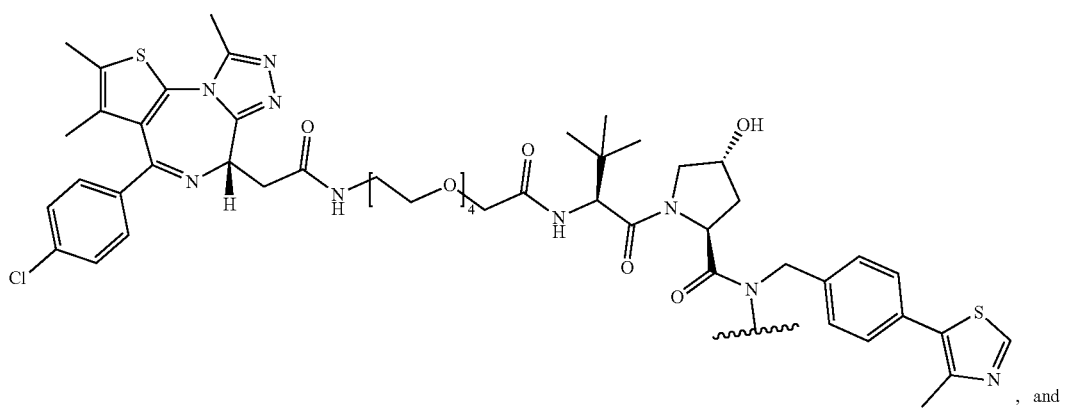
, and
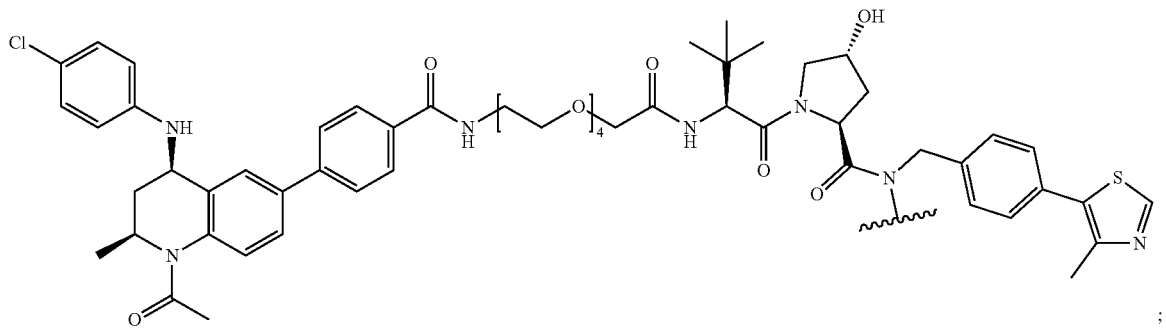
;

wherein the nucleic acid is covalently bonded to the one or more ubiquitin ligase binding compounds.

Embodiment 43

The compound of Embodiment 42, wherein the nucleic acid is SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

Embodiment 44

The compound of Embodiment 42 or 43, wherein the nucleic acid is covalently bonded to the one or more ubiquitin ligase binding compounds through a linking group of the formula: -$L^1$-$L^2$-$L^3$-$L^4$-MC; wherein MC is the ubiquitin ligase binding compound; and $L^1$, $L^2$, $L^3$, and $L^4$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 45

The compound of Embodiment 44, wherein $L^1$ is: —($PO_3OH$—($CH_2$)$_{pm}$)$_{pn}$—$PO_3OH$—, wherein pm is an integer from 1 to 8; and pn is an integer from 1 to 10.

Embodiment 46

The compound of Embodiment 44, wherein $L^1$ is: —($CH_2$)$_{pc}$—($PO_3OH$—($CH_2$)$_{pm}$)$_{pn}$—$PO_3OH$—; wherein pc is an integer from 0 to 6; pm is an integer from 1 to 8; and pn is an integer from 1 to 10.

Embodiment 47

The compound of Embodiment 44, wherein $L^1$ is: —($CH_2$)$_{pc}$—($PO_3OH$—($CH_2$)$_{pm}$)$_{pn}$—; wherein pc is an integer from 0 to 6; pm is an integer from 1 to 8; and pn is an integer from 1 to 10.

Embodiment 48

The compound of Embodiment 44, wherein $L^1$ is: —($PO_3OH$—($CH_2$)$_{pm}$)$_{pn}$—$PO_3OH$—($CH_2$)$_{po}$—NH—; wherein pm is an integer from 1 to 8; pn is an integer from 1 to 10; and po is an integer from 1 to 12.

Embodiment 49

The compound of claim 44, wherein $L^1$ is: —($PO_3OH$—($CH_2$)$_{pm}$)$_{pn}$—$PO_3OH$—[($CH_2$)$_{pa}$—O]$_{pb}$—($CH_2$)$_{po}$—NH—; wherein pm is an integer from 1 to 8; pn is an integer from 1 to 10; po is an integer from 1 to 12; pa is an integer from 1 to 4; and pb is 0, 1, or 2.

Embodiment 50

The compound of any one of Embodiments 44 to 49, wherein $L^2$ is:

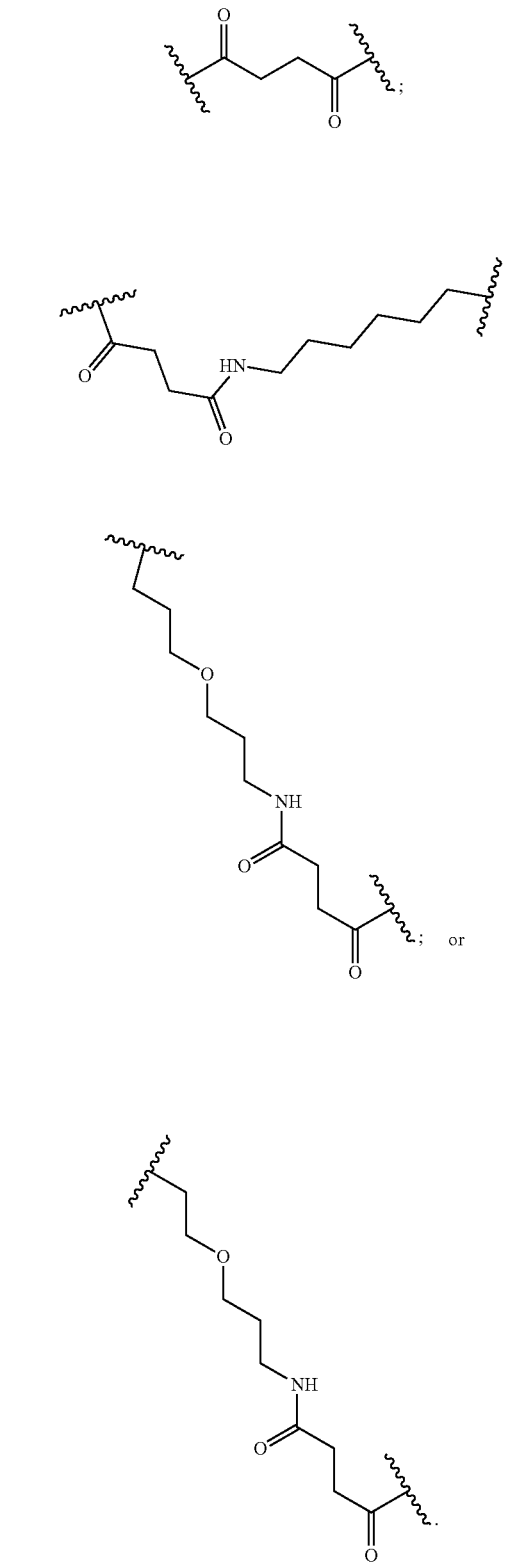

Embodiment 51

The compound of any one of Embodiments 44 to 50, wherein $L^3$ is:

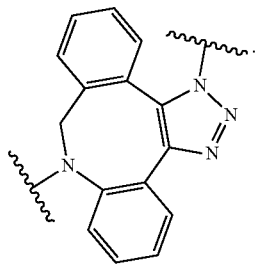 [SMILES: *N1Cc2ccccc2-c2c(nnn2*)-c2ccccc21]

Embodiment 52

The compound of any one of Embodiments 44 to 51, wherein $L^4$ is:

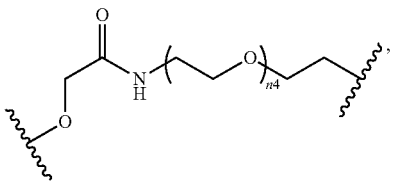

wherein n4 is an integer from 0 to 6.

Embodiment 53

The compound of any one of Embodiments 44 to 49, wherein $-L^2-L^3-L^4-$ is:

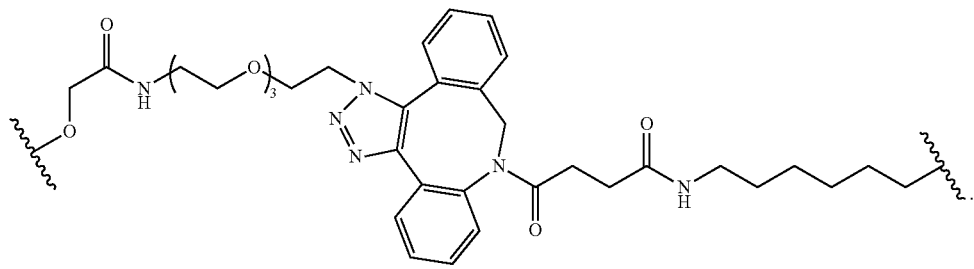

Embodiment 54

The compound of any one of Embodiments 44 to 53, wherein $L^2$ is substituted with $-L^{11}-L^{12}-L^{13}-L^{14}$-MC; wherein MC is the ubiquitin ligase binding compound; and $L^{11}$, $L^{12}$, $L^{13}$, and $L^{14}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 55

The compound of Embodiment 54, wherein $L^{12}$ is substituted with $-L^{101}-L^{102}-L^{103}-L^{104}$-MC; wherein MC is the ubiquitin ligase binding compound; and $L^{101}$, $L^{102}$, $L^{103}$, and $L^{104}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 56

The compound of Embodiment 55, wherein $L^{102}$ is substituted with $-L^{110}-L^{120}-L^{130}-L^{140}$-MC; wherein MC is the ubiquitin ligase binding compound; and $L^{110}$, $L^{120}$, $L^{130}$, and $L^{140}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 57

The compound of Embodiment 56, wherein $L^{120}$ is substituted with $-L^{111}-L^{122}-L^{133}-L^{144}$-MC; wherein MC is the ubiquitin ligase binding compound; and $L^{11}$, $L^{12}$, $L^{133}$, and $L^{144}$ are each independently a bond, substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 58

The compound of any one of Embodiments 42 to 57, wherein the nucleic acid is covalently bonded to one or more of the same ubiquitin ligase binding compound.

Embodiment 59

The compound of any one of Embodiments 42 to 57, wherein the nucleic acid is covalently bonded to two or more different ubiquitin ligase binding compounds.

Embodiment 60

The compound of any one of Embodiments 42 to 59, wherein the nucleic acid is covalently bonded to 1, 2, 3, 4, or 5 ubiquitin ligase binding compound.

Embodiment 61

The compound of any one of Embodiments 42 to 60, further comprising a second nucleic acid selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24; wherein the nucleic acid and the second nucleic acid are linked together via a spacer; wherein the spacer is a substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene

Embodiment 62

A pharmaceutical composition comprising a pharmaceutically acceptable excipient and the compound of any one of Embodiments 42 to 61.

Embodiment 63

A method of treating cancer in a patient in need thereof, the method comprising administering to the patient a therapeutically effective amount of the compound of any one of Embodiments 42 to 61 or the pharmaceutical composition of Embodiment 62.

Embodiment 64

The method of Embodiment 63, wherein the cancer is hematopoietic cell cancer, prostate cancer, bladder cancer, renal cancer, breast cancer, glioblastoma, ovarian cancer, lung cancer, head and neck cancer, esophageal cancer, skin cancer, melanoma, brain cancer, colorectal cancer, leukemia, lymphoma, or myeloma.

Embodiment 65

A method of treating a neurodegenerative disease in a patient in need thereof, the method comprising administering to the patient a therapeutically effective amount of the compound of any one of Embodiments 42 to 61 or the pharmaceutical composition of Embodiment 62.

Embodiment 66

A method of treating an autoimmune disorder in a patient in need thereof, the method comprising administering to the patient a therapeutically effective amount of the compound of any one of Embodiments 42 to 61 or the pharmaceutical composition of Embodiment 62.

EXAMPLES

Oncogenic and tolerogenic transcription factors (TFs), such as STAT3, can be excellent targets for cancer therapy in both cancer cells and in tumor-associated immune cells. See Darnell, Nat. Rev. Cancer, 2(10):740-749 (2002). However, pharmacological inhibition of transcription factors lacking enzymatic activity proved challenging and requires alternative strategies. One of them is to block transcription factor DNA binding and transcriptional activation using competitive inhibitors, such as decoy oligodeoxynucleotides (dODN). See Leong et al, Proc Natl Acad Sci USA, 100(7): 4138-4143 (2003). Decoy ODNs comprise the specific consensus sequence of the transcription factor binding site. The major obstacle in the clinical application of dODNs is difficulty in their targeted delivery. The inventors previously demonstrated that ligand for the intracellular receptor TLR9 (CpG ODN) allows for the delivery of oligonucleotides, such as dODNs, specifically to TLR9-positive target cells without any transfection or packaging reagents both in vitro and in vivo. These include normal myeloid cells or B lymphocytes and malignant cells, such as acute myeloid leukemia (AML) and B cell lymphoma cells. See Zhang et al, Blood, 127(3):1687-1700 (2016); Zhao et al, Mol Ther, 26(3):695-707 (17 Jan. 2018). The CpG-dODN strategy is highly effective in targeting hematologic malignancies and it was shown to induce leukemic and lymphoma cell differentiation and potent immune mediated effects in vivo after systemic administration. However, with target inhibition being reversible, decoys are less effective in generation of cytotoxic effects in cancer cells, which requires more persistent target inhibition.

Example 1

Synthesis and Use of Oligonucleotide-Based Proteolysis Targeting Chimera (Oligo-PROTAC) for Cell-Selective Transcription Factor Knockdown To convert decoys into irreversible transcription factor inhibitors, the inventors equipped CpG-decoy oligodeoxynucleotides with a phthalimide moiety, such as thalidomide or its derivatives (lenalidomide, pomalidomide). Phthalimide moiety acts as a bait to recruit cereblon (CRBN), a component of a cullin-RING ubiquitin ligase (CRL) complex, which can induce proteasomal degradation of the ubiquitinated transcription factor. See Ito et al, Science, 327(5971):1345-1350 (2010); Winter et al, Science, 348 (6241):1376-1381 (2015). The resulting oligonucleotide-based proteolysis targeting chimera (Oligo-PROTAC) can enable cell-selective (TLR9-dependent), transcription factor-specific (decoy-mediated) and irreversible (proteasome-dependent) degradation of the targeted protein. For the proof-of-principal, the inventors developed a method for the chemical synthesis of the STAT3-specific decoy-thalidomide conjugate as described herein. Furthermore, the initial testing of CpG7909-STAT3dODNTHAL (CSI-2BTHAL) indicated reduction of protein levels of STAT3 in B cell lymphoma cells.

Chemical synthesis and structure. $^1$H NMR spectra at 400 MHz and $^{13}$C NMR at 100.6 MHz were recorded in CDCl$_3$/DMSO-d$_6$ unless otherwise noted. All chemical shift values are reported in parts per million (ppm) and referenced to the residual solvent peaks [CDCl$_3$ (7.26 ppm) or DMSO-d6 (2.54 ppm)] for $^1$H NMR and the CDCl$_3$ (77.16 ppm) or DMSO-d$_6$ (39.52 ppm) for $^{13}$C NMR spectra, with coupling constant (J) values reported in Hz. HRMS were obtained in orbitrap (ESI) mode. TLC was performed on Merck Kieselgel 60-F254, and products were detected with 254 nm light. Alfa Aesar Silica gel 60 (230-450 mesh) was used for column chromatography. Purity, yields and ratio of the products (crude and/or purified) were established via NMR with calibrated standards. All reagents and solvents were purchased from commercial suppliers and used without further purification. The derivative of thalidomide (6) was prepared according to the literature reports. Compound 6 was derivatized to obtain the PEG-Azido derivative (8). Compound 8 is a substrate for the click reaction with the DBCO-derivatized oligonucleotide CSI-2B[THAL].

Scheme 1.
Experimental detail for the synthesis of thalidomide-derivatives

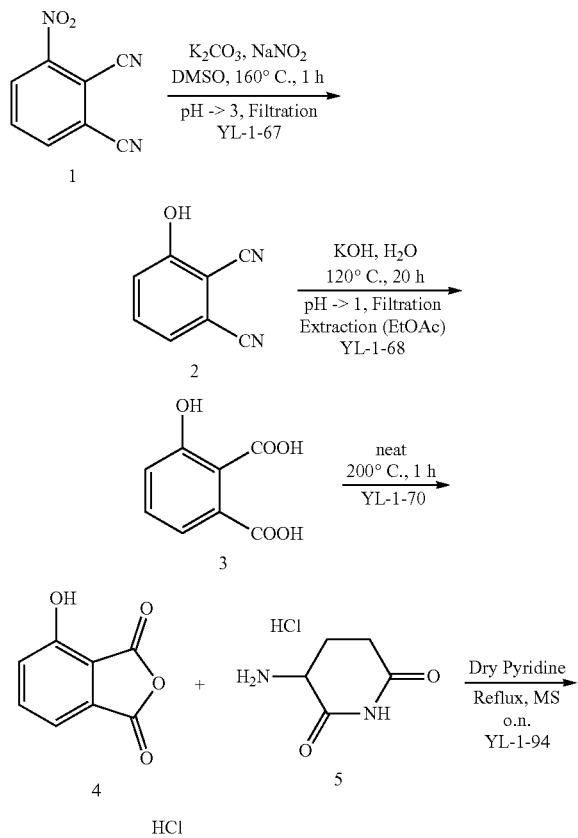

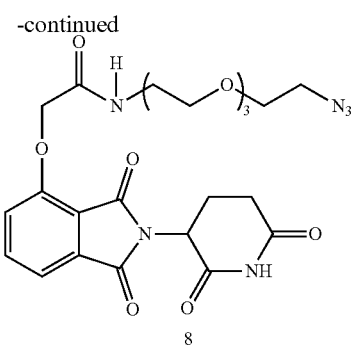

3-hydroxyphthalonitrile (2). The K$_2$CO$_3$ (18.24 g) and NaNO$_2$ (8.27 g) were added to a stirring solution of 3-nitrophthalonitrile (1, 20.8 g, 120 mmol) in DMSO (90 mL) at ambient temperature. The resulting suspension was gently refluxed (oil bath) for 1.5 h. After the resulting hot black reaction mixture was poured into cold water (750 mL), pH was adjusted to 3 with concentrated HCl (~25 mL) to give an orange suspension, which was kept in freezer for 30 min. The precipitate was collected by vacuum filtration, raised with H$_2$O/EtOH and kept under vacuum for overnight to give crude 3-hydroxylphthalonitrile. The product was used for next step without further purification.

3-hydroxyphthalic acid (3). The 3-hydroxylphthalonitrile (2, 17.6 g) was added to a solution of NaOH (38.4 g) in H$_2$O (150 mL) under the ice bath. The resulting suspension was heated at 115° C. for 24 h with air condenser attached. After cooling to ambient temperature, the reaction was adjusted to pH=1 with concentrated HCl (~100 mL) and the pink gel mixture was washed with EtOAc (4×500 mL). Organic layers were combined and dried over anhydrous Na$_2$SO$_4$. Volatiles were removed under the reduced pressure and orange oily residue was dried under vacuum for overnight to give crude 3-hydroxyphthalic acid. The product was used without further purification.

4-hydroxyisobenzofuran-1,3-dione (4). The 3-hydroxyphthalic acid (2 g, 11 mmol) was heated at 198° C. (oil bath) until no sublimation product was generated. The resulting beige crystal was collected and characterized (m.p., NMR). $^1$H NMR (400 MHz, DMSO-d$_6$) δ 7.36 (dd, J=8.4, 0.7 Hz, 1H), 7.47 (dd, J=7.3, 0.7 Hz, 1H), 7.80 (dd, J=8.4, 7.3 Hz, 1H), 11.74 (s, 1H); 13C NMR (100 MHz, DMSO-d$_6$) δ 114.5, 116.1, 124.0, 132.7, 138.1, 157.1, 161.1, 163.4.

Scheme 2. Derivitization of the
3'-amino modified oligonucleotide TH966/CSI-2B[THAL]

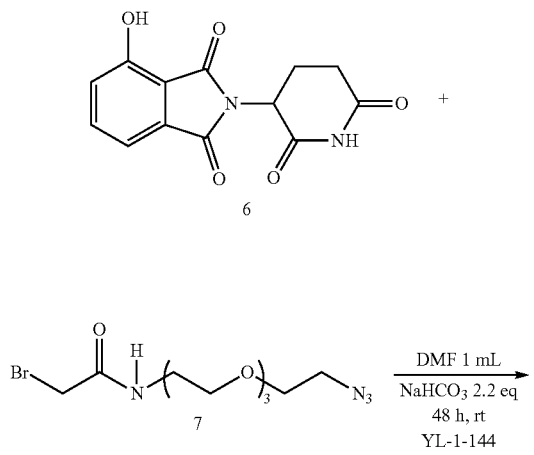

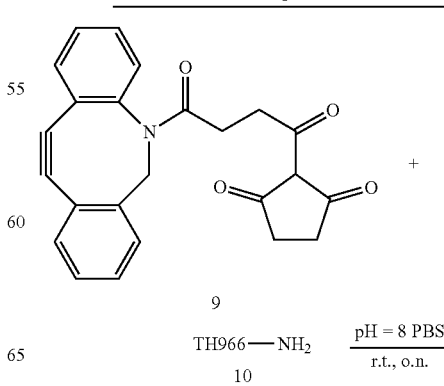

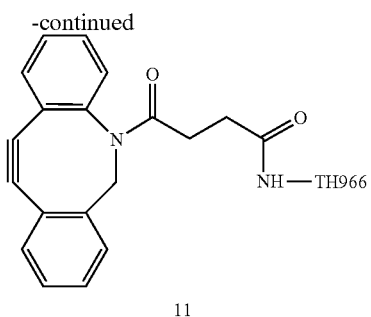

11

CSI-2B$^{THAL}$, other names: CpG(7909)-STAT3 decoy oligodeoxynucleotide-thalidomide conjugate; TH966.

Scheme 3. Conjugation of Thalidomide PEG derivative (8) to a DBCO derivatized oligonucleotide CSI-2B$^{THAL}$

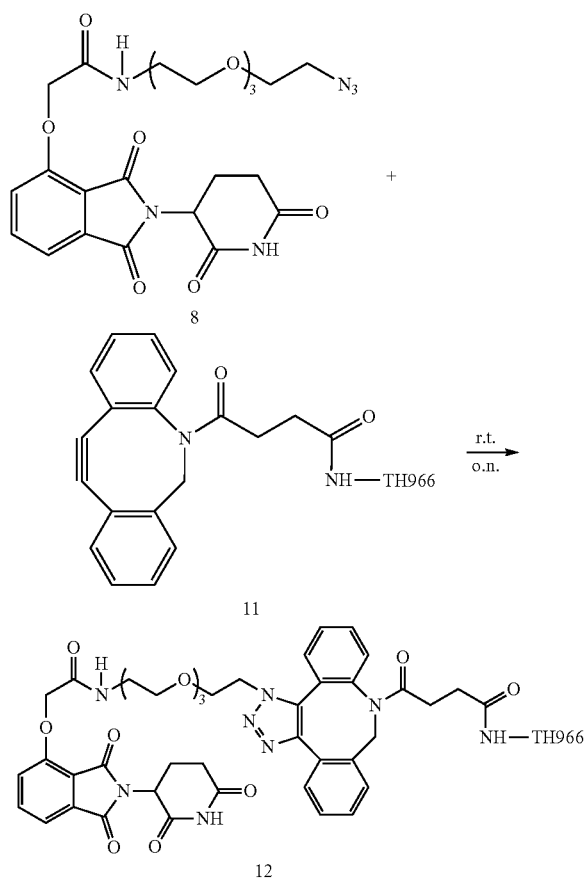

Figure 1B:
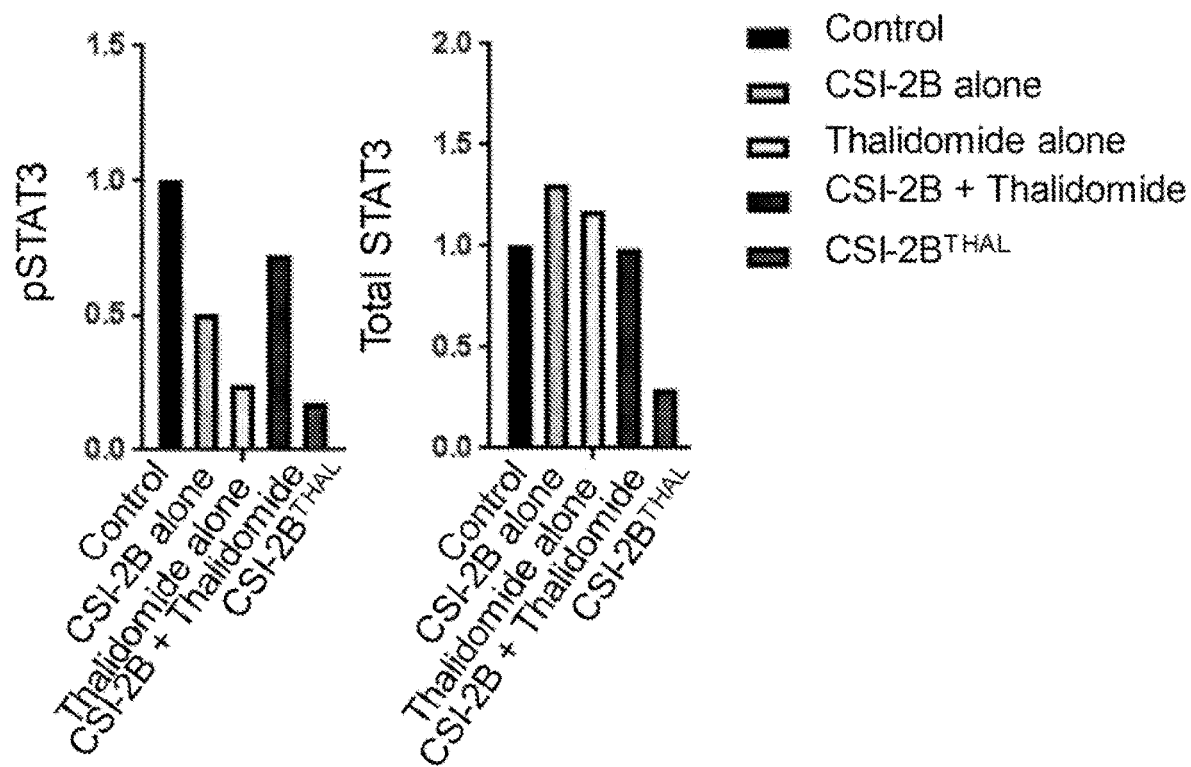
Figure 2:
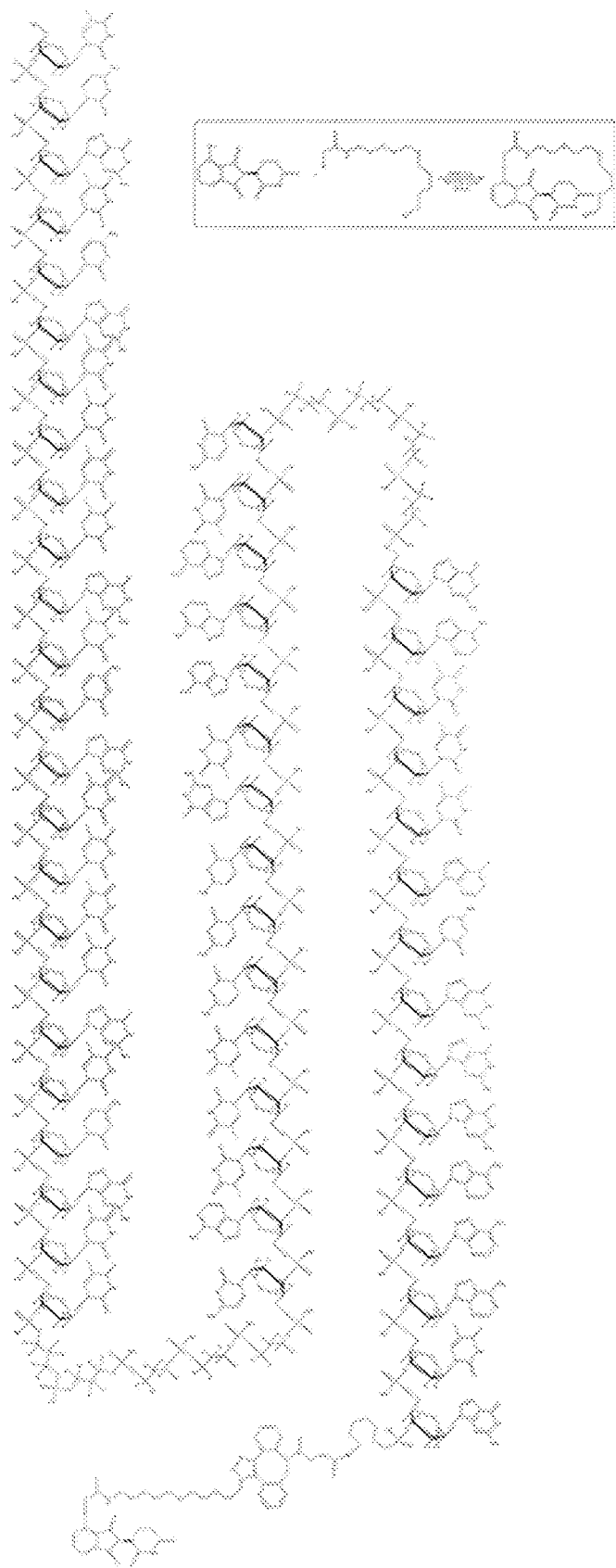
FIG. 2 shows the structure of thalidomide PEG derivative (8) conjugated at the 3'-end to a DBCO derivatized oligonucleotide CSI-2B ODN (SEQ ID NO:1). TH966 CpG (7909)—S3 decoy Click Thalidomide PEG. Chemical formula: $C_{605}H_{790}N_{189}O_{357}P_{63}S_{29}$, exact mass 19291.4843, molecular weight: 19303.0280.
Figure 3A:
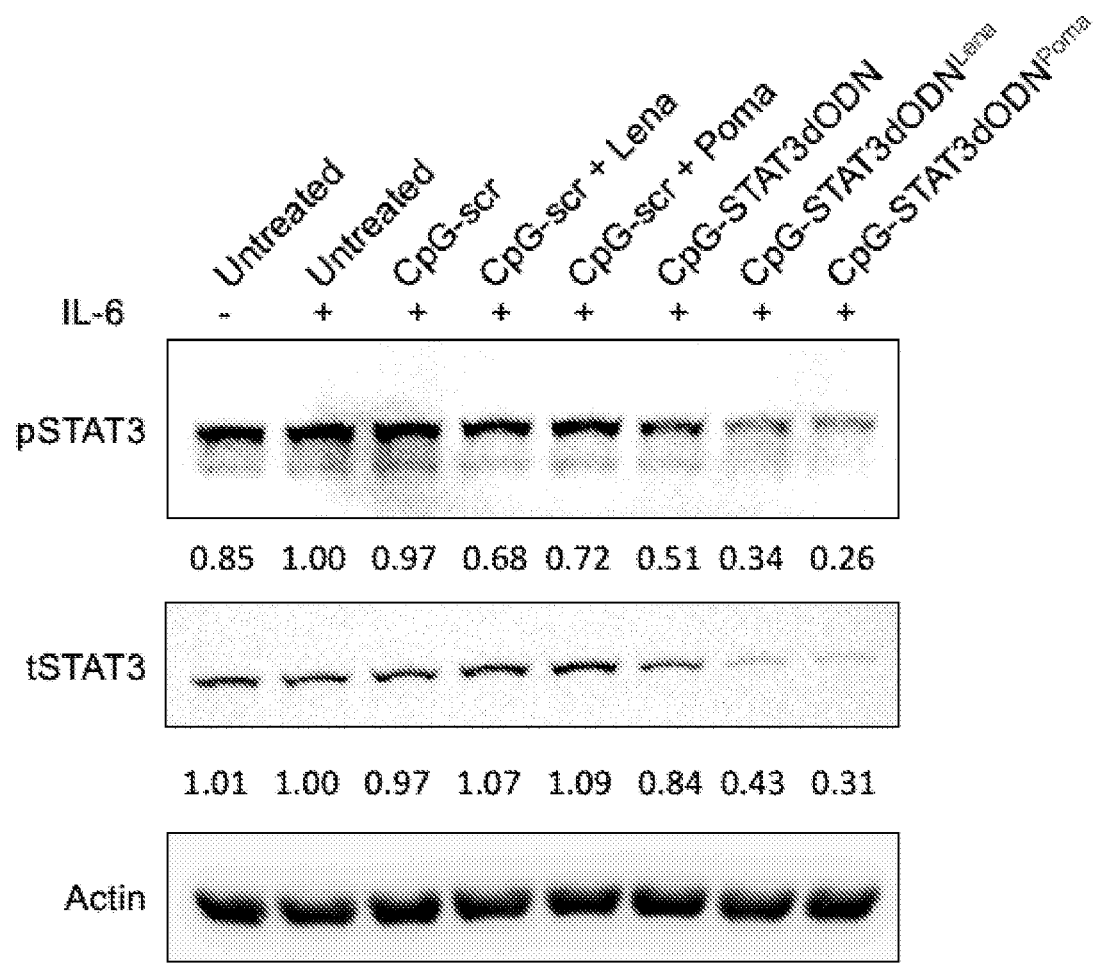
FIGS. 3A-3B shows that CSI-2B conjugates with lenalidomide and pomalidomide (in 1:4 ratio) result in degradation of STAT3 protein in primary mouse splenocytes. Freshly harvested mouse splenocytes were incubated for 3 days with 250 nM CpG7909-STAT3dODN or control CpG7909-scrambledODN conjugated to lenalidomide/pomalidomide or in the presence of unconjugated lenalidomide, pomalidomide (in matched molar ratios).
Figure 3B:
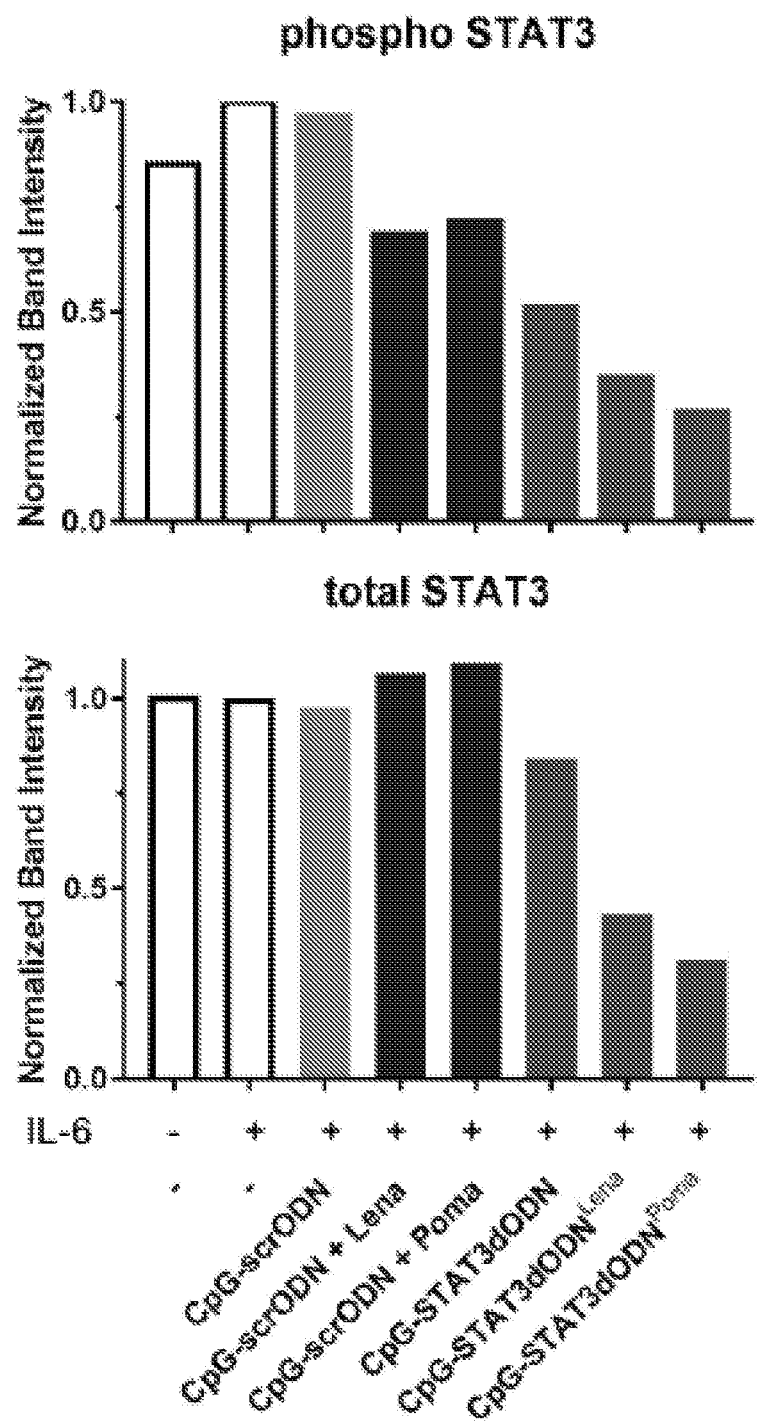
Figure 4:
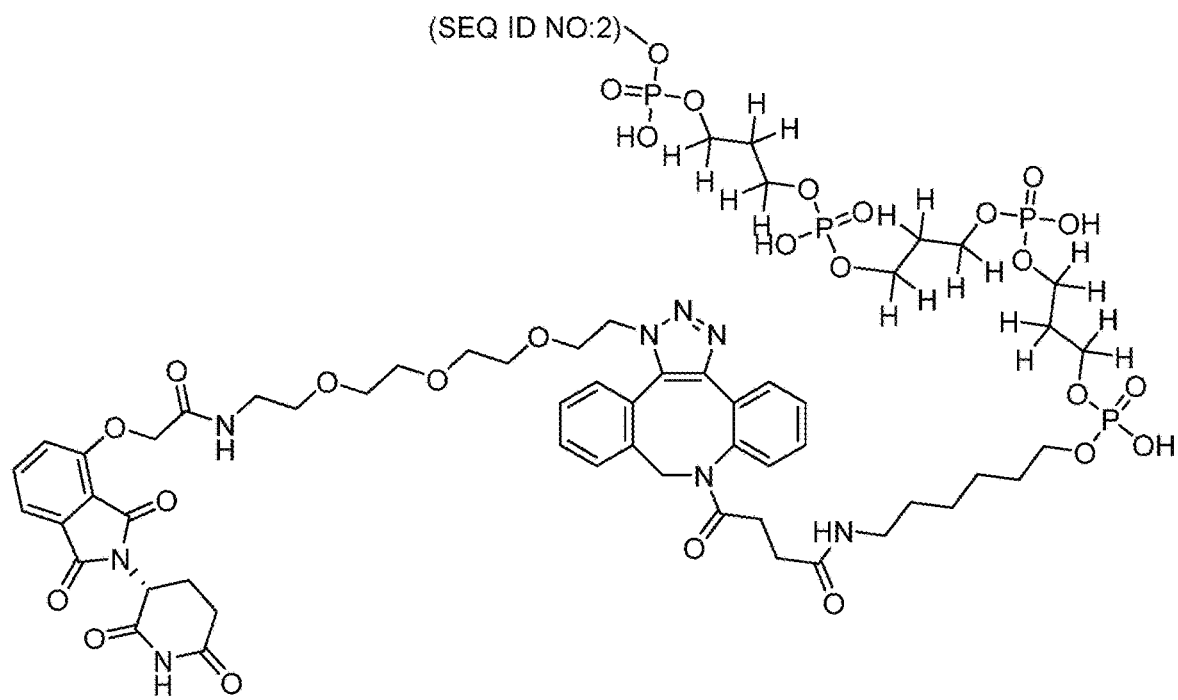
FIG. 4 shows the structure of MK966 CpG(7909)—S3 decoy-mono thalidomide (SEQ ID NO:2 conjugated at the 3' end to one thalidomide moiety via a linking group). Chemical formula: $C_{614}H_{811}N_{189}O_{369}P_{66}S_{29}$, exact mass 19705.51, molecular weight: 19717.20.
Figure 5:
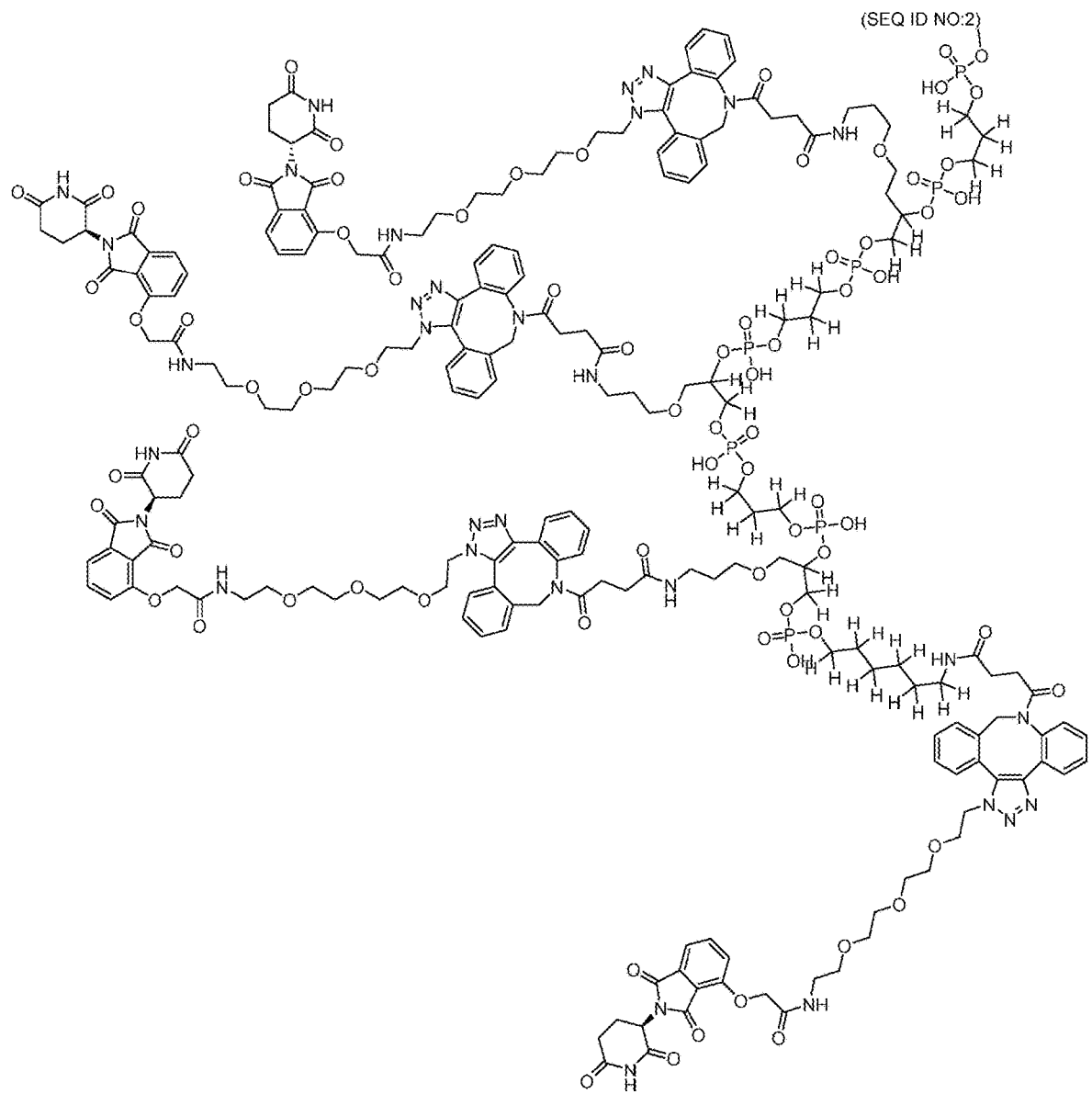
FIG. 5 shows the structure of MK966 CpG(7909)—S3 decoy-tetra thalidomide (SEQ ID NO:2 conjugated at the 3' end to four thalidomide moieties via a linking group). Chemical formula: $C_{759}H_{978}N_{213}O_{416}P_{69}S_{30}$, exact mass 22826.54, molecular weight: 22840.24.
Figure 6:
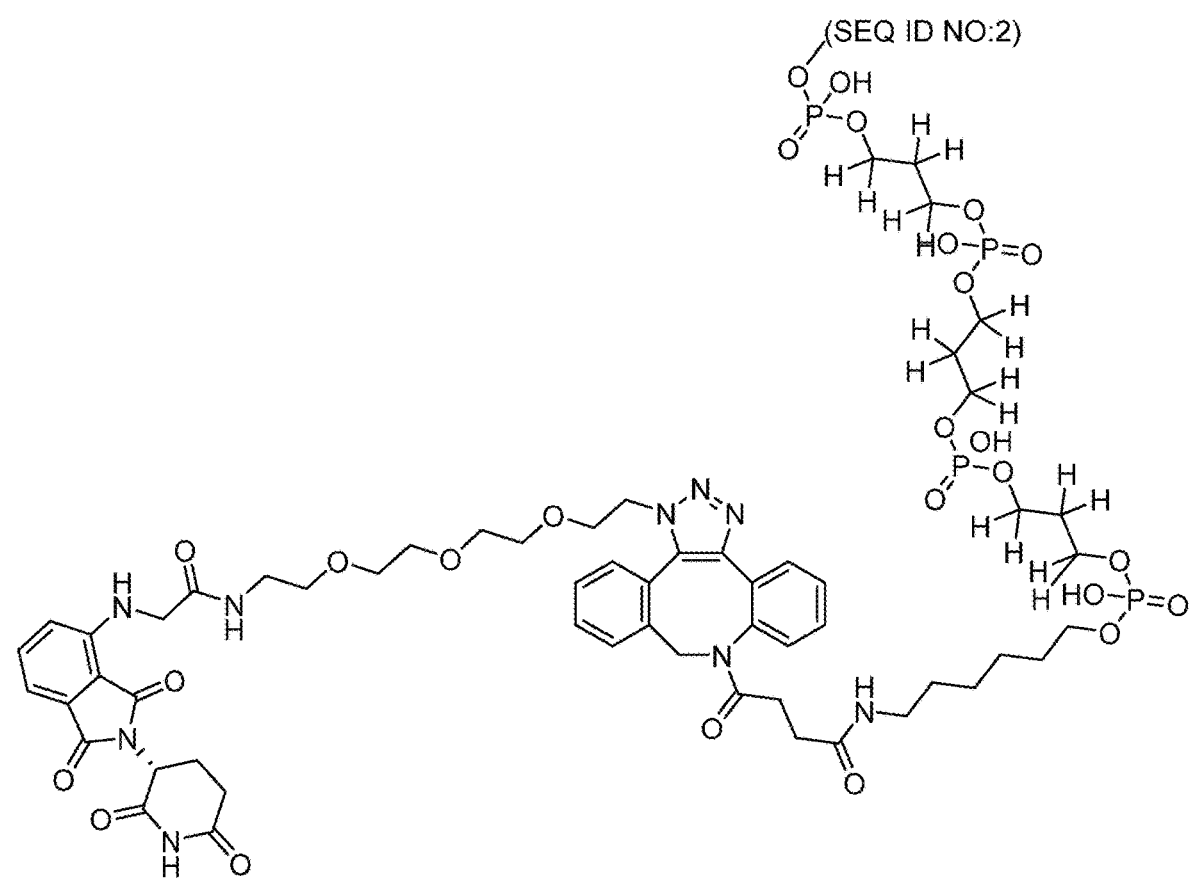
FIG. 6 shows the structure of MK966 CpG(7909)—S3 decoy-mono pomalidomide (SEQ ID NO:2 conjugated at the 3' end to one pomalidomide moiety via a linking group). Chemical formula: $C_{614}H_{812}N_{190}O_{368}P_{66}S_{29}$, exact mass 19704.52, molecular weight: 19716.22.
Figure 7:
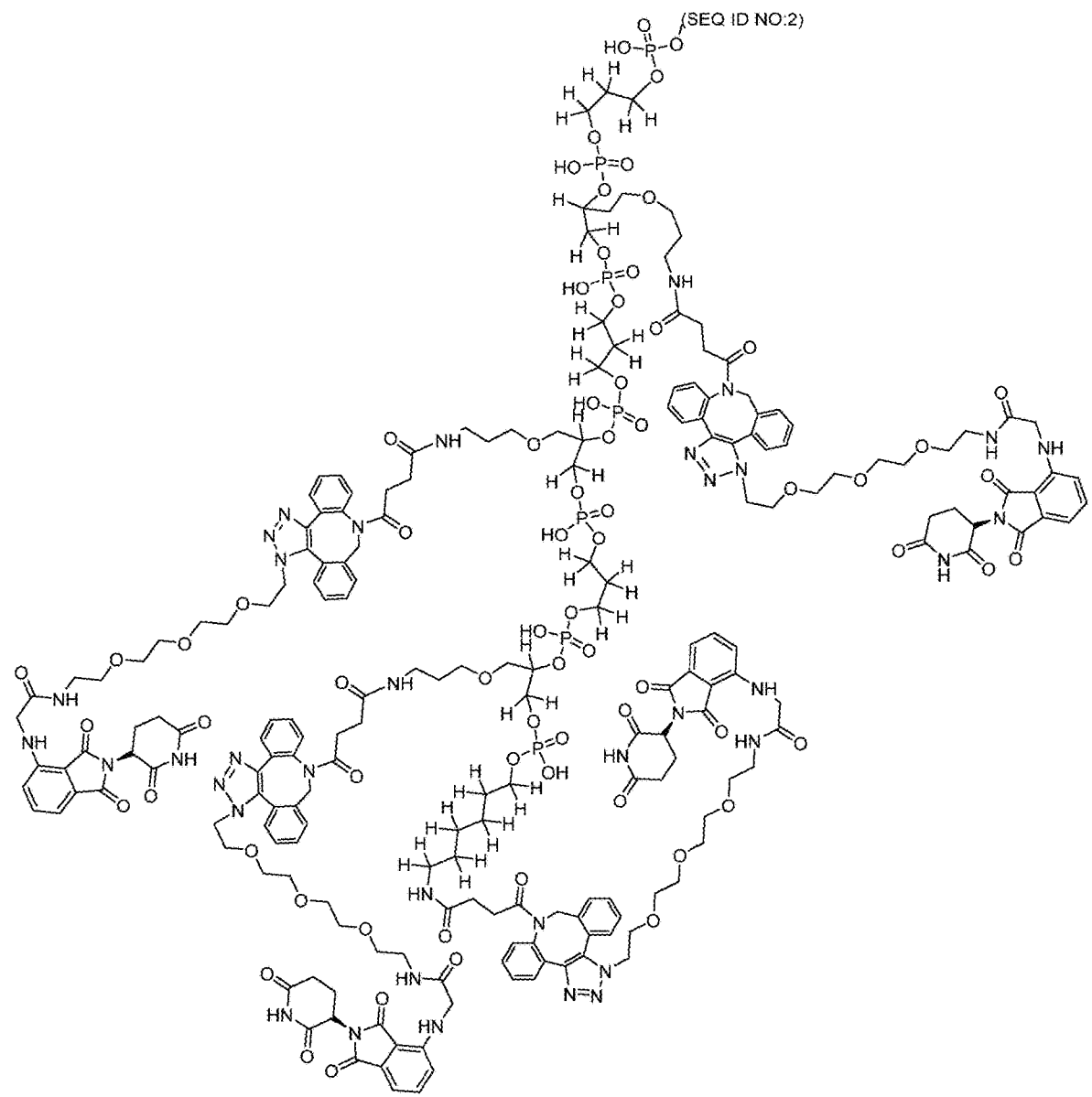
FIG. 7 shows the structure of MK966 CpG(7909)—S3 decoy-tetra pomalidomide (SEQ ID NO:2 conjugated at the 3' end to four pomalidomide moieties via a linking group). Chemical formula: $C_{759}H_{982}N_{217}O_{412}P_{69}S_{30}$, exact mass 22822.61, molecular weight: 22836.30.
Figure 8:
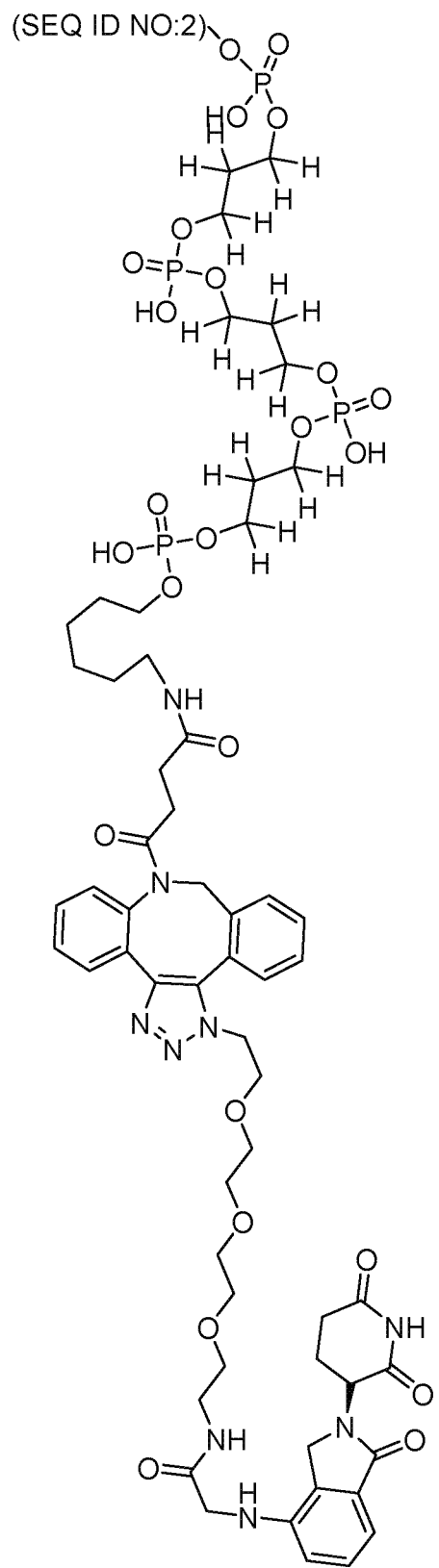
FIG. 8 shows the structure of MK966 CpG(7909)—S3 decoy-mono lenalidomide (SEQ ID NO:2 conjugated at the 3' end to with one lenalidomide moiety via a linking group). Chemical formula: $C_{614}H_{814}N_{190}O_{367}P_{66}S_{29}$, exact mass 19690.5456, molecular weight: 19702.2373.
Figure 9:
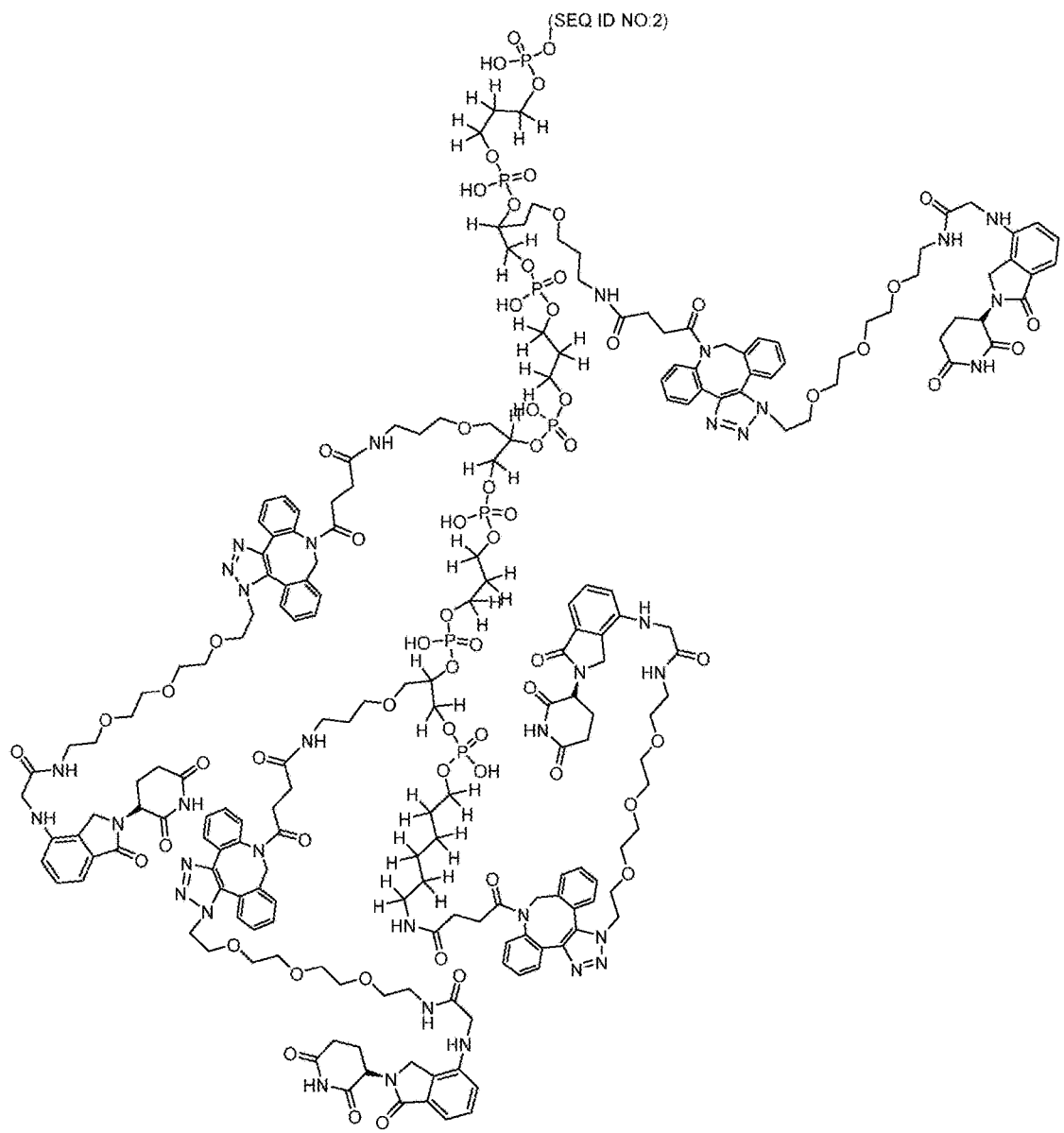
FIG. 9 shows the structure of MK966 CpG(7909)—S3 decoy-tetra lenalidomide (SEQ ID NO:2 conjugated at the 3' end to four lenalidomide moieties via a linking group). Chemical formula: $C_{759}H_{990}N_{217}O_{408}P_{69}S_{30}$, exact mass 22766.69, molecular weight: 22780.37.
Figure 10:
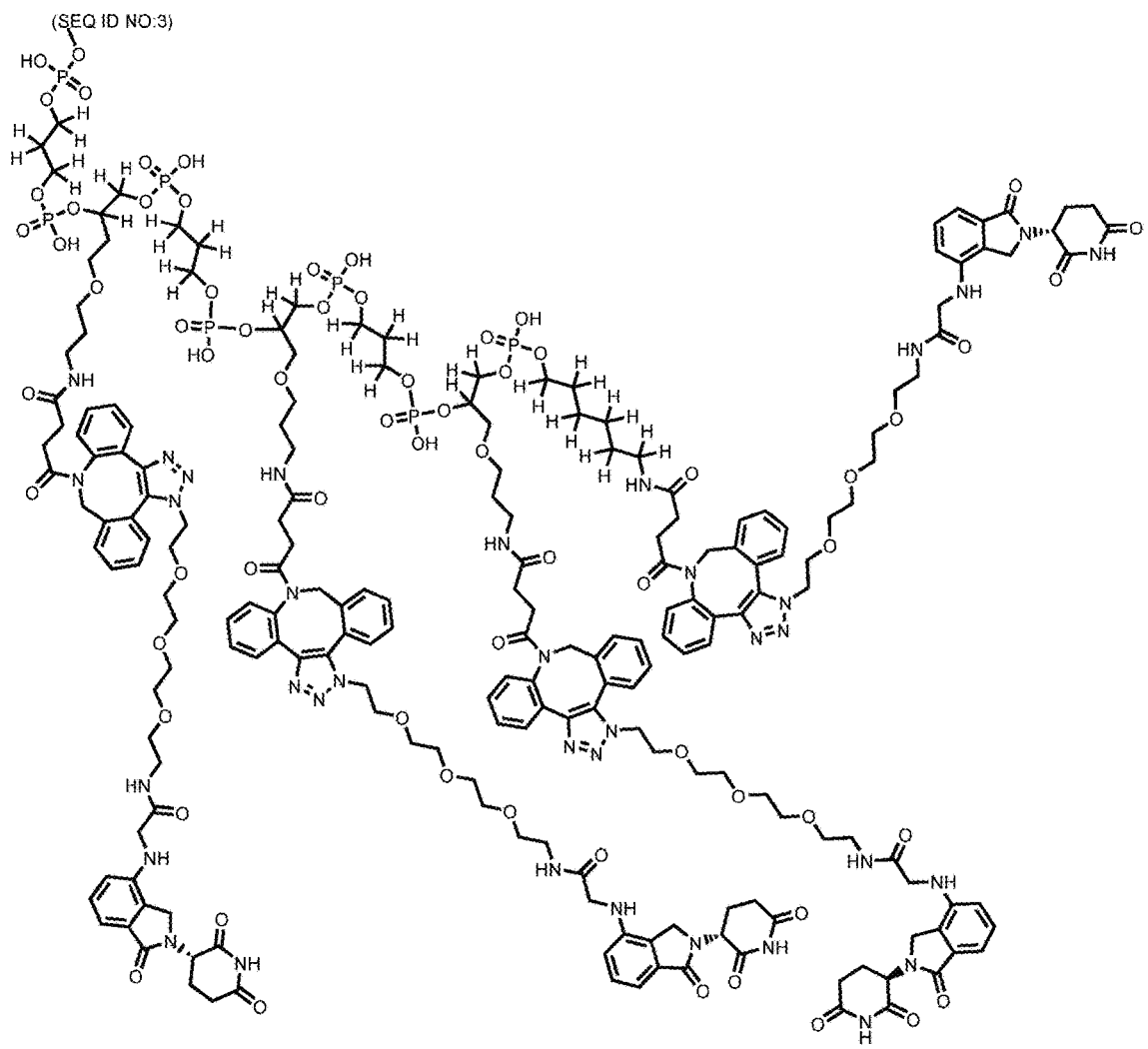
FIG. 10 shows a plurality of monovalent lenalidomide moieties, and their respective linkers, for attachment at the 3' end to a nucleic acid (e.g., NH-TH966, where TH966 is SEQ ID NO:3).

In vitro activity of CSI-2B$^{THAL}$ in human B-cell lymphoma cells. 0.5×10$^6$/ml human OCI-Ly10 ABC-DLBCL cells were seeded in 4 ml RPMI1640 containing 10% FBS on 12-well plates, and treated with 500 nM CSI-2B alone, thalidomide alone, CSI-2B plus thalidomide mixture or CSI-2B$^{THAL}$ conjugate once daily. After 72 h incubation, proteins were extracted and examined using Western blotting. Results were compared to diluent only (DMSO) control to evaluate CSI-2B$^{THAL}$'s effect on target STAT3 protein levels. In Ly10 cells, CSI+Thalidomide mixture moderately reduced the protein level of total STAT3 (t-STAT3), while CSI-2B$^{THAL}$ induced more pronounced degradation effect at higher concentrations. In terms of phosphorylated STAT3 (p-STAT3), CSI-2B$^{THAL}$ induced more profound degradation effect than the mixture or either reagent alone (FIGS. 1A-1B).

FIGS. 13A-13D show the CSI-2B$^{THAL}$ conjugate results in specific reduction of STAT3 but not STAT1 or STAT5 in mouse B-cell lymphoma cells and dendritic cells. Mouse A20 B-cell lymphoma cells with wild-type STAT3 and mouse DC2.4 dendritic cells with or without expression of constitutively active STAT3C mutant (DC2.4/STAT3C cells) were used in the experiment. Cells were seeded in 12-well plates (4×10$^5$ cells in each well) and cultured in 10% FBS/RPMI1640. A20 B-cell lymphoma cells were treated using 250 nM CSI-2B$^{Tha}$ or equimolar mixture of CSI-2B and thalidomide for 2 days followed by 1 hour stimulation with 20 ng/mL IL-6 before harvesting the cells. DC2.4 or DC2.4/STAT3C cells were treated with 500 nM compounds for 3 days followed by 6 hour stimulation using 20 ng/mL IL-6. Phosphorylated and total STAT3 protein, STAT1 protein and STAT5 protein levels were quantified after normalization to β-actin used as a loading control. CSI-2B, CpG (7909)-STAT3 decoy; Tha, thalidomide; CSI-2B$^{Tha}$, Thalidomide-conjugated CpG(7909)-STAT3 decoy; pSTAT3, phosphorylated STAT3 protein.

Figure 11:
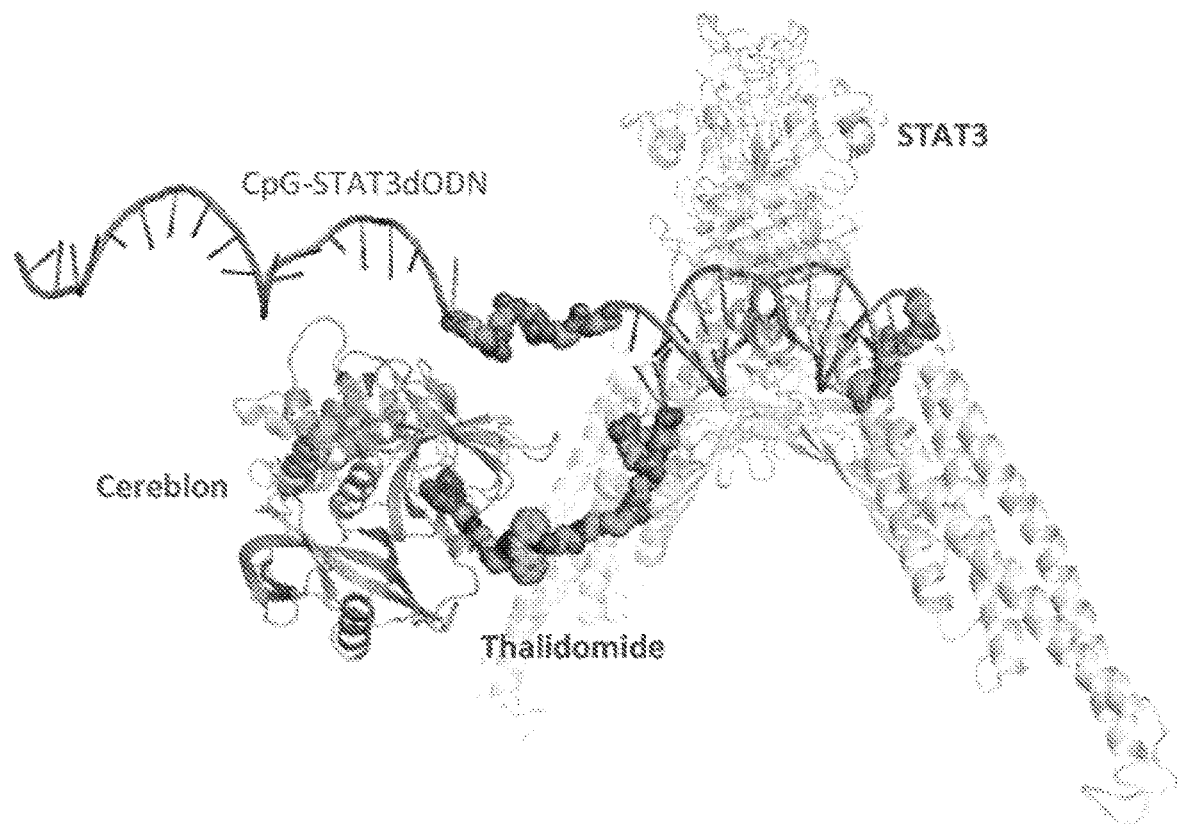
FIG. 11 is a computational model of CSI-2B$^{THAL}$ bound to STAT3 and cereblon proteins.
Figure 12:
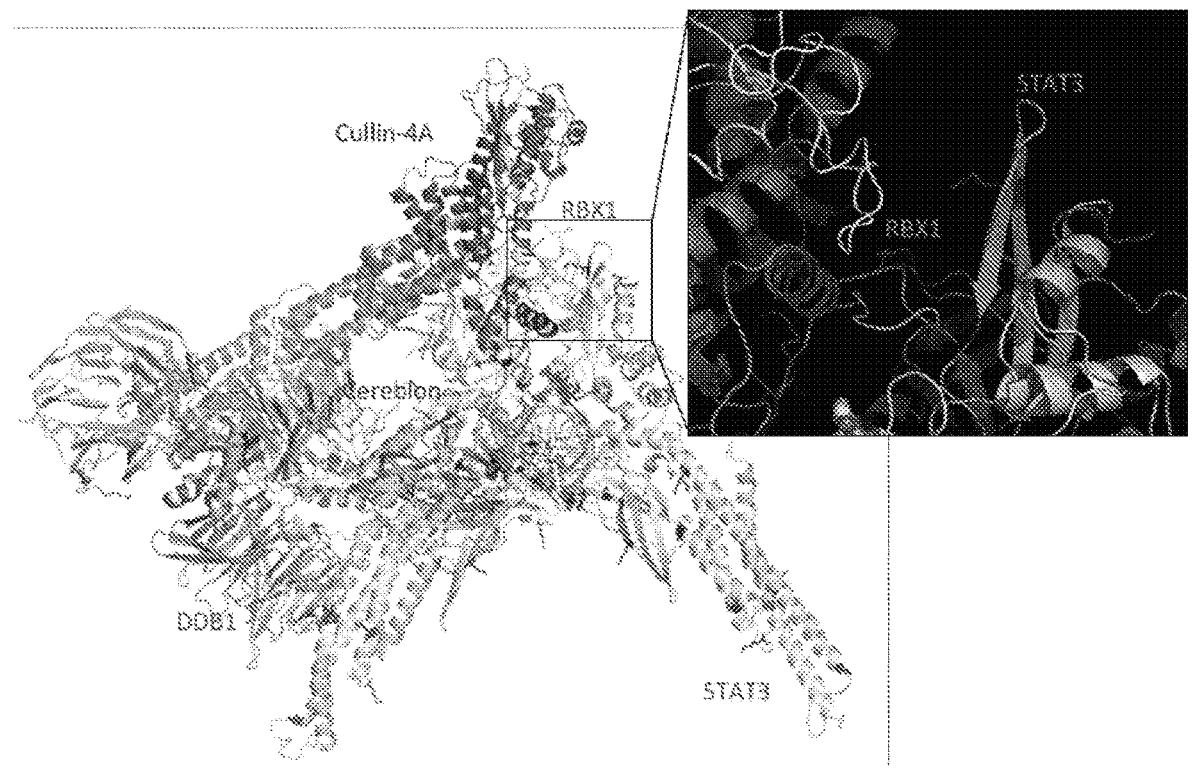
FIG. 12 is a computational modeling of the CSI-2B$^{THAL}$ bridging STAT3 dimer to the E3 ubiquitin ligase complex. Left: Shown is the computational modeling in solution of the CpG-STAT3 decoy$^{THAL}$ (CI-2B) bridging STAT3 with the E3 ubiquitin ligase complex, comprising the cereblon, DDB1, Cullin-4A and RBX1 proteins. Right: close-up of the active site of RBX1 (E3 ubiquitin protein ligase) and the two lysine residues in STAT3 as a potential ubiquitin protein ligase (ubiquitination) sites.
Figure 13A:
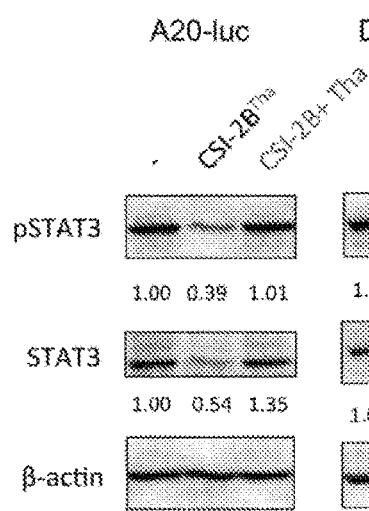
FIGS. 13A-13D show the CSI-2B$^{THAL}$ conjugate results in specific reduction of STAT3 but not STAT1 or STAT5 in mouse A20 B-cell lymphoma cells with wild-type STAT3 and mouse DC2.4 dendritic cells with or without expression of constitutively active STAT3C mutant (DC2.4/STAT3C cells).
Figure 13B:
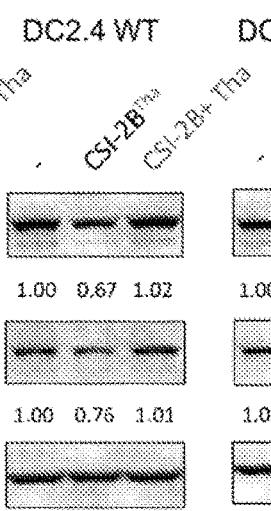
Figure 13C:
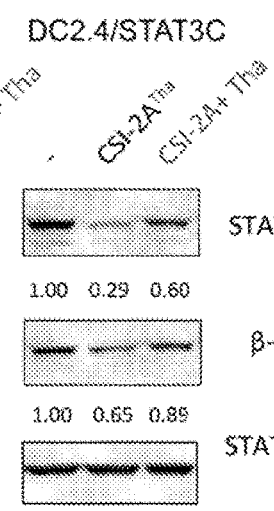
Figure 13D:
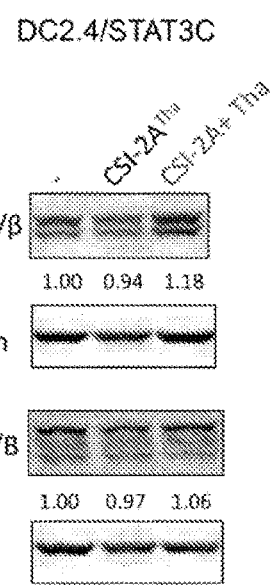

Computational modeling of the CSI-2B$^{THAL}$ with STAT3 and cereblon proteins is shown in FIG. 11. The computational modeling in solution of the tripartite complex of the CpG-STAT3 decoy$^{THAL}$ (conjugated via spacer at the 3'-terminus to a thalidomide molecule) bound to the DNA binding domain of the STAT3 dimer and to the cereblon molecule. Based on these results, the single stranded part of the molecule does not interfere with DNA-protein and thalidomide-protein interactions.

Example 2

Experimental Detail for the Synthesis of Thalidomide and Pomalidomide Derivatives Pomalidomide—General Information. $^1$H NMR spectra at 400 MHz and $^{13}$C NMR at 100.6 MHz were recorded in CDCl$_3$/DMSO-d$_6$ unless otherwise noted. All chemical shift values are reported in parts per million (ppm) and referenced to the residual solvent peaks [CDCl$_3$ (7.26 ppm) or DMSO-d$_6$ (2.54 ppm)] for $^1$H NMR and the CDCl3 (77.16 ppm) or DMSO-d$_6$ (39.52 ppm) for $^{13}$C NMR spectra, with coupling constant (J) values reported in Hz. HRMS were obtained in orbitrap (ESI) mode. TLC was performed on Merck kieselgel 60-F$_{254}$, and products were detected with 254 nm light. Alfa Aesar Silica gel 60 (230-450 mesh) was used for column chromatography. Purity, yields and ratio of the products (crude and/or purified) were established via NMR with calibrated standards. All reagents and solvents were purchased from commercial suppliers and used without further purification.

The 4-nitrophenylchloroformate (2, 230 mg, 1.14 mmol) was added to a stirring suspension of pomalidomide (1, 208 mg, 0.76 mmol) in dry THF (30 mL) at ambient temperature. After the resulting mixture was heated at 70° C. (oil bath) for 4 h. After cool down to ambient temperature, volatiles were removed under the reduced pressure to give yellowish solid, which was washed with DCM to give product 3 in xx mg (xx %). The corresponding product was used without further purification.

Scheme

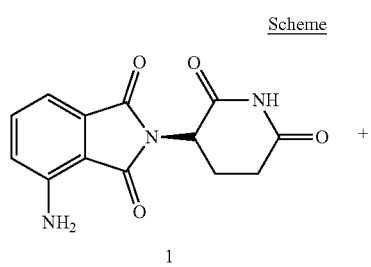

1

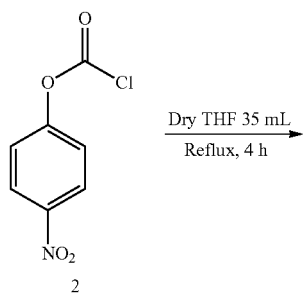

2

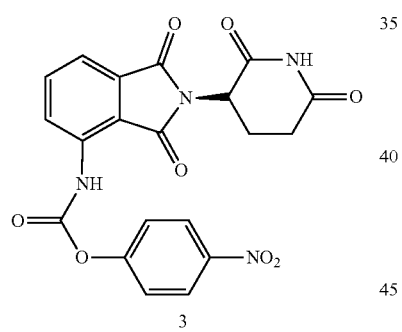

3

Scheme

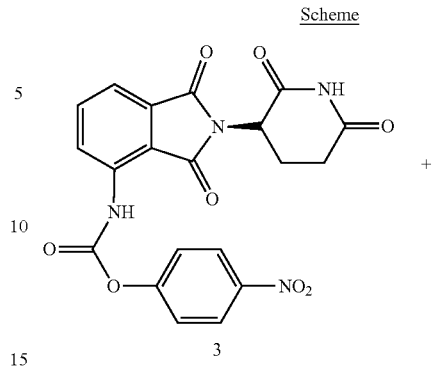

3

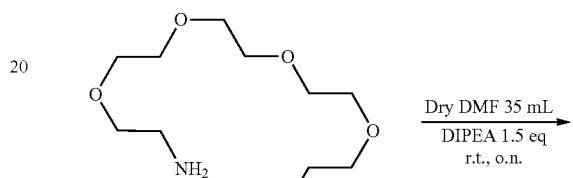

4

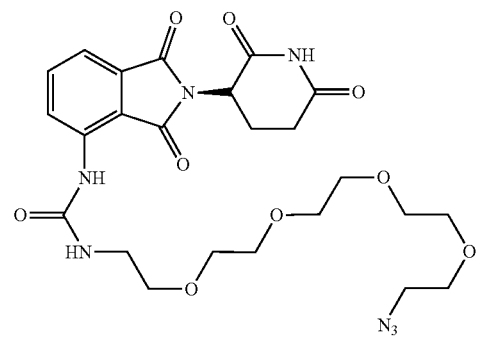

5

The diisopropylamine (39 mg, 27 µL, 0.3 mmol) and activated Lenalidomide 3 (99 mg, 0.2 mmol) were added to a stirring solution of azido-PEG(4)-amine 4 (39 mg, 36 µL, 0.15 mmol) in dry DMF (2 mL) at ambient temperature under Ar atmosphere and the resulting solution was stirred for overnight. Volatiles were removed under the reduced pressure and the oily residue was column chromatographed (EtOAc) to give product 5 in 91% (76 mg). $^1$H NMR (400 MHz, DMSO-$d_6$) δ 2.03-2.11 (m, 1H), 2.52-2.70 (m, 2H), 2.90 (ddd, J=16.9, 13.9, 5.4 Hz, 1H), 3.24-3.29 (m, 2H), 3.36-3.40 (m, 2H), 3.48 (t, J=5.6 Hz, 2H), 3.50-3.56 (m, 12H), 3.56-3.60 (m, 2H), 5.12 (dd, J=12.7, 5.4 Hz, 1H), 7.42 (dd, J=7.2, 0.8 Hz, 1H), 7.73 (dd, J=8.7, 7.2 Hz, 1H), 7.85 (s, 1H), 8.58 (dd, J=8.6, 0.8 Hz, 1H), 8.87 (s, 1H), 11.14 (s, 1H). $^{13}$C NMR (101 MHz, DMSO-$d_6$) δ 22.1, 30.9, 48.8, 50.0, 69.2, 69.4, 69.6, 69.7, 69.8, 69.8, 69.8, 113.8, 115.8, 124.3, 131.4, 135.8, 139.0, 154.3, 166.9, 168.1, 169.9, 172.8.

Example 3

Derivatization of the 3'-amino modified oligonucleotide TH966 (also known as CpG(D19)—S3 decoy; CpG (7909)—S3 Decoy; SEQ ID NO:3).

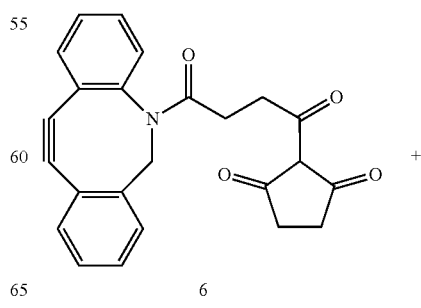

6

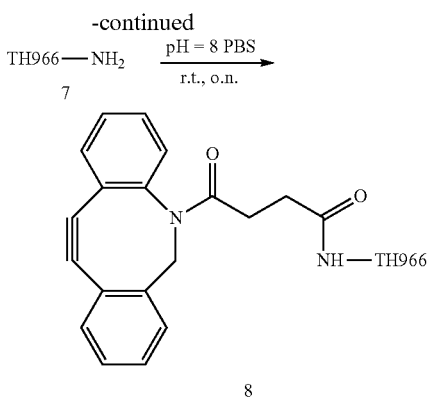

Conjugation of Pomalidomide PEG derivative (5) to a DBCO derivatized oligonucleotide TH966

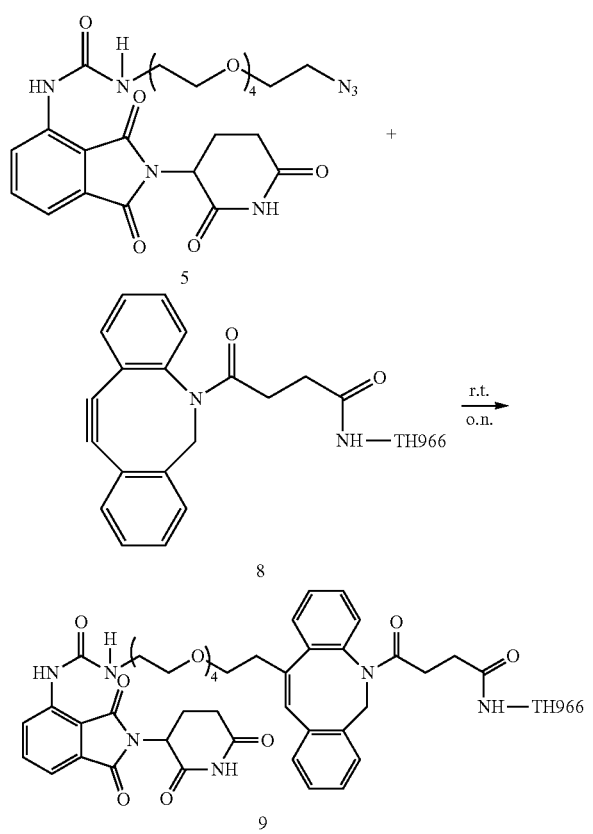

Example 4

The CpG-siRNAs were synthesized in the DNA/RNA Synthesis Core (COH) by linking CpG(B)-ODN (CpG1668), CpG(A) (D19) or GpC(A) to STAT3 decoy or scrambled ODN sequences similarly as previously described (Kortylewski et al. Nat. Biotech. 2009) using 4-5 units of $C_3$ carbon chain, $(CH_2)_3$ (Glen Research, VA). The resulting ODN conjugates are shown below, where asterisks indicate phosphothioation sites in the conjugate backbone; x=single unit of the $C_3$ carbon chain $(CH_2)_3$ bonded to phosphate groups at both ends, except at the 5' end and 3' end where the last 3' x is —$C^6$—$NH_2$ following the final phosphate group and a 5' terminal x has an OH group at the terminus; or combined x's equal an alkylphosphate (e.g. 5x is n=4 or 5x is n1=4, as n and n1 and n2 are used herein for alkylphosphates). A 5' nucleotide has a terminal 5' OH group.

In embodiments, the sequences described herein, 'p' is used in place of 'iSpC3'. Additionally, '/3AmMC6/' has been replaced with 'ppp-C6-amino.' Further, the inventors conducted one experiment where the linkers on 3'-end were eliminated, leaving only 3'-aminoC6 group. This oligo was referred to as TH966, as opposed to MK966 with three 3'-spacers plus amino.

SEQ ID NO:1 5'-T*C*G*T*C*G*T*T*T*T*G*T*C*G*T*T*T*T*T*G*T*C*G*T*T/iSpC3//iSpC3//iSpC3//iSpC3//iSpC3/C*A*T*TTC CCG TAA ATC/iSpC3//iSpC3//iSpC3//iSpC3/GAT TTA CGG GAA*A*T*G/3AmMC6/-3'; wherein/iSpC3/=internal $C_3$ space; *=internal phosphorothioation; /3AmMC6/=3'-C6-amino linker; where 5' C*A*T*TTC CCG TAA ATC 3' is SEQ ID NO:25 and 5' GAT TTA CGG GAA*A*T*G 3' is SEQ ID NO:26.

```
                                    SEQ ID NO: 1
5'- T*C*G* T*C*G* T*T*T* T*G*T* C*G*T* T*T*T*

G*T*C* G*T*T /iSpC3//iSpC3//iSpC3//iSpC3//iSpC3/

C*A*T* TTC CCG TAA ATC /iSpC3//iSpC3//iSpC3// iSpC3/ GAT TTA CGG GAA* A*T*G /3AmMC6/ -3';

wherein /iSpC3/ = internal C3 space; * = internal phosphorothioation; /3AmMC6/ = 3'-C6- amino linker; where 5' C*A*T* TTC CCG TAA ATC

3' is SEQ ID NO: 25 and 5' GAT TTA CGG GAA *A*T*G

3' is SEQ ID NO: 26.

SEQ ID NO: 2
5' T*C*G* T*C*G* T*T*T* T*G*T* C*G*T* T*T*T*

G*T*C* G*T*T ppppp C*A*T* TTC CCG TAA ATC pppp GAT

TTA CGG GAA *A*T*G ppp-C6-amino 3'

SEQ ID NO: 3
SEQ ID NO: 3; 5'-T*C*G* T*C*G* T*T*T* T*G*T*

C*G*T* T*T*T* G*T*C* G*T*T /iSpC3//iSpC3//iSpC3// iSpC3//iSpC3/C*A*T* TTC CCG TAA ATC /iSpC3// iSpC3//iSpC3//iSpC3/GAT TTA CGG GAA* A*T*G

/3AmMC6/ -3'; wherein /iSpC3/ = internal C3 space;

* = internal phosphorothioation; /3AmMC6/ = 3'-

C6-amino linker.

CpG(A)-STAT3dODN
                                    (SEQ ID NO: 4)
5' G*G*TGCATCGATGCAGG*G*G*G*G-xxxxx-C*A*T*TTCCCGTA AATC-xxxx-GATTTACGGGAA*A*T*G-xxxxx 3'

GpC(A)-STAT3dODN
                                    (SEQ ID NO: 5)
5' G*G*TGCATGCATGCAGG*G*G*G*G-xxxxx-C*A*T*TTCCCGTA AATC-xxxx-GATTTACGGGAA*A*T*G-xxxxx 3'
```

-continued

CpG(A)-scrambled ODN
(SEQ ID NO: 6)
5' G*G*TGCATCGATGCAGG*G*G*G*G-xxxxx-A*C*T*CTTGCCAA TTAC-xxxx-GTAATTGGCAAG*A*G*T-xxxxx 3'

CpG(B)-STAT3dODN
(SEQ ID NO: 7)
5' T*C*C*A*T*G*A*C*G*T*T*C*C*T*G*A*T*G*C*T-xxxxx- C*A*T*TTCCCGTAAATC-xxxx-GATTTACGGGAA*A*T*G-xxxxx

3'

CpG(B)-mutSTAT3dODN
(SEQ ID NO: 8)
5' T*C*C*A*T*G*A*C*G*T*T*C*C*T*G*A*T*G*C*T-xxxxx- C*A*T*TTCCCTTAAATC-xxxx-GATTTAAGGGAA*A*T*G-xxxxx

3'

-continued

CpG(B)-scrambled ODN
(SEQ ID NO: 9)
5' T*C*C*A*T*G*A*C*G*T*T*C*C*T*G*A*T*G*C*T-xxxxx- A*C*T*CTTGCCAATTAC-xxxx-GTAATTGGCAAG*A*G*T-xxxxx

3'

STAT3dODN alone
(SEQ ID NO: 10)
5' xxxxx-C*A*T*TTCCCGTAAATC-xxxx-

GATTTACGGGAA*A*T*G-xxxxx 3'

Compound and component sequences.

| NAME | SEQUENCE (* = phosphorothioate linkage), x = (—(CH$_2$)$_3$—) bonded to phosphate groups at both ends except at the termini where terminal phosphates are optionally added and 5'x has an OH terminus and 3' x has a —C$^6$—NH$_2$ bonded to the final phosphate group, other linkages are phosphodiester. |
|---|---|
| CpG(A)-STAT3dODN (SEQ ID NO: 4) | 5' G*G*TGCATCGATGCAGG*G*G*G*G-xxxxx-C*A*T*TTCCCGTAAATC-xxxx-GATTTACGGGAA*A*T*G-xxxxx 3' |
| GpC(A)-STAT3dODN (SEQ ID NO: 5) | 5' G*G*TGCATGCATGCAG G*G*G*G*G-xxxxxx-C*A*T*TTCCCGTAAATC-xxxx-GATTT ACGGGAA*A*T*G-xxxxx 3' |
| CpG(A)-scrambled ODN (SEQ ID NO: 6) | 5' G*G*TGCATCGATGCAGG*G*G*G*G-xxxxx-A*C*T*CTTGCCAATTAC-xxxx-GTAAT TGGCAAG*A*G*T-xxxxx 3' |
| CpG(B)-STAT3dODN (SEQ ID NO: 7) | 5' T*C*C*A*T*G*A*C*G*T*T*C*C*T*G*A*T*G*C*T-xxxxx-C*A*T*TTCCCGTAAATC-xxxx-GATTTACGGGAA*A*T*G-xxxxx 3' |
| CpG(B)-mutSTAT3dODN (SEQ ID NO: 8) | 5' T*C*C*A*T*G*A*C*G*T*T*C*C*T*G*A*T*G*C*T-xxxxxx-C*A*T*TTCCCTTAAATC-xxxx-GATTTAAGGGAA*A*T*G-xxxxx 3' |
| CpG(B)-scrambled ODN (SEQ ID NO: 9) | 5' T*C*C*A*T*G*A*C*G*T*T*C*C*T*G*A*T*G*C*T-xxxxx-A*C*T*CTTGCCAATTAC-xxxx-GTAATTGGCAAG*A*G*T-xxxxx 3' |
| STAT3dODN (SEQ ID NO: 10) | 5' xxxxx-C*A*T*TTCCCGTAAATC-xxxx-GATTTACGGGAA*A*T*G-xxxxx 3' |
| ODN 1585 (SEQ ID NO: 11) | 5'-G*G*GGTCAACGTTGAG*G*G*G*G-3' |
| ODN 1585 (SEQ ID NO: 12) | 5'-G*GGGTCAACGTTGAG*G*G*G*G-3' |
| ODN 2216 (SEQ ID NO: 13) | 5'-G*G*GGGACGATCGTCG*G*G*G*G-3' |
| ODN 2216 (SEQ ID NO: 14) | 5'-G*GGGGACGATCGTCG*G*G*G*G-3' |
| ODN D19 (SEQ ID NO: 15) | 5'-G*G*TGCATCGATGCAGG1*G*G*G*G-3' |
| ODN D19 (SEQ ID NO: 16) | 5'-G*GTGCATCGATGCAGG*G*G*G*G-3' |
| ODN 2336 (SEQ ID NO: 17) | 5'-G*G*G*GACGACGTCGTGG*G*G*G*G-3 |

-continued

| NAME | SEQUENCE (* = phosphorothioate linkage), x = (—(CH$_2$)$_3$—) bonded to phosphate groups at both ends except at the termini where terminal phosphates are optionally added and 5'x has an OH terminus and 3' x has a —C$^6$—NH$_2$ bonded to the final phosphate group, other linkages are phosphodiester. |
|---|---|
| ODN 2336 (SEQ ID NO: 18) | 5'-G*G*GGACGACGTCGTGG*G*G*G*G-3' |
| ODN 1668 (SEQ ID NO: 19) | 5'-T*C*C*A*T*G*A*C*G*T*T*C*C*T*G*A*T*G*C*T-3' |
| ODN 1826 (SEQ ID NO: 20) | 5'- T*C*C*A*T*G*A*C*G*T*T*C*C*T*G*A*C*G*T*T-3' |
| ODN 2006 (ODN7909) (SEQ ID NO: 21) | 5'-T*C*G*T*C*G*T*T*T*T*G*T*C*G*T*T*T*T*G*T*C*G*T*T-3' |
| ODN 2007 (SEQ ID NO: 22) | 5'-T*C*G*T*C*G*T*T*G*T*C*G*T*T*T*T*G*T*C*G*T-3' |
| ODN 2395 (SEQ ID NO: 23) | 5'-T*C*G*T*C*G*T*T*T*T*C*G*G*C*G*C*G*C*G*C*C*G-3' |
| ODN M362 (SEQ ID NO: 24) | 5'- T*C*G*T*C*G*T*C*G*T*T*C*G*A*A*C*G*A*C*G*T*T*G*A*T-3' |

REFERENCES

Darnell, Nat Rev Cancer, 2(10):740-749 (2002);
Leong et al, Proc Natl Acad Sci USA, 100(7):4138-4143 (2003);
Zhang et al, Blood. 127(13):1687-700 (2016);
Zhao et al, Mol Ther. Mol Ther, 26(3):695-707 (17 Jan. 2018);
Ito et al, Science, 327(5971):1345-1350 (2010);
Winter et al, Science, 348(6241):1376-1381 (2015);
Neklesa et al, Pharmacol Ther., 174:138-144 (2017);
Raina et al, Proc Natl Acad Sci USA, 113(26):7124-7129 (2016);
Deshaies, Nat Chem Biol., 11(9):634-635 (2015);
Fischer et al, Nature, 512(7512):49-53 (2014).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound comprising:

(i) a nucleic acid having at least 90% sequence identity to a nucleic acid selected from the group consisting of SEQ ID NO:1, SEQ ID NO:2, SEQ ID NO:3, SEQ ID NO:4, SEQ ID NO:5, SEQ ID NO:7, and SEQ ID NO:8; and (ii) one or more ubiquitin ligase binding compounds selected from the group consisting of:

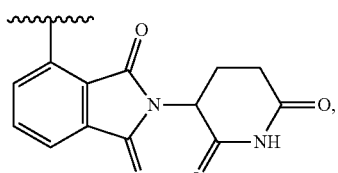

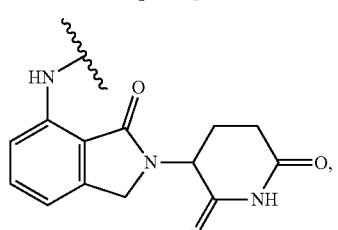

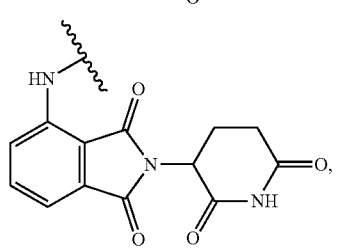

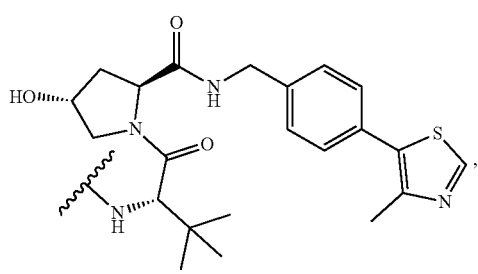

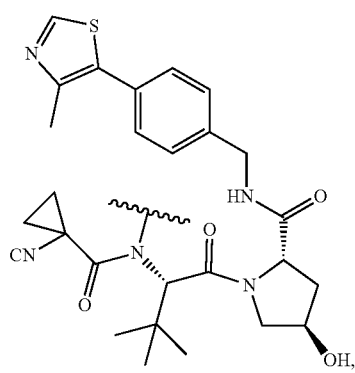

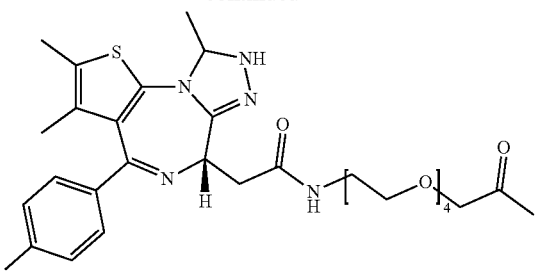

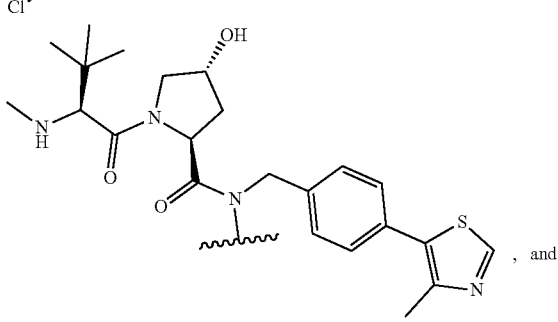, and

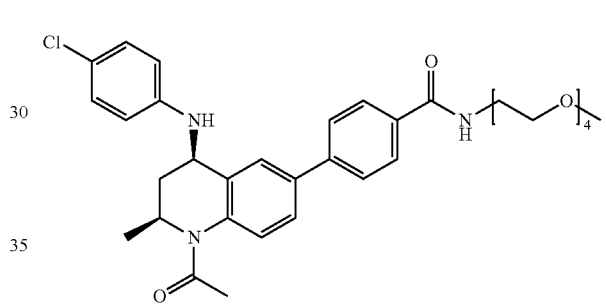

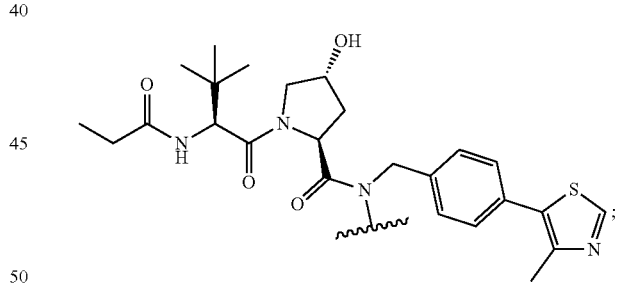

wherein the nucleic acid is covalently bonded to the one or more ubiquitin ligase binding compounds.

2. The compound of claim 1, wherein the one or more ubiquitin ligase binding compounds are selected from the group consisting of:

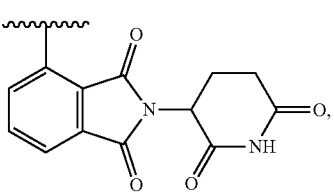 [SMILES: *c1cccc2c1C(=O)N(C1CCC(=O)NC1=O)C2=O]

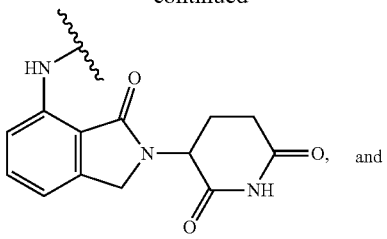

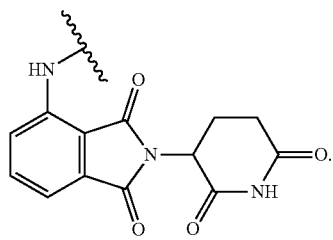

3. The compound of claim 1, wherein the nucleic acid is selected from the group consisting of SEQ ID NO: 1, SEQ ID NO:2, SEQ ID NO:3, SEQ ID NO:4, SEQ ID NO:5, SEQ ID NO:7, and SEQ ID NO: 8.

4. The compound of claim 1, wherein the compound comprises from 1 to 5 ubiquitin ligase binding compounds.

5. The compound of claim 1, wherein the nucleic acid has at least 95% sequence identity to the nucleic acid of SEQ ID NO:2 and the ubiquitin ligase binding compound is

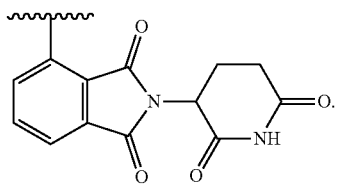

6. A pharmaceutical composition comprising a pharmaceutically acceptable excipient and the compound of claim 1.

7. A method of treating lymphoma in a patient in need thereof, the method comprising administering to the patient a therapeutically effective amount of the compound of claim 1.

8. A compound comprising:
(i) a signal transducer and activator of transcription 3 (STAT3) binding nucleic acid sequence,
(ii) a second nucleic acid sequence selected from the group consisting of a Class A CpG oligodeoxynucleotide, a Class B CpG oligodeoxynucleotide, or a Class C CpG oligodeoxynucleotide, and
(iii) a ubiquitin ligase binding compound capable of binding a cereblon protein;

wherein the ubiquitin ligase binding compound is covalently bound to (i) or (ii) through a linker having the formula:

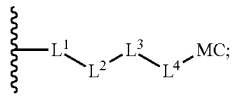

wherein:

MC is the ubiquitin ligase binding compound, $L^1$ is:

(a) —$(PO_3OH$—$(CH_2)_{pm})_{pn}$—$PO_3OH$—, wherein pm is an integer from 1 to 8; and pn is an integer from 1 to 10;

(b) —$(CH_2)_{pc}$—$(PO_3OH$—$(CH_2)_{pm})_{pn}$—$PO_3OH$—; wherein pc is an integer from 0 to 6;
pm is an integer from 1 to 8; and pn is an integer from 1 to 10:

(c) —$(CH_2)_{pc}$—$(PO_3OH$—$(CH_2)_{pm})_{pn}$—; wherein pc is an integer from 0 to 6; pm is an integer from 1 to 8; and pn is an integer from 1 to 10;

(d) —$(PO_3OH$—$(CH_2)_{pm})_{pn}$—$PO_3OH$—$(CH_2)_{po}$—NH—; wherein pm is an integer from 1 to 8; pn is an integer from 1 to 10; and po is an integer from 1 to 12;

(e) —$(PO_3OH$—$(CH_2)_{pm})_{pn}$—$PO_3OH$—$[(CH_2)_{pa}$—$O]_{pb}$—$(CH_2)_{po}$—NH—; wherein pm is an integer from 1 to 8; pn is an integer from 1 to 10; po is an integer from 1 to 12; pa is an integer from 1 to 4; and pb is 0, 1, or 2; or (f)

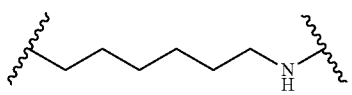 [SMILES: *CCCCCCN*]

$L^2$, $L^3$, and $L^4$ are each independently substituted or unsubstituted polyglycol, substituted or unsubstituted $C_1$-$C_{16}$ alkylene, substituted or unsubstituted 2 to 16 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 6 to 20 membered heteroarylene.

9. The compound of claim 8, wherein:

(i) the STAT3 binding nucleic acid sequence is SEQ ID NO:25 or SEQ ID NO:26;

(ii) the second nucleic acid sequence is SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24; and (iii) the ubiquitin ligase binding compound is selected from the group consisting of:
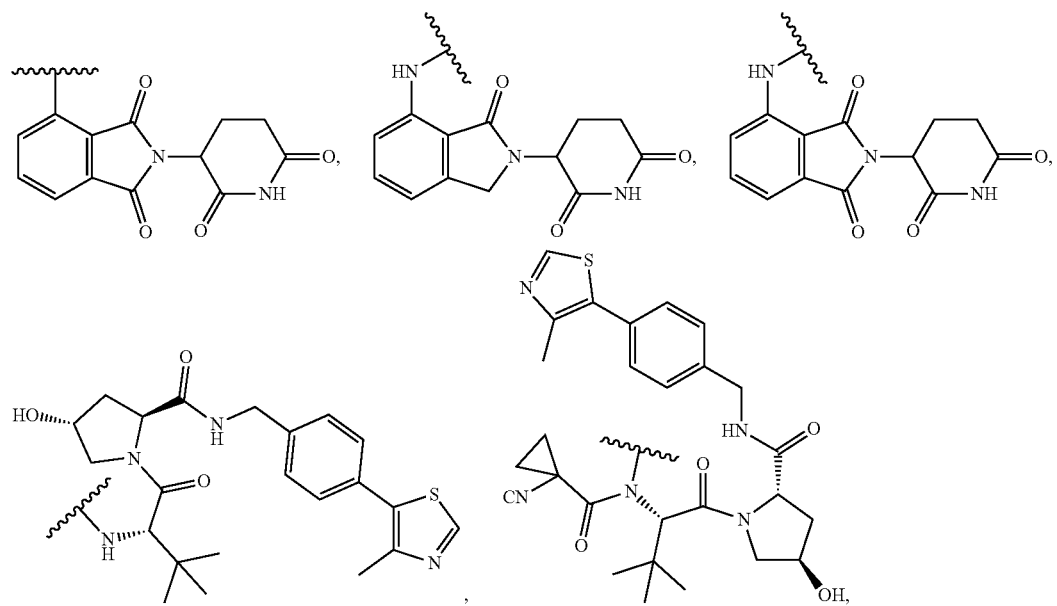
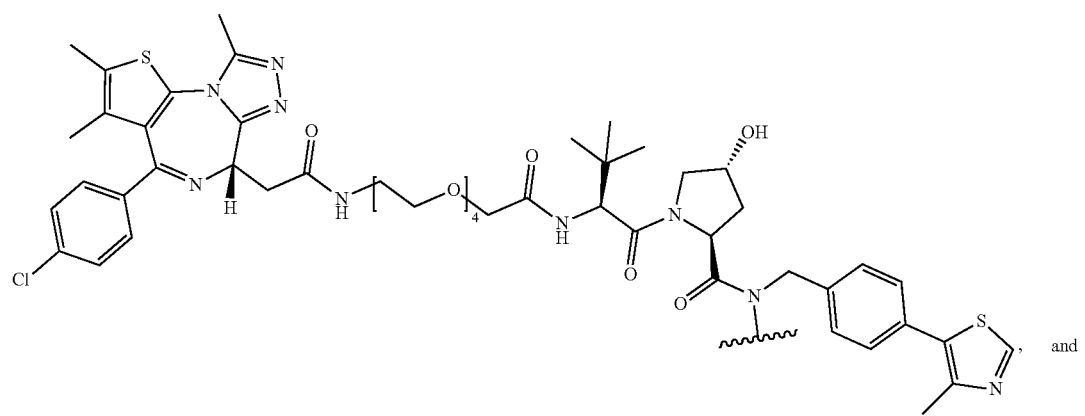
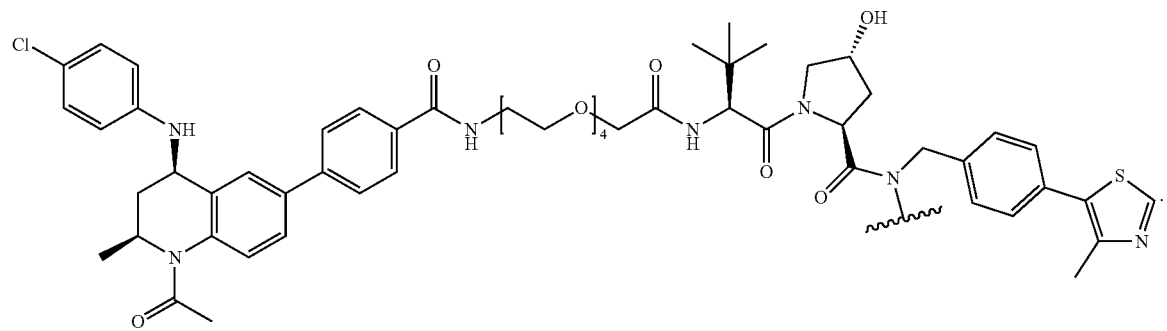

10. The compound of claim 9, wherein the ubiquitin ligase binding compound is selected from the group consisting of:

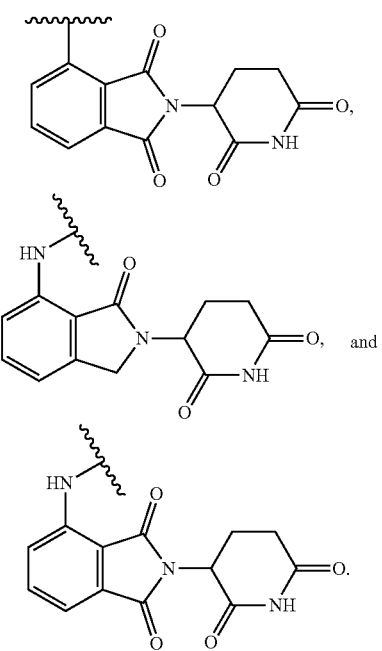

11. The compound of claim 8, wherein the STAT3 binding nucleic acid sequence and the second nucleic acid sequence comprise a nucleic acid selected from the group consisting of SEQ ID NO:1, SEQ ID NO:2, SEQ ID NO:3, SEQ ID NO:4, SEQ ID NO:5, SEQ ID NO:7, and SEQ ID NO:8.

12. The compound of claim 8, wherein the compound comprises from 1 to 5 ubiquitin ligase binding compounds.

13. A pharmaceutical composition comprising a pharmaceutically acceptable excipient and the compound of claim.

14. A method of treating lymphoma in a patient in need thereof, the method comprising administering to the patient a therapeutically effective amount of the compound of claim 8.

15. A compound comprising:
(i) a signal transducer and activator of transcription 3 (STAT3) binding nucleic acid sequence comprising a first STAT3 binding nucleic acid sequence and a second STAT3 binding nucleic acid sequence connected through a spacer, wherein the spacer is substituted or unsubstituted polyglycol, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
(ii) a second nucleic acid sequence selected from the group consisting of a Class A CpG oligodeoxynucleotide, a Class B CpG oligodeoxynucleotide, or a Class C CpG oligodeoxynucleotide, and
(iii) a ubiquitin ligase binding compound capable of binding a cereblon protein; wherein the ubiquitin ligase binding compound is covalently bound to (i) or (ii) through a linker.

16. The compound of claim 15, wherein:
(i) the first STAT3 binding nucleic acid sequence is SEQ ID NO:25 and the second STAT3 binding nucleic acid sequence is SEQ ID NO:26;
(ii) the second nucleic acid sequence is SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24; and
(iii) the ubiquitin ligase binding compound is selected from the group consisting of:

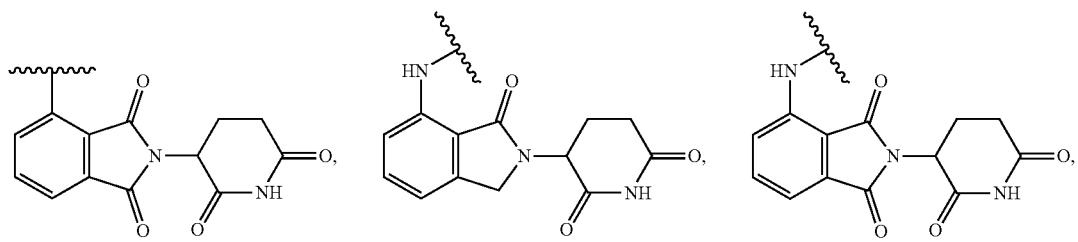

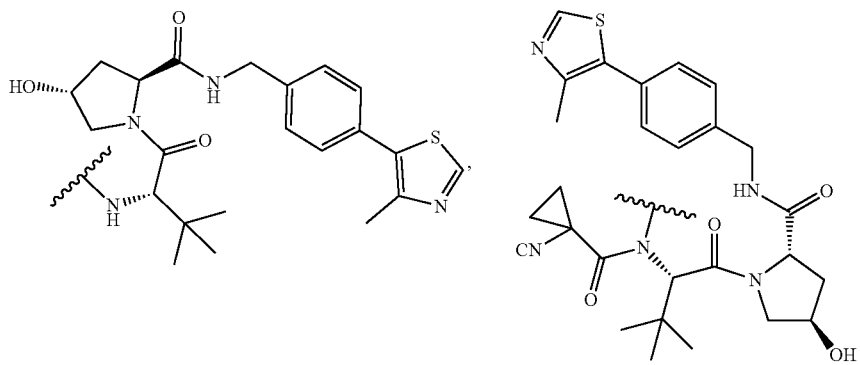

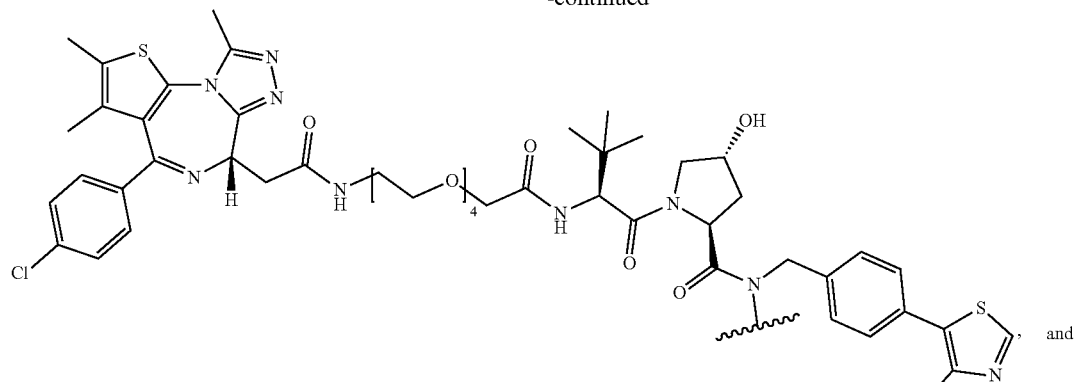

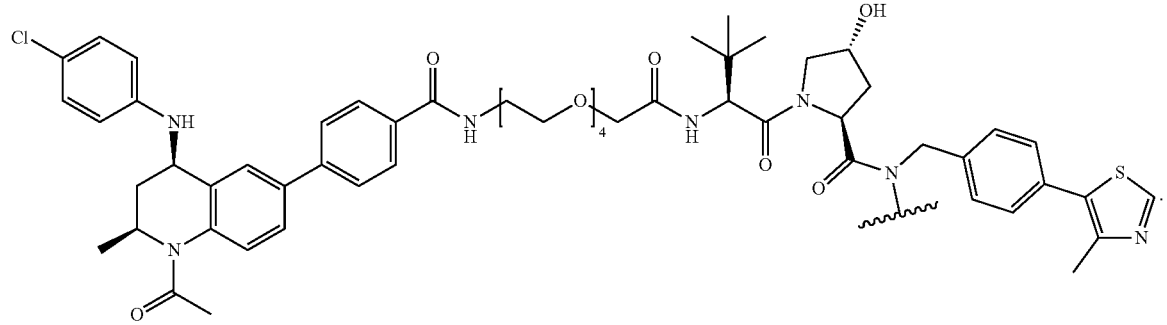
and

17. The compound of claim 16, wherein the ubiquitin ligase binding compound is selected from the group consisting of:

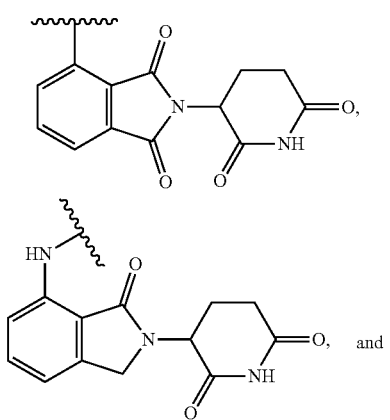
and

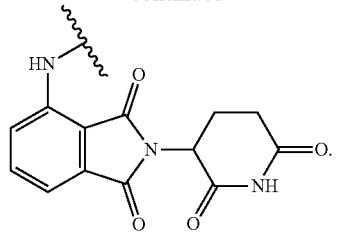

18. The compound of claim 15, wherein the compound comprises from 1 to 5 ubiquitin ligase binding compounds.

19. A pharmaceutical composition comprising a pharmaceutically acceptable excipient and the compound of claim 15.

20. A method of treating lymphoma in a patient in need thereof, the method comprising administering to the patient a therapeutically effective amount of the compound of claim 15.

* * * * *

SEQUENCE LISTING

```
<160> NUMBER OF SEQ ID NOS: 26

<210> SEQ ID NO 1
<211> LENGTH: 54
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: internal phosphorothioation
<220> FEATURE:
<221> NAME/KEY: misc_feature
<222> LOCATION: (2)..(3)
<223> OTHER INFORMATION: internal phosphorothioation
<220> FEATURE:
<221> NAME/KEY: misc_feature
<222> LOCATION: (3)..(4)
<223> OTHER INFORMATION: internal phosphorothioation
<220> FEATURE:
<221> NAME/KEY: misc_feature
<222> LOCATION: (4)..(5)
<223> OTHER INFORMATION: internal phosphorothioation
<220> FEATURE:
<221> NAME/KEY: misc_feature
<222> LOCATION: (5)..(6)
<223> OTHER INFORMATION: internal phosphorothioation
<220> FEATURE:
```

```
<221> NAME/KEY: misc_feature
<222> LOCATION: (6)..(7)
<223> OTHER INFORMATION: internal phosphorothioation
<220> FEATURE:
<221> NAME/KEY: misc_feature
<222> LOCATION: (7)..(8)
<223> OTHER INFORMATION: internal phosphorothioation
<220> FEATURE:
<221> NAME/KEY: misc_feature
<222> LOCATION: (8)..(9)
<223> OTHER INFORMATION: internal phosphorothioation
<220> FEATURE:
<221> NAME/KEY: misc_feature
<222> LOCATION: (9)..(10)
<223> OTHER INFORMATION: internal phosphorothioation
<220> FEATURE:
<221> NAME/KEY: misc_feature
<222> LOCATION: (10)..(11)
<223> OTHER INFORMATION: internal phosphorothioation
<220> FEATURE:
<221> NAME/KEY: misc_feature
<222> LOCATION: (11)..(12)
<223> OTHER INFORMATION: internal phosphorothioation
<220> FEATURE:
<221> NAME/KEY: misc_feature
<222> LOCATION: (12)..(13)
<223> OTHER INFORMATION: internal phosphorothioation
<220> FEATURE:
<221> NAME/KEY: misc_feature
<222> LOCATION: (13)..(14)
<223> OTHER INFORMATION: internal phosphorothioation
<220> FEATURE:
<221> NAME/KEY: misc_feature
<222> LOCATION: (14)..(15)
<223> OTHER INFORMATION: internal phosphorothioation
<220> FEATURE:
<221> NAME/KEY: misc_feature
<222> LOCATION: (15)..(16)
<223> OTHER INFORMATION: internal phosphorothioation
<220> FEATURE:
<221> NAME/KEY: misc_feature
<222> LOCATION: (16)..(17)
<223> OTHER INFORMATION: internal phosphorothioation
<220> FEATURE:
<221> NAME/KEY: misc_feature
<222> LOCATION: (17)..(18)
<223> OTHER INFORMATION: internal phosphorothioation
<220> FEATURE:
<221> NAME/KEY: misc_feature
<222> LOCATION: (18)..(19)
<223> OTHER INFORMATION: internal phosphorothioation
<220> FEATURE:
<221> NAME/KEY: misc_feature
<222> LOCATION: (19)..(20)
<223> OTHER INFORMATION: internal phosphorothioation
<220> FEATURE:
<221> NAME/KEY: misc_feature
<222> LOCATION: (20)..(21)
<223> OTHER INFORMATION: internal phosphorothioation
<220> FEATURE:
<221> NAME/KEY: misc_feature
<222> LOCATION: (21)..(22)
<223> OTHER INFORMATION: internal phosphorothioation
<220> FEATURE:
<221> NAME/KEY: misc_feature
<222> LOCATION: (22)..(23)
<223> OTHER INFORMATION: internal phosphorothioation
<220> FEATURE:
<221> NAME/KEY: misc_feature
<222> LOCATION: (23)..(24)
<223> OTHER INFORMATION: internal phosphorothioation
<220> FEATURE:
<221> NAME/KEY: misc_feature
<222> LOCATION: (24)..(25)
<223> OTHER INFORMATION: ((CH2)3)5
<220> FEATURE:
<221> NAME/KEY: misc_feature
<222> LOCATION: (25)..(26)
<223> OTHER INFORMATION: internal phosphorothioation
```

```
<220> FEATURE:
<221> NAME/KEY: misc_feature
<222> LOCATION: (26)..(27)
<223> OTHER INFORMATION: internal phosphorothioation
<220> FEATURE:
<221> NAME/KEY: misc_feature
<222> LOCATION: (27)..(28)
<223> OTHER INFORMATION: internal phosphorothioation
<220> FEATURE:
<221> NAME/KEY: misc_feature
<222> LOCATION: (39)..(40)
<223> OTHER INFORMATION: ((CH2)3)4
<220> FEATURE:
<221> NAME/KEY: misc_feature
<222> LOCATION: (51)..(52)
<223> OTHER INFORMATION: internal phosphorothioation
<220> FEATURE:
<221> NAME/KEY: misc_feature
<222> LOCATION: (52)..(53)
<223> OTHER INFORMATION: internal phosphorothioation
<220> FEATURE:
<221> NAME/KEY: misc_feature
<222> LOCATION: (53)..(54)
<223> OTHER INFORMATION: internal phosphorothioation
<220> FEATURE:
<221> NAME/KEY: misc_feature
<222> LOCATION: (54)..(54)
<223> OTHER INFORMATION: 3' C6 amino linker

<400> SEQUENCE: 1
tcgtcgtttt gtcgttttgt cgttcatttc ccgtaaatcg atttacggga aatg    54

<210> SEQ ID NO 2
<211> LENGTH: 54
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: internal phosphorothioation
<220> FEATURE:
<221> NAME/KEY: misc_feature
<222> LOCATION: (2)..(3)
<223> OTHER INFORMATION: internal phosphorothioation
<220> FEATURE:
<221> NAME/KEY: misc_feature
<222> LOCATION: (3)..(4)
<223> OTHER INFORMATION: internal phosphorothioation
<220> FEATURE:
<221> NAME/KEY: misc_feature
<222> LOCATION: (4)..(5)
<223> OTHER INFORMATION: internal phosphorothioation
<220> FEATURE:
<221> NAME/KEY: misc_feature
<222> LOCATION: (5)..(6)
<223> OTHER INFORMATION: internal phosphorothioation
<220> FEATURE:
<221> NAME/KEY: misc_feature
<222> LOCATION: (6)..(7)
<223> OTHER INFORMATION: internal phosphorothioation
<220> FEATURE:
<221> NAME/KEY: misc_feature
<222> LOCATION: (7)..(8)
<223> OTHER INFORMATION: internal phosphorothioation
<220> FEATURE:
<221> NAME/KEY: misc_feature
<222> LOCATION: (8)..(9)
<223> OTHER INFORMATION: internal phosphorothioation
<220> FEATURE:
<221> NAME/KEY: misc_feature
<222> LOCATION: (9)..(10)
<223> OTHER INFORMATION: internal phosphorothioation
<220> FEATURE:
<221> NAME/KEY: misc_feature
<222> LOCATION: (10)..(11)
```

```
<223> OTHER INFORMATION: internal phosphorothioation
<220> FEATURE:
<221> NAME/KEY: misc_feature
<222> LOCATION: (11)..(12)
<223> OTHER INFORMATION: internal phosphorothioation
<220> FEATURE:
<221> NAME/KEY: misc_feature
<222> LOCATION: (12)..(13)
<223> OTHER INFORMATION: internal phosphorothioation
<220> FEATURE:
<221> NAME/KEY: misc_feature
<222> LOCATION: (13)..(14)
<223> OTHER INFORMATION: internal phosphorothioation
<220> FEATURE:
<221> NAME/KEY: misc_feature
<222> LOCATION: (14)..(15)
<223> OTHER INFORMATION: internal phosphorothioation
<220> FEATURE:
<221> NAME/KEY: misc_feature
<222> LOCATION: (15)..(16)
<223> OTHER INFORMATION: internal phosphorothioation
<220> FEATURE:
<221> NAME/KEY: misc_feature
<222> LOCATION: (16)..(17)
<223> OTHER INFORMATION: internal phosphorothioation
<220> FEATURE:
<221> NAME/KEY: misc_feature
<222> LOCATION: (17)..(18)
<223> OTHER INFORMATION: internal phosphorothioation
<220> FEATURE:
<221> NAME/KEY: misc_feature
<222> LOCATION: (18)..(19)
<223> OTHER INFORMATION: internal phosphorothioation
<220> FEATURE:
<221> NAME/KEY: misc_feature
<222> LOCATION: (19)..(20)
<223> OTHER INFORMATION: internal phosphorothioation
<220> FEATURE:
<221> NAME/KEY: misc_feature
<222> LOCATION: (20)..(21)
<223> OTHER INFORMATION: internal phosphorothioation
<220> FEATURE:
<221> NAME/KEY: misc_feature
<222> LOCATION: (21)..(22)
<223> OTHER INFORMATION: internal phosphorothioation
<220> FEATURE:
<221> NAME/KEY: misc_feature
<222> LOCATION: (22)..(23)
<223> OTHER INFORMATION: internal phosphorothioation
<220> FEATURE:
<221> NAME/KEY: misc_feature
<222> LOCATION: (23)..(24)
<223> OTHER INFORMATION: internal phosphorothioation
<220> FEATURE:
<221> NAME/KEY: misc_feature
<222> LOCATION: (24)..(25)
<223> OTHER INFORMATION: ((CH2)3)5
<220> FEATURE:
<221> NAME/KEY: misc_feature
<222> LOCATION: (25)..(26)
<223> OTHER INFORMATION: internal phosphorothioation
<220> FEATURE:
<221> NAME/KEY: misc_feature
<222> LOCATION: (26)..(27)
<223> OTHER INFORMATION: internal phosphorothioation
<220> FEATURE:
<221> NAME/KEY: misc_feature
<222> LOCATION: (27)..(28)
<223> OTHER INFORMATION: internal phosphorothioation
<220> FEATURE:
<221> NAME/KEY: misc_feature
<222> LOCATION: (39)..(40)
<223> OTHER INFORMATION: ((CH2)3)4
<220> FEATURE:
<221> NAME/KEY: misc_feature
<222> LOCATION: (51)..(52)
<223> OTHER INFORMATION: internal phosphorothioation
<220> FEATURE:
<221> NAME/KEY: misc_feature
```

<222> LOCATION: (52)..(53)
<223> OTHER INFORMATION: internal phosphorothioation
<220> FEATURE:
<221> NAME/KEY: misc_feature
<222> LOCATION: (53)..(54)
<223> OTHER INFORMATION: internal phosphorothioation
<220> FEATURE:
<221> NAME/KEY: misc_feature
<222> LOCATION: (54)..(54)
<223> OTHER INFORMATION: 3' C6 amino linker

<400> SEQUENCE: 2
tcgtcgtttt gtcgttttgt cgttcatttc ccgtaaatcg atttacggga aatg    54

<210> SEQ ID NO 3
<211> LENGTH: 54
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: internal phosphorothioation
<220> FEATURE:
<221> NAME/KEY: misc_feature
<222> LOCATION: (2)..(3)
<223> OTHER INFORMATION: internal phosphorothioation
<220> FEATURE:
<221> NAME/KEY: misc_feature
<222> LOCATION: (3)..(4)
<223> OTHER INFORMATION: internal phosphorothioation
<220> FEATURE:
<221> NAME/KEY: misc_feature
<222> LOCATION: (4)..(5)
<223> OTHER INFORMATION: internal phosphorothioation
<220> FEATURE:
<221> NAME/KEY: misc_feature
<222> LOCATION: (5)..(6)
<223> OTHER INFORMATION: internal phosphorothioation
<220> FEATURE:
<221> NAME/KEY: misc_feature
<222> LOCATION: (6)..(7)
<223> OTHER INFORMATION: internal phosphorothioation
<220> FEATURE:
<221> NAME/KEY: misc_feature
<222> LOCATION: (7)..(8)
<223> OTHER INFORMATION: internal phosphorothioation
<220> FEATURE:
<221> NAME/KEY: misc_feature
<222> LOCATION: (8)..(9)
<223> OTHER INFORMATION: internal phosphorothioation
<220> FEATURE:
<221> NAME/KEY: misc_feature
<222> LOCATION: (9)..(10)
<223> OTHER INFORMATION: internal phosphorothioation
<220> FEATURE:
<221> NAME/KEY: misc_feature
<222> LOCATION: (10)..(11)
<223> OTHER INFORMATION: internal phosphorothioation
<220> FEATURE:
<221> NAME/KEY: misc_feature
<222> LOCATION: (11)..(12)
<223> OTHER INFORMATION: internal phosphorothioation
<220> FEATURE:
<221> NAME/KEY: misc_feature
<222> LOCATION: (12)..(13)
<223> OTHER INFORMATION: internal phosphorothioation
<220> FEATURE:
<221> NAME/KEY: misc_feature
<222> LOCATION: (13)..(14)
<223> OTHER INFORMATION: internal phosphorothioation
<220> FEATURE:
<221> NAME/KEY: misc_feature
<222> LOCATION: (14)..(15)
<223> OTHER INFORMATION: internal phosphorothioation
<220> FEATURE:

<220> FEATURE:
<221> NAME/KEY: misc_feature
<222> LOCATION: (15)..(16)
<223> OTHER INFORMATION: internal phosphorothioation
<220> FEATURE:
<221> NAME/KEY: misc_feature
<222> LOCATION: (16)..(17)
<223> OTHER INFORMATION: internal phosphorothioation
<220> FEATURE:
<221> NAME/KEY: misc_feature
<222> LOCATION: (17)..(18)
<223> OTHER INFORMATION: internal phosphorothioation
<220> FEATURE:
<221> NAME/KEY: misc_feature
<222> LOCATION: (18)..(19)
<223> OTHER INFORMATION: internal phosphorothioation
<220> FEATURE:
<221> NAME/KEY: misc_feature
<222> LOCATION: (19)..(20)
<223> OTHER INFORMATION: internal phosphorothioation
<220> FEATURE:
<221> NAME/KEY: misc_feature
<222> LOCATION: (20)..(21)
<223> OTHER INFORMATION: internal phosphorothioation
<220> FEATURE:
<221> NAME/KEY: misc_feature
<222> LOCATION: (21)..(22)
<223> OTHER INFORMATION: internal phosphorothioation
<220> FEATURE:
<221> NAME/KEY: misc_feature
<222> LOCATION: (22)..(23)
<223> OTHER INFORMATION: internal phosphorothioation
<220> FEATURE:
<221> NAME/KEY: misc_feature
<222> LOCATION: (23)..(24)
<223> OTHER INFORMATION: internal phosphorothioation
<220> FEATURE:
<221> NAME/KEY: misc_feature
<222> LOCATION: (24)..(25)
<223> OTHER INFORMATION: ((CH2)3)5
<220> FEATURE:
<221> NAME/KEY: misc_feature
<222> LOCATION: (25)..(26)
<223> OTHER INFORMATION: internal phosphorothioation
<220> FEATURE:
<221> NAME/KEY: misc_feature
<222> LOCATION: (26)..(27)
<223> OTHER INFORMATION: internal phosphorothioation
<220> FEATURE:
<221> NAME/KEY: misc_feature
<222> LOCATION: (27)..(28)
<223> OTHER INFORMATION: internal phosphorothioation
<220> FEATURE:
<221> NAME/KEY: misc_feature
<222> LOCATION: (39)..(40)
<223> OTHER INFORMATION: ((CH2)3)4
<220> FEATURE:
<221> NAME/KEY: misc_feature
<222> LOCATION: (51)..(52)
<223> OTHER INFORMATION: internal phosphorothioation
<220> FEATURE:
<221> NAME/KEY: misc_feature
<222> LOCATION: (52)..(53)
<223> OTHER INFORMATION: internal phosphorothioation
<220> FEATURE:
<221> NAME/KEY: misc_feature
<222> LOCATION: (53)..(54)
<223> OTHER INFORMATION: internal phosphorothioation
<220> FEATURE:
<221> NAME/KEY: misc_feature
<222> LOCATION: (54)..(54)
<223> OTHER INFORMATION: 3' C6 amino linker

<400> SEQUENCE: 3
tcgtcgtttt gtcgttttgt cgttcatttc ccgtaaatcg atttacggga aatg    54

<210> SEQ ID NO 4
<211> LENGTH: 50

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: ((CH2)3)5
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage
<220> FEATURE:
<221> NAME/KEY: misc_feature
<222> LOCATION: (35)..(36)
<223> OTHER INFORMATION: ((CH2)3)4
<220> FEATURE:
<221> NAME/KEY: misc_feature
<222> LOCATION: (47)..(48)
<223> OTHER INFORMATION: phosphorothioate linkage
<220> FEATURE:
<221> NAME/KEY: misc_feature
<222> LOCATION: (48)..(49)
<223> OTHER INFORMATION: phosphorothioate linkage
<220> FEATURE:
<221> NAME/KEY: misc_feature
<222> LOCATION: (49)..(50)
<223> OTHER INFORMATION: phosphorothioate linkage
<220> FEATURE:
<221> NAME/KEY: misc_feature
<222> LOCATION: (50)..(50)
<223> OTHER INFORMATION: ((CH2)3)5

<400> SEQUENCE: 4
ggtgcatcga tgcagggggg catttcccgt aaatcgattt acgggaaatg        50

<210> SEQ ID NO 5
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
```

-continued

```
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: ((CH2)3)5
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage
<220> FEATURE:
<221> NAME/KEY: misc_feature
<222> LOCATION: (35)..(36)
<223> OTHER INFORMATION: ((CH2)3)4
<220> FEATURE:
<221> NAME/KEY: misc_feature
<222> LOCATION: (47)..(48)
<223> OTHER INFORMATION: phosphorothioate linkage
<220> FEATURE:
<221> NAME/KEY: misc_feature
<222> LOCATION: (48)..(49)
<223> OTHER INFORMATION: phosphorothioate linkage
<220> FEATURE:
<221> NAME/KEY: misc_feature
<222> LOCATION: (49)..(50)
<223> OTHER INFORMATION: phosphorothioate linkage
<220> FEATURE:
<221> NAME/KEY: misc_feature
<222> LOCATION: (50)..(50)
<223> OTHER INFORMATION: ((CH2)3)5

<400> SEQUENCE: 5
ggtgcatgca tgcagggggg catttcccgt aaatcgattt acgggaaatg    50

<210> SEQ ID NO 6
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
```

<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: ((CH2)3)5
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage
<220> FEATURE:
<221> NAME/KEY: misc_feature
<222> LOCATION: (35)..(36)
<223> OTHER INFORMATION: ((CH2)3)4
<220> FEATURE:
<221> NAME/KEY: misc_feature
<222> LOCATION: (47)..(48)
<223> OTHER INFORMATION: phosphorothioate linkage
<220> FEATURE:
<221> NAME/KEY: misc_feature
<222> LOCATION: (48)..(49)
<223> OTHER INFORMATION: phosphorothioate linkage
<220> FEATURE:
<221> NAME/KEY: misc_feature
<222> LOCATION: (49)..(50)
<223> OTHER INFORMATION: phosphorothioate linkage
<220> FEATURE:
<221> NAME/KEY: misc_feature
<222> LOCATION: (50)..(50)
<223> OTHER INFORMATION: ((CH2)3)5

<400> SEQUENCE: 6
ggtgcatcga tgcagggggg actcttgcca attacgtaat tggcaagagt                50

<210> SEQ ID NO 7
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:

```
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: ((CH2)3)5
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage
<220> FEATURE:
<221> NAME/KEY: misc_feature
<222> LOCATION: (35)..(36)
<223> OTHER INFORMATION: ((CH2)3)4
```

-continued

```
<220> FEATURE:
<221> NAME/KEY: misc_feature
<222> LOCATION: (47)..(48)
<223> OTHER INFORMATION: phosphorothioate linkage
<220> FEATURE:
<221> NAME/KEY: misc_feature
<222> LOCATION: (48)..(49)
<223> OTHER INFORMATION: phosphorothioate linkage
<220> FEATURE:
<221> NAME/KEY: misc_feature
<222> LOCATION: (49)..(50)
<223> OTHER INFORMATION: phosphorothioate linkage
<220> FEATURE:
<221> NAME/KEY: misc_feature
<222> LOCATION: (50)..(50)
<223> OTHER INFORMATION: ((CH2)3)5

<400> SEQUENCE: 7
tccatgacgt tcctgatgct catttcccgt aaatcgattt acgggaaatg                50

<210> SEQ ID NO 8
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
```

```
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: ((CH2)3)5
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage
<220> FEATURE:
<221> NAME/KEY: misc_feature
<222> LOCATION: (35)..(36)
<223> OTHER INFORMATION: ((CH2)3)4
<220> FEATURE:
<221> NAME/KEY: misc_feature
<222> LOCATION: (47)..(48)
<223> OTHER INFORMATION: phosphorothioate linkage
<220> FEATURE:
<221> NAME/KEY: misc_feature
<222> LOCATION: (48)..(49)
<223> OTHER INFORMATION: phosphorothioate linkage
<220> FEATURE:
<221> NAME/KEY: misc_feature
<222> LOCATION: (49)..(50)
<223> OTHER INFORMATION: phosphorothioate linkage
<220> FEATURE:
<221> NAME/KEY: misc_feature
<222> LOCATION: (50)..(50)
<223> OTHER INFORMATION: ((CH2)3)5

<400> SEQUENCE: 8
tccatgacgt tcctgatgct catttccctt aaatcgattt aagggaaatg        50

<210> SEQ ID NO 9
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
```

```
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: (CH2)3)5
<220> FEATURE:
<221> NAME/KEY: misc_feature
<222> LOCATION: (21)..(22)
<223> OTHER INFORMATION: phosphorothioate linkage
<220> FEATURE:
```

```
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage
<220> FEATURE:
<221> NAME/KEY: misc_feature
<222> LOCATION: (35)..(36)
<223> OTHER INFORMATION: (CH2)3 4
<220> FEATURE:
<221> NAME/KEY: misc_feature
<222> LOCATION: (47)..(48)
<223> OTHER INFORMATION: phosphorothioate linkage
<220> FEATURE:
<221> NAME/KEY: misc_feature
<222> LOCATION: (48)..(49)
<223> OTHER INFORMATION: phosphorothioate linkage
<220> FEATURE:
<221> NAME/KEY: misc_feature
<222> LOCATION: (49)..(50)
<223> OTHER INFORMATION: phosphorothioate linkage
<220> FEATURE:
<221> NAME/KEY: misc_feature
<222> LOCATION: (50)..(50)
<223> OTHER INFORMATION: (CH2)3 5

<400> SEQUENCE: 9
tccatgacgt tcctgatgct actcttgcca attacgtaat tggcaagagt            50

<210> SEQ ID NO 10
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: ((CH2)3)5
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (15)..(16)
<223> OTHER INFORMATION: ((CH2)3)4
<220> FEATURE:
<221> NAME/KEY: misc_feature
<222> LOCATION: (27)..(28)
<223> OTHER INFORMATION: phosphorothioate linkage
<220> FEATURE:
<221> NAME/KEY: misc_feature
<222> LOCATION: (28)..(29)
<223> OTHER INFORMATION: phosphorothioate linkage
<220> FEATURE:
<221> NAME/KEY: misc_feature
<222> LOCATION: (29)..(30)
<223> OTHER INFORMATION: phosphorothioate linkage
<220> FEATURE:
<221> NAME/KEY: misc_feature
<222> LOCATION: (30)..(30)
<223> OTHER INFORMATION: ((CH2)3)5

<400> SEQUENCE: 10
catttcccgt aaatcgattt acgggaaatg            30
```

```
<210> SEQ ID NO 11
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage

<400> SEQUENCE: 11
ggggtcaacg ttgagggggg                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage

<400> SEQUENCE: 12
ggggtcaacg ttgagggggg                                               20

<210> SEQ ID NO 13
```

```
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage

<400> SEQUENCE: 13
gggggacgat cgtcgggggg                                                   20

<210> SEQ ID NO 14
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage

<400> SEQUENCE: 14
gggggacgat cgtcgggggg                                                   20

<210> SEQ ID NO 15
<211> LENGTH: 20
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage

<400> SEQUENCE: 15
ggtgcatcga tgcagggggg                                               20

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage

<400> SEQUENCE: 16
ggtgcatcga tgcaggggggg                                              20

<210> SEQ ID NO 17
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
```

-continued

```
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage

<400> SEQUENCE: 17 gggacgacg tcgtgggggg g                                                  21

<210> SEQ ID NO 18
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage

<400> SEQUENCE: 18 gggacgacg tcgtgggggg g                                                  21

<210> SEQ ID NO 19
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
```

```
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage

<400> SEQUENCE: 19
tccatgacgt tcctgatgct                                                      20

<210> SEQ ID NO 20
```

```
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
```

```
<222> LOCATION: (19)..(20)
<223> OTHER INFORMATION: phosphorothioate linkage

<400> SEQUENCE: 20
tccatgacgt tcctgacgtt                                                    20

<210> SEQ ID NO 21
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
```

```
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage

<400> SEQUENCE: 21
tcgtcgtttt gtcgttttgt cgtt                                              24

<210> SEQ ID NO 22
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
```

```
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 22
tcgtcgttgt cgttttgtcg tt                                              22

<210> SEQ ID NO 23
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
```

```
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 23
tcgtcgtttt cggcgcgcgc cg                                          22

<210> SEQ ID NO 24
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
```

```
<222> LOCATION: (2)..(3)
<223> OTHER INFORMATION: phosphorothioate linkage
<220> FEATURE:
<221> NAME/KEY: misc_feature
<222> LOCATION: (3)..(4)
<223> OTHER INFORMATION: phosphorothioate linkage
<220> FEATURE:
<221> NAME/KEY: misc_feature
<222> LOCATION: (4)..(5)
<223> OTHER INFORMATION: phosphorothioate linkage
<220> FEATURE:
<221> NAME/KEY: misc_feature
<222> LOCATION: (5)..(6)
<223> OTHER INFORMATION: phosphorothioate linkage
<220> FEATURE:
<221> NAME/KEY: misc_feature
<222> LOCATION: (6)..(7)
<223> OTHER INFORMATION: phosphorothioate linkage
<220> FEATURE:
<221> NAME/KEY: misc_feature
<222> LOCATION: (7)..(8)
<223> OTHER INFORMATION: phosphorothioate linkage
<220> FEATURE:
<221> NAME/KEY: misc_feature
<222> LOCATION: (8)..(9)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(11)
<223> OTHER INFORMATION: phosphorothioate linkage
<220> FEATURE:
<221> NAME/KEY: misc_feature
<222> LOCATION: (11)..(12)
<223> OTHER INFORMATION: phosphorothioate linkage
<220> FEATURE:
<221> NAME/KEY: misc_feature
<222> LOCATION: (12)..(13)
<223> OTHER INFORMATION: phosphorothioate linkage
<220> FEATURE:
<221> NAME/KEY: misc_feature
<222> LOCATION: (13)..(14)
<223> OTHER INFORMATION: phosphorothioate linkage
<220> FEATURE:
<221> NAME/KEY: misc_feature
<222> LOCATION: (14)..(15)
<223> OTHER INFORMATION: phosphorothioate linkage
<220> FEATURE:
<221> NAME/KEY: misc_feature
<222> LOCATION: (15)..(16)
<223> OTHER INFORMATION: phosphorothioate linkage
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage
<220> FEATURE:
```

```
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage
<220> FEATURE:
<221> NAME/KEY: misc_feature
<222> LOCATION: (24)..(25)
<223> OTHER INFORMATION: phosphorothioate linkage

<400> SEQUENCE: 24
tcgtcgtcgt tcgaacgacg ttgat                                         25

<210> SEQ ID NO 25
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: internal phosphorothioation
<220> FEATURE:
<221> NAME/KEY: misc_feature
<222> LOCATION: (2)..(3)
<223> OTHER INFORMATION: internal phosphorothioation
<220> FEATURE:
<221> NAME/KEY: misc_feature
<222> LOCATION: (3)..(4)
<223> OTHER INFORMATION: internal phosphorothioation

<400> SEQUENCE: 25
catttcccgt aaatc                                                    15

<210> SEQ ID NO 26
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (12)..(13)
<223> OTHER INFORMATION: internal phosphorothioation
<220> FEATURE:
<221> NAME/KEY: misc_feature
<222> LOCATION: (13)..(14)
<223> OTHER INFORMATION: internal phosphorothioation
<220> FEATURE:
<221> NAME/KEY: misc_feature
<222> LOCATION: (14)..(15)
<223> OTHER INFORMATION: internal phosphorothioation

<400> SEQUENCE: 26
gatttacggg aaatg                                                    15
```